United States Patent
Sim et al.

(10) Patent No.: US 7,371,750 B2
(45) Date of Patent: May 13, 2008

(54) COMPOUNDS AND COMPOSITIONS AS PROTEIN KINASE INHIBITORS

(75) Inventors: Taebo Sim, San Diego, CA (US); Hyun Soo Lee, San Diego, CA (US); Pingda Ren, San Diego, CA (US); Qiang Ding, San Diego, CA (US); Guobao Zhang, San Diego, CA (US); Yi Liu, San Diego, CA (US); Xia Wang, San Diego, CA (US); Tetsuo Uno, San Diego, CA (US); Bing Li, San Diego, CA (US); Lintong Li, San Diego, CA (US); Nathanael Schiander Gray, San Diego, CA (US); Shuli You, San Diego, CA (US)

(73) Assignee: IRM LLC, Hamilton (BM)

( * ) Notice: Subject to any disclaimer, the term of this patent is extended or adjusted under 35 U.S.C. 154(b) by 61 days.

(21) Appl. No.: 10/909,227

(22) Filed: Jul. 29, 2004

(65) Prior Publication Data

US 2005/0222177 A1 Oct. 6, 2005

Related U.S. Application Data

(60) Provisional application No. 60/491,133, filed on Jul. 29, 2003.

(51) Int. Cl.
| | |
|---|---|
| *A61K 31/5355* | (2006.01) |
| *A61K 31/53* | (2006.01) |
| *A61K 31/497* | (2006.01) |
| *A61K 31/513* | (2006.01) |
| *C07D 413/12* | (2006.01) |
| *C07D 253/065* | (2006.01) |
| *C07D 487/04* | (2006.01) |
| *C07D 413/14* | (2006.01) |
| *A61P 35/00* | (2006.01) |
| *C07D 471/04* | (2006.01) |

(52) U.S. Cl. ............ 514/234.2; 514/242; 514/252.16; 514/262.1; 544/112; 544/118; 544/182; 544/256; 544/279; 544/81

(58) Field of Classification Search .............. 544/257, 544/258, 256, 112, 118, 182, 81; 514/234.2, 514/262.1, 252.16, 242
See application file for complete search history.

(56) References Cited

U.S. PATENT DOCUMENTS 6,150,373 A * 11/2000 Harris et al. ............ 514/262.1
7,112,676 B2 * 9/2006 Dermatakis et al. ........ 544/256
2004/0019210 A1 * 1/2004 Chivikas Connolly et al. .................... 544/256
2004/0087600 A1 5/2004 Cai et al.
2004/0204427 A1 10/2004 Chen et al.
2007/0232611 A1 10/2007 Engh et al.

FOREIGN PATENT DOCUMENTS

| WO | WO 99/61444 | 12/1999 |
| WO | WO 00/24744 | 5/2000 |
| WO | WO 01/29042 | 4/2001 |
| WO | WO 2004/041821 | 5/2004 |

OTHER PUBLICATIONS

Background Information for the Oct. 2002 ACPS Meeting.*
Wikipedia (Isomer), 2007.*
Souillac, et al., Characterization of Delivery Systems, Differential Scanning Calorimetry, p. 217 (in Encyclopedia of Controlled Drug Delivery, 1999, John Wiley & Sons, pp. 212-227).*
Goldman, et al., N. England J. Med., 344, 14, Apr. 5, 2001.*
Ekman, et al., Oncogene (2000) 19, 4151-58.*
Xu, et al., J. Biol. Chem., 273, 50, Dec. 11, 1998. 33230-38.*
Zhang, et al., J. Biol. Chem., vol. 279, No. 53, Dec. 31, 2004, pp. 55348-55354.*
Lopes de Menezes, et al., Clin. Cancer Res. 2005:11 (14), Jul. 15, 2005, 5281-91.*
Kawahara, et al., J. Clin. Onc., 2006 ASCO Annual Meeting Proceedings, Part I, vol. 27, No. 18S, Jun. 20, 2006, 13163.*
Yoshida, et al., J Neurochem., 2004, 90, 352-58.*
Atlas of Genetics & Cytogenetics in Oncology & Haematology (Sep. 12, 2007) LCK.*
Brandlin, et al., J. Biol. Chem., vol. 277, No. 8, Feb. 22, 2002; 6490-6496.*
Wu, et al., Am. J. Pathol., 156, Jun. 6, 2000.*
Khan, et al., Journal of Allergy and Clinical Immunology, vol. 119, Issue 5, Mar. 6, 2007, p. 1277.*
Webster's Comprehensive Dictionary, 1996, "prevent."*
Graveleau, Nadege et al. Solid-Phase Synthesis of Pyrimido [4,5-d] pyrimidine-2,4(1H,3H)-diones. Synthesis May 8, 2003, No. 11, pp. 1739-1743.

* cited by examiner

*Primary Examiner*—Mark L Berch
*Assistant Examiner*—Cecilia M Jaisle
(74) *Attorney, Agent, or Firm*—Scott W. Reid; Genomics Institute of the Novartis Research Foundation

(57) ABSTRACT

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and Tie2 kinases.

7 Claims, No Drawings

COMPOUNDS AND COMPOSITIONS AS PROTEIN KINASE INHIBITORS

CROSS-REFERENCE TO RELATED APPLICATIONS

This application claims the benefit of priority to U.S. Provisional Patent Application No. 60/491,133, filed 29 Jul. 2003. The full disclosure of this application is incorporated herein by reference in its entirety and for all purposes.

BACKGROUND OF THE INVENTION

1. Field of the Invention

The invention provides a novel class of compounds, pharmaceutical compositions comprising such compounds and methods of using such compounds to treat or prevent diseases or disorders associated with abnormal or deregulated kinase activity, particularly diseases or disorders that involve abnormal activation of the Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and Tie2 kinases.

2. Background

The protein kinases represent a large family of proteins, which play a central role in the regulation of a wide variety of cellular processes and maintaining control over cellular function. A partial, non-limiting, list of these kinases include: receptor tyrosine kinases such as platelet-derived growth factor receptor kinase (PDGF-R), the receptor kinase for stem cell factor, c-kit, the nerve growth factor receptor, trkB, and the fibroblast growth factor receptor, FGFR3; non-receptor tyrosine kinases such Abl and the fusion kinase BCR-Abl, Fes, Lck and Syk; and serine/threonine kinases such as b-RAF, MAP kinases (e.g., MKK6) and SAPK2β. Aberrant kinase activity has been observed in many disease states including benign and malignant proliferative disorders as well as diseases resulting from inappropriate activation of the immune and nervous systems.

The novel compounds of this invention inhibit the activity of one or more protein kinases and are, therefore, expected to be useful in the treatment of kinase-associated diseases.

SUMMARY OF THE INVENTION

In one aspect, the present invention provides compounds of Formula I:

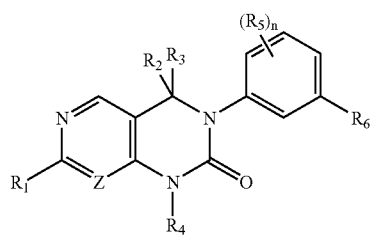

I in which:
n is selected from 0, 1, 2, 3 and 4;
Z is selected from N and CH;
$R_1$ is selected from hydrogen, —$R_8$, —$OR_8$, —$S(O)_{0-2}R_8$, —$NR_7R_8$ and —$NR_7NR_7R_8$; wherein $R_7$ is independently selected from hydrogen and $C_{1-6}$alkyl; $R_8$ is selected from hydrogen, $C_{1-6}$alkyl, $C_{2-6}$alkenyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; or $R_7$ and $R_8$ together with the nitrogen atom to which $R_7$ and $R_8$ are attached form $C_{3-10}$heterocycloalkyl or $C_{5-10}$heteroaryl; wherein any alkyl or alkenyl of $R_8$ is optionally substituted by one to three radicals independently selected from halo, hydroxy, $C_{1-6}$alkyl and —$NR_9R_{10}$; wherein any aryl, heteroaryl, cycloalkyl or heterocycloalkyl of $R_8$, or the combination of $R_7$ and $R_8$, is optionally substituted by one to three radicals selected from halo, hydroxy, cyano, $C_{1-6}$alkyl, $C_{1-6}$alkoxy, $C_{2-6}$alkenyl, halo-substituted-alkyl, halo-substituted-alkoxy, —$XNR_9R_{10}$, —$XOXNR_9R_{10}$, —$XNR_9S(O)_{0-2}R_{10}$, —$XC(O)NR_9R_{10}$, —$XNR_9C(O)XOR_9$, —$XNR_9C(O)NR_9R_{10}$, —$XNR_9XNR_9R_{10}$, —$XC(O)NR_9XNR_9R_{10}$, —$XNR_9XOR_9$, —$XOR_9$, —$XNR_9C(=NR_9)NR_9R_{10}$, —$XS(O)_{0-2}R_{11}$, —$XNR_9C(O)R_9$, —$XNR_9C(O)XNR_9R_{10}$, —$XNR_9C(O)R_{11}$, —$XC(O)R_{11}$, —$XR_{11}$, —$XC(O)OR_{10}$ and —$XS(O)_{0-2}NR_9R_{10}$; wherein X is a bond or $C_{1-4}$alkylene; $R_9$ and $R_{10}$ are independently selected from hydrogen, $C_{1-6}$alkyl and $C_{3-12}$cycloalkyl; and $R_{11}$ is $C_{3-10}$heterocycloalkyl optionally substituted with 1 to 3 radicals selected from $C_{1-6}$alkyl, —$XNR_9R_{10}$, —$XNR_9XNR_9R_9$, $XNR_9XOR_9$ and —$XOR_9$; wherein X, $R_9$ and $R_{10}$ are as described above;

$R_2$ and $R_3$ are independently selected from hydrogen and $C_{1-6}$alkyl; or $R_1$ and $R_2$ together form =O or =S;

$R_4$ is selected from hydrogen, hydroxy, amino, $C_{1-6}$alkyl, —$XOR_9$, —$XC(O)OR_9$, —$XC(O)NR_9R_{10}$, $C_{3-10}$cycloalkyl-$C_{0-4}$alkyl, $C_{5-10}$heteraryl-$C_{0-4}$alkyl, $C_{6-10}$aryl-$C_{0-4}$alkyl and $C_{3-10}$heterocycloalkyl-$C_{0-4}$alkyl; wherein X, $R_9$ and $R_{10}$ are as described above;

$R_5$ is selected from $C_{1-6}$alkyl, $C_{2-6}$alkenyl, $C_{1-6}$alkoxy, halo-substituted-$C_{1-4}$alkyl and halo-substituted-$C_{1-4}$alkoxy;

$R_6$ is selected from —$NR_{12}Y(O)R_{13}$ and —$Y(O)NR_{12}R_{13}$; wherein Y is selected from C, P(O), and S(O); $R_{12}$ is selected from hydrogen and $C_{1-6}$alkyl; and $R_{13}$ is selected from $C_{6-10}$aryl, $C_{5-10}$heteroaryl, $C_{3-10}$cycloalkyl, $C_{3-10}$heterocycloalkyl and $C_{1-6}$alkyl; wherein any aryl, heteroaryl, cycloalkyl or heterocycloalkyl of $R_{13}$ is optionally substituted by one to three radicals independently selected from halo, hydroxy, nitro, cyano, halo-substituted-$C_{1-6}$alkyl, $C_{1-6}$alkyl, $C_{1-6}$alkoxy, halo-substituted-$C_{1-6}$alkoxy, —$XNR_9R_9$, —$XNR_9XNR_9R_9$, —$XNR_9C(O)R_9$, —$XC(O)OR_9$, —$XNR_9S(O)_2R_9$, —$XNR_9S(O)R_9$, —$XNR_9SR_9$ and —$XR_{14}$; wherein X and $R_9$ are as defined above and $R_{14}$ is selected from $C_{5-10}$heteroaryl-$C_{0-4}$alkyl and $C_{3-10}$heterocycloalkyl-$C_{0-4}$alkyl; wherein any heteroaryl or heterocycloalkyl of $R_{14}$ is optionally substituted with a radical selected from $C_{1-6}$alkyl, halo-substituted-$C_{1-6}$alkyl —$NR_9R_9$ and —$C(O)OR_9$; wherein $R_9$ is as described above; and the N-oxide derivatives, prodrug derivatives, protected derivatives, individual isomers and mixture of isomers thereof; and the pharmaceutically acceptable salts and solvates (e.g. hydrates) of such compounds.

In a second aspect, the present invention provides a pharmaceutical composition which contains a compound of Formula I or a N-oxide derivative, individual isomers and mixture of isomers thereof; or a pharmaceutically acceptable salt thereof, in admixture with one or more suitable excipients.

In a third aspect, the present invention provides a method of treating a disease in an animal in which inhibition of kinase activity, particularly Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and/or Tie2 activity, can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides the use of a compound of Formula I in the manufacture of a medicament for treating a disease in an animal in which kinase activity, particularly Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and/or Tie2 activity, contributes to the pathology and/or symptomology of the disease.

In a fifth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

DETAILED DESCRIPTION OF THE INVENTION

Definitions

"Alkyl" as a group and as a structural element of other groups, for example halo-substituted-alkyl and alkoxy, can be either straight-chained or branched. $C_{1-4}$alkoxy includes, methoxy, ethoxy, and the like. Halo-substituted alkyl includes trifluoromethyl, pentafluoroethyl, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group. "Heteroaryl" is as defined for aryl where one or more of the ring members are a heteroatom. For example heteroaryl includes pyridyl, indolyl, indazolyl, quinoxalinyl, quinolinyl, benzofuiranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, etc. "Heterocycloalkyl" means cycloalkyl, as defined in this application, provided that one or more of the ring carbons indicated, are replaced by a moiety selected from —O—, —N=, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, piperazinyl, piperidinyl, piperidinylone, 2-Oxo-pyrrolidin-1-yl, 1,4-dioxa-8-aza-spiro[4.5]dec-8-yl, etc.

"Halogen" (or halo) preferably represents chloro or fluoro, but may also be bromo or iodo.

"Treat", "treating" and "treatment" refer to a method of alleviating or abating a disease and/or its attendant symptoms.

DESCRIPTION OF THE PREFERRED EMBODIMENTS

The fusion protein BCR-Abl is a result of a reciprocal translocation that fuses the Abl proto-oncogene with the Bcr gene. BCR-Abl is then capable of transforming B-cells through the increase of mitogenic activity. This increase results in a reduction of sensitivity to apoptosis, as well as altering the adhesion and homing of CML progenitor cells. The present invention provides compounds, compositions and methods for the treatment of kinase related disease, particularly Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and Tie2 kinase related diseases. For example, leukemia and other proliferation disorders related to BCR-Abl can be treated through the inhibition of wild type and mutant forms of Bcr-Abl.

In one embodiment, with reference to compounds of Formula I:

n is selected from 0, 1 and 2;

Z is selected from N and CH;

$R_1$ is selected from hydrogen, —$R_8$, —$OR_8$, —$S(O)_{0-2}R_8$, —$NR_7R_8$ and —$NR_7NR_7R_8$; wherein $R_7$ is independently selected from hydrogen and $C_{1-6}$alkyl; $R_8$ is selected from hydrogen, $C_{1-6}$alkyl, $C_{2-6}$alkenyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; or $R_7$ and $R_8$ together with the nitrogen atom to which $R_7$ and $R_8$ are attached form $C_{3-10}$heterocycloalkyl or $C_{5-10}$heteroaryl; wherein any alkyl or alkenyl of $R_8$ is optionally substituted by one to three radicals independently selected from halo, hydroxy, $C_{1-6}$alkyl and —$NR_9R_{10}$; wherein any aryl, heteroaryl, cycloalkyl or heterocycloalkyl of $R_8$, or the combination of $R_7$ and $R_8$, is optionally substituted by one to three radicals selected from halo, hydroxy, cyano, $C_{1-6}$alkyl, $C_{1-6}$alkoxy, $C_{2-6}$alkenyl, halo-substituted-alkyl, halo-substituted-alkoxy, —$XNR_9R_{10}$, —$XOXNR_9R_{10}$, —$XNR_9S(O)_{0-2}R_{10}$, —$XC(O)NR_9R_{10}$, —$XNR_9C(O)XOR_9$, —$XNR_9C(O)NR_9R_{10}$, —$XNR_9XNR_9R_{10}$, —$XC(O)NR_9XNR_9R_{10}$, —$XNR_9XOR_9$, —$XOR_9$, —$XNR_9C(=NR_9)NR_9R_{10}$, —$XS(O)_{0-2}R_{11}$, —$XNR_9C(O)R_9$, —$XNR_9C(O)XNR_9R_{10}$, —$XNR_9C(O)R_{11}$, —$XC(O)R_{11}$, —$XR_{11}$, —$XC(O)OR_{10}$ and —$XS(O)_{0-2}NR_9R_{10}$; wherein X is a bond or $C_{1-4}$alkylene; $R_9$ and $R_{10}$ are independently selected from hydrogen, $C_{1-6}$alkyl and $C_{3-12}$cycloalkyl; and $R_{11}$ is $C_{3-10}$heterocycloalkyl optionally substituted with 1 to 3 radicals selected from $C_{1-6}$alkyl, —$XNR_9R_{10}$, —$XNR_9XNR_9R_9$, $XNR_9XOR_9$ and —$XOR_9$; wherein X, $R_9$ and $R_{10}$ are as described above;

$R_2$ and $R_3$ are independently selected from hydrogen and $C_{1-6}$alkyl; or $R_1$ and $R_2$ together form =O;

$R_4$ is selected from hydrogen, $C_{1-6}$alkyl, —$XOR_9$, —$XC(O)OR_9$, —$XC(O)NR_9R_{10}$, $C_{3-10}$cycloalkyl-$C_{0-4}$alkyl, $C_{5-10}$heteraryl-$C_{0-4}$alkyl and $C_{3-10}$heterocycloalkyl-$C_{0-4}$alkyl; wherein X, $R_9$ and $R_{10}$ are as described above;

$R_5$ is selected from $C_{1-6}$alkyl, $C_{2-6}$alkenyl and $C_{1-6}$alkoxy;

$P_6$ is selected from —$NR_{12}C(O)R_{13}$ and —$C(O)NR_{12}R_{13}$; wherein $R_{12}$ is selected from hydrogen and $C_{1-6}$alkyl; and $R_{13}$ is selected from $C_{6-10}$aryl, $C_{5-10}$heteroaryl, $C_{3-10}$cycloalkyl, $C_{3-10}$heterocycloalkyl and $C_{1-6}$alkyl; wherein any aryl, heteroaryl, cycloalkyl or heterocycloalkyl of $R_{13}$ is optionally substituted by one to three radicals independently selected from halo, hydroxy, nitro, cyano, halo-substituted-$C_{1-6}$alkyl, $C_{1-6}$alkyl, $C_{1-6}$alkoxy, halo-substituted-$C_{1-6}$alkoxy, —$XNR_9R_9$, —$XNR_9XNR_9R_9$, —$XNR_9C(O)R_9$, —$XC(O)OR_9$, —$XNR_9S(O)_2R_9$, —$XNR_9S(O)R_9$, —$XNR_9SR_9$ and —$XR_{14}$; wherein X and $R_9$ are as defined above and $R_{14}$ is selected from $C_{5-10}$heteroaryl-$C_{0-4}$alkyl and $C_{3-10}$heterocycloalkyl-$C_{0-4}$alkyl; wherein any heteroaryl or heterocycloalkyl of $R_{14}$ is optionally substituted with a radical selected from $C_{1-6}$alkyl, halo-substituted-$C_{1-6}$alkyl —$NR_9R_9$ and —$C(O)OR_9$; wherein $R_9$ is as described above.

In another embodiment, $R_1$ is selected from hydrogen, —$R_8$, —$OR_8$, —$S(O)_2R_8$, —$NHR_8$ and —$NHNHR_8$;

wherein R$_8$ is selected from hydrogen, methyl, ethyl, isopropyl, cyclopropyl, cyclobutyl, cyclopentyl, cyclohexyl, pyrimidinyl, 3-hydroxy-1-methyl-propyl hydroxy-ethyl, phenyl, morpholino, benzyl, [1,2,4]triazol-4-yl, allyl, 2-methyl-allyl, 2-(2-oxo-pyrrolidin-1-yl)-ethyl, piperazinyl-ethyl, piperazinyl-propyl, thiazolyl, oxazolyl, pyridinyl, pyrazolyl, piperidinyl, thiazolyl, ethyl-pyrrolidinyl-methyl, morpholino-propyl, dimethyl-amino-propyl, diethyl-amino-propyl, diethyl-amino-butyl, ethoxy-carbonyl-methyl and [1,2,4]triazin-3-yl, [1,3,4]thiadiazolyl; wherein any aryl, heteroaryl, cycloalkyl or heterocycloalkyl is optionally substituted with 1 to 3 radicals independently selected from methyl, ethyl, cyano, hydroxy, methoxy, amino-carbonyl-amino, hydroxy-methyl, methyl-piperazinyl, methyl-piperazinyl-carbonyl, ethyl-piperazinyl, methyl-piperazinyl-methyl, morpholino-sulfonyl, methyl-piperazinyl-sulfonyl, methyl-piperazinyl-carbonyl-amino, methyl-sulfonyl-amino, amino-carbonyl, amino-sulfonyl, hydroxy-ethyl, hydroxy-methyl-carbonyl-amino, formyl-amino, dimethyl-amino, dimethyl-amino-methyl, dimethyl-amino-ethyl, isopropyl-amino-ethyl, carboxy, amino-ethyl-amino, methyl-amino-ethyl, morpholino-ethyl, morpholino-methyl, amino-ethyl, imidazolyl-propyl, piperazinyl-ethyl, piperazinyl, trifluoromethyl, diethyl-amino-ethyl, fluoro, morpholino, dimethyl-amino-ethyl-amino-carbonyl, diethyl-amino-ethoxy, 2-amino-propionylamino, dimethyl-amino-pyrrolidinyl, (2-dimethylamino-ethyl)-methyl-amino, 2-dimethylamino-1-methyl-ethoxy and diethyl-amino.

In another embodiment, R$_6$ is selected from —NHC(O)R$_{13}$ and —(O)NHR$_{13}$; wherein R$_{13}$ is selected from methyl, phenyl, pyrazolyl and pyridinyl; wherein any aryl or heteroaryl is optionally substituted with 1 to 2 radicals independently selected from trifluoromethyl, dimethylamino, nitro, amino, morpholino, methyl-piperazinyl-methyl, ethyl-piperazinyl-methyl, methyl-carbonyl-amino, methoxy, methoxy-carbonyl, methyl-piperazinyl, ethyl-piperazinyl, morpholino-methyl, methyl-imidazolyl, dimethylamino-ethoxy, methyl-imidazolyl, diethyl-amino-ethyl, [1,2,4]triazolyl and pyrrolidinyl-methyl.

In another embodiment, R$_4$ is selected from hydrogen, methyl, hydroxy-ethyl, cyclopropyl, carboxymethyl, methoxy-carbonyl-methyl, methyl-amino-carbonyl-methyl, ethyl, morpholino-ethyl, pyridinyl-ethyl, amino-carbonyl-methyl, ethyl-amino-carbonyl-methyl, dimethyl-amino-carbonyl-methyl, cyclopropyl-amino-carbonyl-methyl and isopropyl-amino-carbonyl-methyl.

Preferred compounds of the invention selected from:
N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Amino-phenylamino)-1-methyl-2-oxo-1,4-dihydro-2H-pyrimido[4,5-d]pyrimidin-3-yl]-4-methyl-phenyl}-3-trifluoromethyl-benzamide;

N-[4-Methyl-3-(1-methyl-7-methylamino-2,4-dioxo-1,4-dihydro-2H-pyrimido[4,5-d]pyrimidin-3-yl)-phenyl]-3-trifluoromethyl-benzamide;

N-[3-(7-Benzylamino-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-2-oxo-7-(3-ureido-phenylamino)-1,4-dihydro-2H-pyrimido[4,5-d]pyrimidin-3-yl]-phenyl}-3-trifluoromethyl-benzamide;

N-{3-[7-(3-Hydroxymethyl-phenylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(4-methyl-piperazin-1-yl-methyl)-phenylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-2-oxo-7-(3-sulfamoyl-phenylamino)-1,4-dihydro-2H-pyrimido[4,5-d]pyrimidin-3-yl]-phenyl}-3-trifluoromethyl-benzamide;

N-(3-{7-[3-(2-Hydroxy-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[3-(4-methyl-piperazin-1-yl)-phenylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-2-oxo-7-(N'-phenyl-hydrazino)-1,4-dihydro-2H-pyrimido[4,5-d]pyrimidin-3-yl]-phenyl}-3-trifluoromethyl-benzamide;

N-(3-{7-[3-(2-Hydroxy-acetylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-{4-Methyl-3-[1-methyl-2-oxo-7-([1,2,4]triazol-4-ylamino)-1,4-dihydro-2H-pyrimido[4,5-d]pyrimidin-3-yl]-phenyl}-3-trifluoromethyl-benzamide;

N-{4-Methyl-3-[1-methyl-7-(4-methyl-piperazin-1-ylamino)-2-oxo-1,4-dihydro-2H-pyrimido[4,5-d]pyrimidin-3-yl]-phenyl}-3-trifluoromethyl-benzamide;

N-{3-[7-(3-Formylamino-phenylamino)-1-methyl-2-oxo-1,4-dihydro-2H-pyrimido[4,5-d]pyrimidin-3-yl]-4-methyl-phenyl}-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-trifluoromethyl-benzamide;

N-[3-(7-Cyclopropylamino-1-methyl-2-oxo-1,4-dihydro-2H-pyrimido[4,5-d]pyrimidin-3-yl)-4-methyl-phenyl]-3-trifluoromethyl-benzamide;

N-{3-[7-(2-Hydroxy-ethylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Dimethylamino-phenylamino)-1-(2-hydroxy-ethyl)-2-oxo-1,4-dihydro-2H-pyrimido[4,5-d]pyrimidin-3-yl]-4-methyl-phenyl}-3-trifluoromethyl-benzamide;

N-(3-{7-[3-(2-Isopropylamino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-[3-(7-Methanesulfonyl-1-methyl-2-oxo-1,4-dihydro-2H-pyrimido[4,5-d]pyrimidin-3-yl)-4-methyl-phenyl]-3-trifluoromethyl-benzamide;

3-{8-Methyl-6-[2-methyl-5-(3-trifluoromethyl-benzoylamino)-phenyl-7-oxo-5,6,7,8-tetrahydro-pyrimido[4,5-d]pyrimidin-2-ylamino}-benzoic acid;

N-[3-(7-Cyclobutylamino-1-methyl-2-oxo-1,4-dihydro-2H-pyrimido[4,5-d]pyrimidin-3-yl)-4-methyl-phenyl]-3-trifluoromethyl-benzamide;

N-[3-(7-Cyclopentylamino-1-methyl-2-oxo-1,4-dihydro-2H-pyrimido[4,5-d]pyrimidin-3-yl)-4-methyl-phenyl]-3-trifluoromethyl-benzamide;

N-{3-[7-(2-Hydroxy-1-methyl-ethylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2-Hydroxy-1-methyl-ethylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Allylamino-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-7-(2-methyl-allylamino)-2-oxo-1,4-dihydro-2H-pyrimido[4,5-d]pyrimidin-3-yl]-phenyl}-3-trifluoromethyl-benzamide;

N-(4-Methyl-3-{1-methyl-2-oxo-7-[3-(2-oxo-pyrrolidin-1-yl)-propylamino]-1,4-dihydro-2H-pyrimido(4,5-d]pyrimidin-3-yl}-phenyl)-3-trifluoromethyl-benzamide;

3-Dimethylamino-N-(4-methyl-3-{1-methyl-7-[3-(4-methyl-piperazin-1-ylmethyl)-phenylamino]-2-oxo-1,4-dihydro-2H-pyrimido[4,5-d]pyrimidin-3-yl}-phenyl)-5-trifluoromethyl-benzamide;

3-Dimethylamino-N-{3-[7-(3-dimethylaminomethyl-phenylamino)-1-methyl-2-oxo-1,4-dihydro-2H-pyrimido[4,5-d]pyrimidin-3-yl]-4-methyl-phenyl}-5-trifluoromethyl-benzamide;

N-(3-{7-[3-(2-Dimethylamino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[3-(2-Amino-ethylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[3-(2-methylamino-ethyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[3-(2-morpholin-4-yl-ethyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[4-(2-morpholin-4-yl-ethyl)-phenylamino]-2-oxo-1,4-dihydro-2H-pyrimido[4,5-d]pyrimidin-3-yl}-phenyl)-3-trifluoromethyl-benzamide;

N-(3-{7-[4-(2-Amino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[4-(2-methylamino-ethyl)-phenylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-7-(3-morpholin-4-ylmethyl-phenylamino)-2-oxo-1,4-dihydro-2H-pyrimido[4,5-d]pyrimidin-3-yl]-phenyl}-3-trifluoromethyl-benzamide;

N-(3-{7-[3-(2-Amino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-2-oxo-7-[3-(2-piperazin-1-yl-ethyl)-phenylamino]-1,4-dihydro-2H-pyrimido[4,5-d]pyrimidin-3-yl}-phenyl)-3-trifluoromethyl-benzamide;

N-{3-[7-(3-Imidazol-1-yl-propylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(3-methyl-isoxazol-5-ylamino)-2-oxo-1,4-dihydro-2H-pyrimido[4,5-d]pyrimidin-3-yl]-phenyl}-3-trifluoromethyl-benzamide;

N-(4-Methyl-3-{1-methyl-2-oxo-7-[4-(2-piperazin-1-yl-ethyl)-phenylamino]-1,4-dihydro-2H-pyrimido[4,5-d]pyrimidin-3-yl}-phenyl)-3-trifluoromethyl-benzamide N-{4-Methyl-3-[1-methyl-2-oxo-7-(3-piperazin-1-ylmethyl-phenylamino)-1,4-dihydro-2H-pyrimido[4,5-d]pyrimidin-3-yl]-phenyl}-3-trifluoromethyl-benzamide;

N-{4-Methyl-3-[1-methyl-2-oxo-7-(4-piperazin-1-yl-phenylamino)-1,4-dihydro-2H-pyrimido[4,5-d]pyrimidin-3-yl]-phenyl}-3-trifluoromethyl-benzamide;

N-(3-{7-[4-(4-Ethyl-piperazin-1-yl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-{3-[7-(3-Dimethylamino-phenylamino)-2,4-dioxo-1,4-dihydro-2H-pyrimido[4,5-d]pyrimidin-3-yl]-4-methyl-phenyl}-3-trifluoromethyl-benzamide;

N-{4-Methoxy-3-[1-methyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(6-Ethyl-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Dimethylamino-phenylamino)-1-methyl-2,4-dioxo-1,4-dihydro-2H-pyrimido[4,5-d]pyrimidin-3-yl]-4-methyl-phenyl}-3-trifluoromethyl-benzamide;

N-{4-Methyl-3-[1-methyl-2-oxo-7-(6-trifluoromethyl-pyridin-3-ylamino)-1,4-dihydro-2H-pyrimido[4,5-d]pyrimidin-3-yl]-phenyl}-3-trifluoromethyl-benzamide;

N-{4-Methyl-3-[1-methyl-2-oxo-7-(6-vinyl-pyridin-3-ylamino)-1,4-dihydro-2H-pyrimido[4,5-d]pyrimidin-3-yl]-phenyl}-3-trifluoromethyl-benzamide;

N-{3-[7-(3-Diethylamino-propylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(3-Diethylamino-propylamino)-1-methyl-2-oxo-1,4-dihydro-2H-pyrido[4,3-d]pyrimidin-3-yl]-4-methyl-phenyl}-3-trifluoromethyl-benzamide; N-(3-{7-[6-(2-Diethylamino-ethyl)-pyridin-3-ylamino]-1-methyl-2-oxo-1,4-dihydro-2H-pyrimido[4,5-d]pyrimidin-3-yl}-4-methyl-phenyl)-3-trifluoromethyl-benzamide;

N-{4-Methyl-3-[1-methyl-7-(6-methyl-pyridin-3-ylamino)-2,4-dioxo-1,4-dihydro-2H-pyrimido[4,5-d]pyrimidin-3-yl]-phenyl}-3-trifluoromethyl-benzamide;

N-{3-[7-(4-Fluoro-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(6-methyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(2,5-dimethyl-2H-pyrazol-3-ylamino)-2-oxo-1,4-dihydro-2H-pyrimido[4,5-d]pyrimidin-3-yl]-4-methyl-phenyl}-3-trifluoromethyl-benzamide;

4-Methyl-3-[1-methyl-7-(6-methyl-pyridin-3-ylamino)-2-oxo-1,4-dihydro-2H-pyrimido[4,5-d]pyrimidin-3-yl]-N-(3-trifluoromethyl-phenyl)benzamide;

{7-(6-Methyl-pyridin-3-ylamino)-3-[2-methyl-5-(3-trifluoromethyl-benzoylamino)-phenyl]-2-oxo-3,4-dihydro-2H-pyrimido[4,5-d]pyrimidin-1-yl}-acetic acid methyl ester;

N-{4-Methyl-3-[1-methyl-2-oxo-7-(piperidin-4-ylamino)-1,4-dihydro-2H-pyrimido[4,5-d]pyrimidin-3-yl]-phenyl}-3-trifluoromethyl-benzamide;

{7-(6-Methyl-pyridin-3-ylamino)-3-[2-methyl-5-(3-trifluoromethyl-benzoylamino)-phenyl]-2-oxo-3,4-dihydro-2H-pyrimido[4,5-d]pyrimidin-1-yl}-acetic acid; 60

N-{4-Methyl-3-[1-methylcarbamoylmethyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[1-Cyclopropyl-7-(4-fluoro-phenylamino)-2-oxo-1,4-dihydro-2H-pyrimido[4,5-d]pyrimidin-3-yl]-4-methyl-phenyl}-3-trifluoromethyl-benzamide;

3-[7-(2,6-Dimethyl-pyridin-3-ylamino)-1-methyl-2-oxo-1,4-dihydro-2H-pyrimido[4,5-d]pyrimidin-3-yl]-N-(3-trifluoromethyl-phenyl)-4-vinyl-benzamide;

N-{3-[1-Cyclopropyl-7-(3-methyl-isoxazol-5-ylamino)-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(4-morpholin-4-yl-phenylamino)-2-oxo-1,4-dihydro-2H-pyrimido[4,5-d]pyrimidin-3-yl]-phenyl}-3-trifluoromethyl-benzamide;

N-(3-{1-Cyclopropyl-7-[4-(2-morpholin-4-yl-ethyl)-phenylamino]-2-oxo-1,4-dihydro-2H-pyrimido[4,5-d]pyrimidin-3-yl}-4-methyl-phenyl)-3-trifluoromethyl-benzamide;

N-{3-[1-Cyclopropyl-7-(2,6-dimethyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(2-methyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(4,6-dimethyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-2-oxo-7-(pyridin-3-ylamino)-1,4-dihydro-2H-pyrimido[4,5-d]pyrimidin-3-yl]-4-methyl-phenyl}-3-trifluoromethyl-benzamide;

N-[3-(1-Ethyl-7-methylamino-2-oxo-1,4-dihydro-2H-pyrimido[4,5-d]pyrimidin-3-yl)-4-methyl-phenyl]-3-trifluoromethyl-benzamide;

N-[3-(1-Ethyl-7-ethylamino-2-oxo-1,4-dihydro-2H-pyrimido[4,5-d]pyrimidin-3-yl)-4-methyl-phenyl]-3-trifluoromethyl-benzamide;

N-{3-[7-(2,6-Dimethyl-pyridin-3-ylamino)-1-ethyl-2-oxo-1,4-dihydro-2H-pyrimido[4,5-d]pyrimidin-3-yl]-4-methyl-phenyl}-3-trifluoromethyl-benzamide;

N-{3-[1-Ethyl-7-(2-methyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[7-(2,6-Dimethyl-pyridin-3-ylamino)-1-methyl-2-oxo-1,4-dihydro-2H-pyrimido[4,5-d]pyrimidin-3-yl]-4-ethyl-phenyl}-3-trifluoromethyl-benzamide;

N-[3-Methoxy-5-(1-methyl-7-methylamino-2-oxo-1,4-dihydro-2H-pyrimido[4,5-d]pyrimidin-3-yl)-phenyl]-3-trifluoromethyl-benzamide;

N-(3-Methoxy-5-{1-methyl-2-oxo-7-[3-(2-oxo-pyrrolidin-1-yl)-propylamino]-1,4-hydro-2H-pyrimido[4,5-d]pyrimidin-3-yl}-phenyl)-3-trifluoromethyl-benzamide;

N-[3-Methoxy-5-(1-methyl-7-methylamino-2-oxo-1,4-dihydro-2H-pyrimido[4,5-]pyrimidin-3-yl)-phenyl]-3-morpholin-4-yl-5-trifluoromethyl-benzamide;

N-(3-Methoxy-5-{1-methyl-2-oxo-7-[3-(2-oxo-pyrrolidin-1-yl)-propylamino]-1,4-dihydro-2H-pyrimido[4,5-d]pyrimidin-3-yl}-phenyl)-3-morpholin-4-yl-5-trifluoromethyl-benzamide;

N-[4-Methyl-3-(1-methyl-7-methylamino-2,4-dioxo-1,4-dihydro-2H-pyrimido[4,5-]pyrimidin-3-yl)-phenyl]-3-trifluoromethyl-benzamide;

N-[3-(7-Amino-1-methyl-2,4-dioxo-1,4-dihydro-2H-pyrimido[4,5-d]pyrimidin-3-yl)-4-methyl-phenyl]-3-trifluoromethyl-benzamide;

N-{3-[7-(2,6-Dimethyl-pyridin-3-ylamino)-1-methyl-2,4-dioxo-1,4-dihydro-2H-pyrimido[4,5-d]pyrimidin-3-yl]-4-methyl-phenyl}-3-trifluoromethyl-benzamide;

4-(4-Ethyl-piperazin-1-ylmethyl)-N-[3-methoxy-5-(1-methyl-7-methylamino-2-oxo-1,4-dihydro-2H-pyrimido[4,5-d]pyrimidin-3-yl)-phenyl]-3-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-4-(4-ethyl-piperazin-1-yl)-3-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-3-(4-ethyl-piperazin-1-yl)-5-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-3-morpholin-4-yl-5-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-4-(4-ethyl-piperazin-1-ylmethyl)-3-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-4-morpholin-4-ylmethyl-3-trifluoromethyl-benzamide;

N-[4-Methyl-3-(1-methyl-7-methylamino-2,4-dioxo-1,4-dihydro-2H-pyrimido[4,5-d]pyrimidin-3-yl)-phenyl]-3-morpholin-4-yl-5-trifluoromethyl-benzamide;

4-(4-Ethyl-piperazin-1-yl)-N-[4-methyl-3-(1-methyl-7-methylamino-2,4-dioxo-1,4-dihydro-2H-pyrimido[4,5-d]pyrimidin-3-yl)-phenyl]-3-trifluoromethyl-benzamide;

3-(4-Ethyl-piperazin-1-yl)-N-[4-methyl-3-(1-methyl-7-methylamino-2,4-dioxo-1,4-dihydro-2H-pyrimido[4,5-d]pyrimidin-3-yl)-phenyl]-5-trifluoromethyl-benzamide;

4-(4-Ethyl-piperazin-1-ylmethyl)-N-[4-methyl-3-(1-methyl-7-methylamino-2,4-dioxo-1,4-dihydro-2H-pyrimido[4,5-d]pyrimidin-3-yl)-phenyl]-3-trifluoromethyl-benzamide;

N-[4-Methyl-3-(1-methyl-7-methylamino-2,4-dioxo-1,4-dihydro-2H-pyrimido[4,5-d]pyrimidin-3-yl)-phenyl]-4-morpholin-4-ylmethyl-3-trifluoromethyl-benzamide;

N-(2-Hydroxy-5-trifluoromethyl-pyridin-3-yl)-4-methyl-3-[1-methyl-7-(6-methyl-pyridin-3-ylamino)-2-oxo-1,4-dihydro-2H-pyrimido[4,5-d]pyrimidin-3-yl]-benzamide;

N-[3-(1-Ethyl-7-methylamino-2-oxo-1,4-dihydro-2H-pyrimido[4,5-d]pyrimidin-3-yl)-5-methoxy-phenyl]-4-(4-ethyl-piperazin-1-ylmethyl)-benzamide;

N-{3-Methoxy-5-[7-methylamino-1-(2-morpholin-4-yl-ethyl)-2-oxo-1,4-dihydro-2H-pyrimido[4,5-d]pyrimidin-3-yl]-phenyl}-3-trifluoromethyl-benzamide;

N-{3-[7-Ethylamino-1-(2-morpholin-4-yl-ethyl)-2-oxo-1,4-dihydro-2H-pyrimido[4,5-d]pyrimidin-3-yl]-5-methoxy-phenyl}-3-trifluoromethyl-benzamide;

N-{3-[7-Cyclopropylamino-1-(2-morpholin-4-yl-ethyl)-2-oxo-1,4-dihydro-2H-pyrimido[4,5-d]pyrimidin-3-yl]-5-methoxy-phenyl}-3-trifluoromethyl-benzamide;

N-{3-Methoxy-5-[7-(2-methyl-allylamino)-1-(2-morpholin-4-yl-ethyl)-2-oxo-1,4-dihydro-2H-pyrimido[4,5-d]pyrimidin-3-yl]-phenyl}-3-trifluoromethyl-benzamide;

N-{3-Methoxy-5-[1-(2-morpholin-4-yl-ethyl)-2-oxo-7-phenylamino-1,4-dihydro-2H-pyrimido[4,5-d]pyrimidin-3-yl]-phenyl}-3-trifluoromethyl-benzamide;

N-{3-Methoxy-5-[1-(2-morpholin-4-yl-ethyl)-7-(4-morpholin-4-yl-phenylamino)-2-oxo-1,4-dihydro-2H-pyrimido[4,5-d]pyrimidin-3-yl]-phenyl}-3-trifluoromethyl-benzamide;

N-{3-Methoxy-5-[7-methylamino-2-oxo-1-(2-pyridin-2-yl-ethyl)-1,4-dihydro-2H-pyrimido[4,5-d]pyrimidin-3-yl]-phenyl}-3-trifluoromethyl-benzamide;

N-{3-[7-Ethylamino-2-oxo-1-(2-pyridin-2-yl-ethyl)-1,4-dihydro-2H-pyrimido[4,5-d]pyrimidin-3-yl]-5-methoxy-phenyl}-3-trifluoromethyl-benzamide;

N-{3-[7-Cyclopropylamino-2-oxo-1-(2-pyridin-2-yl-ethyl)-1,4-dihydro-2H-pyrimido[4,5-d]pyrimidin-3-yl]-5-methoxy-phenyl}-3-trifluoromethyl-benzamide;

N-{3-Methoxy-5-[7-(2-methyl-pyridin-3-ylamino)-1-(2-morpholin-4-yl-ethyl)-2-oxo-1,4-dihydro-2H-pyrimido[4,5-d]pyrimidin-3-yl]-phenyl}-3-trifluoromethyl-benzamide;

N-[3-(1-Ethyl-7-ethylamino-2-oxo-1,4-dihydro-2H-pyrimido[4,5-d]pyrimidin-3-yl)-5-methoxy-phenyl]-4-(4-ethyl-piperazin-1-ylmethyl)-3-trifluoromethyl-benzamide;

N-[3-(1-Ethyl-7-isopropylamino-2-oxo-1,4-dihydro-2H-pyrimido[4,5-d]pyrimidin-3-yl)-5-methoxy-phenyl]-4-(4-ethyl-piperazin-1-ylmethyl)-3-trifluoromethyl-benzamide;

{3-[3-Methoxy-5-(3-trifluoromethyl-benzoylamino)-phenyl]-7-methylamino-2-oxo-,3,4-dihydro-2H-pyrimido[4,5-d]pyrimidin-1-yl}-acetic acid methyl ester;

N-[3-Methoxy-5-(7-methylamino-1-methylcarbamoylmethyl-2-oxo-1,4-dihydro-2H-pyrimido[4,5-d]pyrimidin-3-yl)-phenyl]-3-trifluoromethyl-benzamide;

{3-[3-Methoxy-5-(3-trifluoromethyl-benzoylamino)-phenyl]-7-methylamino-2-oxo-3,4-dihydro-2H-pyrimido[4,5-d]pyrimidin-1-yl}-acetic acid;

N-[3-(1-Carbamoylmethyl-7-methylamino-2-oxo-1,4-dihydro-2H-pyrimido[4,5-d]pyrimidin-3-yl)-5-methoxy-phenyl]-3-trifluoromethyl-benzamide;

N-[3-(1-Ethylcarbamoylmethyl-7-methylamino-2-oxo-1,4-dihydro-2H-pyrimido[4,5-d]pyrimidin-3-yl)-5-methoxy-phenyl]-3-trifluoromethyl-benzamide;

N-[3-(1-Dimethylcarbamoylmethyl-7-methylamino-2-oxo-1,4-dihydro-2H-pyrimido[4,5-d]pyrimidin-3-yl)-5-methoxy-phenyl]-3-trifluoromethyl-benzamide;

N-[3-(1-Cyclopropylcarbamoylmethyl-7-methylamino-2-oxo-1,4-dihydro-2H-pyrimido[4,5-d]pyrimidin-3-yl)-S-methoxy-phenyl]-3-trifluoromethyl-benzamide;

N-{3-[1-(Isopropylcarbamoyl-methyl)-7-methylamino-2-oxo-1,4-dihydro-2H-pyrimido[4,5-d]pyrimidin-3-yl]-5-methoxy-phenyl}-3-trifluoromethyl-benzamide;

N-[3-(7-Ethylamino-1-methylcarbamoylmethyl-2-oxo-1,4-dihydro-2H-pyrimido[4,5-d]pyrimidin-3-yl)-5-methoxy-phenyl]-3-trifluoromethyl-benzamide;

N-{3-[7-(2,5-Dimethyl-2H-pyrazol-3-ylamino)-1-methylcarbamoylmethyl-2-oxo-1,4-dihydro-2H-pyrimido[4,5-d]pyrimidin-3-yl]-5-methoxy-phenyl}-3-trifluoromethyl-benzamide;

N-{3-[7-(4,6-Dimethyl-pyridin-3-ylamino)-1-methylcarbamoylmethyl-2-oxo-1,4-dihydro-2H-pyrimido[4,5-d]pyrimidin-3-yl]-5-methoxy-phenyl}-3-trifluoromethyl-benzamide;

N-{3-Methoxy-5-[1-methylcarbamoylmethyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

3-(7-Amino-1-ethyl-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxy-benzamide;

3-(1-Ethyl-7-methylamino-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxy-benzamide;

3-(1-Ethyl-7-ethylamino-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxy-benzamide;

3-(1-Ethyl-7-isopropylamino-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxy-benzamide;

3-(7-Cyclopropylamino-1-ethyl-2-oxo-1,4-dihydro-2H-pyrimido[4,5-d]pyrimidin-3-yl)-N-[4-(4-ethyl-piperazin-1-ylmethyl)3-trifluoromethyl-phenyl]-5-methoxy-benzamide;

3-(1-Ethyl-7-methylamino-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-[1-Ethyl-7-(6-methyl-pyridin-3-ylamino)-2-oxo-1,4-dihydro-2H-pyrimido[4,5-d]pyrimidin-3-yl]-N-[4-(4-ethyl-piperazin-1-ylmethyl)-3-trifluoromethyl-phenyl]-5-methoxy-benzamide;

3-(7-Amino-1-ethyl-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-(1-Ethyl-7-ethylamino-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-(7-Cyclopropylamino-1-ethyl-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-(1-Ethyl-7-isopropylamino-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

N-[3-(7-Amino-1-ethyl-2-oxo-1,4-dihydro-2H-pyrimido[4,5-d]pyrimidin-3-yl)-2,5-dimethoxy-phenyl]-acetamide;

N-{3-[1-Ethyl-7-(4-morpholin-4-yl-phenylamino)-2-oxo-1,4-dihydro-2H-pyrimido[4,5-d]pyrimidin-3-yl]-2,5-dimethoxy-phenyl}-acetamide;

N-[3-(1-Ethyl-7-ethylamino-2-oxo-1,4-dihydro-2H-pyrimido[4,5-d]pyrimidin-3-yl)-2,5-dimethoxy-phenyl]-acetamide;

N-[3-(1-Ethyl-7-methylamino-2-oxo-1,4-dihydro-2H-pyrimido[4,5-d]pyrimidin-3-yl)-2,5-dimethoxy-phenyl]-acetamide;

N-[3-(7-Cyclopropylamino-1-ethyl-2-oxo-1,4-dihydro-2H-pyrimido[4,5-d]pyrimidin-3-yl)-2,5-dimethoxy-phenyl]-acetamide;

N-{3-[1-Ethyl-7-(2-ethyl-2H-pyrazol-3-ylamino)-2-oxo-1,4-dihydro-2H-pyrimido[4,5-d]pyrimidin-3-yl]-5-methoxy-phenyl}-3-trifluoromethyl-benzamide;

N-{3-[7-(2,5-Dimethyl-2H-pyrazol-3-ylamino)-1-ethyl-2-oxo-1,4-dihydro-2H-pyrimido[4,5-d]pyrimidin-3-yl]-5-methoxy-phenyl}-3-trifluoromethyl-benzamide;

N-[4-Dimethyl-aminoethyl-amino-carbonyl-3-(1-methyl-2-oxo-7-p-tolylamino-1,4-dihydro-2H-pyrimido[4,5-d]pyrimidin-3-yl)-phenyl]-3-trifluoromethyl-benzamide;

N-(4-Methyl-3-{1-methyl-7-[4-(4-methyl-piperazin-1-yl)-phenylamino]-2-oxo-1,4-dihydro-2H-pyrimido[4,5-d]pyrimidin-3-yl}-phenyl)-3-trifluoromethyl-benzamide;

N-[3-(7-Hydroxy-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-7-(2-methyl-pyridin-4-ylamino)-2-oxo-1,4-dihydro-2H-pyrimido[4,5-d]pyrimidin-3-yl]-phenyl}-3-trifluoromethyl-benzamide;

N-[4-Methyl-3-(1-methyl-2-oxo-7-pyridin-3-yl-1,4-dihydro-2H-pyrimido[4,5-d]pyrimidin-3-yl)-phenyl]-3-trifluoromethyl-benzamide;

N-{3-[1-Ethyl-7-(2-methyl-pyridin-3-ylamino)-2-oxo-1,4-dihydro-2H-pyrimido[4,5-d]pyrimidin-3-yl]-5-methoxy-phenyl}-3-trifluoromethyl-benzamide;

N-{3-[7-(4,6-Dimethyl-pyridin-3-ylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(2,6-Dimethyl-pyridin-3-ylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[1-Ethyl-7-(6-methyl-pyridin-3-ylamino)-2-oxo-1,4-dihydro-2H-pyrimido[4,5-d]pyrimidin-3-yl]-5-methoxy-phenyl}-3-trifluoromethyl-benzamide;

N-{3-[7-(5-Dimethylaminomethyl-thiazol-2-ylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[4-(4-methyl-piperazin-1-ylmethyl)-phenylamino]-2-oxo-1,4-dihydro-2H-pyrimido[4,5-d]pyrimidin-3-yl }-phenyl)-3-trifluoromethyl-benzamide;

N-{3-[7-(4-Dimethylaminomethyl-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Cyano-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(5-Cyano-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2,6-Dimethyl-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(4,6-Dimethyl-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(4-Methoxy-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2-Methoxy-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(2-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(2,4-Dimethyl-thiazol-5-ylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Amino-1,4-dimethyl-2-oxo-1,4-dihydro-2H-pyrimido[4,5-d]pyrimidin-3-yl)-4-methyl-phenyl]-3-trifluoromethyl-benzamide;

N-[3-(7-Amino-1,4-dimethyl-2-oxo-1,4-dihydro-2H-pyrimido[4,5-d]pyrimidin-3-yl)-phenyl]-3-trifluoromethyl-benzamide;

N-{3-[1,4-Dimethyl-2-oxo-7-(pyridin-3-ylamino)-1,4-dihydro-2H-pyrimido[4,5-d]pyrimidin-3-yl]-4-methyl-phenyl}-3-trifluoromethyl-benzamide;

N-{3-[1,4-Dimethyl-2-oxo-7-(pyridin-3-ylamino)-1,4-dihydro-2H-pyrimido[4,5-d]pyrimidin-3-yl]-phenyl}-3-trifluoromethyl-benzamide;

N-{4-Methyl-3-[7-methylamino-1-(morpholin-4-yl-ethyl)2-oxo-1,4-dihydro-2H-pyrimido[4,5-d]pyrimidin-3-yl]-phenyl}-3-trifluoromethyl-benzamide;

N-{3-[7-Amino-1-(2-morpholin-4-yl-ethyl)-2-oxo-1,4-dihydro-2H-pyrimido[4,5-d]pyrimidin-3-yl]-4-methyl-phenyl}-3-trifluoromethyl-benzamide;

N-[3-(7-Amino-1-methyl-2-oxo-1,4-dihydro-2H-pyrimido[4,5-d]pyrimidin-3-yl)-5-methoxy-phenyl]-3-trifluoromethyl-benzamide;

N-[3-(7-Ethylamino-1-methyl-2-oxo-1,4-dihydro-2H-pyrimido[4,5-d]pyrimidin-3-yl)-5-methoxy-phenyl]-3-trifluoromethyl-benzamide;

N-(3-{7-[4-(2-Diethylamino-ethoxy)-phenylamino]-1-methyl-2-oxo-1,4-dihydro-2H-pyrimido[4,5-d]pyrimidin-3-yl}-5-methoxy-phenyl)-3-trifluoromethyl-benzamide;

N-[3-(7-Amino-1-ethyl-2-oxo-1,4-dihydro-2H-pyrimido[4,5-d]pyrimidin-3-yl)-5-methoxy-phenyl]-3-trifluoromethyl-benzamide;

N-[3-(1-Ethyl-7-ethylamino-2-oxo-1,4-dihydro-2H-pyrimido[4,5-d]pyrimidin-3-yl)-5-methoxy-phenyl]-3-trifluoromethyl-benzamide;

N-{3-[1-Ethyl-7-(3-morpholin-4-yl-propylamino)-2-oxo-1,4-dihydro-2H-pyrimido[4,5-d]pyrimidin-3-yl]-5-methoxy-phenyl}-3-trifluoromethyl-benzamide;

N-{3-[1-Ethyl-7-(4-morpholin-4-yl-phenylamino)-2-oxo-1,4-dihydro-2H-pyrimido[4,5-d]pyrimidin-3-yl]-5-methoxy-phenyl}-3-trifluoromethyl-benzamide;

N-{3-[1-Ethyl-2-oxo-7-(pyridin-3-ylamino)-1,4-dihydro-2H-pyrimido[4,5-d]pyrimidin-3-yl]-5-methoxy-phenyl}-3-trifluoromethyl-benzamide;

N-[3-(7-Cyclopropylamino-1-ethyl-2-oxo-1,4-dihydro-2H-pyrimido[4,5-d]pyrimidin-3-yl)-5-methoxy-phenyl]-3-trifluoromethyl-benzamide;

N-{3-[1-Ethyl-7-(2-methyl-allylamino)-2-oxo-1,4-dihydro-2H-pyrimido[4,5-d]pyrimidin-3-yl]-5-methoxy-phenyl}-3-trifluoromethyl-benzamide;

N-{3-[7-(3-Diethylamino-propylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(4-Diethylamino-butylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(3-Dimethylamino-phenylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-nitro-5-trifluoromethyl-benzamide;

3-Amino-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

N-(3-{7-[3-(2-Amino-propionylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[3-(2-Amino-3-methyl-butyrylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[6-(3-Dimethylamino-pyrrolidin-1-yl)-pyridin-3-ylamino]-1-methyl-2-oxo-1,4-dihydro-2H-pyrimido[4,5-d]pyrimidin-3-yl}-4-methyl-phenyl)-3-trifluoromethyl-benzamide;

N-[3-(7-{6-[(2-Dimethylamino-ethyl)-methyl-amino]-pyridin-3-ylamino}-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-2-oxo-7-(pyrimidin-2-ylamino)-1,4-dihydro-2H-pyrimido[4,5-d]pyrimidin-3-yl]-phenyl}-3-trifluoromethyl-benzamide;

N-{3-[7-(5,6-Dimethyl-[1,2,4]triazin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(pyrazin-2-ylamino)-2-oxo-1,4-dihydro-2H-pyrimido[4,5-d]pyrimidin-3-yl]-phenyl}-3-trifluoromethyl-benzamide;

N-{3-[7-(2,5-Dimethyl-2H-pyrazol-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(3-methyl-isothiazol-5-ylamino)-2-oxo-1,4-dihydro-2H-pyrimido[4,5-d]pyrimidin-3-yl]-phenyl}-3-trifluoromethyl-benzamide;

N-{3-[7-(2-Ethyl-2H-pyrazol-3-ylamino)-1-methyl-2-oxo-1,4-dihydro-2H-pyrimido[4,5-d]pyrimidin-3-yl]-4-methyl-phenyl}-3-trifluoromethyl-benzamide;

N-(3-{7-[6-(2-Dimethylamino-1-methyl-ethoxy)-pyridin-3-ylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[4-(2-Diethylamino-ethoxy)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[3-(4-methyl-piperazin-1-yl)-propylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-2-oxo-7-(pyridin-3-ylamino)-1,4-dihydro-2H-pyrido[4,3-d]pyrimidin-3-yl]-phenyl}-3-trifluoromethyl-benzamide;

N-{4-Methyl-3-[1-methyl-7-(4-methyl-pyridin-3-ylamino)-2-oxo-1,4-dihydro-2H-pyrimido[4,5-d]pyrimidin-3-yl]-phenyl}-3-trifluoromethyl-benzamide;

N-{4-Methyl-3-[1-methyl-7-(3-methyl-pyridin-4-ylamino)-2-oxo-1,4-dihydro-2H-pyrimido[4,5-d]pyrimidin-3-yl]-phenyl}-3-trifluoromethyl-benzamide;

N-{4-Methyl-3-[1-methyl-7-(5-morpholin-4-ylmethyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(6-Diethylamino-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(6-Ethylamino-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2,6-Dimethyl-pyridin-4-ylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(4-methyl-imidazol-1-yl)-5-trifluoromethyl-benzamide;

N-{3-[7-(5-Ethyl-[1,3,4]thiadiazol-2-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(6-methyl-pyridin-3-ylamino)-2-oxo-1,4-dihydro-2H-pyrido[4,3-d]pyrimidin-3-yl]-phenyl}-3-trifluoromethyl-benzamide;

N-{4-Methyl-3-[7-(6-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(2,5-Dimethyl-2H-pyrazol-3-ylamino)-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(5-methyl-1H-pyrazol-3-ylamino)-2-oxo-1,4-dihydro-2H-pyrimido[4,5-d]pyrimidin-3-yl]-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-[1,2,4]triazol-4-yl-5-trifluoromethyl-benzamide;

N-{3-[7-(2,5-Dimethyl-2H-pyrazol-3-ylamino)-1-methyl-2-oxo-1,4-dihydro-2H-pyrido[4,3-d]pyrimidin-3-yl]-4-methyl-phenyl}-3-trifluoromethyl-benzamide;

N-{4-Methyl-3-[1-methyl-7-(1-methyl-1H-pyrazol-3-ylamino)-2-oxo-1,4-dihydro-2H-pyrimido[4,5-d]pyrimidin-3-yl]-phenyl}-3-trifluoromethyl-benzamide;

N-{4-Methyl-3-[1-methyl-7-(2-methyl-2H-pyrazol-3-ylamino)-2-oxo-1,4-dihydro-2H-pyrimido[4,5-d]pyrimidin-3-yl]-phenyl}-3-trifluoromethyl-benzamide;

N-{3-[7-(2,4-Dimethyl-thiazol-5-ylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-morpholin-4-yl-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-(2-methyl-imidazol-1-yl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-morpholin-4-yl-3-trifluoromethyl-benzamide;

N-{4-Methyl-3-[1-methyl-2-oxo-7-(pyrazin-2-ylamino)-1,4-dihydro-2H-pyrido[4,3-d]pyrimidin-3-yl]-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-dimethylamino-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-diethylaminomethyl-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-morpholin-4-ylmethyl-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-morpholin-4-yl-5-trifluoromethyl-benzamide;

3-Dimethylamino-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-[1,2,4]triazol-4-yl-5-trifluoromethyl-benzamide;

4-(2-Methyl-imidazol-1-yl)-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-morpholin-4-yl-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-(4-methyl-piperazin-1-yl)-3-trifluoromethyl-benzamide;

4-(4-Ethyl-piperazin-1-yl)-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

4-Cyclopropylaminomethyl-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

4-(4-Ethyl-piperazin-1-ylmethyl)-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-pyrrolidin-1-ylmethyl-3-trifluoromethyl-benzamide;

N-[4-Methyl-3-(1-methyl-7-methylamino-2-oxo-1,4-dihydro-2H-pyrimido[4,5-]pyrimidin-3-yl)-phenyl]-4-morpholin-4-ylmethyl-3-trifluoromethyl-benzamide;

4-Diethylaminomethyl-N-[4-methyl-3-(1-methyl-7-methylamino-2-oxo-1,4-dihydro-H-pyrimido[4,5-d]pyrimidin-3-yl)-phenyl]-3-trifluoromethyl-benzamide;

N-[3-(7-Amino-1-methyl-2-oxo-1,4-dihydro-2H-pyrimido[4,5-d]pyrimidin-3-yl)-4-ethyl-phenyl]-4-(4-methyl-piperazin-1-yl)-3-trifluoromethyl-benzamide;

N-[3-(7-Amino-1-methyl-2-oxo-1,4-dihydro-2H-pyrimido[4,5-d]pyrimidin-3-yl)-4-ethyl-phenyl]-4-(4-ethyl-piperazin-1-yl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-(4-ethyl-piperazin-1-ylmethyl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-pyrrolidin-1-ylmethyl-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-(4-methyl-piperazin-1-ylmethyl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(4-methyl-piperazin-1-yl)-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(3-dimethylamino-pyrrolidin-1-yl)-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(4-ethyl-piperazin-1-yl)-5-trifluoromethyl-benzamide;

3-(4-Methyl-imidazol-1-yl)-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

3-(4-Ethyl-piperazin-1-yl)-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

3-(3-Dimethylamino-pyrrolidin-1-yl)-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-(4-methyl-piperazin-1-yl)-5-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-(4-methyl-piperazin-1-ylmethyl)-3-trifluoromethyl-benzamide;

N-{4-Methyl-3-[1-methyl-7-(3-morpholin-4-yl-propylamino)-2-oxo-1,4-dihydro-2H-pyrido[4,3-d]pyrimidin-3-yl]-phenyl}-3-trifluoromethyl-benzamide;

N-{3-[7-(3-Diethylamino-propylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(4-Diethylamino-butylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(4,6-Dimethyl-pyridin-3-ylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(2,6-Dimethyl-pyridin-3-ylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(2,6-Dimethyl-pyridin-4-ylamino)-1-methyl-2-oxo-1,4-dihydro-2H-pyrido[4,3-d]pyrimidin-3-yl]-4-methyl-phenyl}-3-trifluoromethyl-benzamide;

N-[4-Methyl-3-(1-methyl-2-oxo-1,4-dihydro-2H-pyrido[4,3-d]pyrimidin-3-yl)-phenyl]-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-4-(4-methyl-piperazin-1-ylmethyl)-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-trifluoromethyl-benzamide;

N-{3-[7-(3-Carbamoyl-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(2-Fluoro-5-trifluoromethyl-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(2-Fluoro-3-trifluoromethyl-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Methanesulfonylamino-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Methanesulfonylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-propylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-acetamide;

N-{3-[7-(3-Dimethylamino-phenylamino)-2-oxo-1,4-dihydro-2H-pyrimido[4,5-d]pyrimidin-3-yl]-4-methyl-phenyl}-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-fluoro-benzamide;

N-{4-Methyl-3-[1-methyl-7-(4-methyl-thiazol-2-ylamino)-2-oxo-1,4-dihydro-2H-pyrimido[4,5-d]pyrimidin-3-yl]-phenyl}-3-trifluoromethyl-benzamide;

(2-{8-Methyl-6-[2-methyl-5-(3-trifluoromethyl-benzoylamino)-phenyl]-7-oxo-5,6,7,8-tetrahydro-pyrimido[4,5-d]pyrimidin-2-ylamino}-thiazol-4-yl)-acetic acid ethyl ester;

N-{3-[7-(3-Amino-phenylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Cyclohexylamino-1-methyl-2-oxo-1,4-dihydro-2H-pyrimido[4,5-d]pyrimidin-3-yl)-4-methyl-phenyl]-3-trifluoromethyl-benzamide;

N-[4-Methyl-3-(1-methyl-7-morpholin-4-yl-2-oxo-1,4-dihydro-2H-pyrimido[4,5-d]pyrimidin-3-yl)-phenyl]-3-trifluoromethyl-benzamide;

N-[4-Methyl-3-(1-methyl-2-oxo-7-phenylamino-1,4-dihydro-2H-pyrimido[4,5-d]pyrimidin-3-yl)-phenyl]-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3,5-bis-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-isophthalamic acid methyl ester;

N-{3-[7-(3-Dimethylamino-phenylamino)-2-oxo-1,4-dihydro-2H-pyrimido[4,5-d]pyrimidin-3-yl]-4-methyl-phenyl}-2,5-bis-trifluoromethyl-benzamide;

N-{3-[7-(3-Dimethylamino-phenylamino)-1-ethyl-2-oxo-1,4-dihydro-2H-pyrimido[4,5-d]pyrimidin-3-yl]-4-methyl-phenyl}-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-fluoro-5-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-4-fluoro-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-4-methoxy-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-methyl-benzamide;

N-{3-[7-(3-Hydroxy-phenylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(morpholine-4-sulfonyl)-phenylamino]-2-oxo-1,4-dihydro-2H-pyrimido[4,5-d]pyrimidin-3-yl}-phenyl)-3-trifluoromethyl-benzamide;

N-{3-[7-(3-Dimethylaminomethyl-phenylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(4-methyl-piperazin-1-ylmethyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[3-(4-methyl-piperazine-1-sulfonyl)-phenylamino]-2-oxo-1,4-dihydro-2H-pyrimido[4,5-d]pyrimidin-3-yl }-phenyl)-3-trifluoromethyl-benzamide;

N-(4-Methyl-3-{1-methyl-7-[2-(4-methyl-piperazin-1-yl)-pyridin-4-ylamino]-2-oxo-1,4-dihydro-2H-pyrimido[4,5-d]pyrimidin-3-yl}-phenyl)-3-trifluoromethyl-benzamide;

4-Methyl-piperazine-1-carboxylic acid (3-{8-methyl-6-[2-methyl-5-(3-trifluoromethyl-benzoylamino)-phenyl]-7-oxo-5,6,7,8-tetrahydro-pyrimido[4,5-d]pyrimidin-2-ylamino}-phenyl)-amide;

N-(3-{7-[(1-Ethyl-pyrrolidin-2-ylmethyl)-amino]-1-methyl-2-oxo-1,4-dihydro-2H-pyrimido[4,5-d]pyrimidin-3-yl}-4-methyl-phenyl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-2-oxo-7-(pyridin-4-ylamino)-1,4-dihydro-2H-pyrimido[4,5-d]pyrimidin-3-yl]-phenyl}-3-trifluoromethyl-benzamide;

N-{4-Methyl-3-[1-methyl-2-oxo-7-(pyridin-3-ylamino)-1,4-dihydro-2H-pyrimido[4,5-]pyrimidin-3-yl]-phenyl}-3-trifluoromethyl-benzamide;

N-{3-[7-(2-Dimethylamino-pyridin-4-ylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(4-methyl-piperazine-1-carbonyl)-phenylamino]-2-oxo-1,4-dihydro-2H-pyrimido[4,5-d]pyrimidin-3-yl }-phenyl)-3-trifluoromethyl-benzamide;

N-{4-Methyl-3-[1-methyl-2-oxo-7-(pyrimidin-5-ylamino)-1,4-dihydro-2H-pyrimido[4,5-d]pyrimidin-3-yl]-phenyl}-3-trifluoromethyl-benzamide;

N-{4-Methyl-3-[1-methyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

3-Acetylamino-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

3-(2-Dimethylamino-ethoxy)-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(2-morpholin-4-yl-ethoxy)-5-trifluoromethyl-benzamide;

3-(2-Dimethylamino-ethylamino)-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(4-methyl-piperazin-1-yl)-5-trifluoromethyl-benzamide; and 2-Methyl-5-trifluoromethyl-2H-pyrazole-3-carboxylic acid -{3-[7-(3-dimethylamino-phenylamino)-1-methyl-2-oxo-1,4-dihydro-2H-pyrimido[4,5-d]pyrimidin-3-yl]-4-methyl-phenyl}-amide.

Further preferred compounds of Formula I are detailed in the Examples and Table I, infra.

Pharmacology and Utility

Compounds of the invention modulate the activity of protein tyrosine kinases and, as such, are useful for treating diseases or disorders in which protein tyrosine kinases, particularly Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and Tie2 kinases, contribute to the pathology and/or symptomology of the disease.

Abelson tyrosine kinase (i.e. Abl, c-Abl) is involved in the regulation of the cell cycle, in the cellular response to genotoxic stress, and in the transmission of information about the cellular environment through integrin signaling. Overall, it appears that the Abl protein serves a complex role as a cellular module that integrates signals from various extracellular and intracellular sources and that influences decisions in regard to cell cycle and apoptosis. Abelson tyrosine kinase includes sub-types derivatives such as the chimeric fusion (oncoprotein) BCR-Abl with deregulated tyrosine kinase activity or the v-Abl. BCR-Abl is critical in the pathogenesis of 95% of chronic myelogenous leukemia (CML) and 10% of acute lymphocytic leukemia. STI-571 (Gleevec) is an inhibitor of the oncogenic BCR-Abl tyrosine kinase and is used for the treatment of chronic myeloid leukemia (CML). However, some patients in the blast crisis stage of CML are resistant to STI-571 due to mutations in the BCR-Abl kinase. Over 22 mutations have been reported to date with the most common being G250E, E255V, T315I, F317L and M351T.

Compounds of the present invention inhibit abl kinase, especially v-abl kinase. The compounds of the present invention also inhibit wild-type BCR-Abl kinase and mutations of BCR-Abl kinase and are thus suitable for the treatment of Bcr-abl-positive cancer and tumor diseases, such as leukemias (especially chronic myeloid leukemia and acute lymphoblastic leukemia, where especially apoptotic mechanisms of action are found), and also shows effects on the subgroup of leukemic stem cells as well as potential for the purification of these cells in vitro after removal of said cells (for example, bone marrow removal) and reimplantation of the cells once they have been cleared of cancer cells (for example, reimplantation of purified bone marrow cells).

PDGF (Platelet-derived Growth Factor) is a very commonly occurring growth factor, which plays an important role both in normal growth and also in pathological cell proliferation, such as is seen in carcinogenesis and in diseases of the smooth-muscle cells of blood vessels, for example in atherosclerosis and thrombosis. Compounds of the invention can inhibit PDGF receptor (PDGFR) activity and are, therefore, suitable for the treatment of tumor diseases, such as gliomas, sarcomas, prostate tumors, and tumors of the colon, breast, and ovary.

Compounds of the present invention, can be used not only as a tumor-inhibiting substance, for example in small cell lung cancer, but also as an agent to treat non-malignant proliferative disorders, such as atherosclerosis, thrombosis, psoriasis, scleroderma and fibrosis, as well as for the protection of stem cells, for example to combat the hemotoxic effect of chemotherapeutic agents, such as 5-fluoruracil, and in asthma. Compounds of the invention can especially be used for the treatment of diseases, which respond to an inhibition of the PDGF receptor kinase.

Compounds of the present invention show useful effects in the treatment of disorders arising as a result of transplantation, for example, allogenic transplantation, especially tissue rejection, such as especially obliterative bronchiolitis (OB), i.e. a chronic rejection of allogenic lung transplants. In contrast to patients without OB, those with OB often show an elevated PDGF concentration in bronchoalveolar lavage fluids.

Compounds of the present invention are also effective in diseases associated with vascular smooth-muscle cell migration and proliferation (where PDGF and PDGF-R often also play a role), such as restenosis and atherosclerosis. These effects and the consequences thereof for the proliferation or migration of vascular smooth-muscle cells in vitro and in vivo can be demonstrated by administration of the compounds of the present invention, and also by investigating its effect on the thickening of the vascular intima following mechanical injury in vivo.

The compounds of the present invention also inhibit cellular processes involving stem-cell factor (SCF, also known as the c-kit ligand or steel factor), such as inhibiting SCF receptor (kit) autophosphorylation and SCF-stimulated activation of MAPK kinase (mitogen-activated protein kinase). MO7e cells are a human promegakaryocytic leukemia cell line, which depends on SCF for proliferation. Compounds of the invention can inhibit the autophosphorylation of SCF receptors.

The trk family of neurotrophin receptors (trkA, trkB, trkC) promotes the survival, growth and differentiation of the neuronal and non-neuronal tissues. The TrkB protein is expressed in neuroendocrine-type cells in the small intestine and colon, in the alpha cells of the pancreas, in the monocytes and macrophages of the lymph nodes and of the spleen, and in the granular layers of the epidermis (Shibayama and Koizumi, 1996). Expression of the TrkB protein has been associated with an unfavorable progression of Wilms tumors and of neuroblastomas. TkrB is, moreover, expressed in cancerous prostate cells but not in normal cells. The signaling pathway downstream of the trk receptors involves the cascade of MAPK activation through the Shc, activated Ras, ERK-1 and ERK-2 genes, and the PLC-gammal transduction pathway (Sugimoto et al., 2001).

The kinase, c-Src transmits oncogenic signals of many receptors. For example, over-expression of EGFR or HER2/neu in tumors leads to the constitutive activation of c-src, which is characteristic for the malignant cell but absent from the normal cell. On the other hand, mice deficient in the expression of c-src exhibit an osteopetrotic phenotype, indicating a key participation of c-src in osteoclast function and a possible involvement in related disorders.

The Tec family kinase, Bmx, a non-receptor protein-tyrosine kinase, controls the proliferation of mammary epithelial cancer cells.

Fibroblast growth factor receptor 3 was shown to exert a negative regulatory effect on bone growth and an inhibition of chondrocyte proliferation. Thanatophoric dysplasia is caused by different mutations in fibroblast growth factor receptor 3, and one mutation, TDII FGFR3, has a constitutive tyrosine kinase activity which activates the transcription factor Stat1, leading to expression of a cell-cycle inhibitor, growth arrest and abnormal bone development (Su et al., Nature, 1997, 386, 288-292). FGFR3 is also often expressed in multiple myeloma-type cancers.

The activity of serum and glucocorticoid-regulated kinase (SGK), is correlated to perturbed ion-channel activities, in particular, those of sodium and/or potassium channels and compounds of the invention can be useful for treating hypertension.

Lin et al (1997) J. Clin. Invest. 100, 8: 2072-2078 and P. Lin (1998) PNAS 95, 8829-8834, have shown an inhibition of tumor growth and vascularization and also a decrease in lung metastases during adenoviral infections or during injections of the extracellular domain of Tie-2 (Tek) in breast tumor and melanoma xenograft models. Tie2 inhibitors can be used in situations where neovascularization takes place inappropriately (i.e. in diabetic retinopathy, chronic inflammation, psoriasis, Kaposi's sarcoma, chronic neovascularization due to macular degeneration, rheumatoid arthritis, infantile haemangioma and cancers).

Lck plays a role in T-cell signaling. Mice that lack the Lck gene have a poor ability to develop thymocytes. The function of Lck as a positive activator of T-cell signaling suggests that Lck inhibitors may be useful for treating autoimmune disease such as rheumatoid arthritis.

JNKs, along with other MAPKs, have been implicated in having a role in mediating cellular response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, cancer and neurodegenerative diseases. As a result of the importance of JNK activation associated with liver disease or episodes of hepatic ischemia, compounds of the invention may also be useful to treat various hepatic disorders. A role for JNK in cardiovascular disease such as myocardial infarction or congestive heart failure has also been reported as it has been shown JNK mediates hypertrophic responses to various forms of cardiac stress. It has been demonstrated that the JNK cascade also plays a role in T-cell activation, including activation of the IL-2 promoter. Thus, inhibitors of JNK may have therapeutic value in altering pathologic immune responses. A role for JNK activation in various cancers has also been established, suggesting the potential use of JNK inhibitors in cancer. For example, constitutively activated JNK is associated with HTLV-1 mediated tumorigenesis [Oncogene 13:135-42 (1996)]. JNK may play a role in Kaposi's sarcoma (KS). Other proliferative effects of other cytokines implicated in KS proliferation, such as vascular endothelial growth factor (VEGF), IL-6 and TNF□, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) [Blood 92:2450-60 (1998)].

Certain abnormal proliferative conditions are believed to be associated with raf expression and are, therefore, believed to be responsive to inhibition of raf expression. Abnormally high levels of expression of the raf protein are also implicated in transformation and abnormal cell proliferation. These abnormal proliferative conditions are also believed to be responsive to inhibition of raf expression. For example, expression of the c-raf protein is believed to play a role in abnormal cell proliferation since it has been reported that 60% of all lung carcinoma cell lines express unusually high levels of c-raf mRNA and protein. Further examples of abnormal proliferative conditions are hyper-proliferative disorders such as cancers, tumors, hyperplasia, pulmonary fibrosis, angiogenesis, psoriasis, atherosclerosis and smooth muscle cell proliferation in the blood vessels, such as stenosis or restenosis following angioplasty. The cellular signaling pathway of which raf is a part has also been implicated in inflammatory disorders characterized by T-cell proliferation (T-cell activation and growth), such as tissue graft rejection, endotoxin shock, and glomerular nephritis, for example.

The stress activated protein kinases (SAPKs) are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Therefore, agents that inhibit SAPK activity in a cell prevent DNA repair and sensitize the cell to agents that induce DNA damage or inhibit DNA synthesis and induce apoptosis of a cell or that inhibit cell proliferation.

Mitogen-activated protein kinases (MAPKs) are members of conserved signal transduction pathways that activate transcription factors, translation factors and other target molecules in response to a variety of extracellular signals. MAPKs are activated by phosphorylation at a dual phosphorylation motif having the sequence Thr-X-Tyr by mitogen-activated protein kinase kinases (MKKs). In higher eukaryotes, the physiological role of MAPK signaling has been correlated with cellular events such as proliferation, oncogenesis, development and differentiation. Accordingly, the ability to regulate signal transduction via these pathways (particularly via MKK4 and MKK6) could lead to the development of treatments and preventive therapies for human diseases associated with MAPK signaling, such as inflammatory diseases, autoimmune diseases and cancer.

Syk is a tyrosine kinase that plays a critical role in mast cell degranulation and eosinophil activation. Accordingly, Syk kinase is implicated in various allergic disorders, in particular asthma. It has been shown that Syk binds to the phosphorylated gamma chain of the Fc☐R1 receptor via N-terminal SH2 domains and is essential for downstream signaling.

Inhibition of eosinophil apoptosis has been proposed as a key mechanism for the development of blood and tissue eosinophilia in asthma. IL-5 and GM-CSF are upregulated in asthma and are proposed to cause blood and tissue eosinophilia by inhibition of eosinophil apoptosis. Inhibition of eosinophil apoptosis has been proposed as a key mechanism for the development of blood and tissue eosinophilia in asthma. It has been reported that Syk kinase is required for the prevention of eosinophil apoptosis by cytokines (using antisense) [Yousefi, et al., J. Exp. Med. 1996, 183, 1407].

The family of human ribosomal S6 protein kinases consists of at least 8 members (RSK1, RSK2, RSK3, RSK4, MSK1, MSK2, p70S6K and p70S6 Kb). Ribosomal protein S6 protein kinases play important pleotropic functions, among them is a key role in the regulation of mRNA translation during protein biosynthesis (Eur. J. Biochem 2000 November; 267(21): 6321-30, Exp Cell Res. Nov. 25, 1999; 253 (1):100-9, Mol Cell Endocrinol. May 25, 1999; 151(1-2):65-77). The phosphorylation of the S6 ribosomal protein by p70S6 has also been implicated in the regulation of cell motility (Immunol. Cell Biol. 2000 August; 78(4): 447-51) and cell growth (Prog. Nucleic Acid Res. Mol. Biol., 2000;65:101-27), and hence, may be important in tumor metastasis, the immune response and tissue repair as well as other disease conditions.

The SAPK's (also called "jun N-terminal kinases" or "JNK's") are a family of protein kinases that represent the penultimate step in signal transduction pathways that result in activation of the c-jun transcription factor and expression of genes regulated by c-jun. In particular, c-jun is involved in the transcription of genes that encode proteins involved in the repair of DNA that is damaged due to genotoxic insults. Agents that inhibit SAPK activity in a cell prevent DNA repair and sensitize the cell to those cancer therapeutic modalities that act by inducing DNA damage. In accordance with the foregoing, the present invention further provides a method for preventing or treating any of the diseases or disorders described above in a subject in need of such treatment, which method comprises administering to said subject a therapeutically effective amount (See, "Administration and Pharmaceutical Compositions", infra) of a compound of Formula I or a pharmaceutically acceptable salt thereof. For any of the above uses, the required dosage will vary depending on the mode of administration, the particular condition to be treated and the effect desired.

Administration and Pharmaceutical Compositions

In general, compounds of the invention will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. In general, satisfactory results are indicated to be obtained systemically at daily dosages of from about 0.03 to 2.5 mg/kg per body weight. An indicated daily dosage in the larger mammal, e.g. humans, is in the range from about 0.5 mg to about 100 mg, conveniently administered, e.g. in divided doses up to four times a day or in retard form. Suitable unit dosage forms for oral administration comprise from ca. 1 to 50 mg active ingredient.

Compounds of the invention can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present invention in free form or in a pharmaceutically acceptable salt form in association with at least one pharmaceutically acceptable carrier or diluent can be manufactured in a conventional manner by mixing, granulating or coating methods. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

Compounds of the invention can be administered in therapeutically effective amounts in combination with one or more therapeutic agents (pharmaceutical combinations). For example, synergistic effects can occur with other immunomodulatory or anti-inflammatory substances, for example when used in combination with cyclosporin, rapamycin, or ascomycin, or immunosuppressant analogues thereof, for example cyclosporin A (CsA), cyclosporin G, FK-506, rapamycin, or comparable compounds, corticosteroids, cyclophosphamide, azathioprine, methotrexate, brequinar, leflunomide, mizoribine, mycophenolic acid, mycophenolate mofetil, 15-deoxyspergualin, immunosuppressant antibodies, especially monoclonal antibodies for leukocyte receptors, for example MHC, CD2, CD3, CD4, CD7, CD25, CD28, B7, CD45, CD58 or their ligands, or other immunomodulatory compounds, such as CTLA41 g. Where the compounds of the invention are administered in conjunction with other therapies, dosages of the co-administered compounds will of course vary depending on the type of co-drug employed, on the specific drug employed, on the condition being treated and so forth.

The invention also provides for a pharmaceutical combinations, e.g. a kit, comprising a) a first agent which is a compound of the invention as disclosed herein, in free form or in pharmaceutically acceptable salt form, and b) at least one co-agent. The kit can comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of Formula I and a co-agent, are both administered to a patient simultaneously in the form of a single entity or dosage. The term "non-fixed combination" means that the active ingredients, e.g. a compound of Formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, in which $R_{12}$ is hydrogen, $R_1$ is —$NR_7R_8$ and $R_6$ is —$NHY(O)R_{13}$, can be prepared by proceeding as in the following Reaction Scheme I:

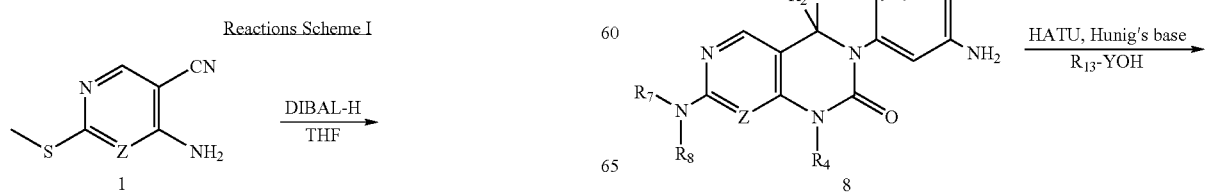

-continued

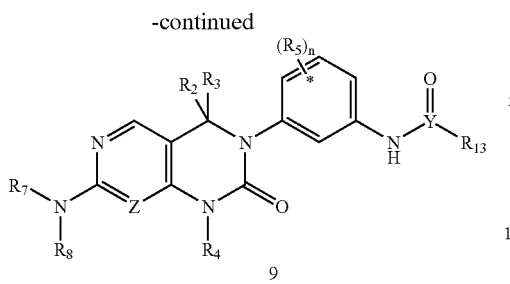
9 in which n, $R_2$, $R_3$, $R_4$, $R_5$, $R_7$, $R_8$, $R_{13}$, Y and Z are as defined for Formula I in the Summary of the Invention and X represents a halo group, for example iodo or chloro, preferably iodo.

A compound of Formula 2 can be prepared by reducing a nitrile of formula 1 with diisobutylaluminum hydride (DIBAL-H) in the presence of a suitable solvent (e.g., THF). Compounds of formula 3 can be prepared by reductive amination of a compound of formula 2 in the presence of a solvent mixture (e.g., DMF, AcOH, EtOH, and the like) using an appropriate reducing agent (e.g., sodium cyanoborohydride ($NaBH_3CN$)).

Compounds of formula 4 can be prepared by formation of a cyclic urea from compounds of formula 3 with triphosgene in the presence of a suitable base (e.g., triethylamine) in a suitable solvent (e.g., THF) and can take up to 4 hours to complete. Compounds of formula 4 can be further oxidized to give compounds of formula 5 with a suitable oxidizing agent (e.g., m-chloroperoxybenzoic acid (mCPBA)) and can take up to 6 hours to complete. A detailed example of the synthesis of a compound of formula 5 can be found in Reference 1, infra.

Compounds of formula 6 can be prepared by reacting a compound of Formula 5 with a suitable halo-alkane (e.g., iodomethane). The reaction can be effected in an appropriate solvent (e.g., DMF) and requires up to 5 hours to complete. Compounds of formula 7 can be prepared by reacting a compound of formula 6 with an appropriate amine (e.g., 3-dimethylaminoaniline). The reaction is carried out in a temperature range of 100-150° C. and can take up to 3 hours to complete. Compounds of formula 8 can be prepared by hydrogenation of compounds of formula 7 in the presence of a suitable catalyst (e.g., Pd/C, or the like) in an appropriate solvent (e.g., DMF, methanol, or the like) and can take up to 15 hours to complete. Compounds of Formula I can be prepared by coupling compounds of formula 8 with $R_{13}YOH$ using a suitable acyl activating reagent (e.g., HATU) in the presence of a suitable base (e.g., DIEA, or the like) and an appropriate solvent (e.g., DMF) and can take up to 3 hours to complete.

Compounds of Formula I, in which $R_1$ is $-NR_7R_8$, can be prepared by proceeding as in the following Reaction Scheme II:

Reactions Scheme II

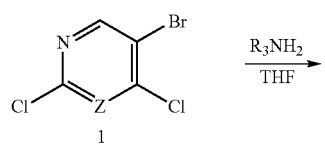
1

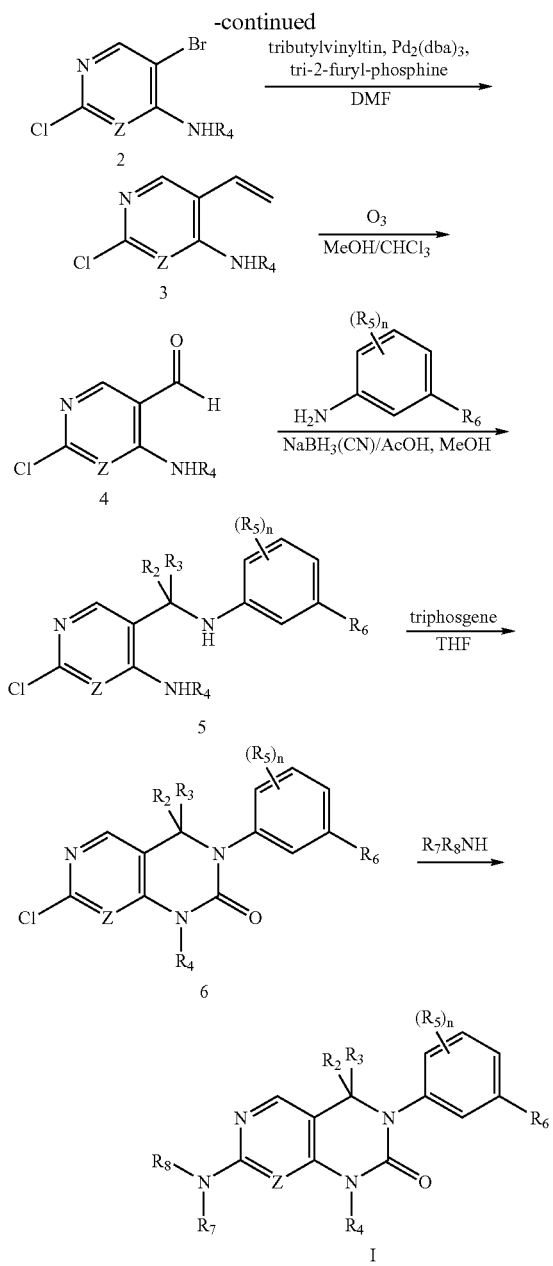

in which n, $R_2$, $R_3$, $R_4$, $R_5$, $R_6$, and Z are as defined for Formula I in the Summary of the Invention.

A compound of formula 2 can be regioselectively prepared by reacting a compound of formula 1 with a suitable amine at a temperature below −20° C. in the presence of an appropriate solvent (e.g., THF). A compound of formula 3 can be prepared via a Stille coupling reaction from a compound of formula 2 in the presence of a suitable solvent (e.g., DMF, 1-methyl-2-pyrrolidinone, and the like) at a temperature of about 70° C. The reaction can take up to 15 hours to complete. A compound of formula 4 can be prepared through ozonolysis of a compound of formula 3 at a temperature of about −78° C. A compound of formula 5 can be readily prepared by reductive amination of a compound of formula 4 with a suitable amine in methanol solvent that can facilitate the corresponding imine formation. A compound of formula 5 is treated with triphosgene to afford a compound of formula 6 at elevated temperature in the presence of an appropriate solvent (e.g., THF). A compound of Formula I can be prepared by reacting a compound of formula 6 with a suitable amine in the absence or presence of an appropriate solvent (e.g., AcOH-water). A compound of Formula I can be also prepared by reacting a compound of formula 6 with a suitable amine in the presence of a suitable solvent (e.g., 1-butanol) with the aid of p-toluenesulfonic acid at elevated temperatures.

Alternatively, a compound of Formula I can be prepared by reacting a compound of formula 6 with a compound of formula $R_7R_8NH$ by three methods. For the heteroaryl amine or aryl amine, the reaction proceeds in the presence of a suitable catalyst (e.g., Pd (II) salt, or the like) and a suitable solvent (e.g., 1,4-dioxane, or the like), in a temperature range of about 80 to about 150° C. and can take up to about 20 hours to complete. The reaction conditions for alkyl amine displacement involves heating a compound of formula 6 with 5-10 equivalents of amine in a suitable solvent (e.g. DMSO, DMF, or the like). For condensations of formula 6 with aryl amine, these are carried out in the presence of acid (e.g., TsOH, HOAc, HCl, or the like) in a suitable solvent (e.g., DMSO, DMF, alcohol or the like).

Detailed examples of the synthesis of a compound of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base. Alternatively, the salt forms of the compounds of the invention can be prepared using salts of the starting materials or intermediates.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.)

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:

(a) those of reaction schemes I and II; and (b) optionally converting a compound of the invention into a pharmaceutically acceptable salt;

(c) optionally converting a salt form of a compound of the invention to a non-salt form;

(d) optionally converting an unoxidized form of a compound of the invention into a pharmaceutically acceptable N-oxide;

(e) optionally converting an N-oxide form of a compound of the invention to its unoxidized form;

(f) optionally resolving an individual isomer of a compound of the invention from a mixture of isomers;

(g) optionally converting a non-derivatized compound of the invention into a pharmaceutically acceptable prodrug derivative; and (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The present invention is further exemplified, but not limited, by the following examples that illustrate the preparation of compounds of Formula I (Examples) and intermediates (References) according to the invention.

Reference 1

7-Methanesulfonyl-3-(2-methyl-5-nitro-phenyl)-3,4-dihydro-1H-pyrimido[4,5-d]pyrimidin-2-one

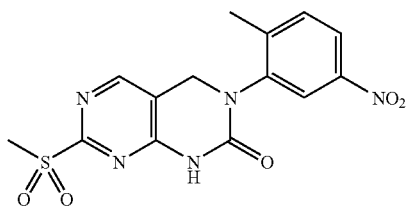

To a stirred solution of 4-amino-2-methylsulfanyl-pyrimidine-5-carbonitrile (4.50 g, 27.1 mmol) in 120 mL of THF is slowly added 27 mL of a 1 M solution of diisobutylaluminum hydride in dichloromethane for 5 minutes at 0° C. The ice bath is removed, and an additional 27 mL of 1M solution of diisobutylaluminum hydride in dichloromethane is added. After 30 minutes an additional 13 mL of 1 M solution of diisobutylaluminum hydride in dichloromethane is added. After 30 minutes the reaction is carefully quenched by the addition of 45 mL of methanol. This mixture is partitioned between 250 mL of EtOAc and 160 mL of 1 N HCl. The aqueous layer is treated with 80 mL of 2 N NaOH and extracted with EtOAc. The organic layer is dried over MgSO₄, filtered, concentrated under reduced pressure and purified by flash column chromatography (SiO₂, EtOAc/hexane=1/3) to give pure 4-amino-2-methylsulfanyl-pyrimidine-5-carbaldehyde (1.80 g, 39%) as a white solid.

4-amino-2-methylsulfanyl-pyrimidine-5-carbaldehyde (1.80 g, 10.6 mmol) and 2-methyl-4-nitrophenylamine (1.94 g, 12.8 mmol) is dissolved in the mixed solvent of DMF (18 mL), AcOH (18 mL), and EtOH (36 mL), and the reaction mixture is stirred for 2 hours at 40° C. To the reaction mixture is added sodium cyanoborohydride (2.01 g, 31.2 mmol) and the mixture is stirred for 30 minutes at room temperature. The reaction mixture is diluted with EtOAc (80 mL), and washed with saturated aqueous sodium bicarbonate solution. The organic layer is dried over MgSO₄, and concentrated under reduced pressure. The residue is purified by flash column chromatography (SiO₂, EtOAc/hexane=1/2) to give 5-[(2-methyl-5-nitro-phenylamino)-methyl]-2-methylsulfanyl-pyrimidin-4-ylamine (1.10 g, 34%) as an orange solid.

To a stirred solution of 5-[(2-methyl-5-nitro-phenylamino)-methyl]-2-methylsulfanyl-pyrimidin-4-ylamine (112 mg, 0.37 mmol) and triethylamine (112 μL, 0.80 mmol) in THF (5 mL) is added a solution of triphosgene (38 mg, 0.13 mmol) in THF (1 mL) at 0° C., and the mixture is stirred for 3 hours at room temperature. The reaction mixture is diluted with EtOAc (10 mL), and washed with saturated aqueous sodium bicarbonate solution. The organic layer is dried over MgSO₄, concentrated under reduced pressure and recrystallized from dichloromethane to give 3-(2-methyl-5-nitro-phenyl)-7-methylsulfanyl-3,4-dihydro-1H-pyrimido[4,5-d]pyrimidin-2-one (94 mg, 76%) as a white crystalline solid.

To a stirred solution of 3-(2-methyl-5-nitro-phenyl)-7-methylsulfanyl-3,4-dihydro-1H-pyrimido[4,5-d]pyrimidin-2-one (240 mg, 0.72 mmol) in chloroform (15 mL) is added m-chloroperoxybenzoic acid (77% max., 400 mg, 1.8 mmol) and the mixture is stirred for 4 hours at room temperature. The white precipitate is collected and washed with chloroform to give 7-methanesulfonyl-3-(2-methyl-5-nitro-phenyl)-3,4-dihydro-1H-pyrimido[4,5-d]pyrimidin-2-one (195 mg, 75%) as a white solid.

Example 1

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide

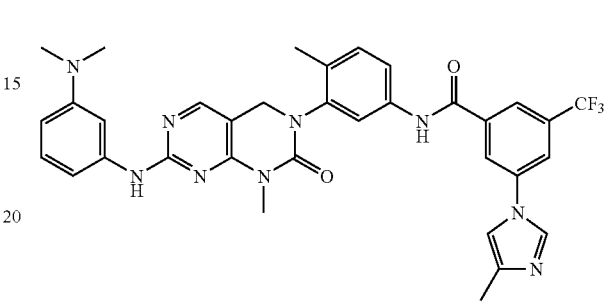

To the suspension of NaH (60% dispersion in mineral oil, 139 mg, 3.5 mmol) in DMF is added 7-methanesulfonyl-3-(2-methyl-5-nitro-phenyl)-3,4-dihydro-1H-pyrimido[4,5-d]pyrimidin-2-one (1.15 g, 3.2 mmol), prepared as in Reference 1, at 0° C. When H₂ evolution has ceased, iodomethane (0.99 ml, 15.8 mmol) is added and the reaction mixture is stirred for 3 hours at room temperature. The mixture is diluted with ethyl acetate, and washed with 5% aqueous Na₂S₂O₃ solution to remove DMF. The organic layer is dried over MgSO₄ and concentrated under reduced pressure. The crude product is purified by flash column chromatography (SiO₂, EtOAc/hexane=1/1) to give 7-methanesulfonyl-1-methyl-3-(2-methyl-5-nitro-phenyl)-3,4-dihydro-1H-pyrimido[4,5-d]pyrimidin-2-one (0.85 g, 70%) as a white solid.

A mixture of 7-methanesulfonyl-1-methyl-3-(2-methyl-5-nitro-phenyl)-3,4-dihydro-1H-pyrimido[4,5-d]pyrimidin-2-one (148 mg, 0.39 mmol) and 3-dimethylaminoaniline (530 mg, 3.9 mmol) is stirred for 1 hour at 130° C. The mixture is cooled down to room temperature and suspended in methanol. The precipitate is collected and washed with methanol to give 7-(3-dimethylamino-phenylamino)-1-methyl-3-(2-methyl-5-nitro-phenyl)-3,4-dihydro-1H-pyrimido[4,5-d]pyrimidin-2-one (98 mg, 58%) as a yellow solid.

To a solution of 7-(3-dimethylamino-phenylamino)-1-methyl-3-(2-methyl-5-nitro-phenyl)-3,4-dihydro-1H-pyrimido[4,5-d]pyrimidin-2-one (80 mg, 0.18 mmol) in the mixed solvent of DMF (3 ml) and methanol (3 mL) is added 10% Pd/C, and the reaction mixture was stirred for 12 hours at room temperature under a hydrogen balloon. The reaction mixture is filtered and the filtrate is concentrated in vacuo to give 3-(5-amino-2-methyl-phenyl)-7-(3-dimethylamino-phenylamino)-1-methyl-3,4-dihydro-1H-pyrimido[4,5-d]pyrimidin-2-one (60 mg, 81%) as a dark yellow solid.

To a solution of 3-(5-amino-2-methyl-phenyl)-7-(3-dimethylamino-phenylamino)-1-methyl-3,4-dihydro-1H-pyrimido[4,5-d]pyrimidin-2-one (52 mg, 0.13 mmol), 3-(4-methyl-imidazol-1-yl)-5-trifluoromethylbenzoic acid (42 mg, 0.15 mmol), and DIEA (78 μL, 0.45 mmol) in DMF is added HATU (59 mg, 0.15 mmol), and the mixture is stirred for 1 hour at room temperature. The reaction mixture is diluted with EtOAc and washed with 5% aqueous Na₂S₂O₃ solution, saturated aqueous NaHCO₃ solution, and brine. The organic layer is dried over MgSO₄ and concentrated in reduced pressure. The residue is purified by recrystallization from methanol to give N-{3-[7-(3-dimethylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide (25 mg, 30%) as a yellowish solid; $^1$H NMR 400 MHz (DMSO-$d_6$) δ 9.34 (s, 1H), 8.43 (s, 1H), 8.38 (s, 1H), 8.23 (s, 1H), 8.16 (s, 1H), 8.13 (s, 1H), 7.74 (s, 1H), 7.69 (s, 1H), 7.65 (d, 1H), 7.34-7.30 (m, 2H), 7.08-7.03 (m, 2H), 6.33 (d, 1H), 4.68 (d, 1H), 4.51 (d, 1H), 3.35 (s, 3H), 2.88 (s, 6H), 2.17 (s, 3H), 2.14 (s, 3H); MS m/z 656.3 (M+1).

Example 2

N-{3-[7-(3-Amino-phenylamino)-1-methyl-2-oxo-1,4-dihydro-2H-pyrimido[4,5-d]pyrimidin-3-yl]-4-methyl-phenyl}-3-trifluoromethyl-benzamide

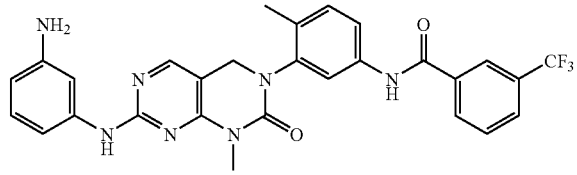

5-Bromo-2,4-dichloro-pyrimidine (2.41 g, 10.6 mmol) is slowly treated with methylamine (8 M in EtOH, 3.3 mL) in THF (15 mL) at about −20° C. After stirring for 30 minutes at about −20° C., the reaction mixture is partitioned between CHCl₃ and saturated NaHCO₃. The aqueous layer is extracted with additional CHCl₃ twice and the combined organic layer is dried over MgSO₄, filtered and concentrated. The crude product is purified by column chromatography (SiO₂, EtOAc/Hexane=3/7) to give 1.76 g (75%) of (5-bromo-2-chloro-pyrimidin-4-yl)-methylamine as a white solid.

A mixture of (5-bromo-2-chloro-pyrimidin-4-yl)-methylamine (3.75 g, 16.9 mmol), tris(dibenzylidineacetone)dipalladium(0) (388 mg, 0.4 mmol), and tri-2-furylphosphine (777 mg, 3.3 mmol) in DMF is stirred for 20 minutes at room temperature and then tributylvinyltin (5.93 mL, 20.3 mmol) is added. After stirring for 16 hours at about 65° C., the reaction mixture is cooled to room temperature and stirred with a 10% aqueous solution of potassium fluoride (800 mL) and diethyl ether (600 mL) for 1 hour before filtering through a pad of Celite. The pad of Celite is rinsed with a further portion of diethyl ether (200 mL). The aqueous layer is separated and extracted with CHCl₃. The combined organic extract is dried over MgSO₄ and concentrated under reduced pressure to give crude oil which is purified by flash column chromatography (SiO₂, EtOAc/Hx=1/4) to afford (2-chloro-5-vinyl-pyrimidin-4-yl)-methylamine (2.63 g, 92%) as a white solid.

A solution of (2-chloro-5-vinyl-pyrimidin-4-yl)-methylamine (2.50 g, 14.7 mmol) in CHCl₃/MeOH (15 mL/15 mL) is bubbled by ozone for 30 minutes and then passed by a stream of argon for 3 minutes at −78° C. The reaction mixture is allowed to warm up to room temperature and treated with dimethyl sulfide (3.24 mL, 44.1 mmol). The reaction mixture is concentrated under reduced pressure to give colorless oil that is purified by flash column chromatography (SiO₂, EtOAc/Hx=1/3) over silica gel to give 2-chloro-4-methylamino-pyrimidine-5-carbaldehyde (2.40 g, 95%) as a white solid.

A solution of 2-chloro-4-methylamino-pyrimidine-5-carbaldehyde (1.08 g, 6.3 mmol) and N-(3-amino-4-methylphenyl)-3-trifluoromethylbenzamide (2.04 g, 6.9 mmol) in MeOH (70 mL) is stirred for 2 hours at 45° C. and then treated with sodium cyanoborohydride (1.19 g, 18.9 mmol) and acetic acid (1 mL) sequentially. After stirring for 2 hours at room temperature, the reaction mixture is diluted with CHCl₃ and washed with saturated NaHCO₃ The organic layer is dried over MgSO₄ and concentrated under reduced pressure. The residue is purified by flash column chromatography (SiO₂, EtOAc/hexane=1/2) to give N-{3-[(2-chloro-4-methylaminopyrimidin-5-ylmethyl)amino]-4-methylphenyl}-3-trifluoromethylbenzamide (1.80 g, 64%) as a white solid.

To a stirred solution of N-{3-[(2-chloro-4-methylaminopyrimidin-5-ylmethyl)amino]-4-methylphenyl}-3-trifluoromethylbenzamide (559 mg, 1.24 mmol) and triethylamine (693 μL, 4.97 mmol) in THF (15 mL) is added triphosgene (147 mg, 0.49 mmol) in THF (5 mL) at 0° C., and the mixture is stirred for 30 minutes at room temperature. The precipitate is filtered off and the filtrate is stirred for 3 hours at 110° C. The reaction mixture is then diluted with EtOAc and washed with saturated NaHCO₃. The organic layer is dried over MgSO₄ and concentrated under reduced pressure to give crude oil which is purified by flash column chromatography (SiO₂, EtOAc/hexane=1/2) to give N-[3-(7-chloro-2-oxo-1,4-dihydro-2H-pyrimido[4,5-d]pyrimidin-3-yl)-4-methylphenyl]-3-trifluoromethylbenzamide (420 mg, 71%) as a white solid.

A mixture of N-[3-(7-chloro-2-oxo-1,4-dihydro-2H-pyrimido[4,5-d]pyrimidin-3-yl)-4-methylphenyl]-3-trifluoromethylbenzamide (35.0 mg, 73.6 mmol) and phenylenediamine (79.5 mg, 736 mmol) is stirred for 1 hour at 100° C. The mixture is cooled to room temperature and suspended in methanol. The precipitate is collected and washed with methanol to give N-{3-[7-(3-amino-phenylamino)-1-methyl-2-oxo-1,4-dihydro-2H-pyrimido[4,5-d]pyrimidin-3-yl]-4-methyl-phenyl}-3-trifluoromethyl-benzamide (34 mg, 84%) as a white solid; $^1$H NMR 400 MHz (DMSO-$d_6$) δ 9.22 (s, 1H), 8.29 (s, 1H), 8.25 (d, 1H), 8.10 (s, 1H), 7.95 (d, 1H), 7.78-7.76 (m, 2H), 7.62 (dd, 1H), 7.30 (d, 1H), 7.05 (d, 1H), 6.88 (d, 1H), 6.87 (s, 1H), 6.17 (dd, 1H), 4.92 (s, 2H), 4.67 (d, 1H), 4.49 (d, 1H), 3.33 (s, 3H), 2.12 (s, 3H); MS m/z 548.3 (M+1).

Example 3

N-[4-Methyl-3-(1-methyl-7-methylamino-2,4-dioxo-1,4-dihydro-2H-pyrimido[4,5-d]pyrimidin-3-yl)-phenyl]-3-trifluoromethyl-benzamide

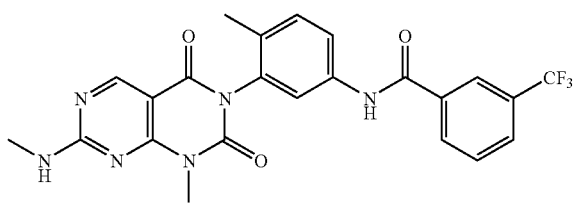

To a stirred solution of ethyl 4-chloro-2-methylsulfanyl-5-pyrimidinecarboxylate (4.50 g, 19.4 mmol) in MeOH is added 7 N NH₃ (13.9 mL) in MeOH at 0° C. and the mixture is stirred for 2 h at room temperature. The reaction mixture is diluted with EtOAc and washed with saturated NaHCO₃ solution. The organic layer is dried over MgSO₄, filtered and concentrated. The crude product is crystrallized from the mixed solvent of EtOAc and hexanes to give 2.90 g (66%) of ethyl 4-amino-2-methylsulfanyl-5-pyrimidinecarboxylate as a white solid.

To a stirred solution of ethyl 4-amino-2-methylsulfanyl-5-pyrimidinecarboxylate (2.79 g, 13.1 mmol) is added 4 N NaOH (3.9 mL) and the mixture is stirred for 3 h at 60° C. The reaction mixture is concentrated to give 4-amino-2-methylsulfanyl-5-pyrimidinecarboxylate in a sodium salt form in quantitative yield.

To a solution of 4-amino-2-methylsulfanyl-5-pyrimidinecarboxylate in a sodium salt form (1.28 g, 6.2 mmol), N-(3-Amino-4-methyl-phenyl)-3-trifluoromethyl-benzamide (1.82 g, 6.2 mmol), and DIEA (3.22 mL, 18.5 mmol) in DMF is added HATU (2.82 g, 7.42 mmol), and the mixture is stirred for 1 h at room temperature. The reaction mixture is diluted with EtOAc and washed with 5% aqueous Na₂S₂O₃ solution, saturated aqueous NaHCO₃ solution, and brine. The organic layer is dried over MgSO₄ and concentrated in reduced pressure. The crude product is crystallized from MeOH to give 4-amino-2-methylsulfanyl-pyrimidine-5-carboxylic acid [2-methyl-5-(3-trifluoromethyl-benzoylamino)-phenyl]-amide (1.79 g, 61%) as a white solid.

To a stirred solution of 4-amino-2-methylsulfanyl-pyrimidine-5-carboxylic acid [2-methyl-5-(3-trifluoromethyl-benzoylamino)-phenyl]-amide (286 mg, 0.62 mmol) and diisopropylethylamine (864 μL, 4.96 mmol) in dioxane (10 mL) is added a solution of triphosgene (184 mg, 0.62 mmol) in dioxane (2 mL) at 0 C, and the mixture is stirred for 12 h at 100° C. The reaction mixture is diluted with EtOAc (50 mL), and washed with saturated NaHCO₃ solution. The organic layer is dried over MgSO₄, filtered, concentrated under reduced pressure, and crystallized from MeOH to give N-[4-Methyl-3-(7-methylsulfanyl-2,4-dioxo-1,4-dihydro-2H-pyrimido[4,5-d]pyrimidin-3-yl)-phenyl]-3-trifluoromethyl-benzamide (166 mg, 55%) as a white crystalline solid.

To the suspension of NaH (60% dispersion in mineral oil, 19.7 mg, 0.49 mmol) in DMF is added N-[4-Methyl-3-(7-methylsulfanyl-2,4-dioxo-1,4-dihydro-2H-pyrimido[4,5-d]pyrimidin-3-yl)-phenyl]-3-trifluoromethyl-benzamide (218 mg, 0.45 mmol) at 0° C. When H₂ evolution has ceased, iodomethane (84 μl, 1.35 mmol) is added and the reaction mixture is stirred for 3 hours at room temperature. The mixture is diluted with ethyl acetate, and washed with 5% aqueous Na₂S₂O₃ solution to remove DMF. The organic layer is dried over MgSO₄ and concentrated under reduced pressure. The crude product is crystallized from MeOH to give N-[4-Methyl-3-(1-methyl-7-methylsulfanyl-2,4-dioxo-1,4-dihydro-2H-pyrimido[4,5-d]pyrimidin-3-yl)-phenyl]-3-trifluoromethyl-benzamide (184 mg, 82%) as a white solid.

To a stirred solution of N-[4-Methyl-3-(1-methyl-7-methylsulfanyl-2,4-dioxo-1,4-dihydro-2H-pyrimido[4,5-d]pyrimidin-3-yl)-phenyl]-3-trifluoromethyl-benzamide (184 mg, 0.37 mmol) in the mixed solvent of DMF (4 mL) and chloroform (4 mL) is added m-chloroperoxybenzoic acid (77% max., 97 mg, 44 mmol) and the mixture is stirred for 1 h at room temperature. The mixture is diluted with chloroform, and washed with 5% aqueous Na₂S₂O₃ solution and saturated NaHCO₃ solution. The organic layer is dried over MgSO₄ and concentrated under reduced pressure to give N-[3-(7-Methanesulfinyl-1-methyl-2,4-dioxo-1,4-dihydro-2H-pyrimido[4,5-d]pyrimidin-3-yl)-4-methyl-phenyl]-3-trifluoromethyl-benzamide (167 mg, 88%).

N-[3-(7-Methanesulfinyl-1-methyl-2,4-dioxo-1,4-dihydro-2H-pyrimido[4,5-d]pyrimidin-3-yl)-4-methyl-phenyl]-3-trifluoromethyl-benzamide (30 mg, 58 μmol) is dissolved in 2 M methylamine solution (1 mL) in THF and the mixture is stirred for 1 h at 60° C. The reaction mixture is concentrated, dissolved in DMSO, and purified by preparative LCMS to give N-[4-Methyl-3-(1-methyl-7-methylamino-2,4-dioxo-1,4-dihydro-2H-pyrimido[4,5-d]pyrimidin-3-yl)-phenyl]-3-trifluoromethyl-benzamide (20 mg, 71%); $^1$H NMR 400 MHz (DMSO-d₆) δ 10.70 (s, 1H), 8.95 (s, 0.33H), 8.85 (s, 0.66H), 8.39 (m, 3H), 8.11 (d, 1H), 7.93 (t, 1H), 7.84 (m, 2H), 7.49 (d, 1H), 3.65 (d, 2H), 3.58 (s, 1H), 3.08 (m, 3H), 2.17 (s, 3H); MS m/z 485.3 (M+1).

By repeating the procedures described in the above examples, using appropriate starting materials, the following compounds of Formula I, as identified in Table 1, are obtained.

TABLE 1

| Compound Number | Structure | Physical Data $^1$H NMR 400 MHz (DMSO-d₆) and/or MS (m/z) |
|---|---|---|
| 1 | 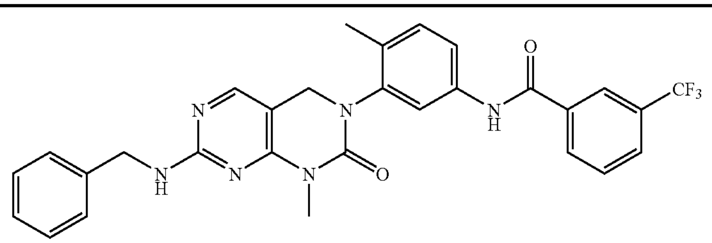 | MS m/z 547.2 (M + 1) |
| 2 | 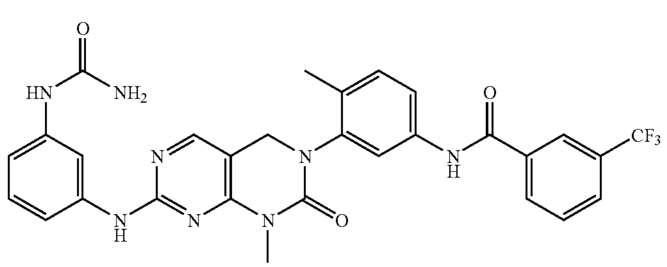 | MS m/z 591.2 (M + 1) |

TABLE 1-continued

| Compound Number | Structure | Physical Data $^1$H NMR 400 MHz (DMSO-$d_6$) and/or MS (m/z) |
|---|---|---|
| 3 | 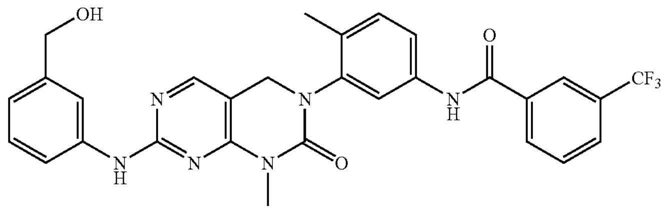 | MS m/z 563.2 (M + 1) |
| 4 | 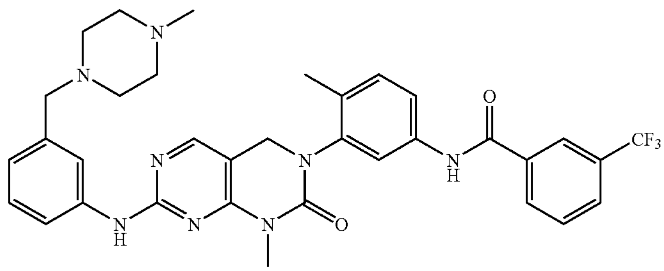 | MS m/z 645.3 (M + 1) |
| 5 | 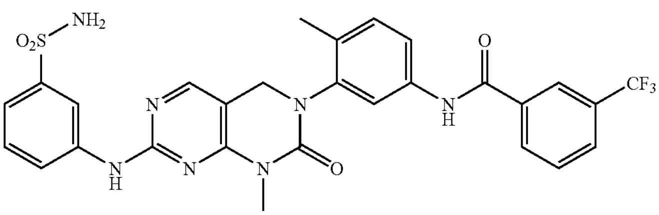 | MS m/z 612.1 (M + 1) |
| 6 | 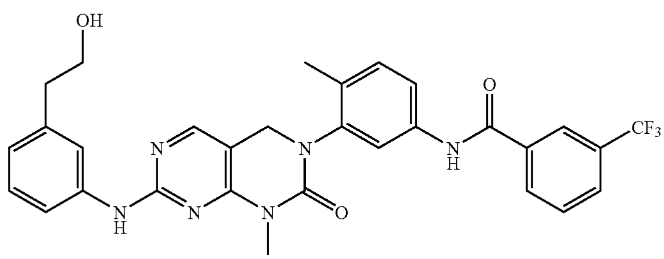 | MS m/z 577.2 (M + 1) |
| 7 | 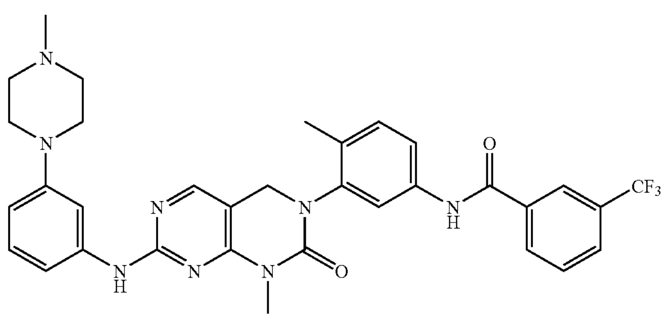 | MS m/z 631.3 (M + 1) |
| 8 | 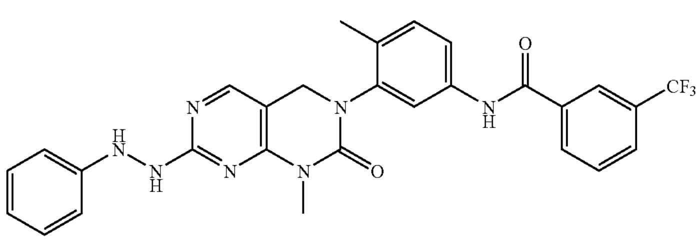 | MS m/z 548.2 (M + 1) |

TABLE 1-continued

| Compound Number | Structure | Physical Data ¹H NMR 400 MHz (DMSO-d$_6$) and/or MS (m/z) |
|---|---|---|
| 9 | 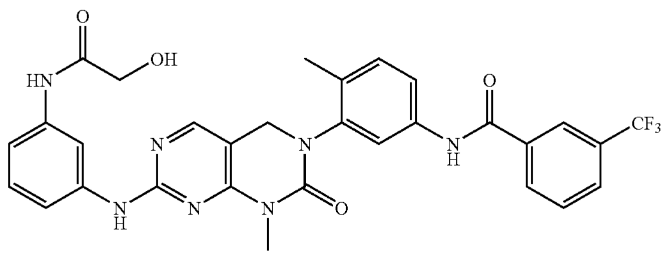 | MS m/z 606.2 (M + 1) |
| 10 | 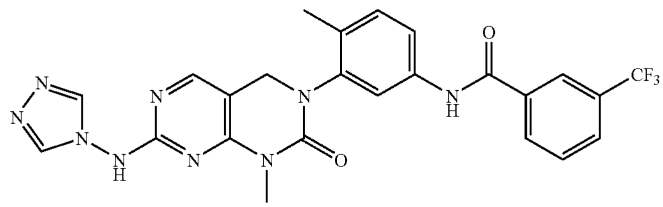 | MS m/z 524.2 (M + 1) |
| 11 | 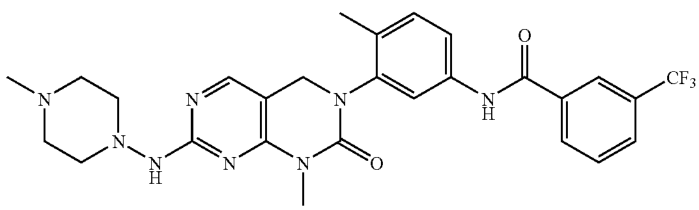 | MS m/z 555.2 (M + 1) |
| 12 | 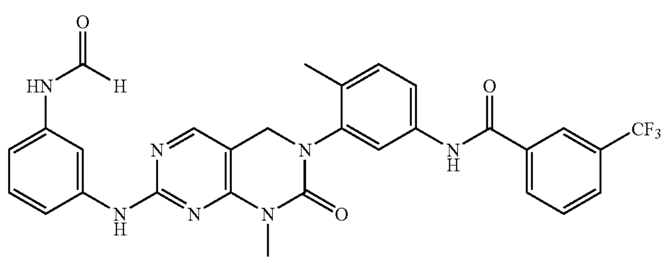 | MS m/z 576.2 (M + 1) |
| 13 | 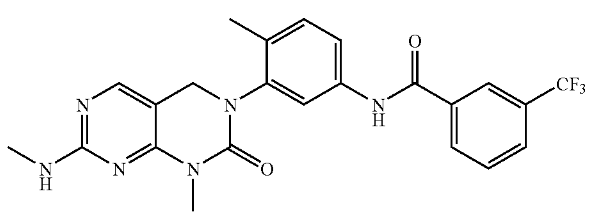 | MS m/z 471.2 (M + 1) |
| 14 | 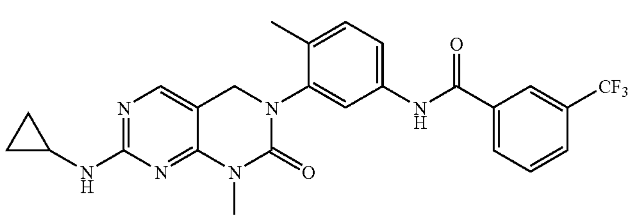 | MS m/z 497.2 (M + 1) |

TABLE 1-continued

| Compound Number | Structure | Physical Data $^1$H NMR 400 MHz (DMSO-$d_6$) and/or MS (m/z) |
|---|---|---|
| 15 | 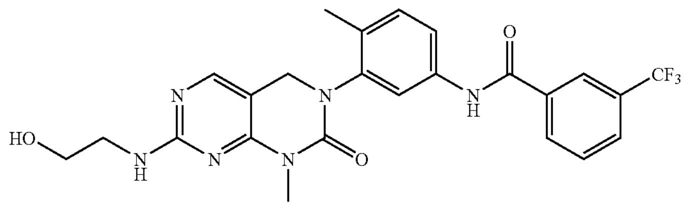 | MS m/z 501.2 (M + 1) |
| 16 | 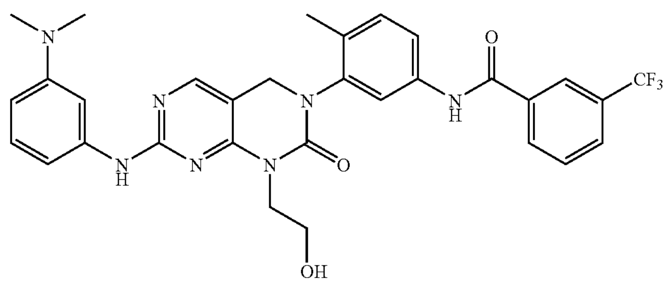 | MS m/z 606.2 (M + 1) |
| 17 | 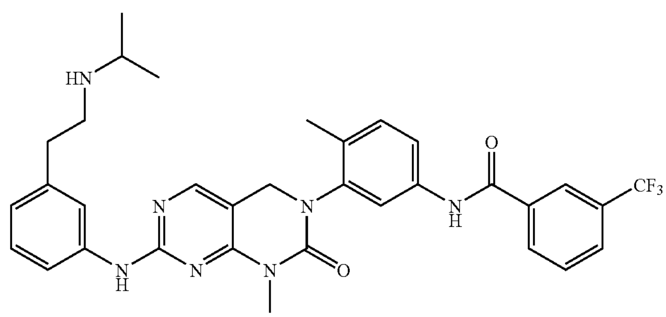 | MS m/z 618.3 (M + 1) |
| 18 | 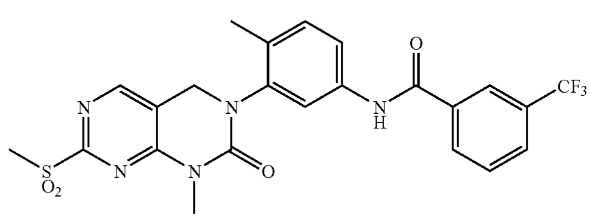 | MS m/z 520.1 (M + 1) |
| 19 | 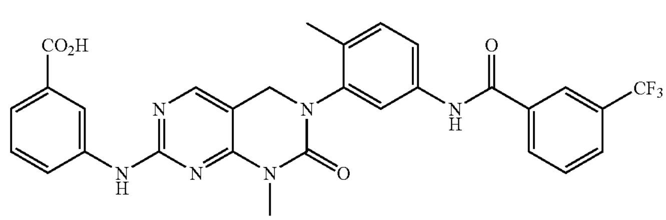 | MS m/z 577.2 (M + 1) |
| 20 | 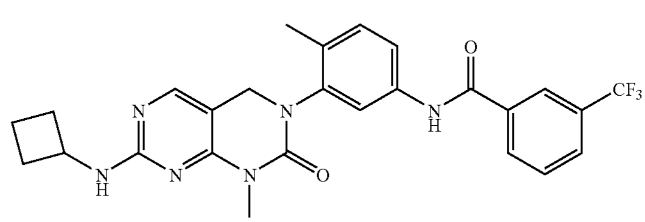 | MS m/z 511.2 (M + 1) |

TABLE 1-continued

| Compound Number | Structure | Physical Data<br>¹H NMR 400 MHz<br>(DMSO-d₆) and/or MS (m/z) |
| --- | --- | --- |
| 21 | 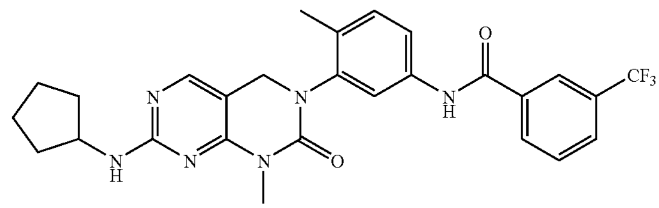 | MS m/z 525.2 (M + 1) |
| 22 | 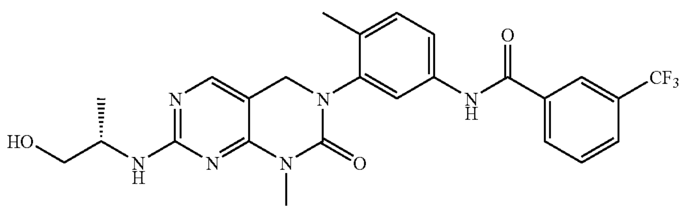 | MS m/z 515.1 (M + 1) |
| 23 | 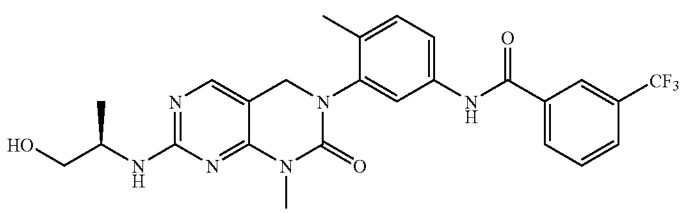 | MS m/z 515.1 (M + 1) |
| 24 | 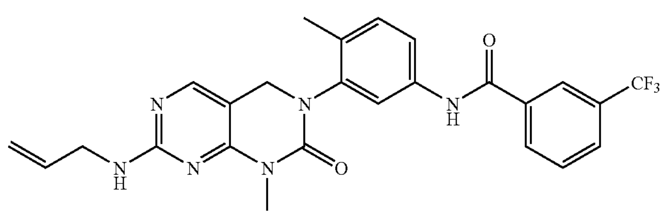 | MS m/z 497.1 (M + 1) |
| 25 | 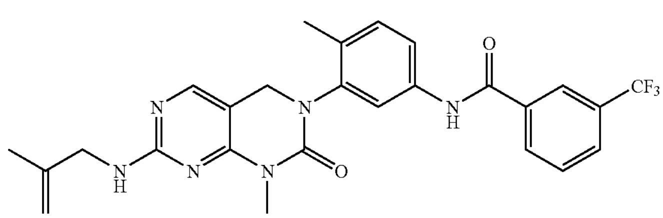 | MS m/z 511.1 (M + 1) |
| 26 | 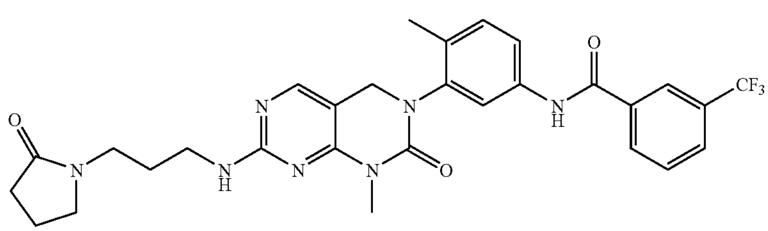 | MS m/z 582.2 (M + 1) |

TABLE 1-continued

| Compound Number | Structure | Physical Data ¹H NMR 400 MHz (DMSO-$d_6$) and/or MS (m/z) |
|---|---|---|
| 27 | 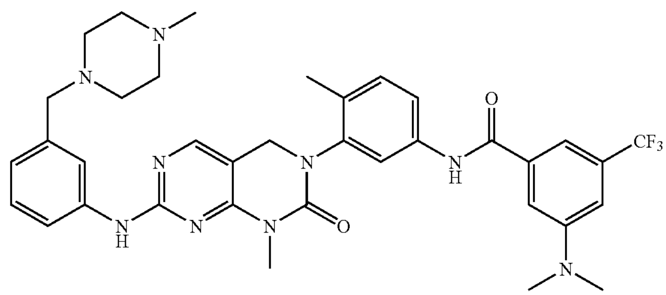 | MS m/z 688.3 (M + 1) |
| 28 | 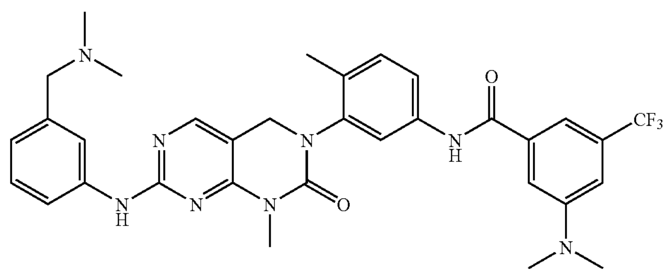 | MS m/z 633.3 (M + 1) |
| 29 | 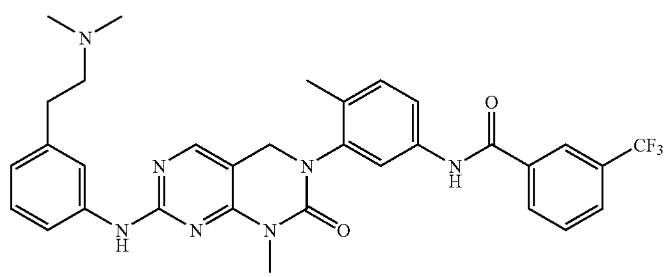 | MS m/z 604.2 (M + 1) |
| 30 | 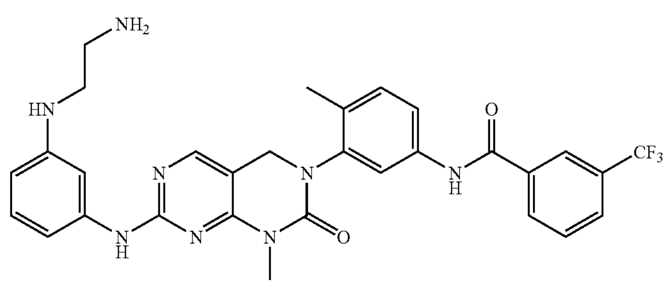 | MS m/z 591.2 (M + 1) |
| 31 | 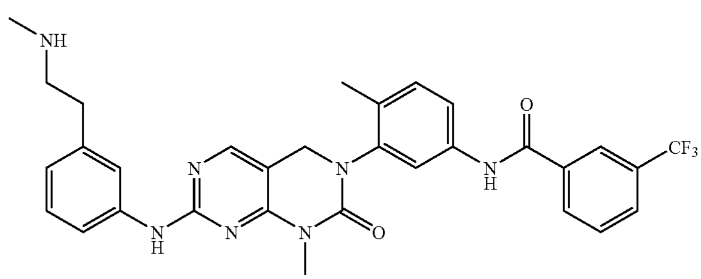 | MS m/z 590.2 (M + 1) |

TABLE 1-continued

| Compound Number | Structure | Physical Data<br>$^1$H NMR 400 MHz<br>(DMSO-$d_6$) and/or MS (m/z) |
| --- | --- | --- |
| 32 | 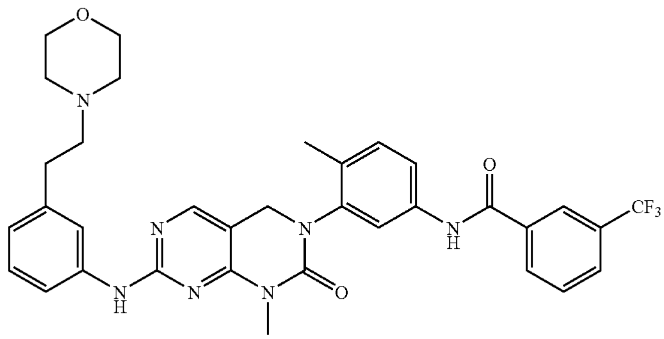 | MS m/z 646.2 (M + 1) |
| 33 | 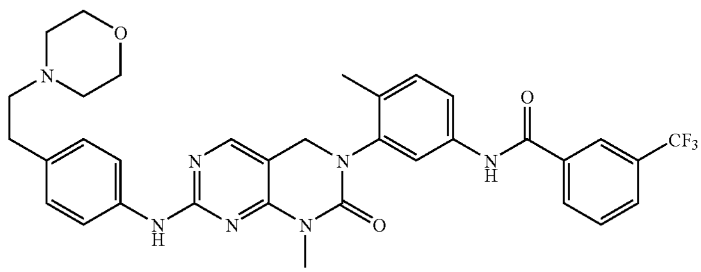 | MS m/z 646.2 (M + 1) |
| 34 | 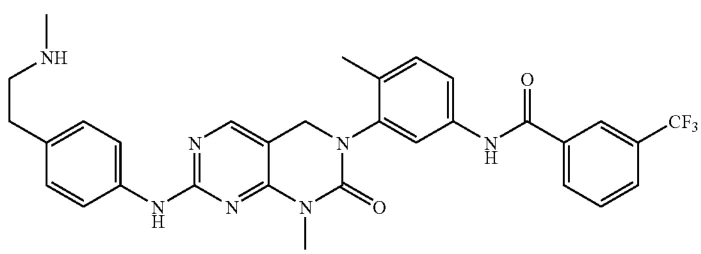 | MS m/z 590.2 (M + 1) |
| 35 | 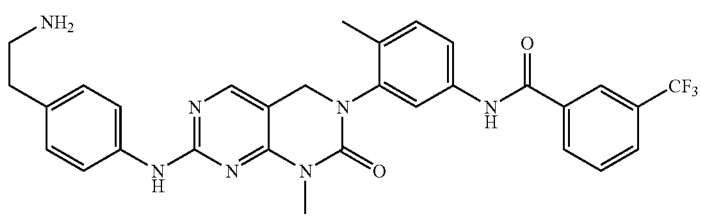 | MS m/z 576.1 (M + 1) |
| 36 | 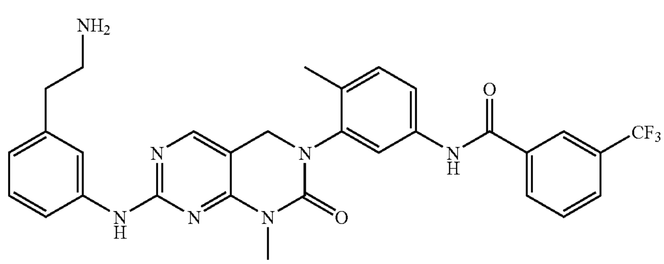 | MS m/z 576.1 (M + 1) |

TABLE 1-continued

| Compound Number | Structure | Physical Data $^1$H NMR 400 MHz (DMSO-$d_6$) and/or MS (m/z) |
|---|---|---|
| 37 | 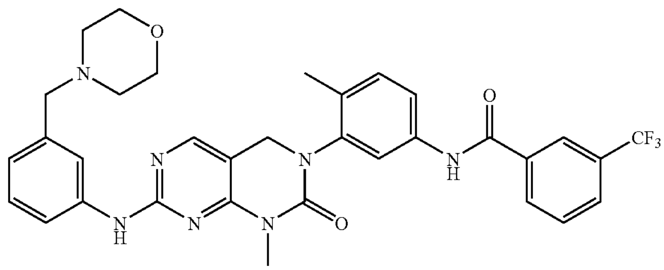 | MS m/z 632.2 (M + 1) |
| 38 | 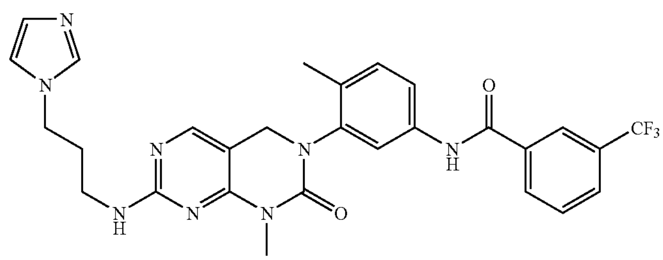 | MS m/z 565.2 (M + 1) |
| 39 | 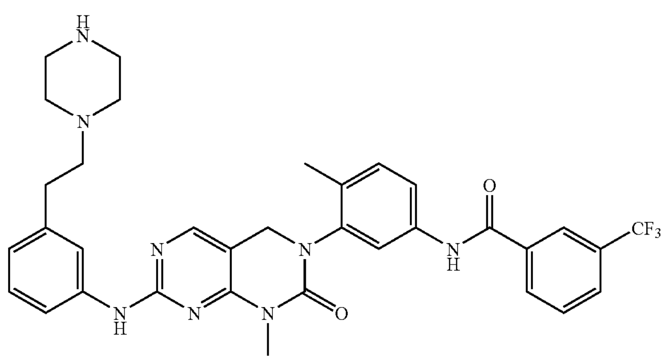 | MS m/z 645.2 (M + 1) |
| 40 | 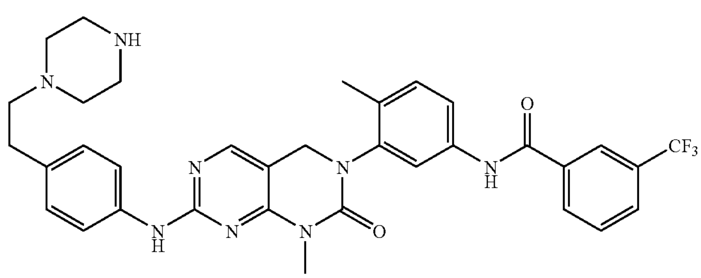 | MS m/z 645.2 (M + 1) |
| 41 | 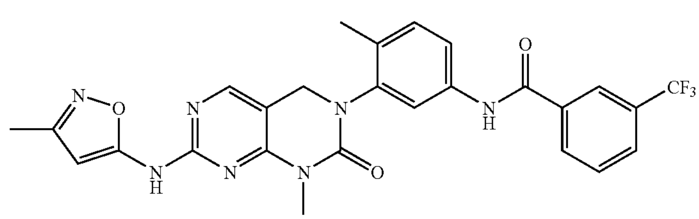 | MS m/z 538.1 (M + 1) |

TABLE 1-continued

| Compound Number | Structure | Physical Data<br>¹H NMR 400 MHz<br>(DMSO-d₆) and/or MS (m/z) |
|---|---|---|
| 42 | 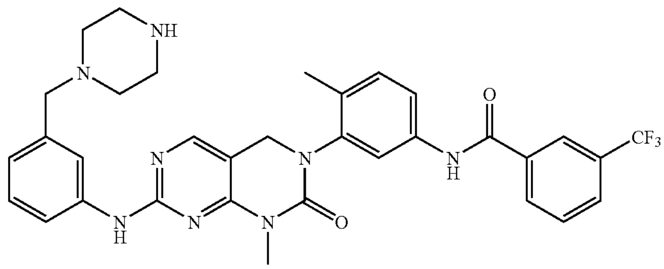 | MS m/z 631.3 (M + 1) |
| 43 | 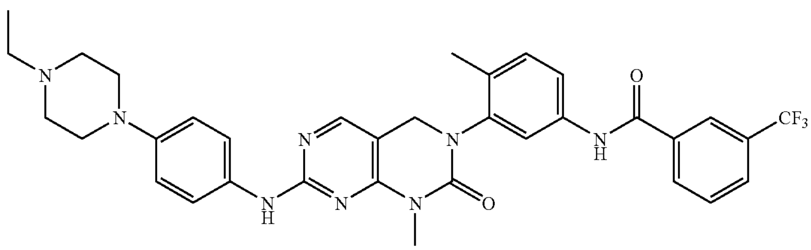 | MS m/z 645.3 (M + 1) |
| 44 | 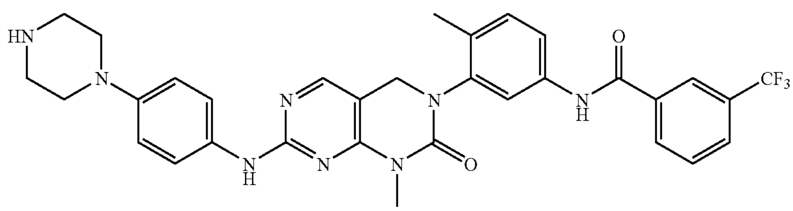 | MS m/z 617.3 (M + 1) |
| 45 | 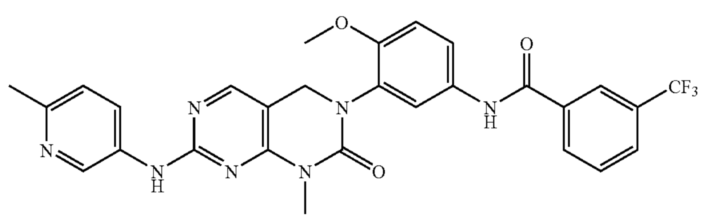 | MS m/z 564.2 (M + 1) |
| 46 | 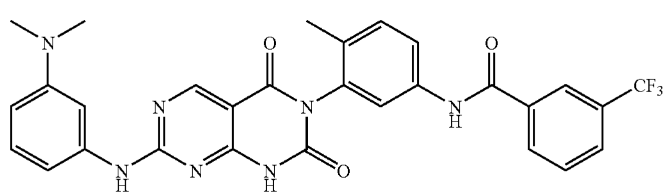 | MS m/z 576.1 (M + 1) |
| 47 | 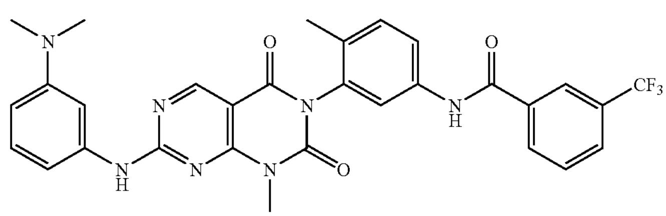 | MS m/z 590.2 (M + 1) |

TABLE 1-continued

| Compound Number | Structure | Physical Data<br>¹H NMR 400 MHz<br>(DMSO-d$_6$) and/or MS (m/z) |
| --- | --- | --- |
| 48 | 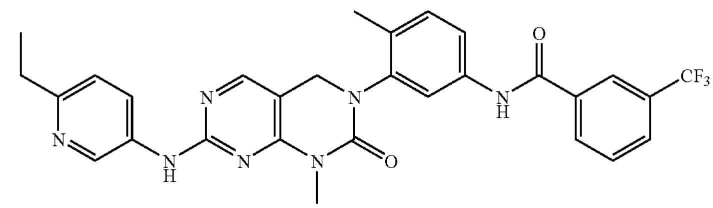 | MS m/z 562.2 (M + 1) |
| 49 | 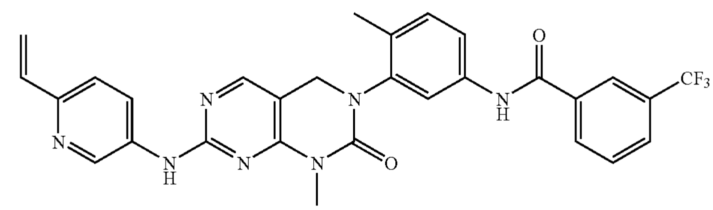 | MS m/z 560.2 (M + 1) |
| 50 | 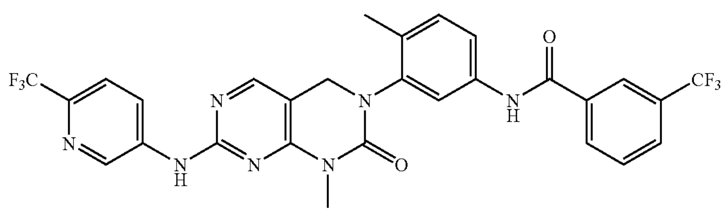 | MS m/z 602.2 (M + 1) |
| 51 | 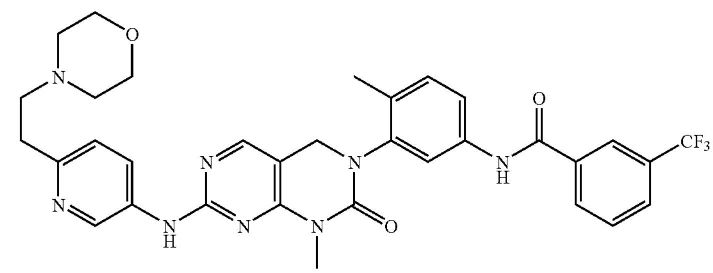 | MS m/z 647.3 (M + 1) |
| 52 | 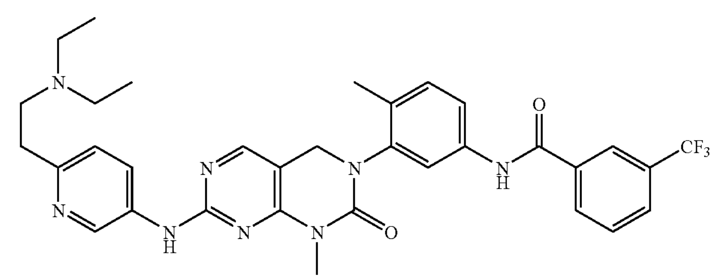 | MS m/z 633.3 (M + 1) |
| 53 | 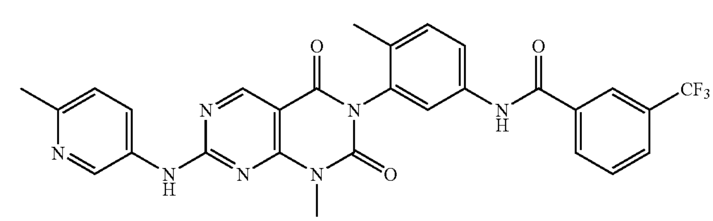 | MS m/z 562.1 (M + 1) |

TABLE 1-continued

| Compound Number | Structure | Physical Data $^1$H NMR 400 MHz (DMSO-$d_6$) and/or MS (m/z) |
|---|---|---|
| 54 | 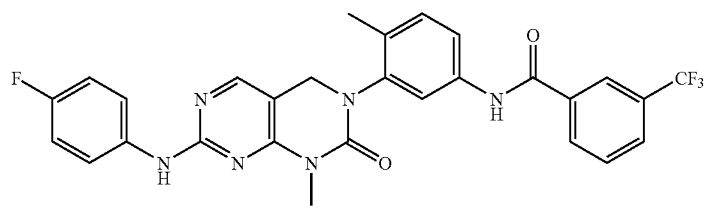 | MS m/z 551.1 (M + 1) |
| 55 | 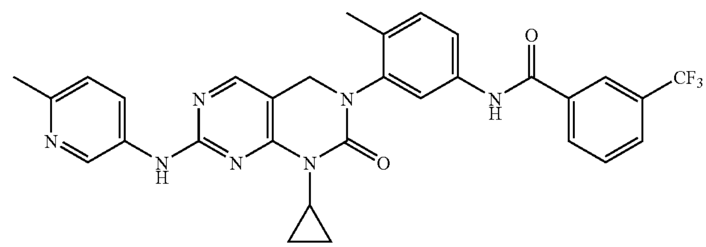 | MS m/z 574.1 (M + 1) |
| 56 | 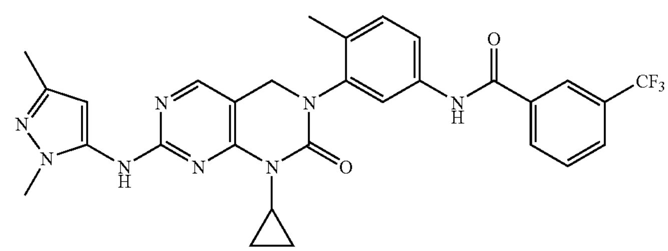 | MS m/z 577.1 (M + 1) |
| 57 | 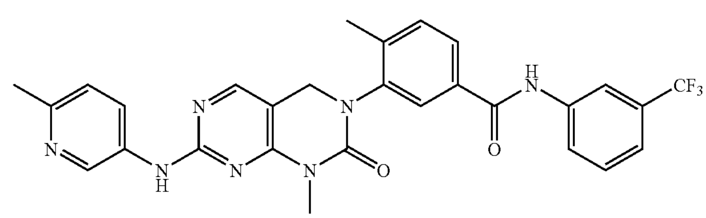 | MS m/z 584.4 (M + 1) |
| 58 | 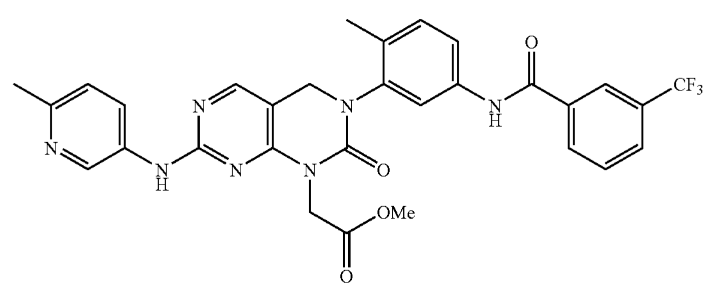 | MS m/z 606.4 (M + 1) |
| 59 | 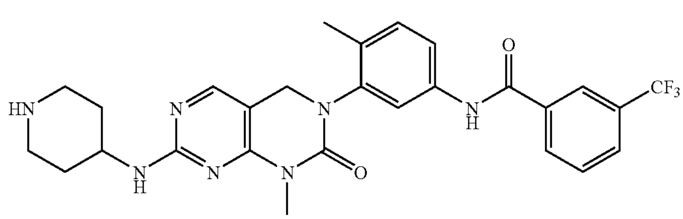 | MS m/z 540.4 (M + 1) |

TABLE 1-continued

| Compound Number | Structure | Physical Data<br>¹H NMR 400 MHz<br>(DMSO-d₆) and/or MS (m/z) |
|---|---|---|
| 60 | 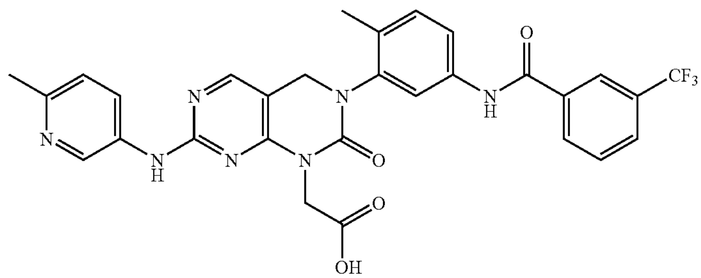 | MS m/z 592.4 (M + 1) |
| 61 | 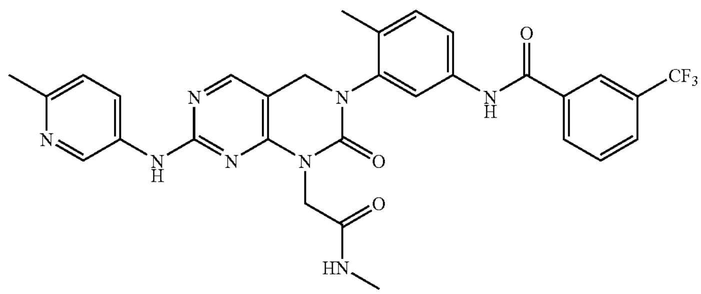 | MS m/z 605.4 (M + 1) |
| 62 | 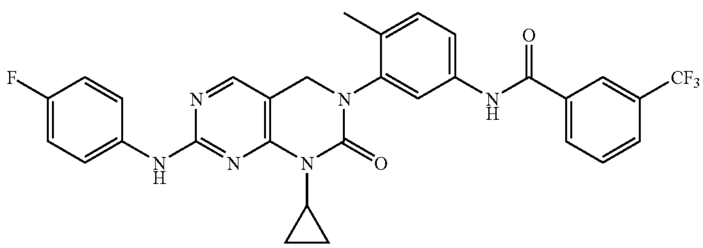 | MS m/z 577.4 (M + 1) |
| 63 | 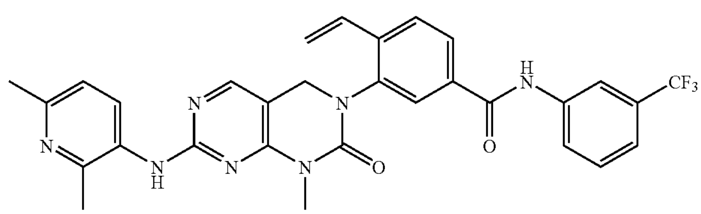 | MS m/z 574.4 (M + 1) |
| 64 | 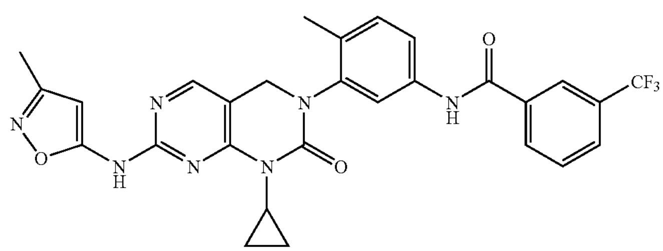 | MS m/z 564.4 (M + 1) |
| 65 | 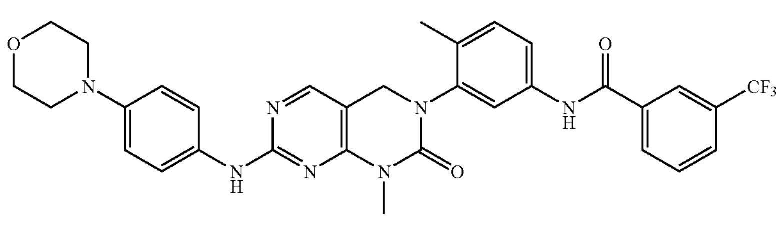 | MS m/z 618.4 (M + 1) |

TABLE 1-continued
| Compound Number | Structure | Physical Data $^1$H NMR 400 MHz (DMSO-$d_6$) and/or MS (m/z) |
|---|---|---|
| 66 | 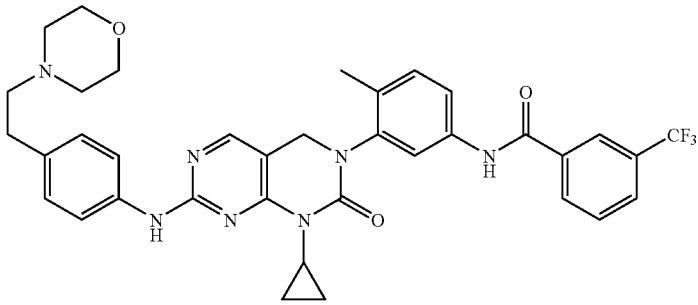 | MS m/z 672.5 (M + 1) |
| 67 | 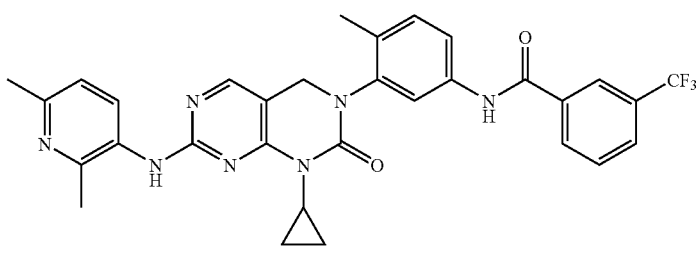 | MS m/z 588.4 (M + 1) |
| 68 | 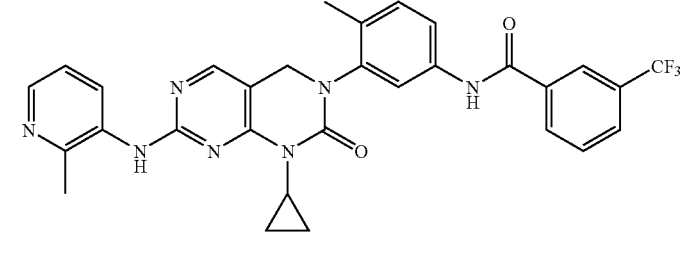 | MS m/z 574.4 (M + 1) |
| 69 | 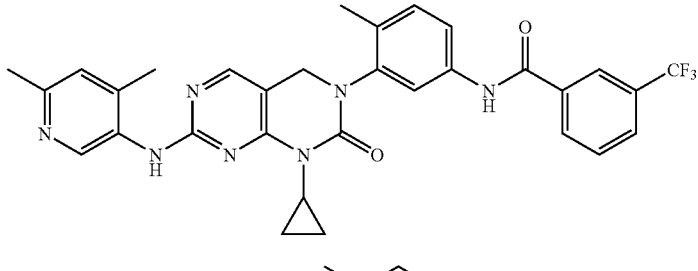 | MS m/z 588.4 (M + 1) |
| 70 | 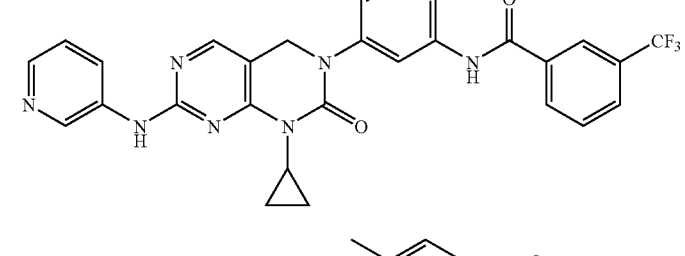 | MS m/z 560.4 (M + 1) |
| 71 | 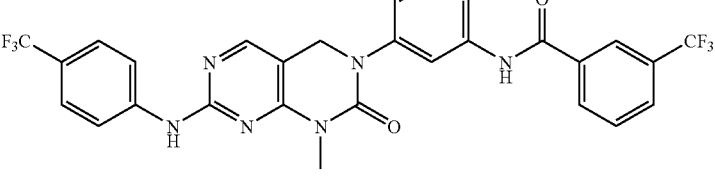 | MS m/z 601.3 (M + 1) |

TABLE 1-continued

| Compound Number | Structure | Physical Data<br>¹H NMR 400 MHz<br>(DMSO-d₆) and/or MS (m/z) |
|---|---|---|
| 72 | 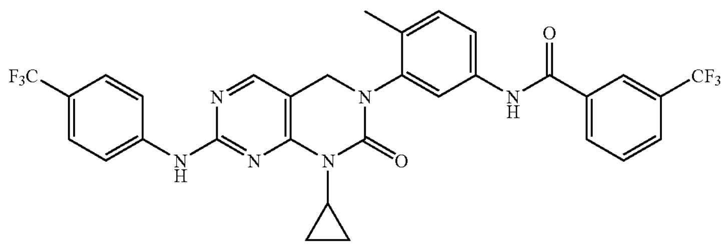 | MS m/z 627.4 (M + 1) |
| 73 | 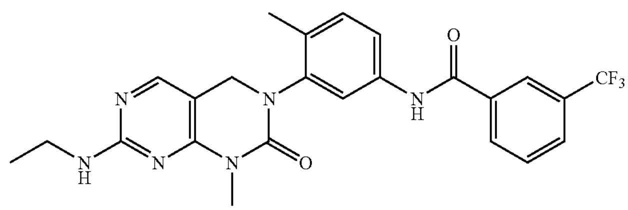 | MS m/z 485.4 (M + 1) |
| 74 | 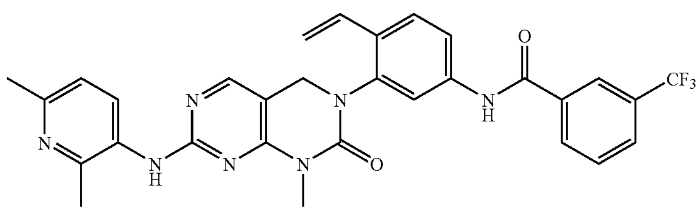 | MS m/z 574.4 (M + 1) |
| 75 | 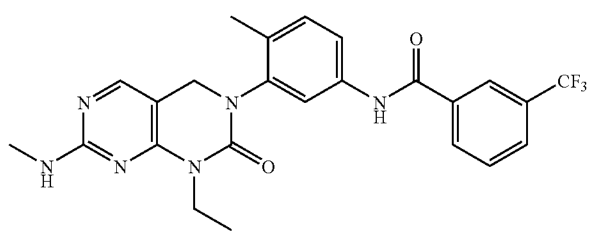 | MS m/z 485.4 (M + 1) |
| 76 | 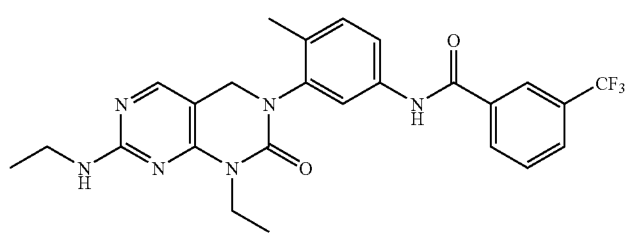 | MS m/z 499.4 (M + 1) |
| 77 | 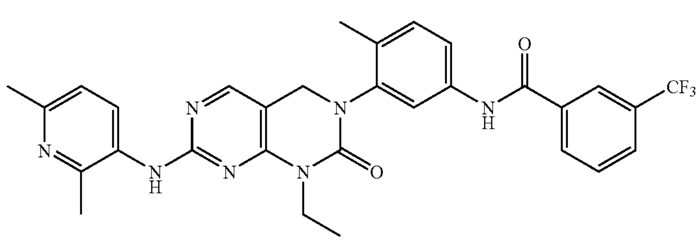 | MS m/z 576.4 (M + 1) |

TABLE 1-continued

| Compound Number | Structure | Physical Data $^1$H NMR 400 MHz (DMSO-$d_6$) and/or MS (m/z) |
|---|---|---|
| 78 | 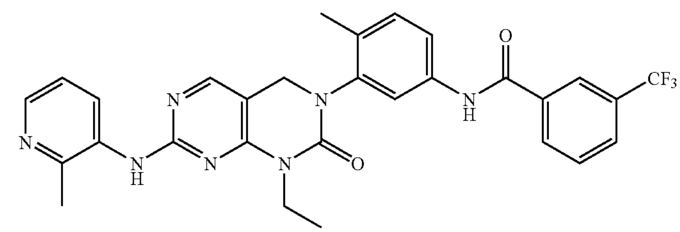 | MS m/z 562.4 (M + 1) |
| 79 | 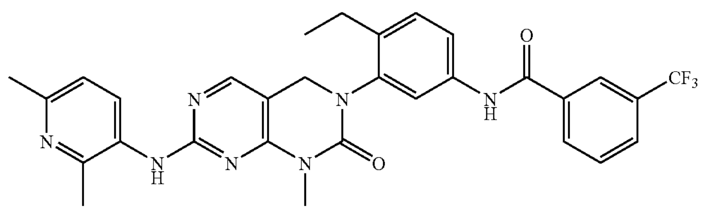 | MS m/z 576.4 (M + 1) |
| 80 | 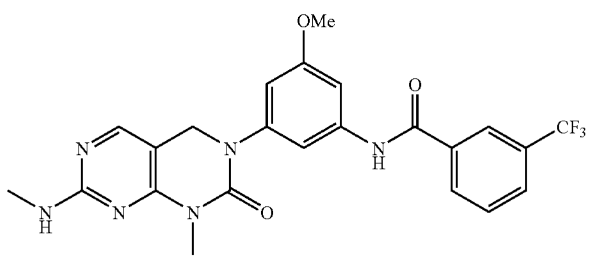 | MS m/z 487.1 (M + 1) |
| 81 | 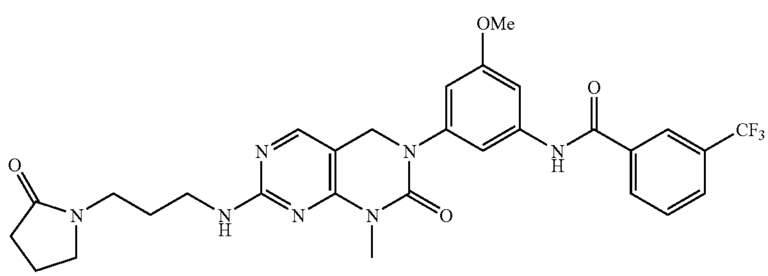 | MS m/z 598.2 (M + 1) |
| 82 | 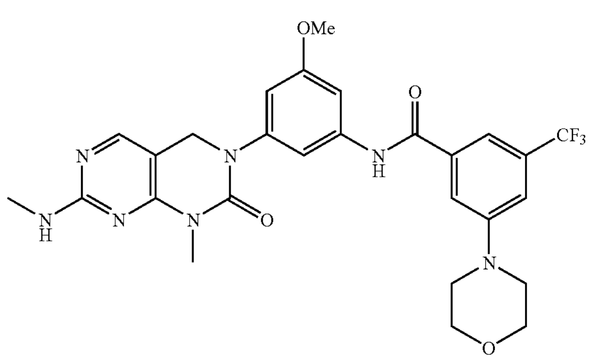 | MS m/z 572.4 (M + 1) |

TABLE 1-continued

| Compound Number | Structure | Physical Data<br>¹H NMR 400 MHz<br>(DMSO-d₆) and/or MS (m/z) |
|---|---|---|
| 83 | 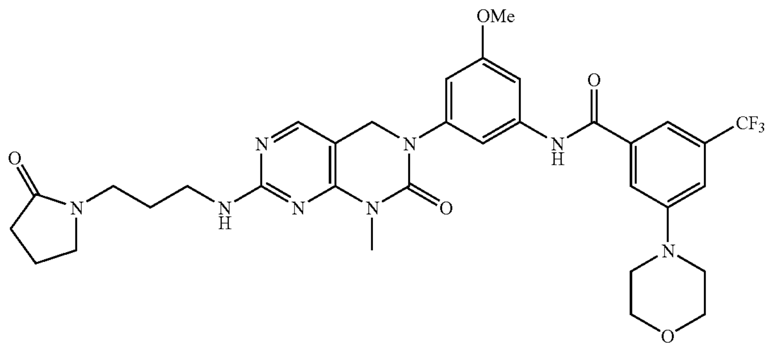 | MS m/z 683.5 (M + 1) |
| 84 | 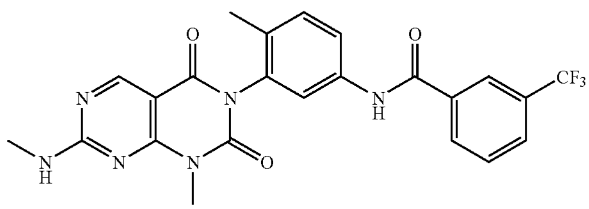 | MS m/z 485.3 (M + 1) |
| 85 | 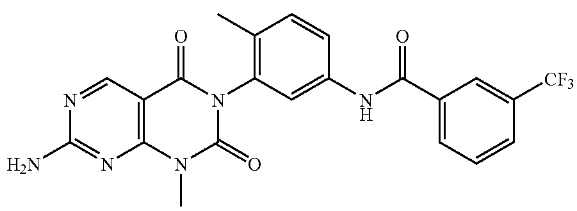 | MS m/z 471.3 (M + 1) |
| 86 | 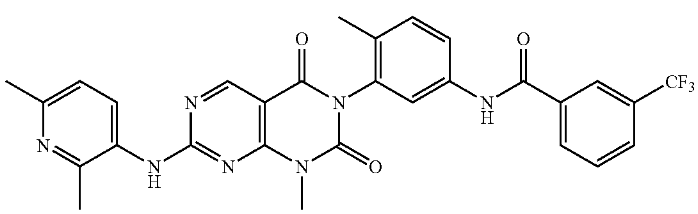 | MS m/z 576.4 (M + 1) |
| 87 | 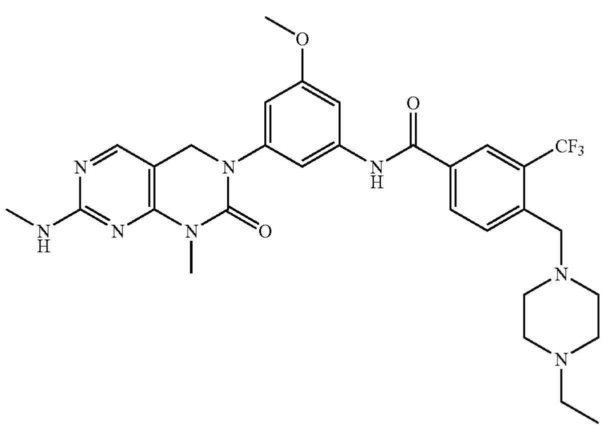 | MS m/z 613.5 (M + 1) |

TABLE 1-continued

| Compound Number | Structure | Physical Data<br>$^1$H NMR 400 MHz<br>(DMSO-$d_6$) and/or MS (m/z) |
|---|---|---|
| 88 | 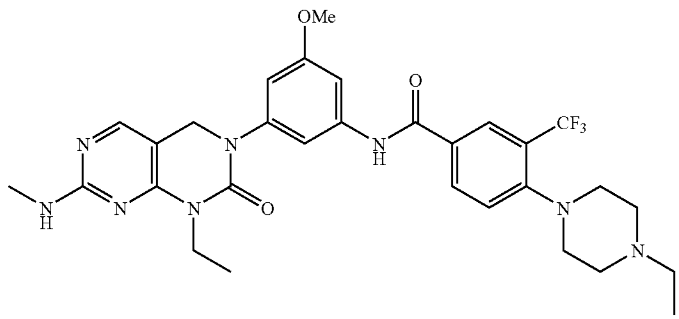 | MS m/z 613.3 (M + 1) |
| 89 | 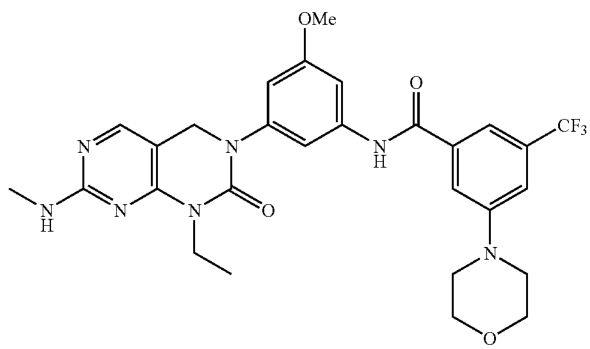 | MS m/z 586.1 (M + 1) |
| 90 | 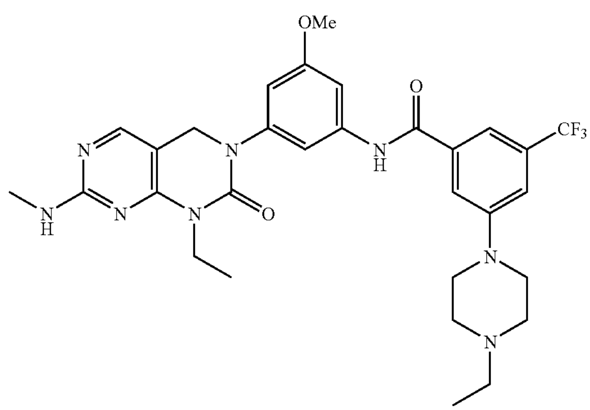 | MS m/z 613.2 (M + 1) |
| 91 | 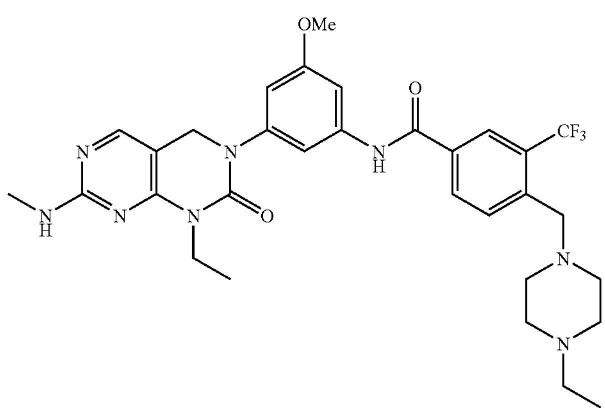 | MS m/z 627.4 (M + 1) |

TABLE 1-continued

| Compound Number | Structure | Physical Data<br>$^1$H NMR 400 MHz<br>(DMSO-$d_6$) and/or MS (m/z) |
|---|---|---|
| 92 | 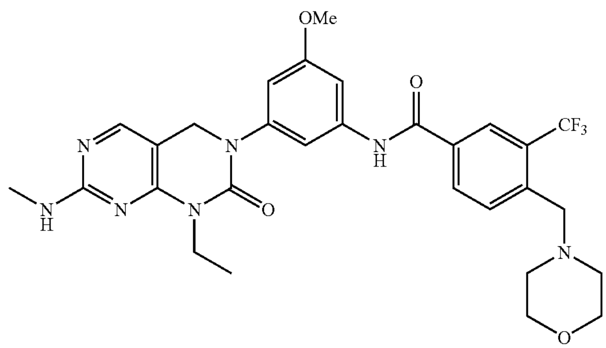 | MS m/z 600.3 (M + 1) |
| 93 | 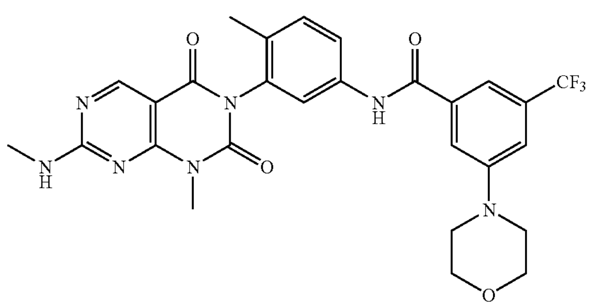 | MS m/z 570.2 (M + 1) |
| 94 | 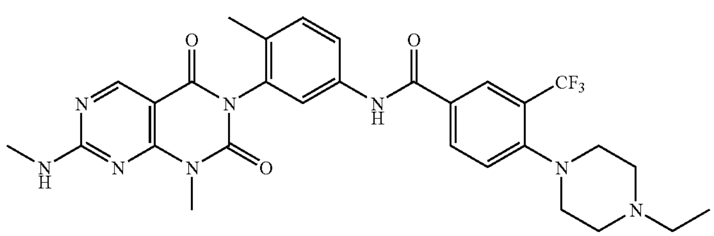 | MS m/z 597.2 (M + 1) |
| 95 | 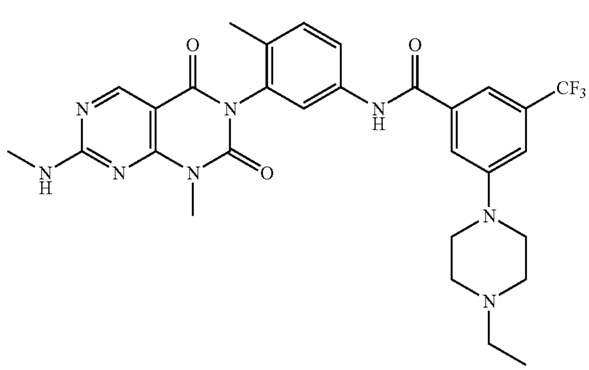 | MS m/z 597.2 (M + 1) |

TABLE 1-continued
| Compound Number | Structure | Physical Data $^1$H NMR 400 MHz (DMSO-$d_6$) and/or MS (m/z) |
|---|---|---|
| 96 | 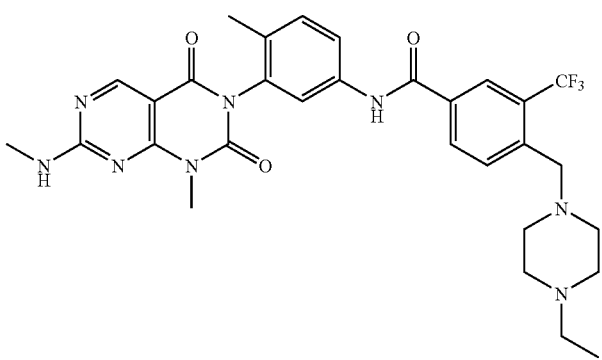 | MS m/z 611.4 (M + 1) |
| 97 | 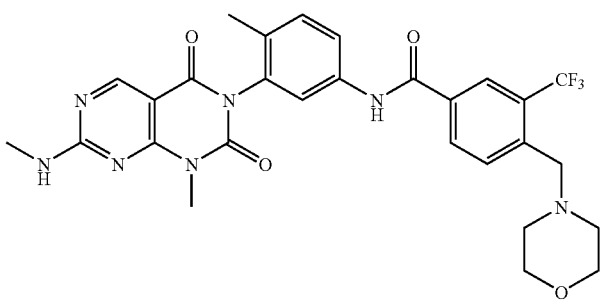 | MS m/z 584.3 (M + 1) |
| 98 | 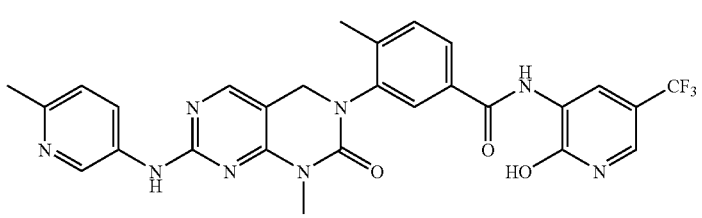 | MS m/z 565.3 (M + 1) |
| 99 | 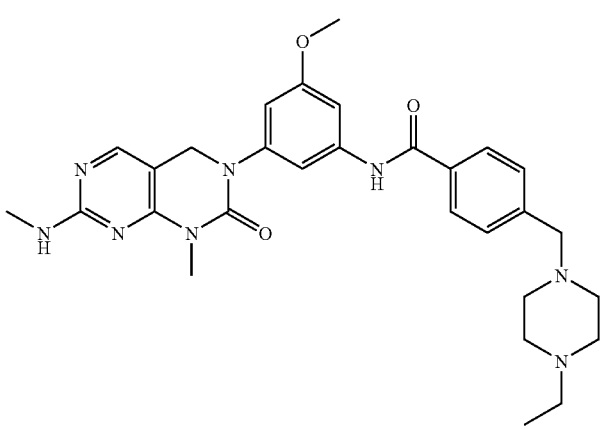 | MS m/z 559.6 (M + 1) |

TABLE 1-continued
| Compound Number | Structure | Physical Data<br>¹H NMR 400 MHz<br>(DMSO-d₆) and/or MS (m/z) |
|---|---|---|
| 100 | 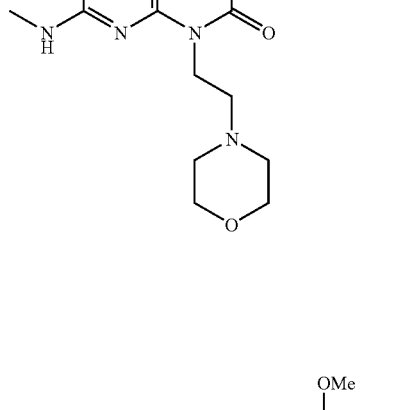 | MS m/z 586.5 (M + 1) |
| 101 | 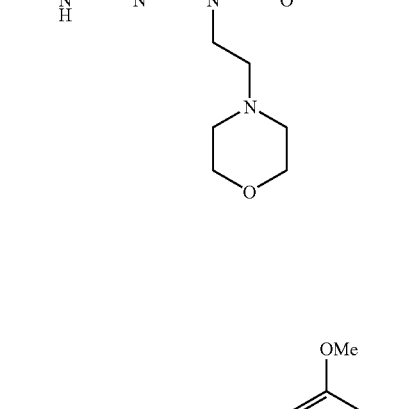 | MS m/z 600.5 (M + 1) |
| 102 | 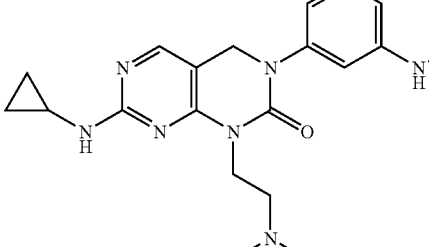 | MS m/z 612.5 (M + 1) |

TABLE 1-continued

| Compound Number | Structure | Physical Data<br>¹H NMR 400 MHz<br>(DMSO-$d_6$) and/or MS (m/z) |
|---|---|---|
| 103 | 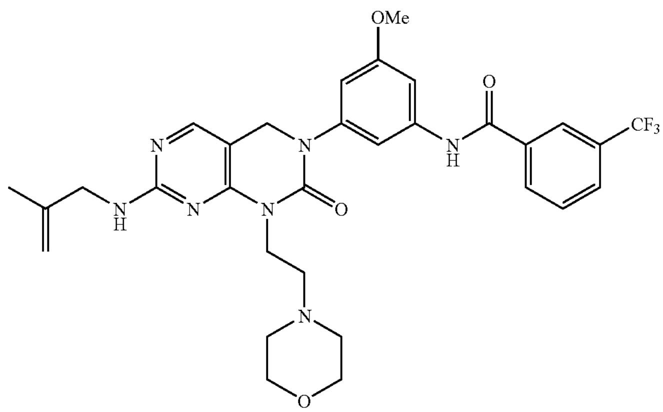 | MS m/z 626.5 (M + 1) |
| 104 | 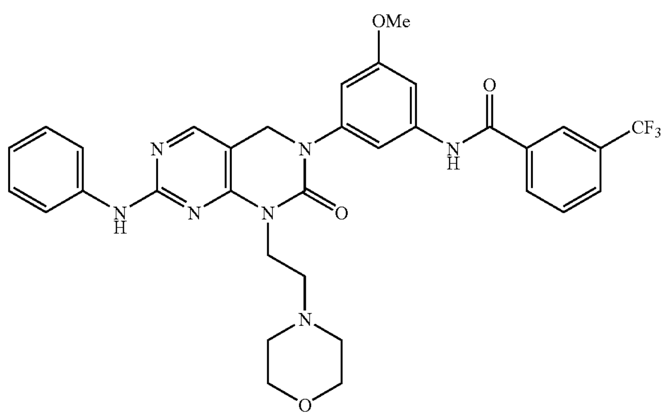 | MS m/z 648.5 (M + 1) |
| 105 | 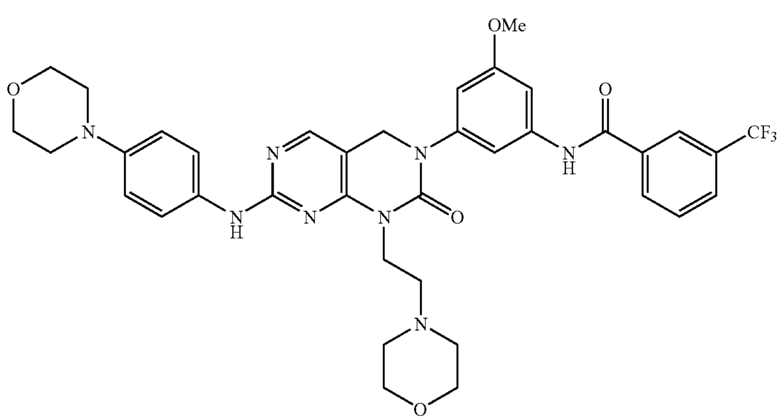 | MS m/z 733.5 (M + 1) |

TABLE 1-continued
| Compound Number | Structure | Physical Data<br>$^1$H NMR 400 MHz<br>(DMSO-$d_6$) and/or MS (m/z) |
|---|---|---|
| 106 | 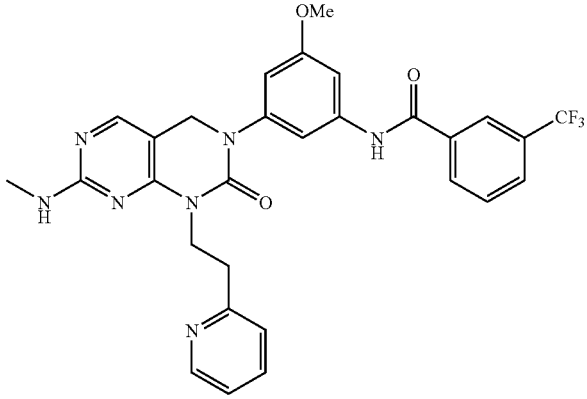 | MS m/z 578.4 (M + 1) |
| 107 | 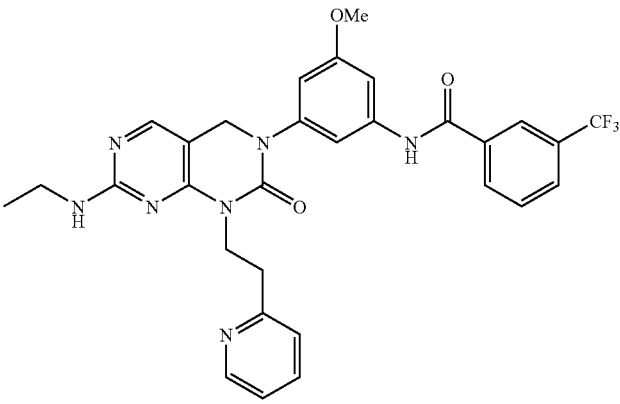 | MS m/z 592.5 (M + 1) |
| 108 | 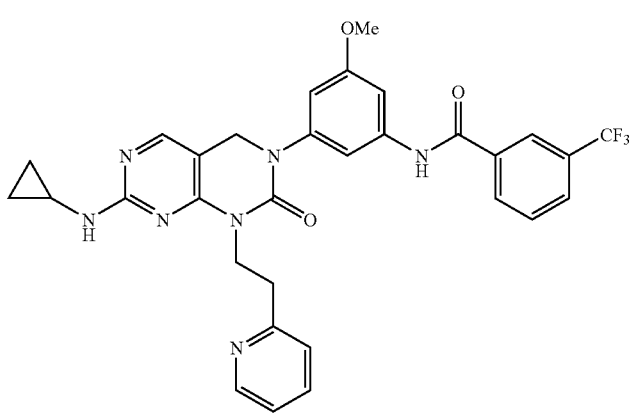 | MS m/z 604.5 (M + 1) |

TABLE 1-continued

| Compound Number | Structure | Physical Data <br> $^1$H NMR 400 MHz (DMSO-$d_6$) and/or MS (m/z) |
|---|---|---|
| 109 | 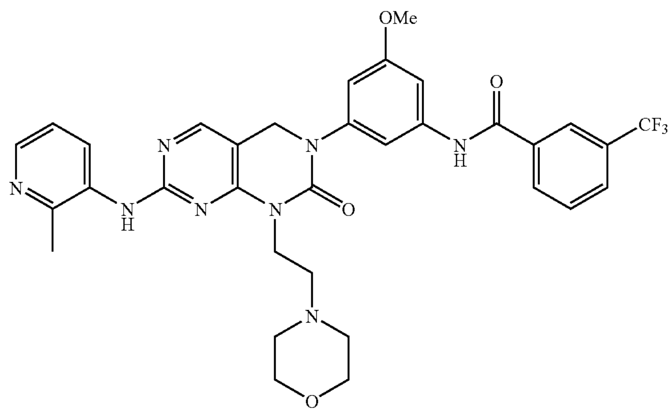 | MS m/z 663.5 (M + 1) |
| 110 | 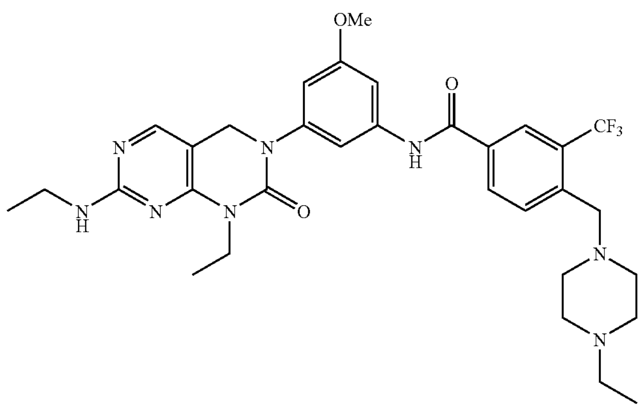 | MS m/z 641.5 (M + 1) |
| 111 | 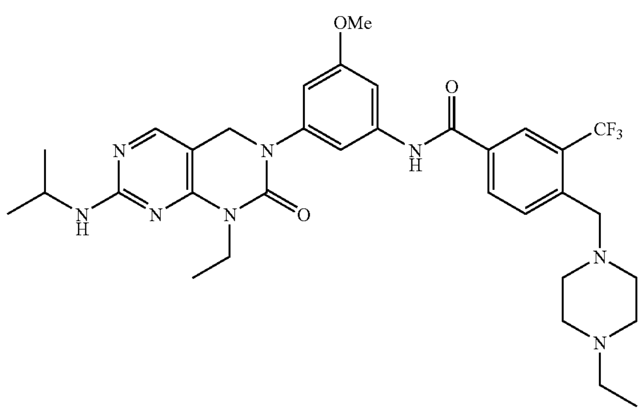 | MS m/z 655.5 (M + 1) |
| 112 | 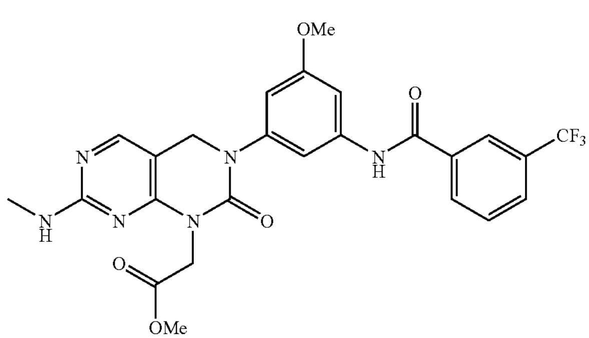 | MS m/z 545.4 (M + 1) |

TABLE 1-continued

| Compound Number | Structure | Physical Data $^1$H NMR 400 MHz (DMSO-$d_6$) and/or MS (m/z) |
|---|---|---|
| 113 | 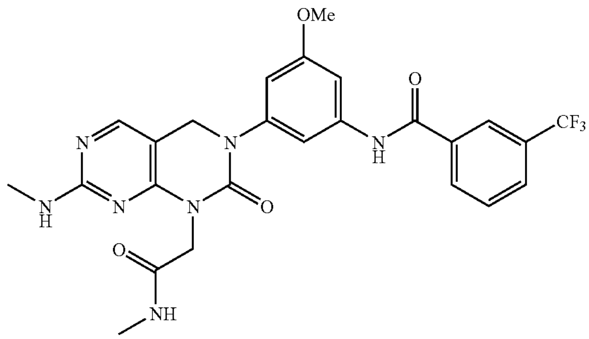 | MS m/z 544.4 (M + 1) |
| 114 | 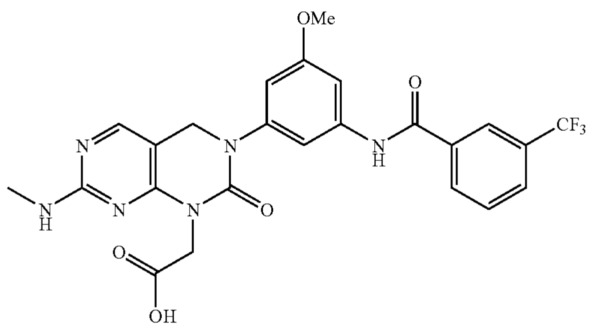 | MS m/z 531.4 (M + 1) |
| 115 | 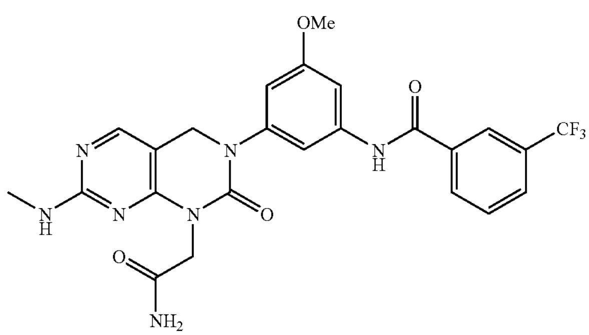 | MS m/z 530.4 (M + 1) |
| 116 | 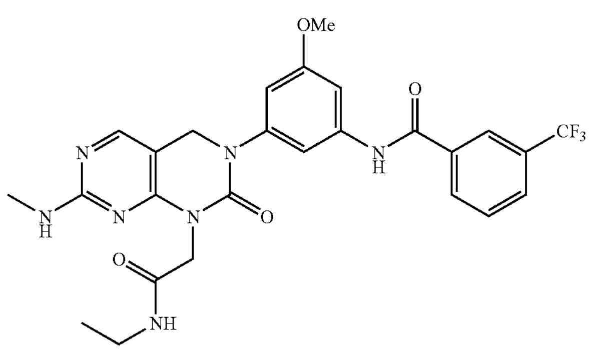 | MS m/z 558.4 (M + 1) |

TABLE 1-continued
| Compound Number | Structure | Physical Data $^1$H NMR 400 MHz (DMSO-$d_6$) and/or MS (m/z) |
|---|---|---|
| 117 | 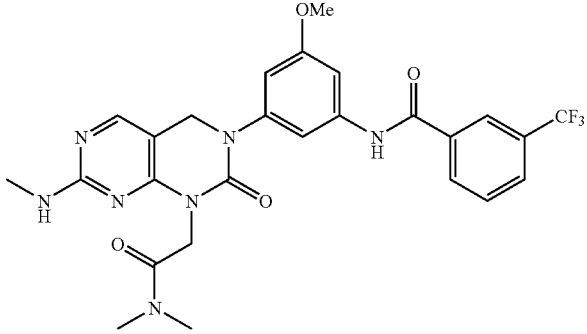 | MS m/z 558.4 (M + 1) |
| 118 | 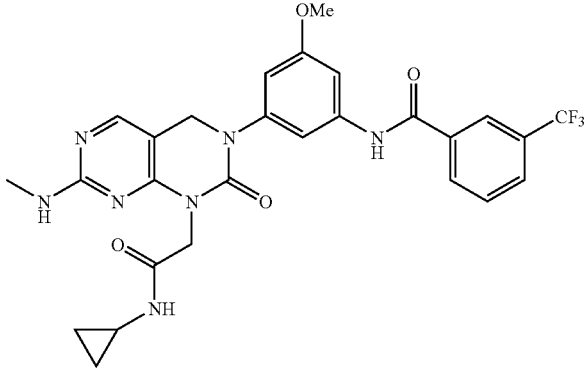 | MS m/z 570.4 (M + 1) |
| 119 | 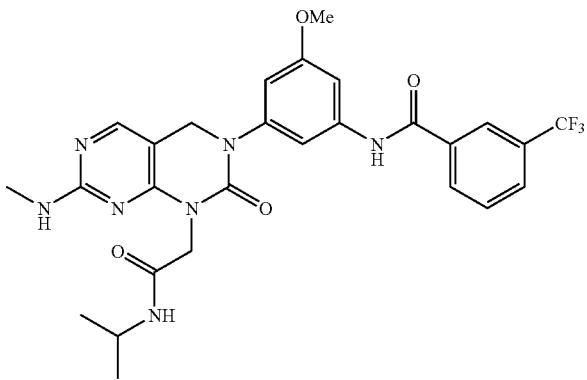 | MS m/z 572.5 (M + 1) |
| 120 | 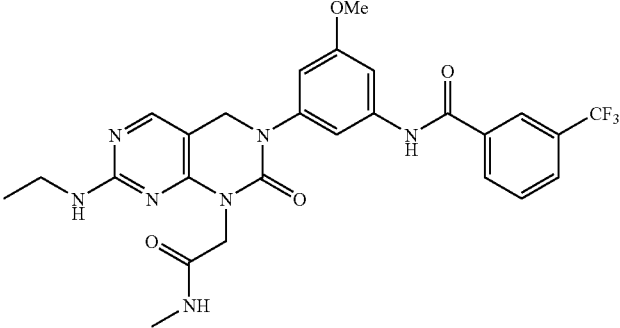 | MS m/z 558.4 (M + 1) |

TABLE 1-continued
| Compound Number | Structure | Physical Data<br>$^1$H NMR 400 MHz<br>(DMSO-$d_6$) and/or MS (m/z) |
|---|---|---|
| 121 | 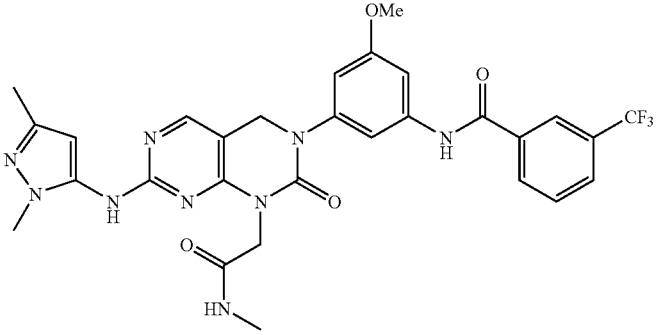 | MS m/z 624.5 (M + 1) |
| 122 | 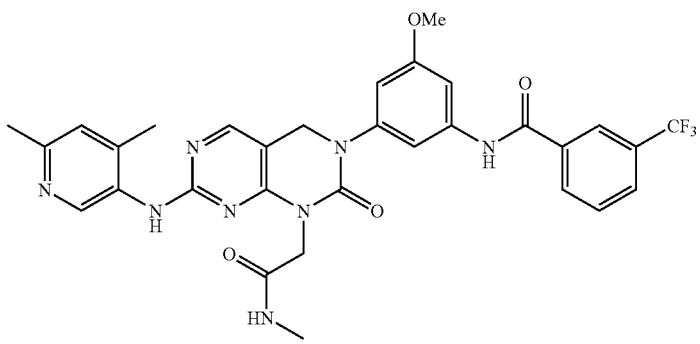 | MS m/z 635.5 (M + 1) |
| 123 | 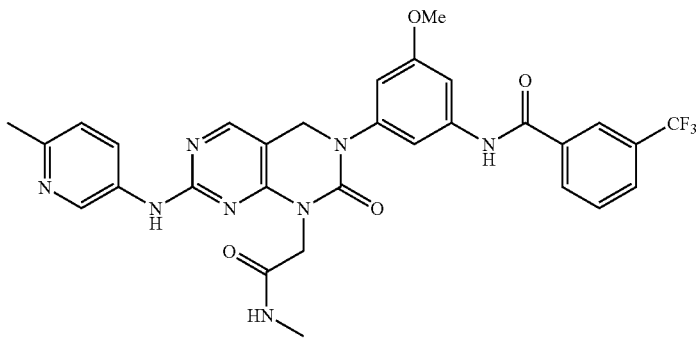 | MS m/z 621.5 (M + 1) |
| 124 | 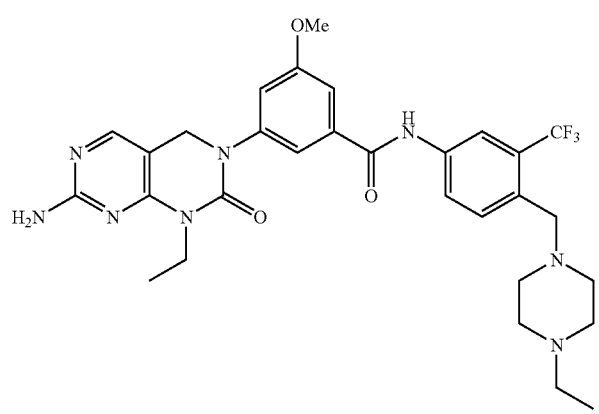 | MS m/z 613.5 (M + 1) |

TABLE 1-continued

| Compound Number | Structure | Physical Data $^1$H NMR 400 MHz (DMSO-$d_6$) and/or MS (m/z) |
|---|---|---|
| 125 | 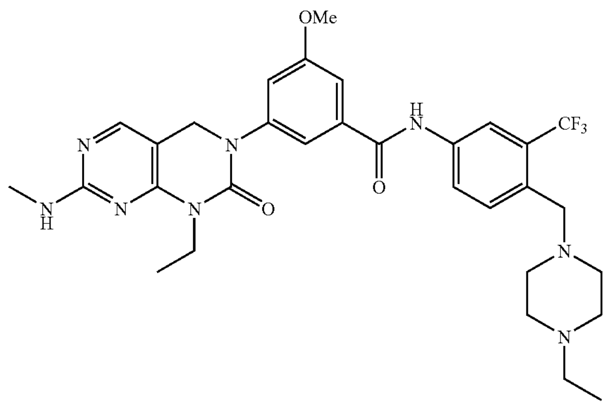 | MS m/z 627.5 (M + 1) |
| 126 | 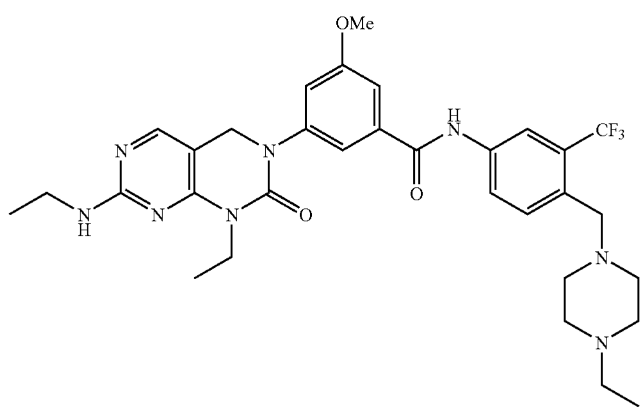 | MS m/z 641.5 (M + 1) |
| 127 | 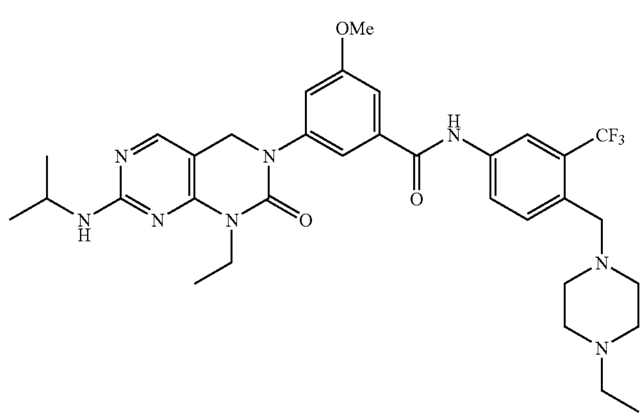 | MS m/z 655.5 (M + 1) |

TABLE 1-continued

| Compound Number | Structure | Physical Data $^1$H NMR 400 MHz (DMSO-$d_6$) and/or MS (m/z) |
|---|---|---|
| 128 | 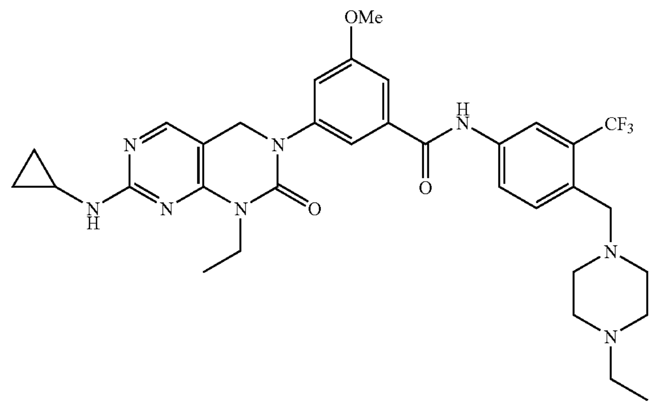 | MS m/z 653.5 (M + 1) |
| 129 | 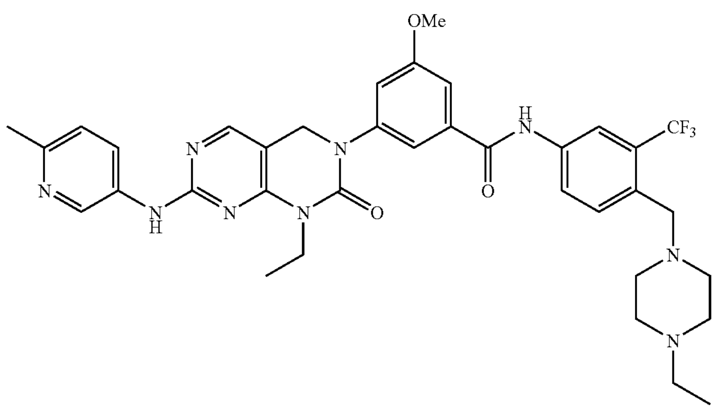 | MS m/z 704.5 (M + 1) |
| 130 | 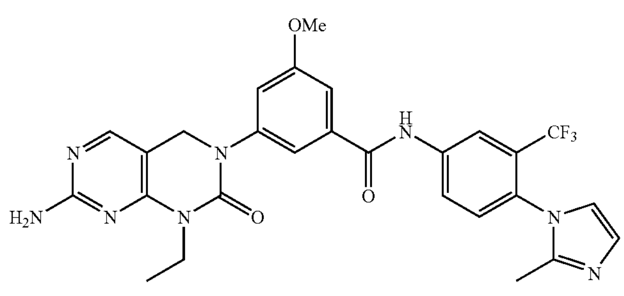 | MS m/z 567.5 (M + 1) |
| 131 | 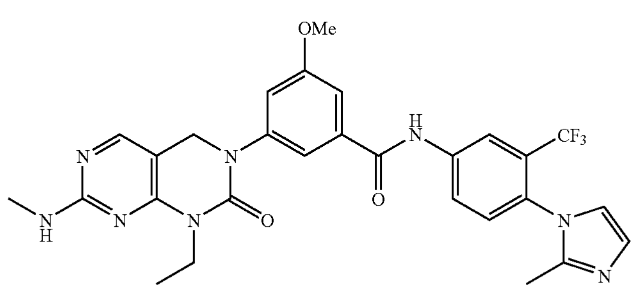 | MS m/z 581.5 (M + 1) |

TABLE 1-continued

| Compound Number | Structure | Physical Data $^1$H NMR 400 MHz (DMSO-$d_6$) and/or MS (m/z) |
|---|---|---|
| 132 | 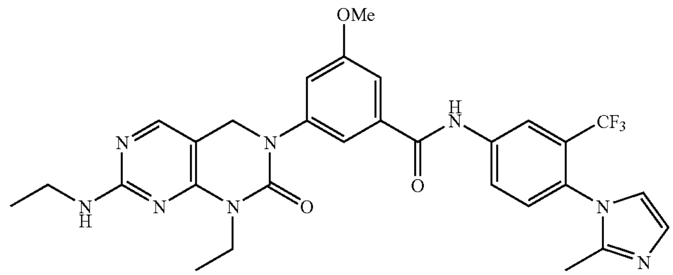 | MS m/z 595.5 (M + 1) |
| 133 | 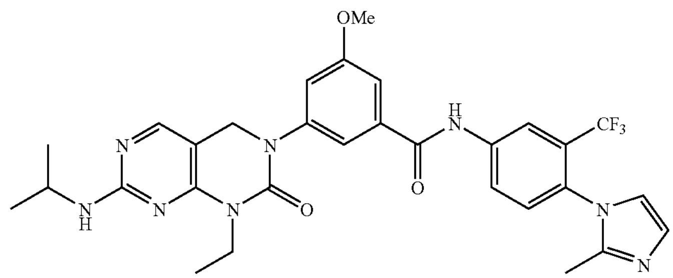 | MS m/z 609.5 (M + 1) |
| 134 | 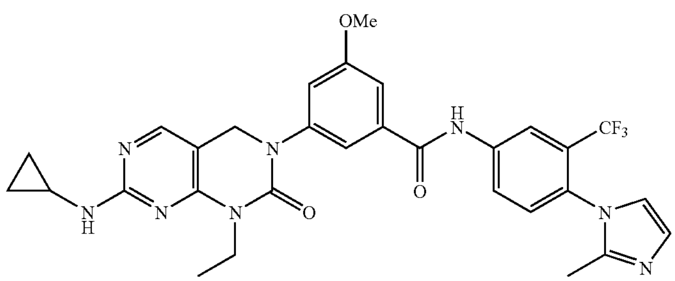 | MS m/z 607.5 (M + 1) |
| 135 | 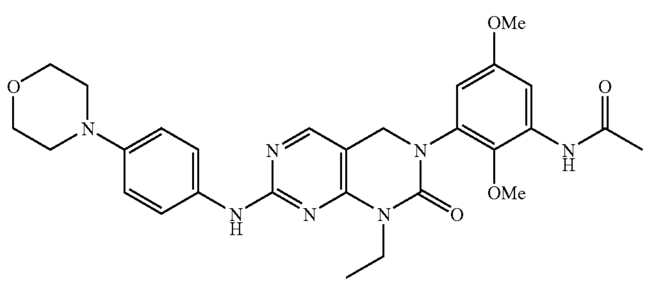 | MS m/z 548.5 (M + 1) |
| 136 | 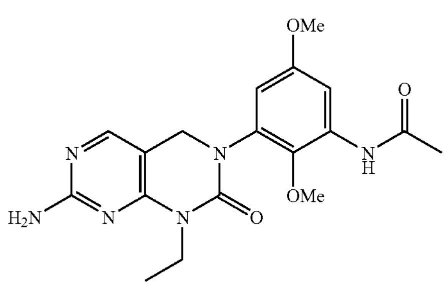 | MS m/z 387.4 (M + 1) |

TABLE 1-continued

| Compound Number | Structure | Physical Data ¹H NMR 400 MHz (DMSO-d$_6$) and/or MS (m/z) |
|---|---|---|
| 137 | 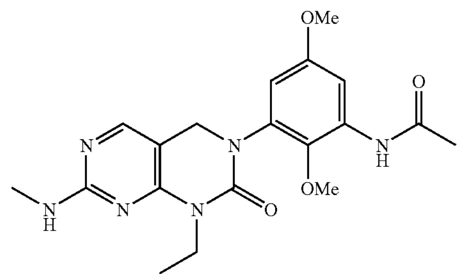 | MS m/z 401.4 (M + 1) |
| 138 | 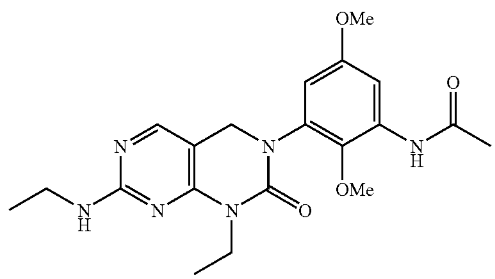 | MS m/z 415.5 (M + 1) |
| 139 | 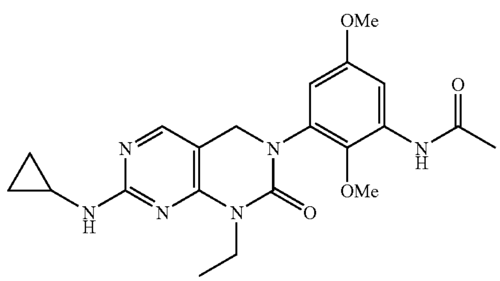 | MS m/z 427.4 (M + 1) |
| 140 | 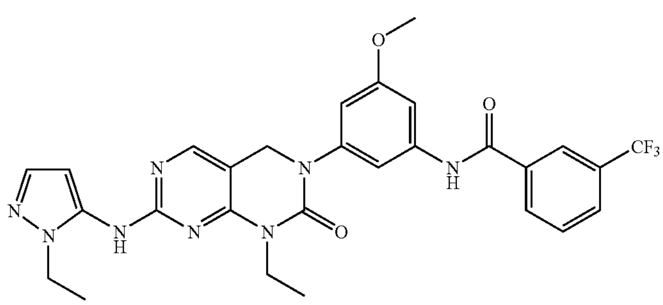 | ¹H NMR 400 MHz (DMSO-d$_6$) δ 10.47 (s, 1H), 9.33 (s, 1H), 8.23 (s, 1H), 8.20 (m, 1H), 8.05 (s, 1H), 7.92 (d, 1H), 7.73 (t, 1H), 7.36–7.33 (m, 3H), 6.70 (s, 1H), 6.16 (d, 1H), 4.65 (s, 2H), 3.98 (q, 2H), 3.88 (q, 2H), 3.72 (s, 3H), 1.22 (t, 3H), 1.10 (t, 3H); MS m/z 581.5 (M + 1). |
| 141 | 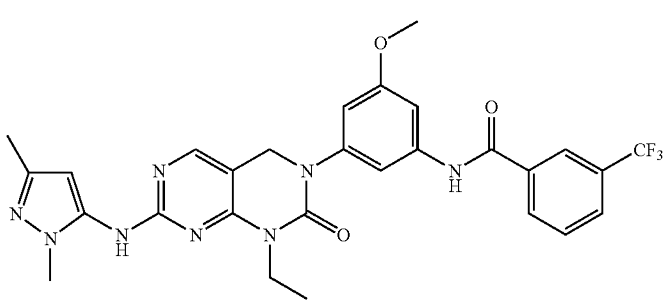 | ¹H NMR 400 MHz (DMSO-d$_6$) δ 9.34 (s, 1H), 9.03 (s, 1H), 8.23 (s, 1H), 8.19 (d, 1H), 8.14 (s, 1H), 7.92 (d, 1H), 7.74 (d, 1H), 7.71 (s, 1H), 7.40 (t, 1H), 7.30 (t, 1H), 6.71 (t, 1H), 4.69 (s, 2H), 3.89 (q, 2H), 3.72 (s, 3H), 2.56 (s, 3H), 2.45 (s, 3H), 1.13 (t, 3H); MS m/z 581.5 (M + 1). |

TABLE 1-continued

| Compound Number | Structure | Physical Data<br>¹H NMR 400 MHz<br>(DMSO-d₆) and/or MS (m/z) |
|---|---|---|
| 142 | 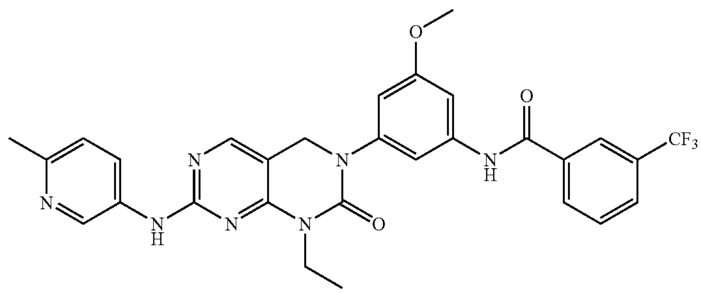 | ¹H NMR 400 MHz (DMSO-d₆) δ 10.45 (s, 1H), 10.30 (s, 1H), 9.14 (s, 1H), 8.39 (d, 1H), 8.23–8.19 (m, 3H), 7.92 (d, 1H), 7.73 (t, 2H), 7.41 (d, 1H), 7.32 (s, 1H), 6.73 (s, 1H), 4.72 (s, 2H), 3.99 (q, 2H), 3.73 (s, 3H), 2.56 (s, 3H), 1.20 (t, 3H); MS m/z 578.2 (M + 1). |
| 143 | 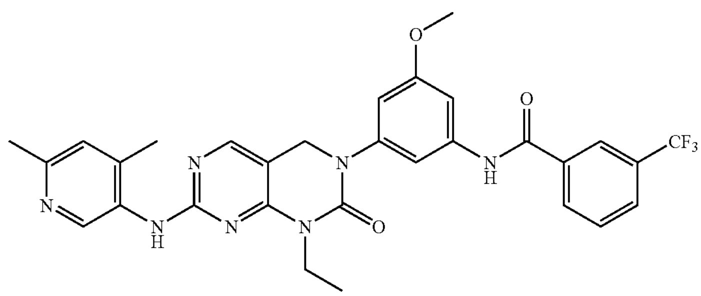 | ¹H NMR 400 MHz (DMSO-d₆) δ 10.48 (s, 1H), 9.43 (s, 1H), 8.23 (s, 1H), 8.19 (d, 1H), 8.07 (s, 1H), 7.92 (d, 1H), 7.73 (t, 1H), 7.36 (s, 1H), 7.33 (s, 1H), 6.71 (t, 1H), 6.04 (s, 1H), 5.30 (br, 1H), 4.65 (s, 2H), 3.90 (q, 2H), 3.72 (s, 3H), 3.57 (s, 3H), 2.07 (s, 3H), 1.13 (t, 3H); MS m/z 592.2 (M + 1). |
| 144 | 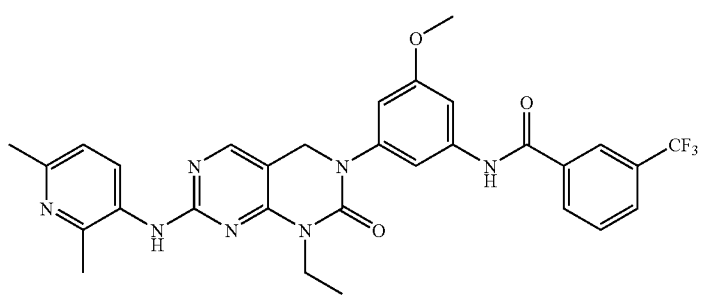 | ¹H NMR 400 MHz (DMSO-d₆) δ 10.49 (s, 1H), 9.47 (s, 1H), 8.56 (d, 1H), 8.23 (s, 1H), 8.19 (d, 1H), 8.11 (s, 1H), 7.92 (d, 1H), 7.73 (t, 1H), 7.63 (d, 1H), 7.39 (s, 1H), 7.30 (s, 1H), 6.71 (t, 1H), 4.68 (s, 2H), 3.87 (q, 2H), 3.72 (s, 3H), 2.59 (s, 6H), 1.10 (t, 3H); MS m/z 592.5 (M + 1). |
| 145 | 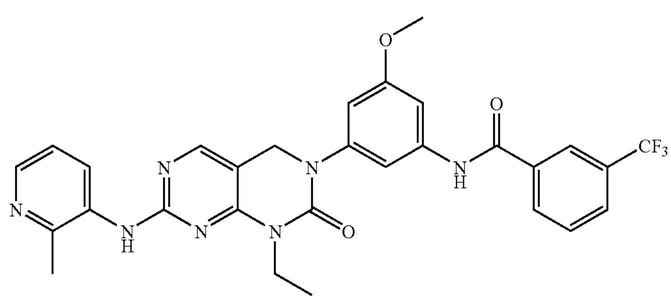 | ¹H NMR 400 MHz (DMSO-d₆) δ 10.58 (s, 1H), 9.56 (s, 1H), 8.74 (d, 1H), 8.51 (d, 1H), 8.33 (s, 1H), 8.29 (d, 1H), 8.23 (s, 1H), 8.02 (d, 1H), 7.85–7.80 (m, 2H), 7.49 (s, 1H), 7.41 (s, 1H), 6.81 (s, 1H), 4.78 (s, 2H), 3.99 (q, 2H), 3.83 (s, 3H), 2.71 (s, 3H), 1.22 (t, 3H); MS m/z 578.2 (M + 1). |
| 146 | 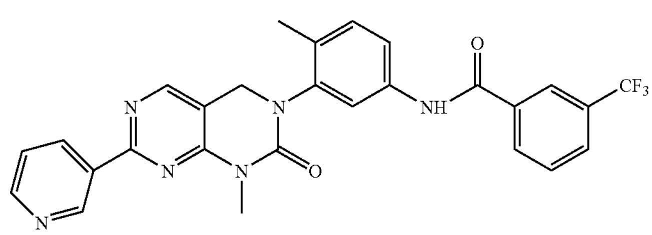 | MS m/z 519.1 (M + 1). |

TABLE 1-continued

| Compound Number | Structure | Physical Data $^1$H NMR 400 MHz (DMSO-$d_6$) and/or MS (m/z) |
|---|---|---|
| 147 | 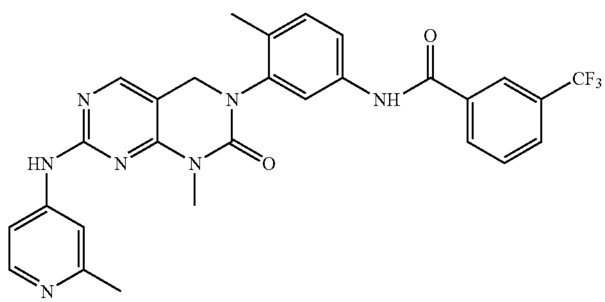 | MS m/z 548.2 (M + 1). |
| 148 | 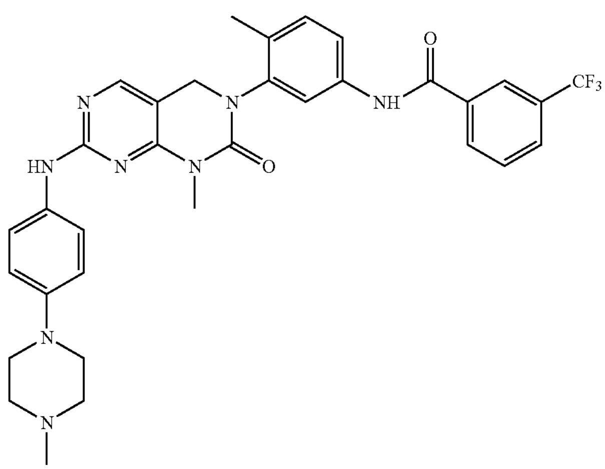 | MS m/z 631.3 (M + 1). |
| 149 | 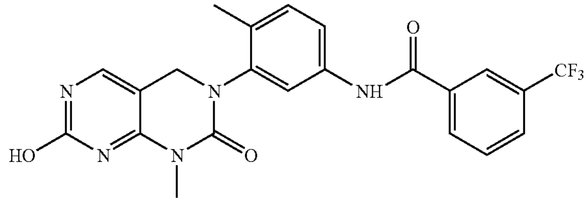 | MS m/z 458.1 (M + 1). |
| 150 | 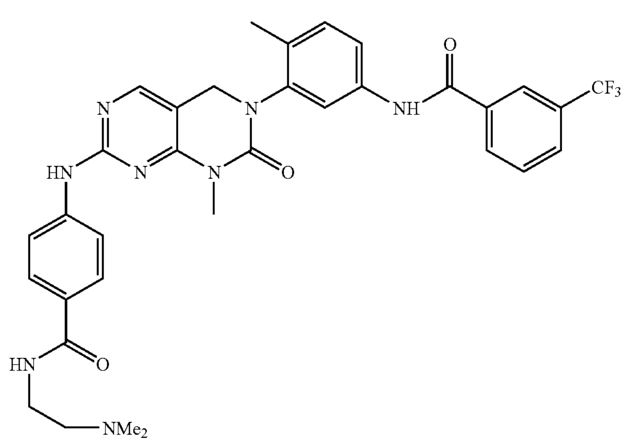 | MS m/z 647.3 (M + 1). |

TABLE 1-continued

| Compound Number | Structure | Physical Data<br>¹H NMR 400 MHz<br>(DMSO-d₆) and/or MS (m/z) |
|---|---|---|
| 151 | 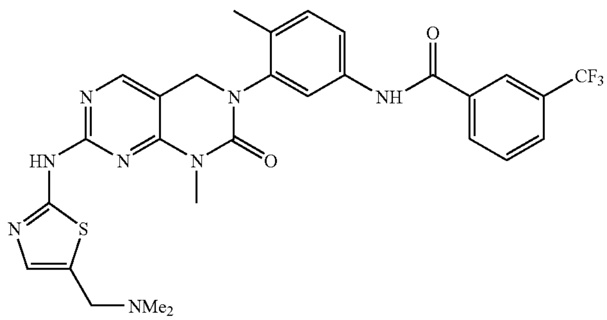 | MS m/z 597.2 (M + 1). |
| 152 | 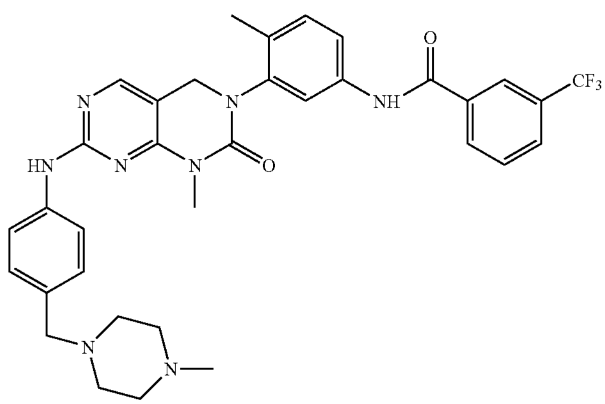 | MS m/z 645.2 (M + 1). |
| 153 | 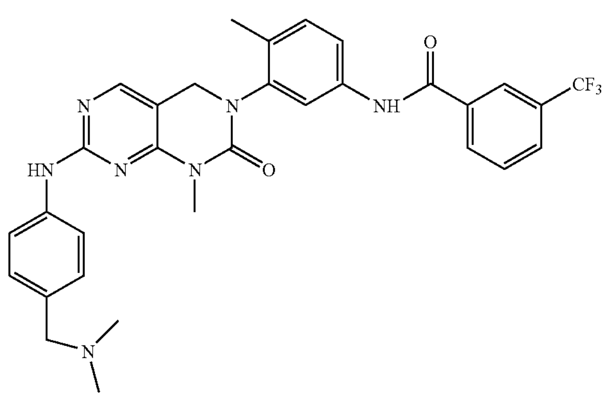 | MS m/z 590.3 (M + 1). |
| 154 | 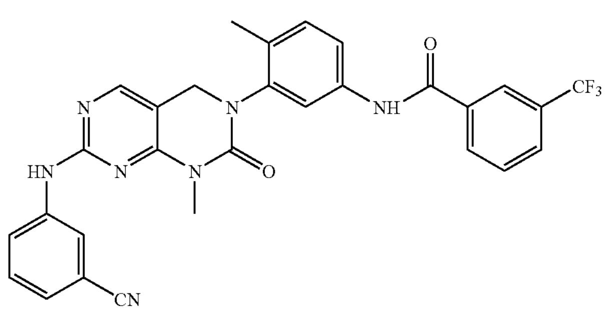 | MS m/z 558.1 (M + 1). |

TABLE 1-continued

| Compound Number | Structure | Physical Data $^1$H NMR 400 MHz (DMSO-$d_6$) and/or MS (m/z) |
|---|---|---|
| 155 | 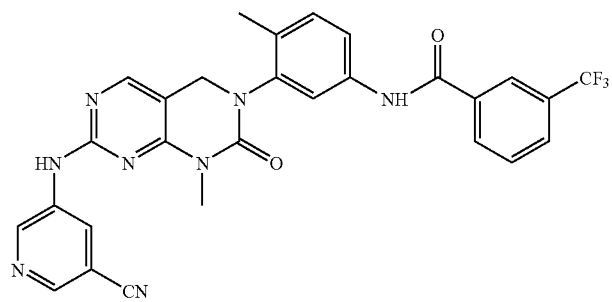 | MS m/z 559.1 (M + 1). |
| 156 | 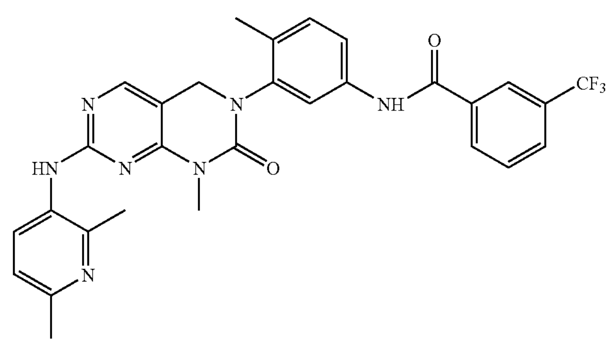 | MS m/z 562.2 (M + 1). |
| 157 | 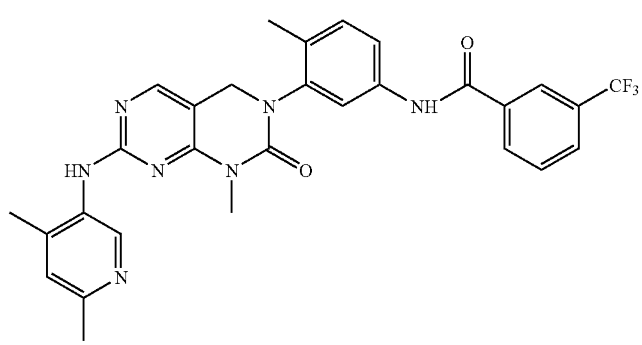 | MS m/z 562.2 (M + 1). |
| 158 | 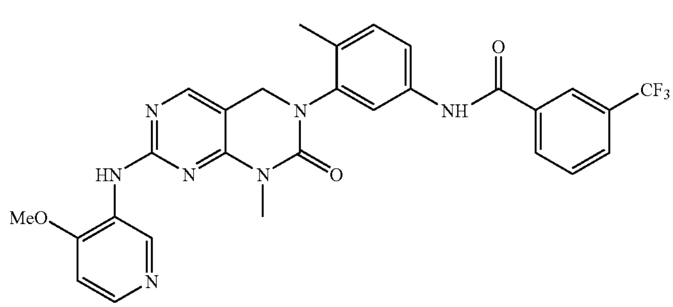 | MS m/z 564.1 (M + 1). |

TABLE 1-continued
| Compound Number | Structure | Physical Data<br>¹H NMR 400 MHz<br>(DMSO-d$_6$) and/or MS (m/z) |
| --- | --- | --- |
| 159 | 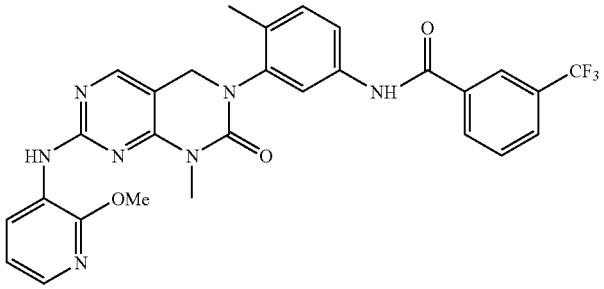 | MS m/z 564.1 (M + 1). |
| 160 | 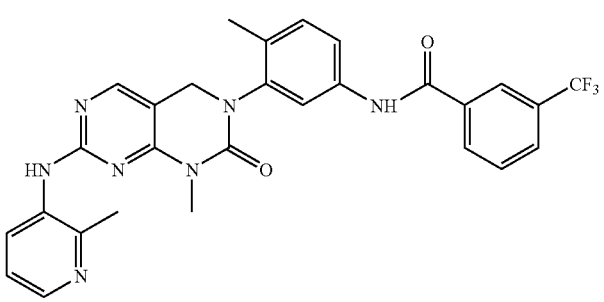 | MS m/z 548.1 (M + 1). |
| 161 | 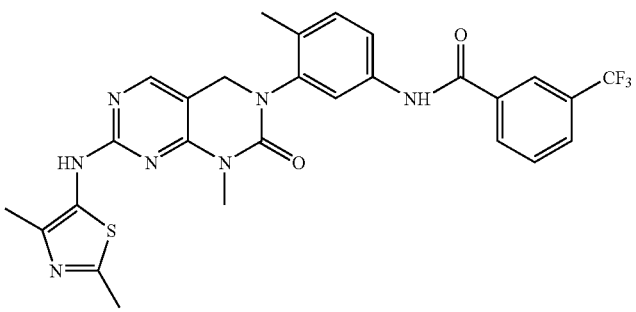 | MS m/z 568.2 (M + 1). |
| 162 | 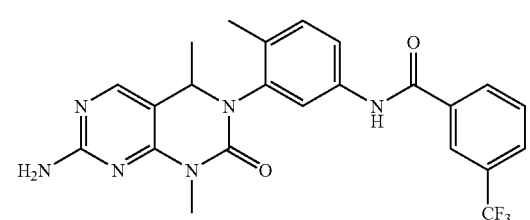 | MS m/z 471.1 (M + 1). |
| 163 | 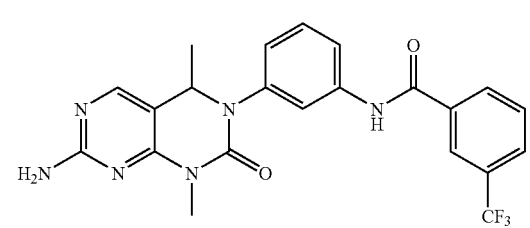 | MS m/z 457.1 (M + 1). |

TABLE 1-continued

| Compound Number | Structure | Physical Data<br>$^1$H NMR 400 MHz<br>(DMSO-$d_6$) and/or MS (m/z) |
|---|---|---|
| 164 | 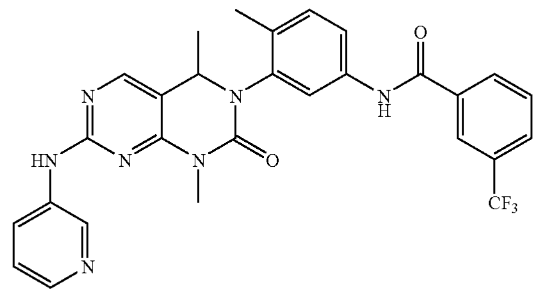 | MS m/z 548.2 (M + 1). |
| 165 | 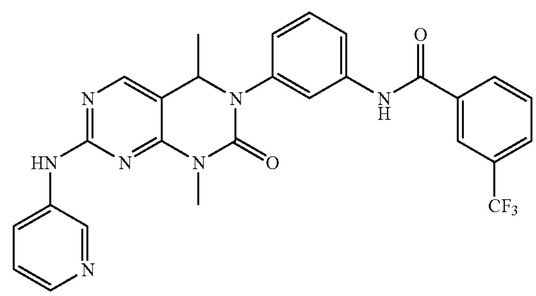 | MS m/z 534.2 (M + 1). |
| 166 | 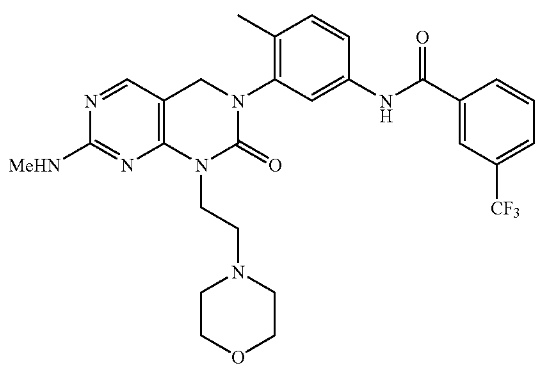 | MS m/z 570.2 (M + 1). |
| 167 | 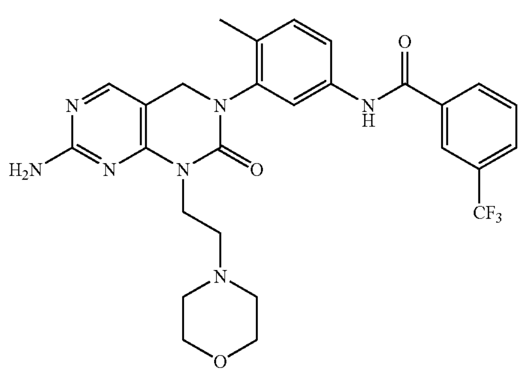 | MS m/z 556.2 (M + 1). |

TABLE 1-continued

| Compound Number | Structure | Physical Data<br>¹H NMR 400 MHz<br>(DMSO-d₆) and/or MS (m/z) |
|---|---|---|
| 168 | 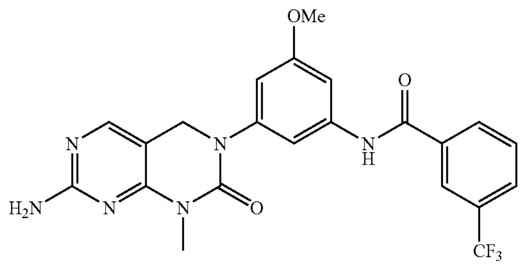 | MS m/z 511.2 (M + 1). |
| 169 | 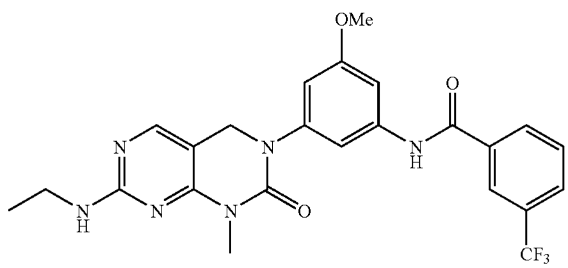 | MS m/z 539.2 (M + 1). |
| 170 | 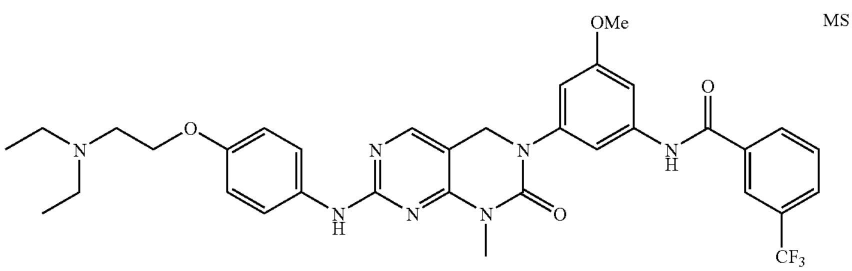 | MS m/z 702.3 (M + 1). |
| 171 | 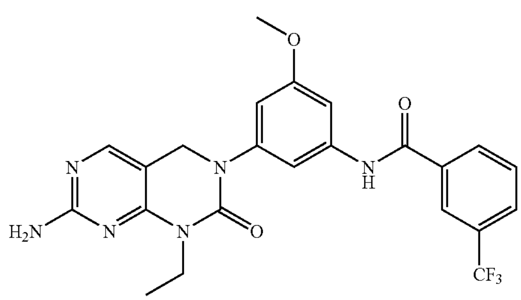 | MS m/z 487.2 (M + 1). |
| 172 | 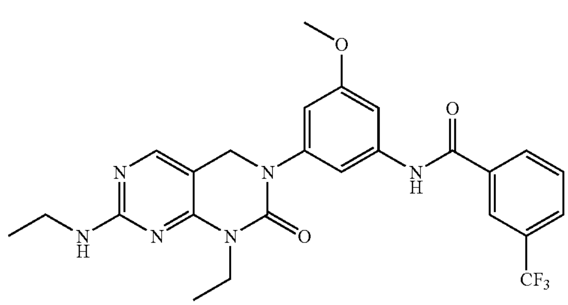 | MS m/z 515.3 (M + 1). |

TABLE 1-continued

| Compound Number | Structure | Physical Data ¹H NMR 400 MHz (DMSO-d$_6$) and/or MS (m/z) |
|---|---|---|
| 173 | 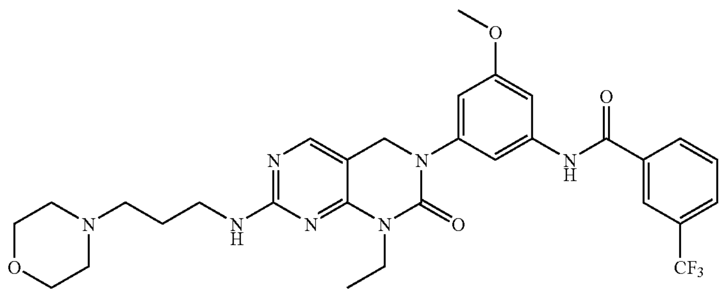 | MS m/z 614.2 (M + 1). |
| 174 | 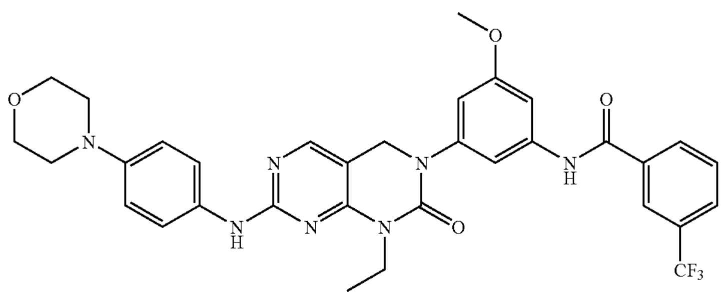 | MS m/z 648.3 (M + 1). |
| 175 | 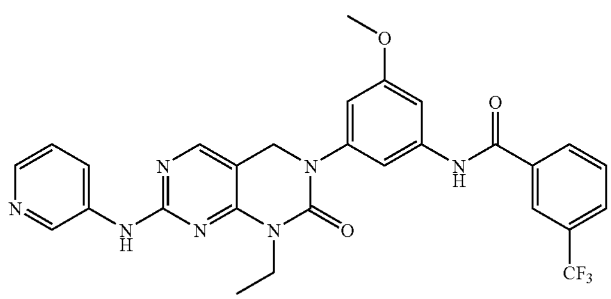 | MS m/z 564.2 (M + 1). |
| 176 | 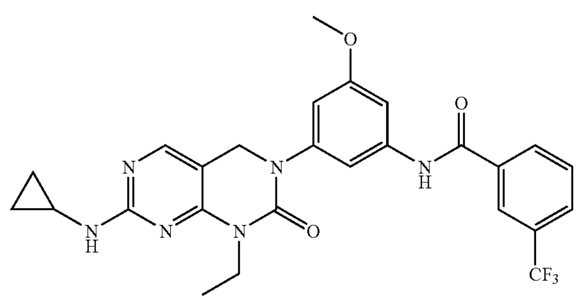 | MS m/z 527.2 (M + 1). |
| 177 | 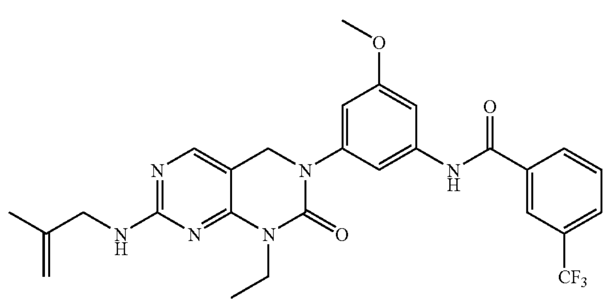 | MS m/z 541.2 (M + 1). |

TABLE 1-continued

| Compound Number | Structure | Physical Data $^1$H NMR 400 MHz (DMSO-$d_6$) and/or MS (m/z) |
|---|---|---|
| 178 | 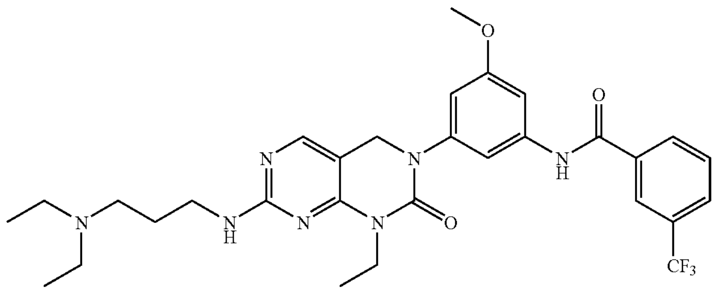 | MS m/z 600.3 (M + 1). |
| 179 | 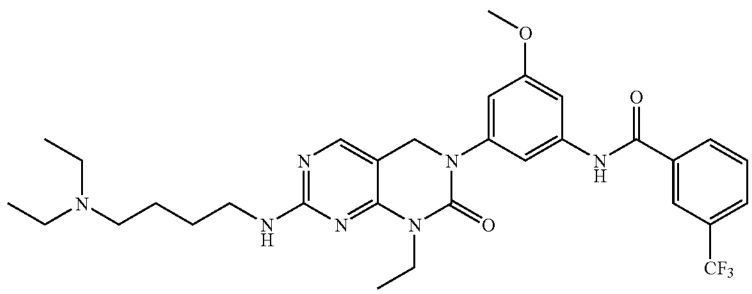 | MS m/z 614.3 (M + 1). |
| 180 | 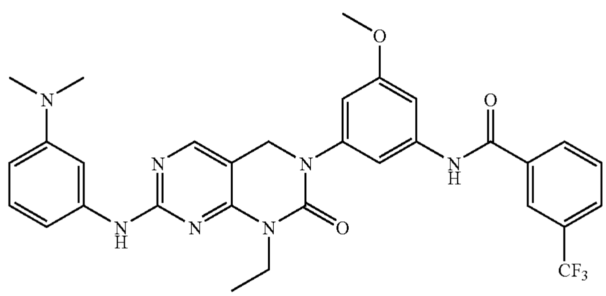 | MS m/z 606.3 (M + 1). |
| 181 | 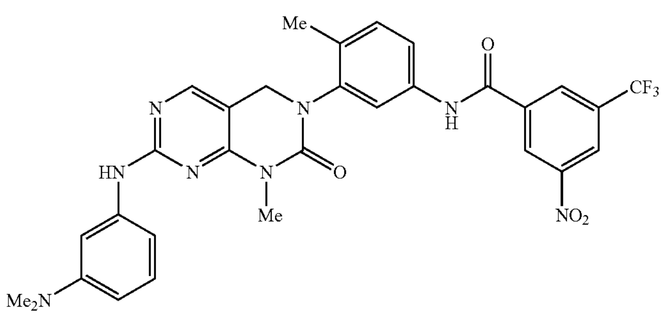 | MS m/z 621.2 (M + 1). |
| 182 | 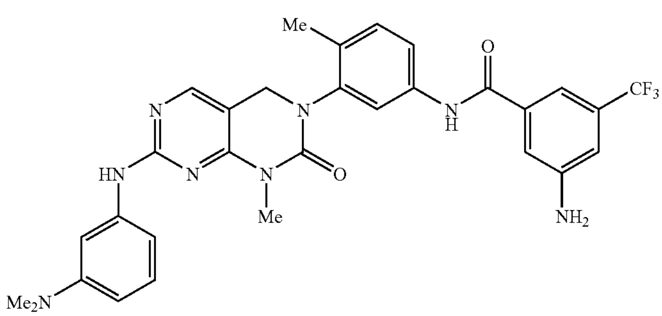 | MS m/z 591.2 (M + 1). |

TABLE 1-continued

| Compound Number | Structure | Physical Data<br>¹H NMR 400 MHz<br>(DMSO-d₆) and/or MS (m/z) |
|---|---|---|
| 183 | 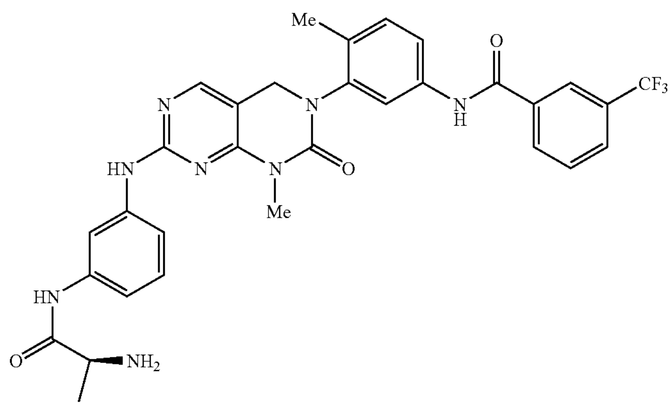 | MS m/z 619.2 (M + 1). |
| 184 | 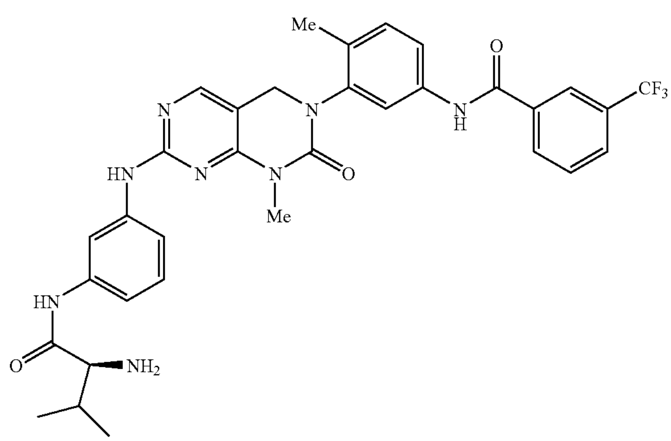 | MS m/z 647.3 (M + 1). |
| 185 | 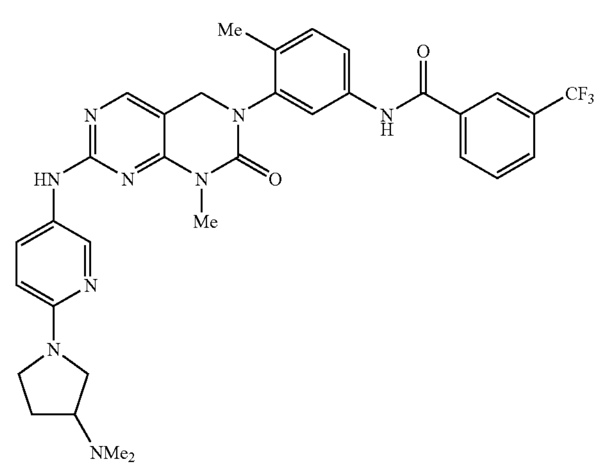 | MS m/z 646.3 (M + 1). |

TABLE 1-continued

| Compound Number | Structure | Physical Data<br>¹H NMR 400 MHz<br>(DMSO-d$_6$) and/or MS (m/z) |
|---|---|---|
| 186 | 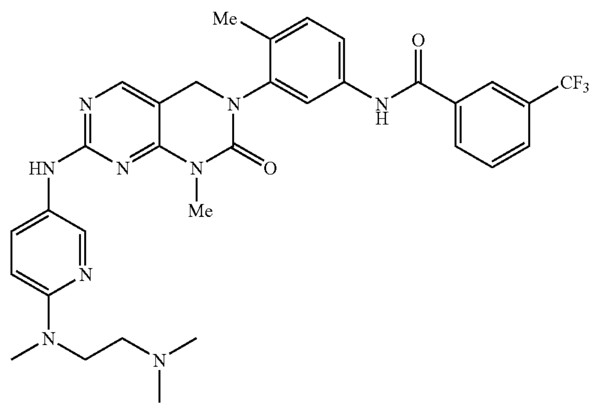 | MS m/z 634.3 (M + 1). |
| 187 | 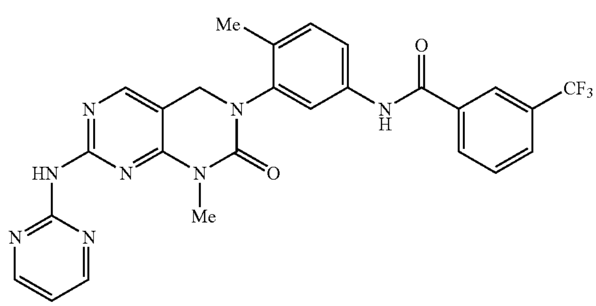 | MS m/z 535.1 (M + 1). |
| 188 | 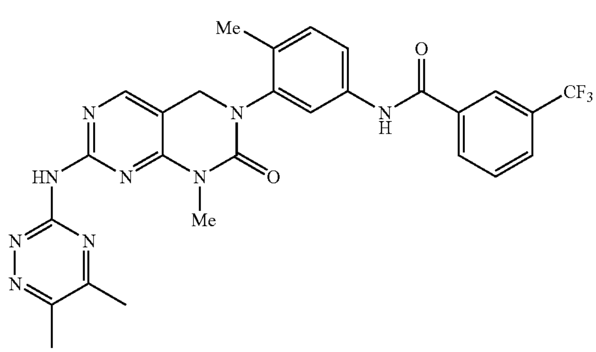 | MS m/z 564.1 (M + 1). |
| 189 | 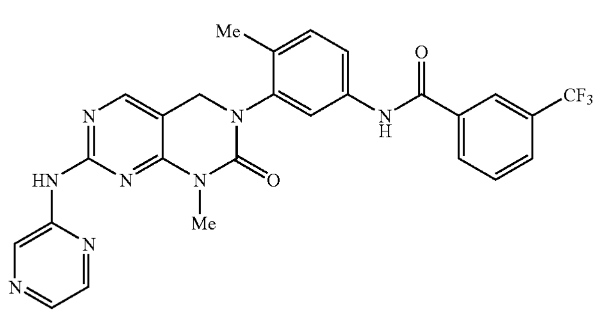 | MS m/z 535.1 (M + 1). |

TABLE 1-continued

| Compound Number | Structure | Physical Data<br>¹H NMR 400 MHz<br>(DMSO-d₆) and/or MS (m/z) |
| --- | --- | --- |
| 190 | 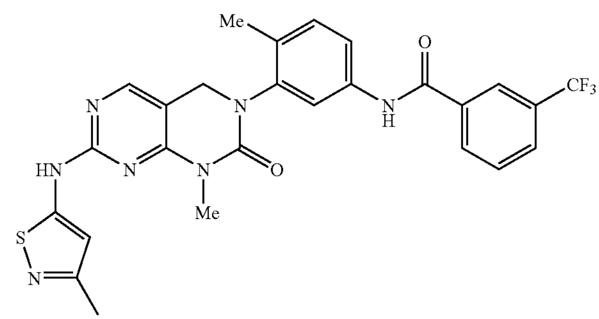 | MS m/z 554.1 (M + 1). |
| 191 | 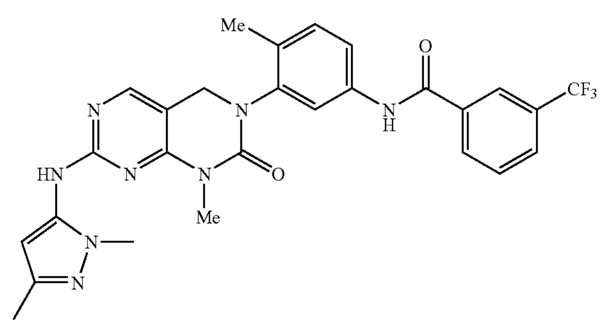 | MS m/z 551.1 (M + 1). |
| 192 | 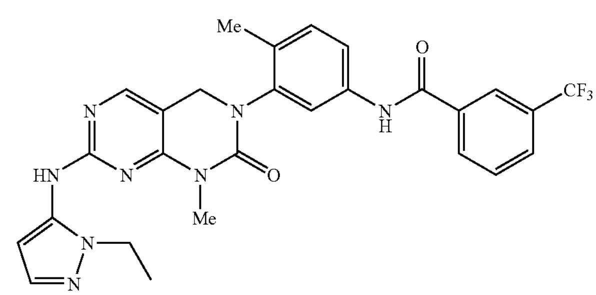 | MS m/z 551.1 (M + 1). |
| 193 | 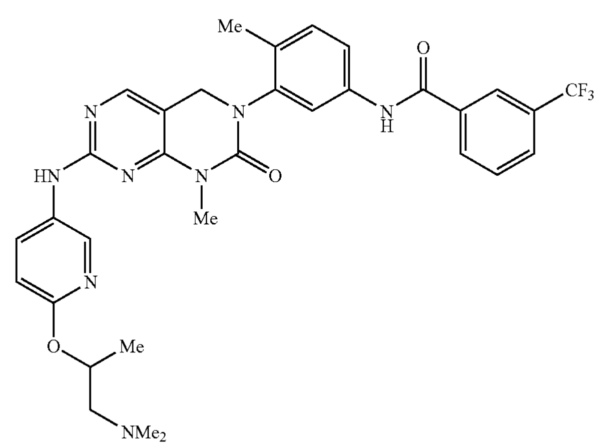 | MS m/z 635.2 (M + 1). |

TABLE 1-continued

| Compound Number | Structure | Physical Data $^1$H NMR 400 MHz (DMSO-$d_6$) and/or MS (m/z) |
|---|---|---|
| 194 | 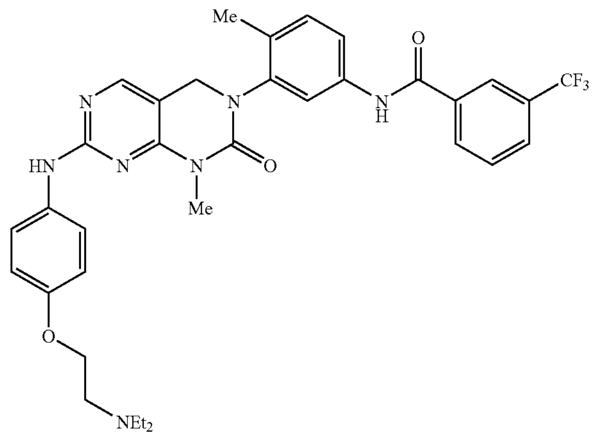 | MS m/z 648.2 (M + 1). |
| 195 | 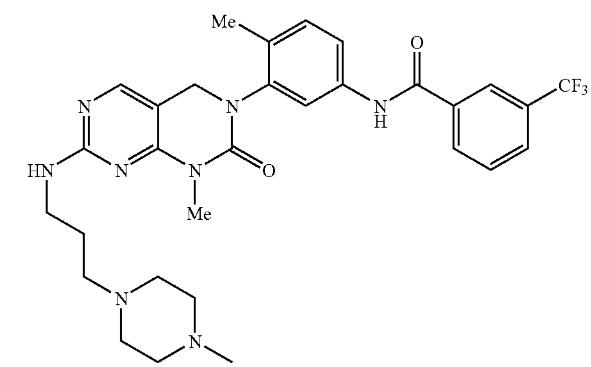 | MS m/z 597.2 (M + 1). |
| 196 | 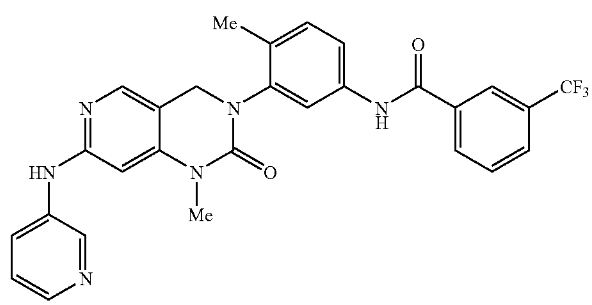 | MS m/z 533.2 (M + 1). |
| 197 | 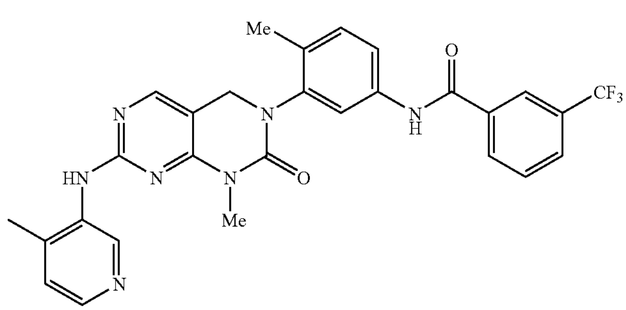 | MS m/z 548.2 (M + 1). |

TABLE 1-continued

| Compound Number | Structure | Physical Data<br>¹H NMR 400 MHz<br>(DMSO-d₆) and/or MS (m/z) |
| --- | --- | --- |
| 198 | 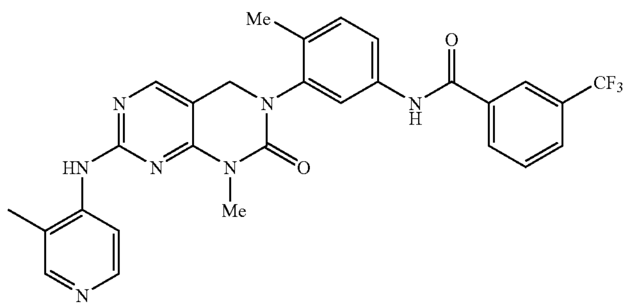 | MS m/z 548.2 (M + 1). |
| 199 | 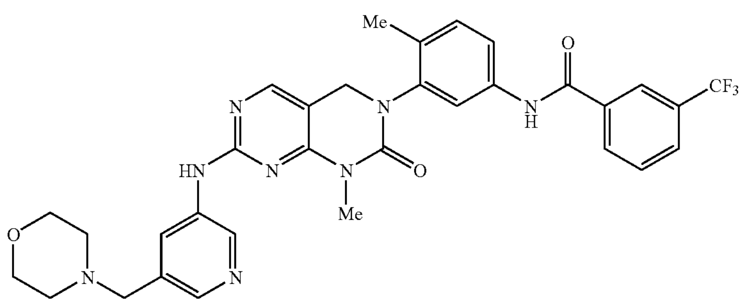 | MS m/z 633.2 (M + 1). |
| 200 | 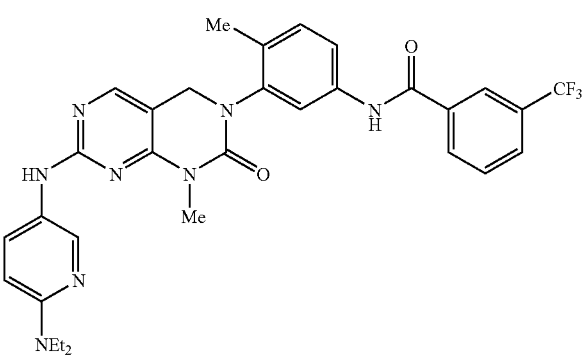 | MS m/z 605.2 (M + 1). |
| 201 | 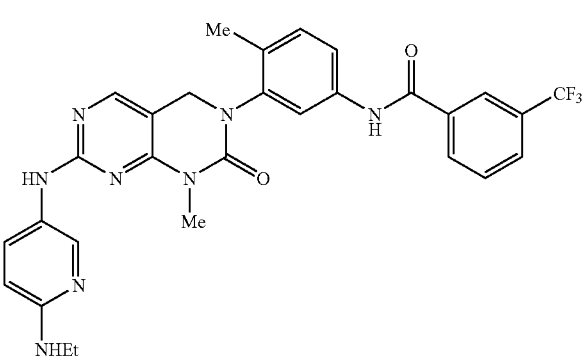 | MS m/z 577.1 (M + 1). |

TABLE 1-continued

| Compound Number | Structure | Physical Data $^1$H NMR 400 MHz (DMSO-$d_6$) and/or MS (m/z) |
|---|---|---|
| 202 | 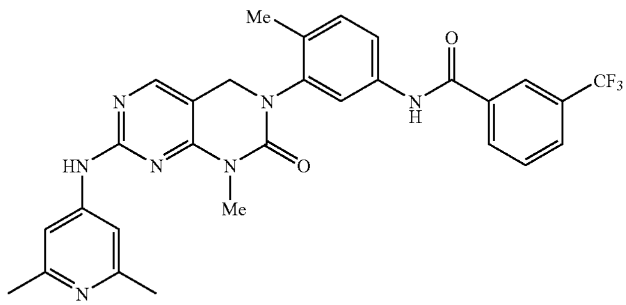 | MS m/z 562.1 (M + 1). |
| 203 | 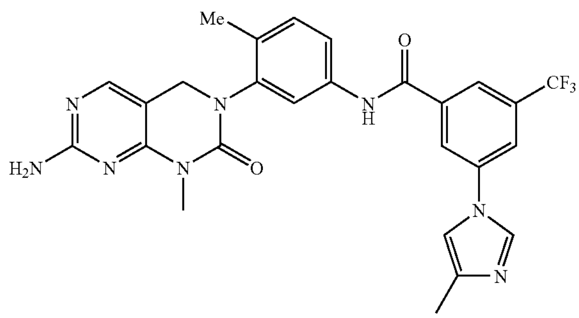 | MS m/z 537.2 (M + 1). |
| 204 | 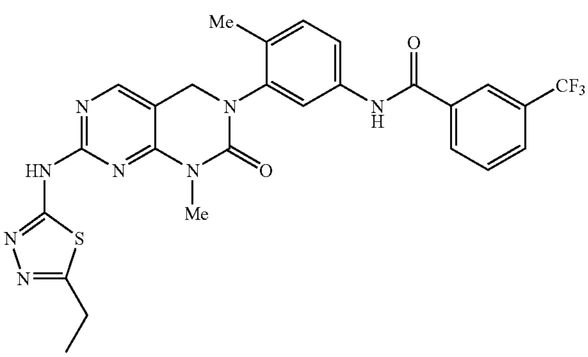 | MS m/z 569.1 (M + 1). |
| 205 | 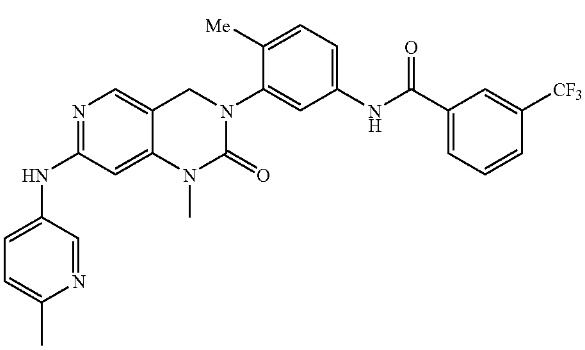 | MS m/z 547.1 (M + 1). |

TABLE 1-continued

| Compound Number | Structure | Physical Data<br>¹H NMR 400 MHz<br>(DMSO-d₆) and/or MS (m/z) |
|---|---|---|
| 206 | 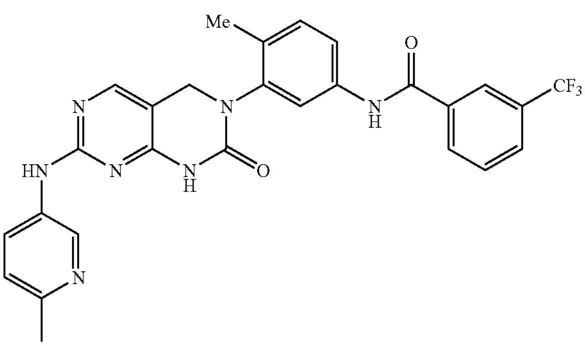 | MS m/z 534.1 (M + 1). |
| 207 | 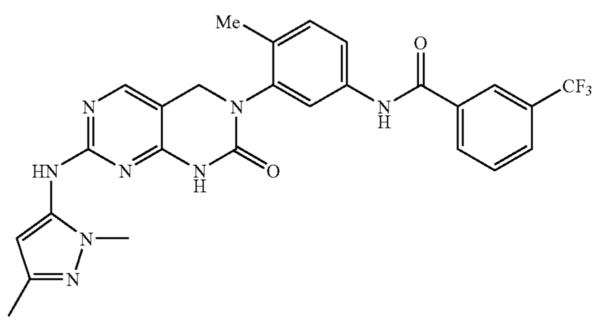 | MS m/z 537.1 (M + 1). |
| 208 | 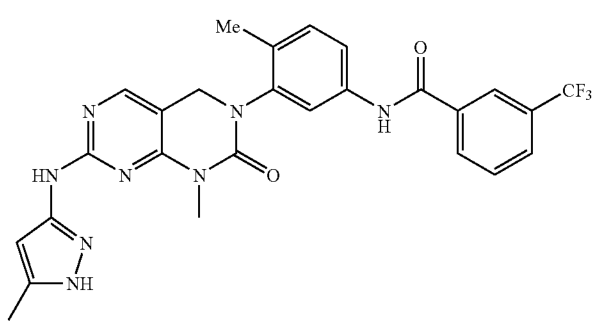 | MS m/z 537.1 (M + 1). |
| 210 | 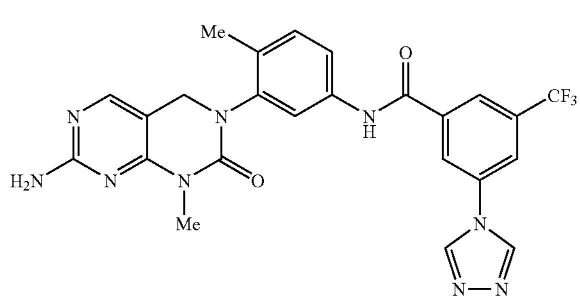 | MS m/z 524.1 (M + 1). |

TABLE 1-continued

| Compound Number | Structure | Physical Data $^1$H NMR 400 MHz (DMSO-$d_6$) and/or MS (m/z) |
|---|---|---|
| 211 | 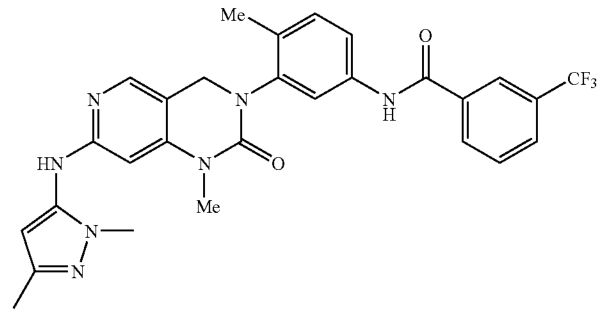 | MS m/z 550.1 (M + 1). |
| 212 | 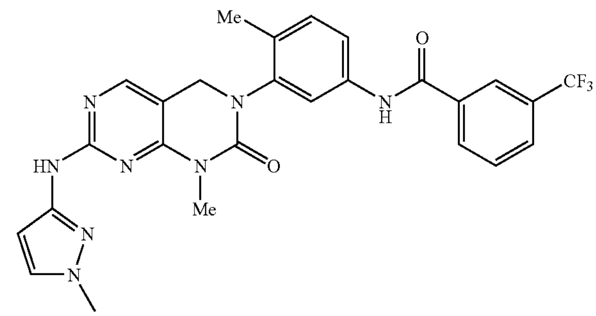 | MS m/z 537.1 (M + 1). |
| 213 | 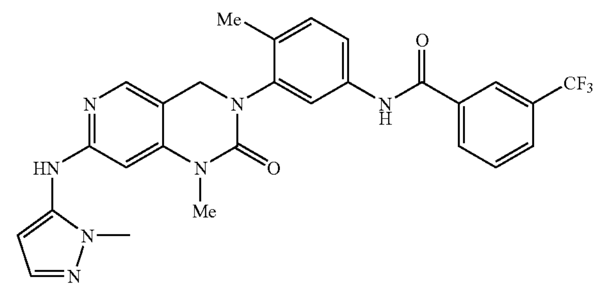 | MS m/z 537.1 (M + 1). |
| 214 | 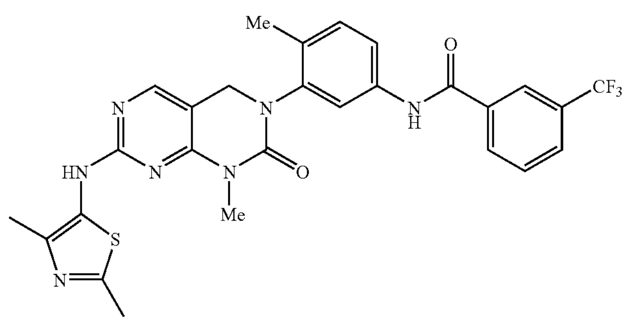 | MS m/z 568.1 (M + 1). |
| 215 | 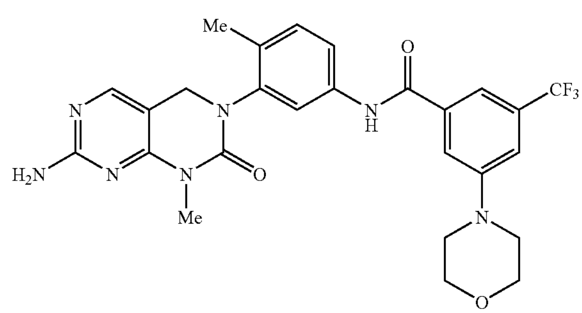 | MS m/z 542.1 (M + 1). |

TABLE 1-continued

| Compound Number | Structure | Physical Data<br>¹H NMR 400 MHz<br>(DMSO-d₆) and/or MS (m/z) |
|---|---|---|
| 216 | 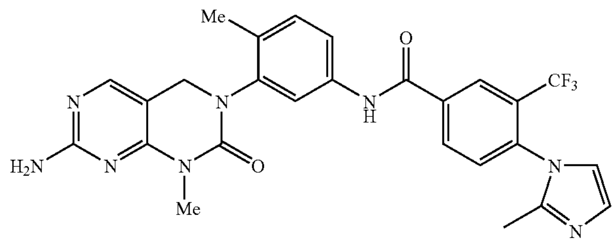 | MS m/z 537.1 (M + 1). |
| 217 | 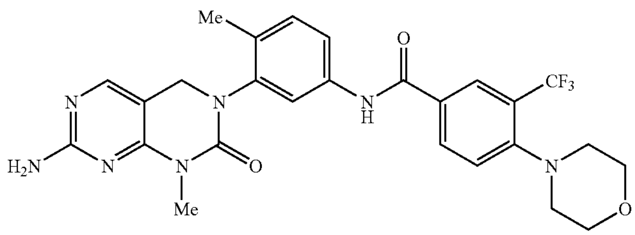 | MS m/z 542.1 (M + 1). |
| 218 | 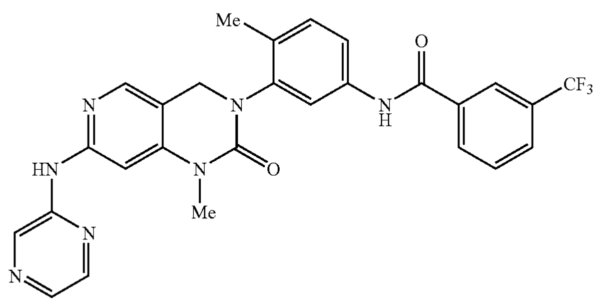 | MS m/z 534.1 (M + 1). |
| 219 | 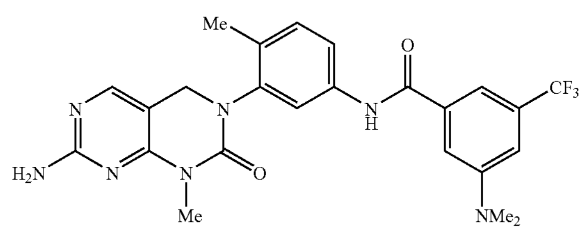 | MS m/z 500.1 (M + 1). |
| 220 | 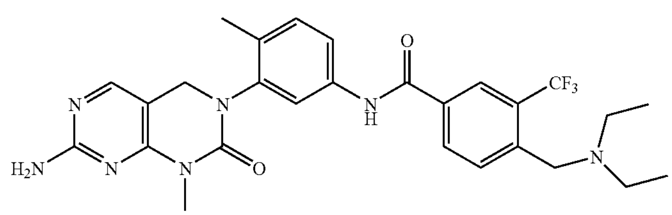 | MS m/z 542.1 (M + 1). |
| 221 | 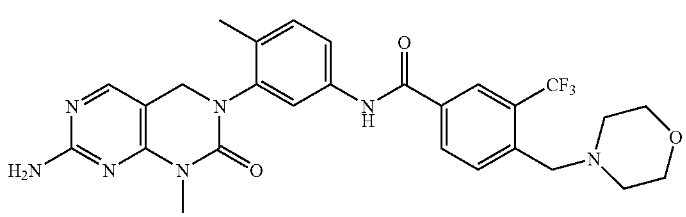 | MS m/z 556.1 (M + 1). |

TABLE 1-continued
| Compound Number | Structure | Physical Data<br>¹H NMR 400 MHz<br>(DMSO-d₆) and/or MS (m/z) |
|---|---|---|
| 222 | 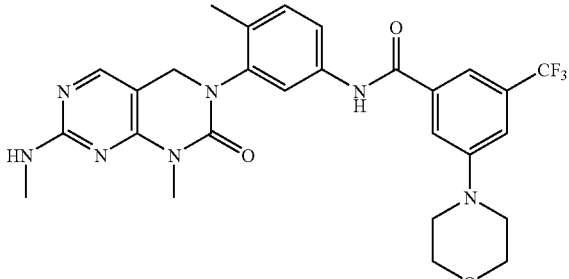 | MS m/z 556.1 (M + 1). |
| 223 | 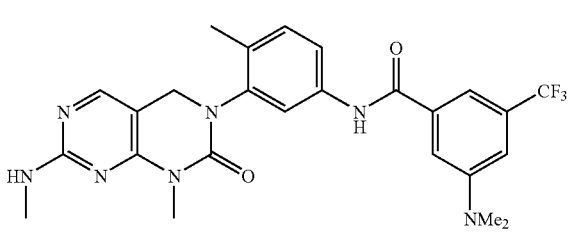 | MS m/z 514.1 (M + 1). |
| 224 | 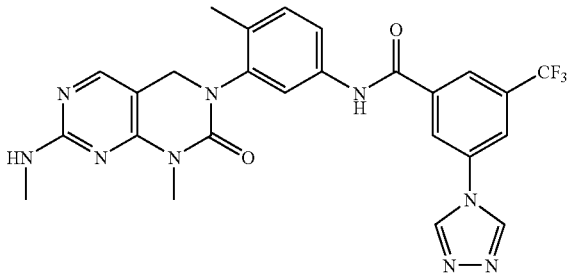 | MS m/z 538.1 (M + 1). |
| 225 | 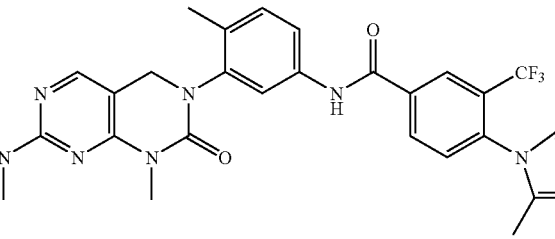 | MS m/z 551.1 (M + 1). |
| 226 | 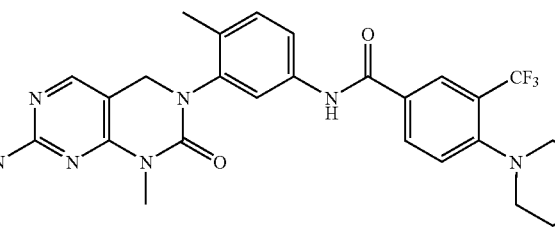 | MS m/z 556.1 (M + 1). |
| 227 | 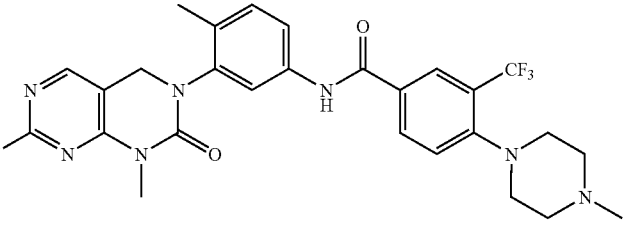 | MS m/z 569.2 (M + 1). |

TABLE 1-continued

| Compound Number | Structure | Physical Data $^1$H NMR 400 MHz (DMSO-$d_6$) and/or MS (m/z) |
|---|---|---|
| 228 | 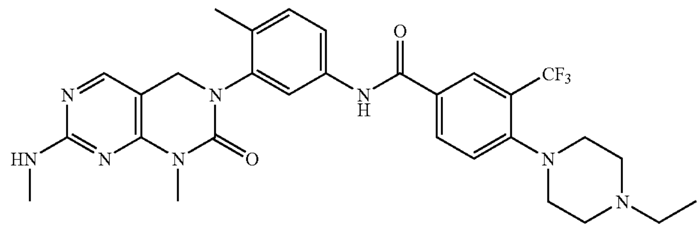 | MS m/z 583.2 (M + 1). |
| 229 | 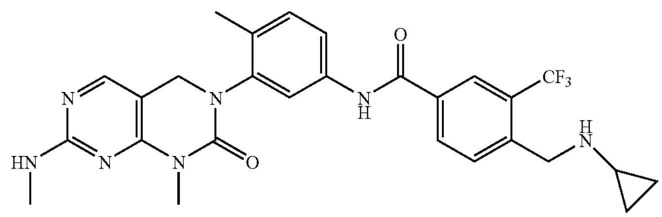 | MS m/z 540.1 (M + 1). |
| 230 | 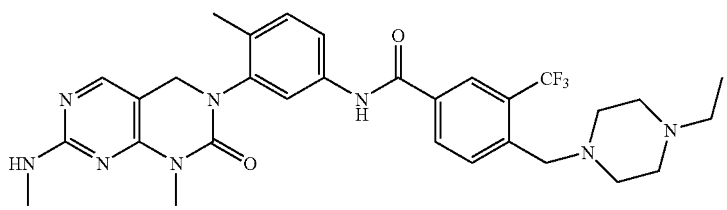 | MS m/z 597.2 (M + 1). |
| 231 | 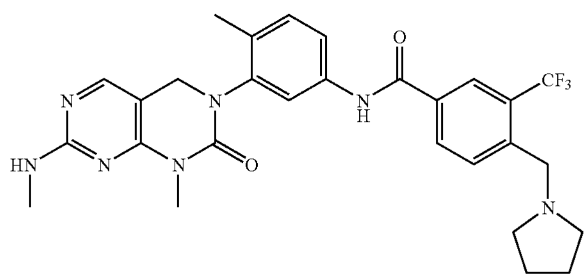 | MS m/z 554.2 (M + 1). |
| 232 | 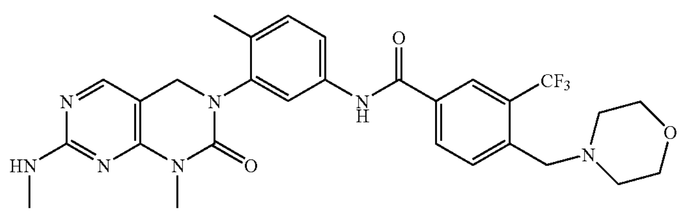 | MS m/z 570.2 (M + 1). |
| 233 | 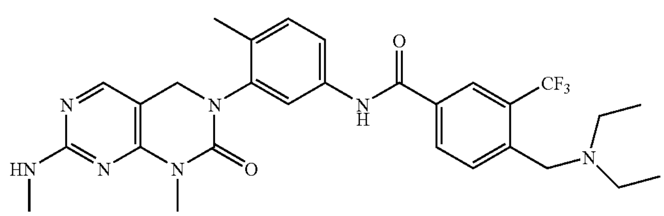 | MS m/z 556.2 (M + 1). |

TABLE 1-continued

| Compound Number | Structure | Physical Data $^1$H NMR 400 MHz (DMSO-$d_6$) and/or MS (m/z) |
|---|---|---|
| 234 | 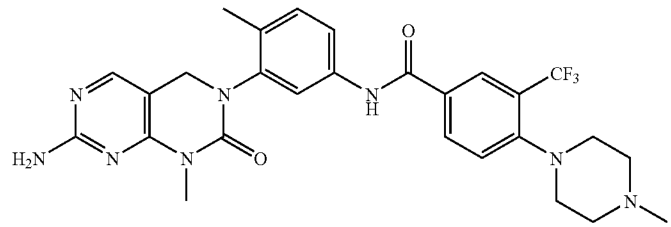 | MS m/z 555.2 (M + 1). |
| 235 | 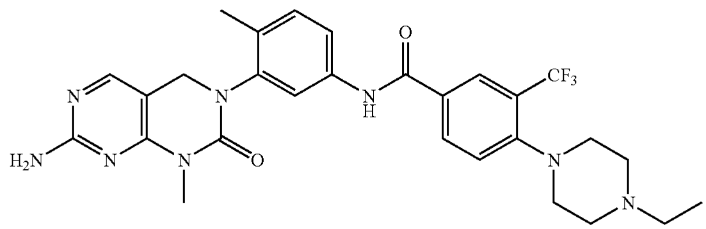 | MS m/z 569.2 (M + 1). |
| 236 | 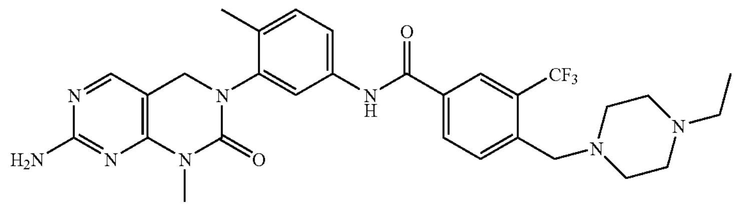 | MS m/z 583.2 (M + 1). |
| 237 | 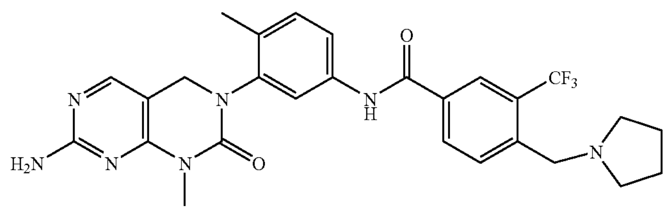 | MS m/z 540.2 (M + 1). |
| 238 | 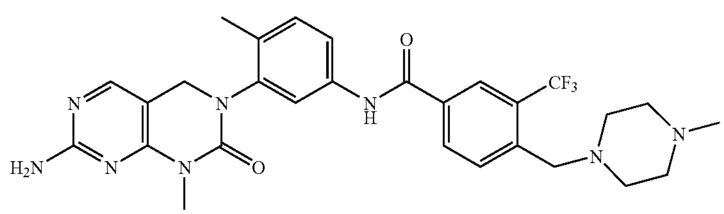 | MS m/z 569.2 (M + 1). |
| 239 | 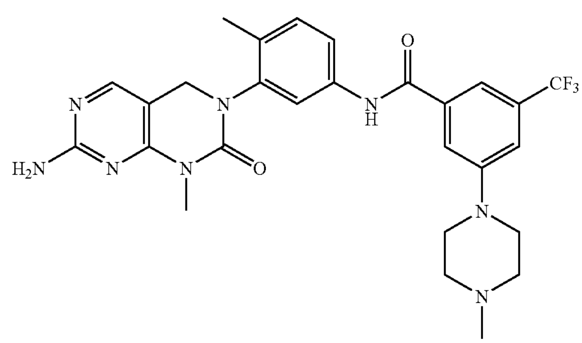 | MS m/z 555.2 (M + 1). |

TABLE 1-continued
| Compound Number | Structure | Physical Data<br>$^1$H NMR 400 MHz<br>(DMSO-$d_6$) and/or MS (m/z) |
|---|---|---|
| 240 | 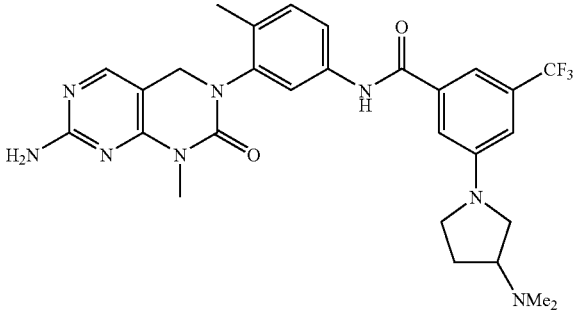 | MS m/z 569.2 (M + 1). |
| 241 | 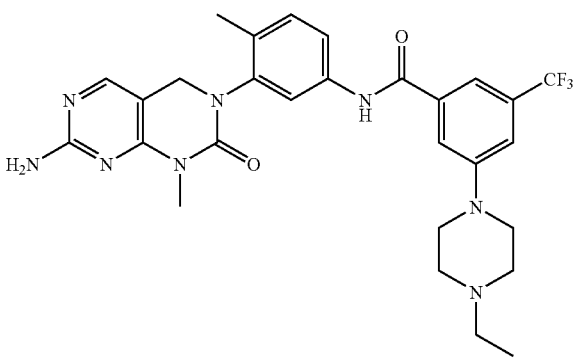 | MS m/z 569.2 (M + 1). |
| 242 | 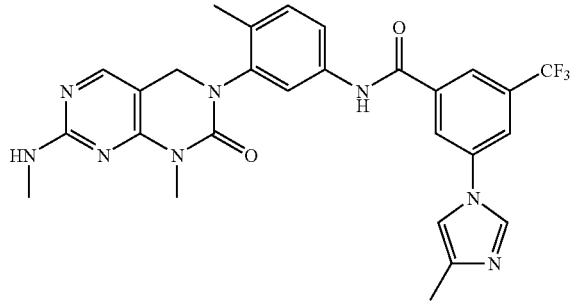 | MS m/z 551.2 (M + 1). |
| 243 | 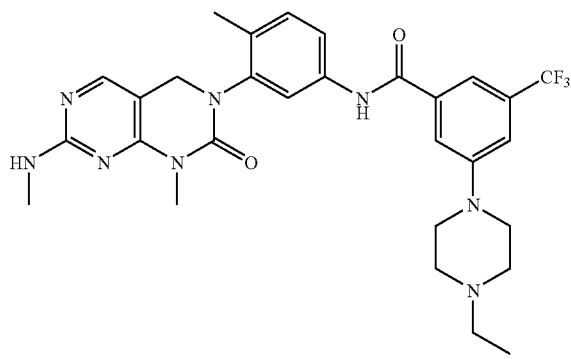 | MS m/z 583.2 (M + 1). |

TABLE 1-continued

| Compound Number | Structure | Physical Data $^1$H NMR 400 MHz (DMSO-$d_6$) and/or MS (m/z) |
|---|---|---|
| 244 | 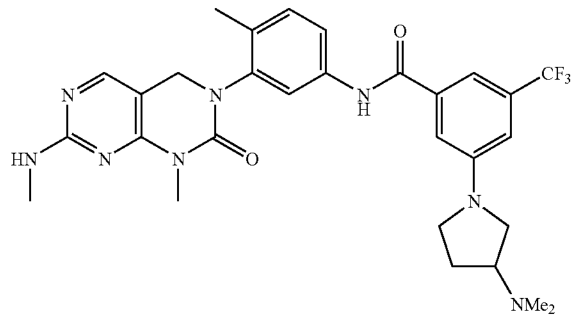 | MS m/z 583.2 (M + 1). |
| 245 | 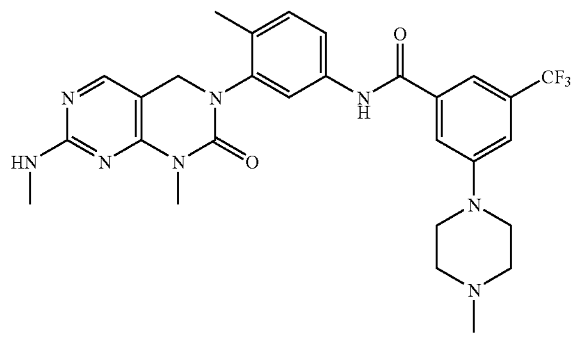 | MS m/z 569.2 (M + 1). |
| 246 | 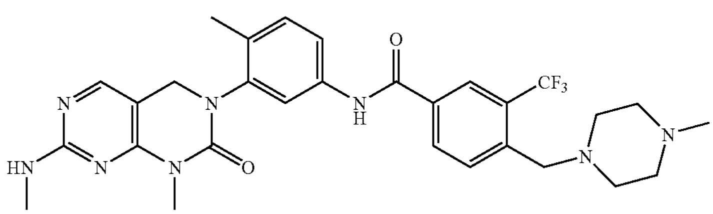 | MS m/z 583.2 (M + 1). |
| 247 | 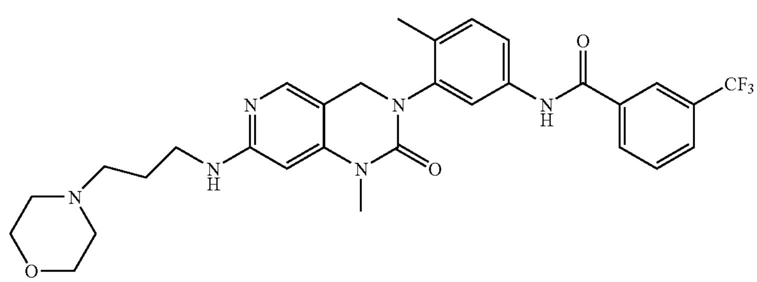 | MS m/z 583.2 (M + 1). |
| 248 | 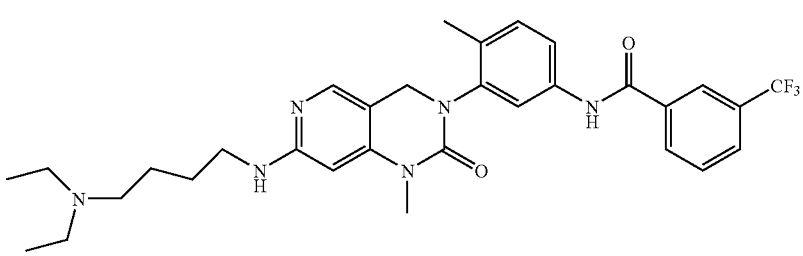 | MS m/z 583.2 (M + 1). |

TABLE 1-continued

| Compound Number | Structure | Physical Data<br>¹H NMR 400 MHz<br>(DMSO-d₆) and/or MS (m/z) |
|---|---|---|
| 249 | 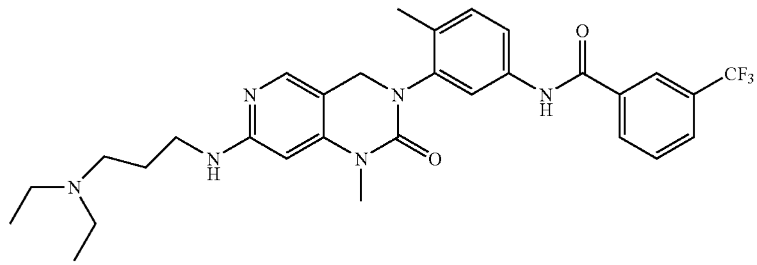 | MS m/z 569.2 (M + 1). |
| 250 | 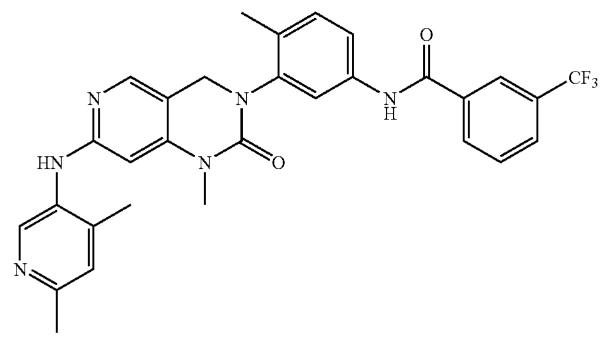 | MS m/z 561.1 (M + 1). |
| 251 | 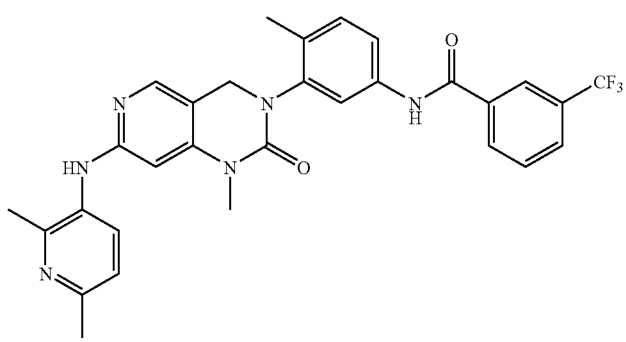 | MS m/z 561.1 (M + 1). |
| 252 | 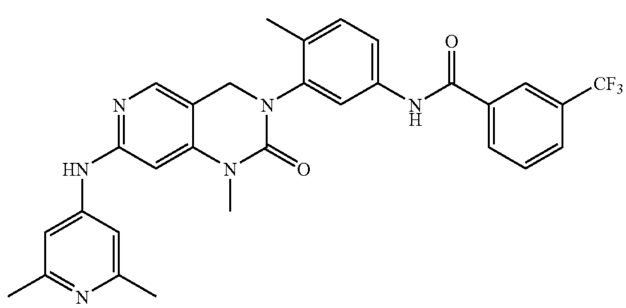 | MS m/z 561.1 (M + 1). |
| 253 | 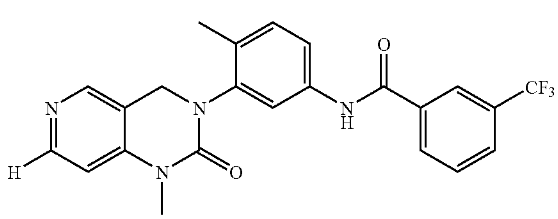 | MS m/z 441.1 (M + 1). |

TABLE 1-continued

| Compound Number | Structure | Physical Data $^1$H NMR 400 MHz (DMSO-$d_6$) and/or MS (m/z) |
|---|---|---|
| 254 | 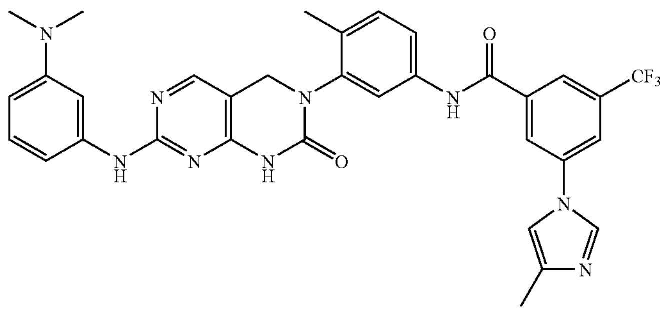 | $^1$H NMR 400 MHz (DMSO-$d_6$) γ 9.14 (s, 1H), 8.43 (s, 1H), 8.37 (s, 1H), 8.22 (s, 1H), 8.16 (s, 1H), 8.10 (s, 1H), 7.74–7.65 (m, 3H), 7.32 (d, 1H), 7.20 (s, 1H), 7.14 (d, 1H), 7.02 (t, 1H), 6.31 (d, 1H), 4.68 (d, 1H), 4.51 (d, 1H), 2.87 (s, 6H), 2.18 (s, 3H), 2.16 (s, 3H); MS m/z 642.3 (M + 1). |
| 255 | 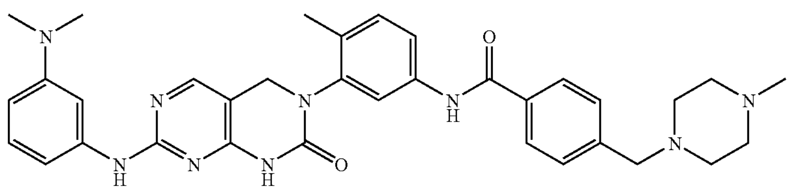 | $^1$H NMR 400 MHz (DMSO-$d_6$) δ 9.13 (s, 1H), 8.09 (s, 1H), 7.90 (s, 1H), 7.89 (s, 1H), 7.77 (d, 1H), 7.61 (dd, 1H), 7.43 (s, 1H), 7.42 (s, 1H), 7.26 (d, 1H), 7.20 (s, 1H), 7.14 (d, 1H), 7.02 (t, 1H), 6.31 (dd, 1H), 4.68 (d, 1H), 4.49 (d, 1H), 3.53 (s, 2H), 2.86 (s, 6H), 2.40 (m, 8H), 2.21 (s, 3H), 2.14 (s, 3H); MS m/z 606.4 (M + 1). |
| 256 | 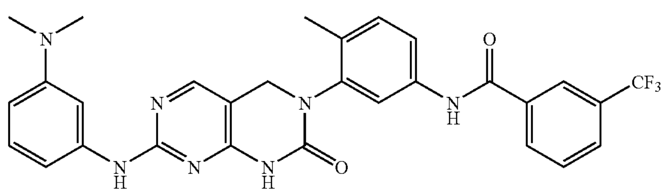 | $^1$H NMR 400 MHz (DMSO-$d_6$) δ 9.16 (s, 1H), 8.29 (s, 1H), 8.25 (d, 1H), 8.10 (s, 1H), 7.96 (d, 1H), 7.79 (d, 1H), 7.76 (s, 1H), 7.64 (d, 1H), 7.30 (d, 1H), 7.20 (s, 1H), 7.14 (d, 1H), 7.01 (t, 1H), 6.31 (d, 1H), 4.68 (d, 1H), 4.50 (d, 1H), 2.86 (s, 6H), 2.15 (s, 3H); MS m/z 562.3 (M + 1). |
| 257 | 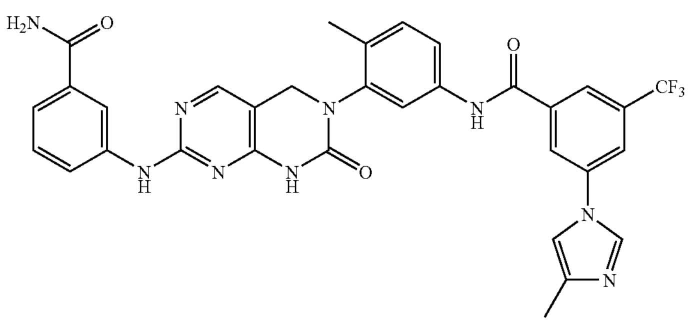 | $^1$H NMR 400 MHz (DMSO-$d_6$) δ 9.57 (s, 1H), 8.58 (s, 1H), 8.40 (s, 1H), 8.39 (s, 1H), 8.21 (s, 1H), 8.14 (s, 1H), 8.10 (s, 1H), 7.88 (d, 1H), 7.75 (s, 1H), 7.67 (d, 1H), 7.40 (d, 1H), 7.34–7.28 (m, 3H), 4.69 (d, 1H), 4.50 (d, 1H), 2.32 (s, 3H), 2.17 (s, 3H); MS m/z 642.2 (M + 1). |
| 258 | 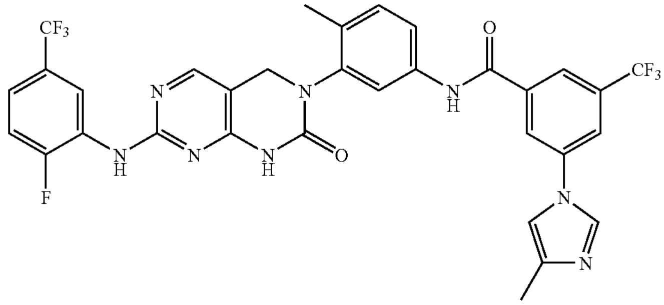 | $^1$H NMR 400 MHz (DMSO-$d_6$) δ 9.08 (s, 1H), 8.43 (s, 1H), 8.39 (s, 1H), 8.30 (d, 1H), 8.23 (s, 1H), 8.16 (s, 1H), 8.13 (s, 1H), 7.74 (s, 1H), 7.69 (s, 1H), 7.65 (dd, 1H), 7.45 (s, 1H), 7.43 (s, 1H), 7.30 (d, 1H), 4.67 (d, 1H), 4.53 (d, 1H), 2.18 (s, 3H), 2.16 (s, 3H); MS m/z 685.2 (M + 1). |

| Compound Number | Structure | Physical Data <br> ¹H NMR 400 MHz (DMSO-d₆) and/or MS (m/z) |
|---|---|---|
| 259 | 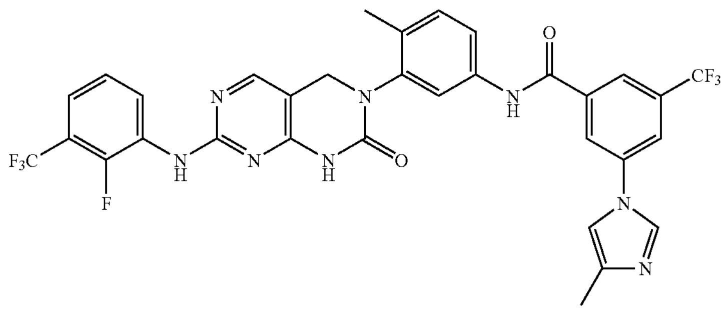 | ¹H NMR 400 MHz (DMSO-d₆) δ 9.15 (s, 1H), 8.43 (s, 1H), 8.38 (s, 1H), 8.25 (d, 1H), 8.23 (s, 1H), 8.16 (s, 1H), 8.11 (s, 1H), 7.74 (s, 1H), 7.69 (s, 1H), 7.65 (dd, 1H), 7.42 (t, 1H), 7.33 (s, 1H), 7.31 (d, 1H), 4.68 (d, 1H), 4.53 (d, 1H), 2.18 (s, 3H), 2.15 (s, 3H); MS m/z 685.2 (M + 1). |
| 260 | 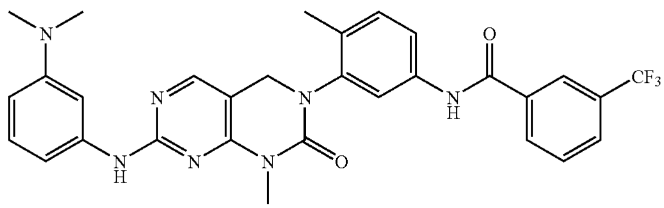 | ¹H NMR 400 MHz (MeOH-d₄) δ 8.25 (s, 1H), 8.19 (d, 1H), 8.05 (s, 1H), 7.87 (d, 1H), 7.76–7.72 (m, 2H), 7.60 (dd, 1H), 7.33 (d, 1H), 7.24 (t, 1H), 7.13 (t, 1H), 7.01 (d, 1H), 6.48 (dd, 1H), 4.77 (d, 1H), 4.55 (d, 1H), 3.46 (s, 3H), 2.94 (s, 6H), 2.23 (s, 3H); MS m/z 576.3 (M + 1). |
| 261 | 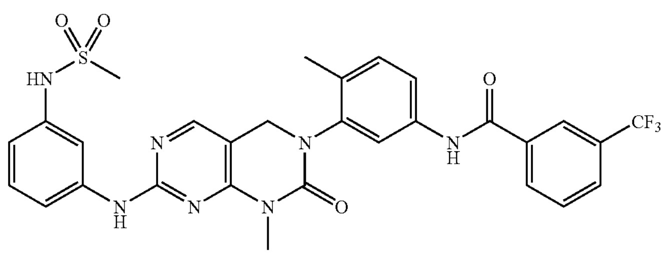 | ¹H NMR 400 MHz (DMSO-d₆) δ 9.64 (s, 1H), 9.60 (d, 1H), 8.29 (s, 1H), 8.21 (d, 1H), 8.14 (s, 1H), 7.95 (d, 1H), 7.78 (m, 3H), 7.63 (d, 1H), 7.42 (d, 1H), 7.31 (d, 1H), 7.20 (t, 1H), 6.77 (d, 1H), 4.68 (d, 1H), 4.53 (d, 1H), 3.35 (s, 3H), 2.97 (s, 3H), 2.13 (s, 3H); MS m/z 626.3 (M + 1). |
| 262 | 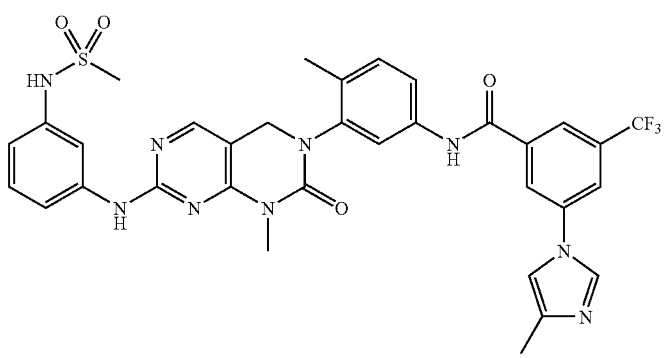 | ¹H NMR 400 MHz (DMSO-d₆) δ 9.64 (s, 1H), 9.60 (d, 1H), 8.43 (s, 1H), 8.38 (s, 1H), 8.22 (s, 1H), 8.15 (s, 1H), 8.14 (s, 1H), 7.77 (s, 1H), 7.75 (s, 1H), 7.69 (s, 1H), 7.65 (d, 1H), 7.42 (d, 1H), 7.33 (d, 1H), 7.20 (t, 1H), 6.78 (d, 1H), 4.69 (d, 1H), 4.52 (d, 1H), 3.35 (s, 3H), 2.97 (s, 3H), 2.17 (s, 3H), 2.14 (s, 3H); MS m/z 706.3 (M + 1). |
| 263 | 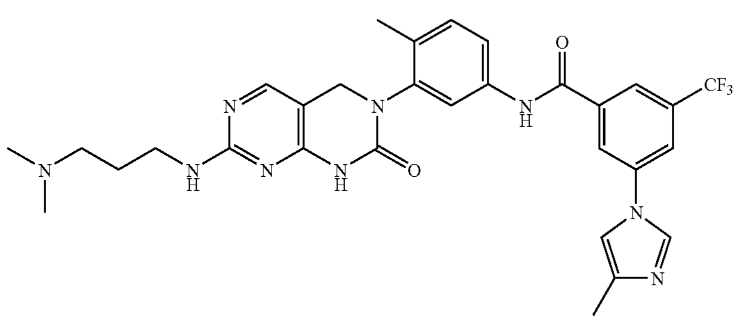 | ¹H NMR 400 MHz (DMSO-d₆) δ 8.43 (s, 1H), 8.38 (s, 1H), 8.22 (s, 1H), 8.15 (s, 1H), 7.93 (s, 1H), 7.70 (s, 1H), 7.69 (s, 1H), 7.65 (dd, 1H), 7.30 (d, 1H), 6.92 (br, 1H), 4.59 (d, 1H), 4.41 (d, 1H), 3.23 (t, 2H), 2.24 (t, 2H), 2.17 (s, 3H), 2.13 (s, 3H), 2.12 (s, 6H), 1.62 (m, 2H); MS m/z 608.2 (M + 1). |

TABLE 1-continued

| Compound Number | Structure | Physical Data<br>¹H NMR 400 MHz<br>(DMSO-d₆) and/or MS (m/z) |
|---|---|---|
| 264 | 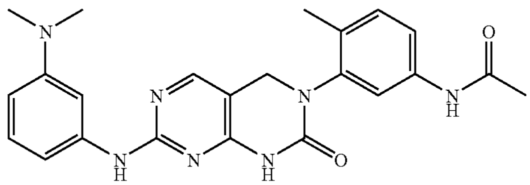 | ¹H NMR 400 MHz (DMSO-d₆) δ 9.19 (s, 1H), 8.07 (s, 1H), 7.57 (s, 1H), 7.37 (d, 1H), 7.20 (m, 2H), 7.13 (d, 1H), 7.01 (t, 1H), 6.30 (d, 1H), 4.63 (d, 1H), 4.45 (d, 1H), 2.86 (s, 6H), 2.10 (s, 3H), 2.02 (s, 3H); MS m/z 432.3 (M + 1). |
| 265 | 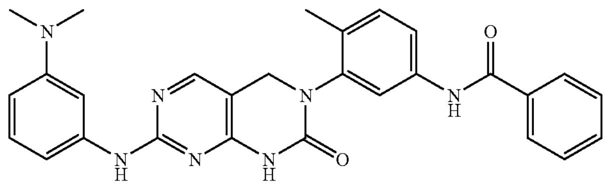 | ¹H NMR 400 MHz (DMSO-d₆) δ 10.24 (s, 1H), 10.18 (s, 1H), 9.12 (s, 1H), 8.05 (s, 1H), 7.90 (s, 1H), 7.88 (s, 1H), 7.74 (s, 1H), 7.59–7.45 (m, 4H), 7.22 (d, 1H), 7.15 (s, 1H), 7.08 (d, 1H), 6.97 (t, 1H), 6.26 (dd, 1H), 4.63 (d, 1H), 4.45 (d, 1H), 2.82 (s, 6H), 2.09 (s, 3H); MS m/z 494.3 (M + 1). |
| 266 | 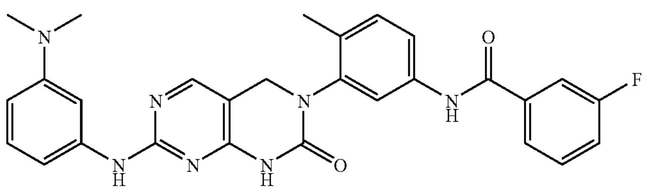 | ¹H NMR 400 MHz (DMSO-d₆) δ 10.31 (s, 1H), 10.19 (s, 1H), 9.12 (s, 1H), 8.05 (s, 1H), 7.76–7.72 (m, 3H), 7.58–7.52 (m, 2H), 7.35 (t, 1H), 7.23 (d, 1H), 7.16 (s, 1H), 7.08 (d, 1H), 6.97 (t, 1H), 6.26 (dd, 1H), 4.63 (d, 1H), 4.45 (d, 1H), 2.82 (s, 6H), 2.09 (s, 3H); MS m/z 512.3 (M + 1). |
| 267 | 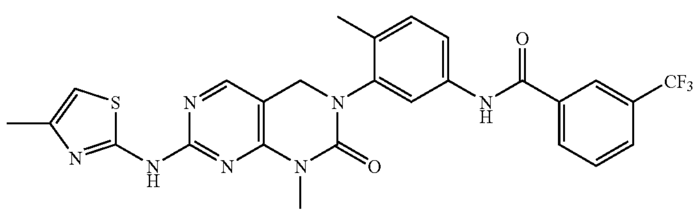 | ¹H NMR 400 MHz (DMSO-d₆) δ 8.28 (s, 1H), 8.24 (d, 1H), 8.22 (s, 1H), 7.97 (d, 1H), 7.79–7.76 (m, 2H), 7.62 (dd, 1H), 7.30 (d, 1H), 6.66 (s, 1H), 4.77 (d, 1H), 4.53 (d, 1H), 3.43 (s, 3H), 2.13 (s, 3H), 1.16 (t, 3H); MS m/z 626.3 (M + 1). |
| 268 | 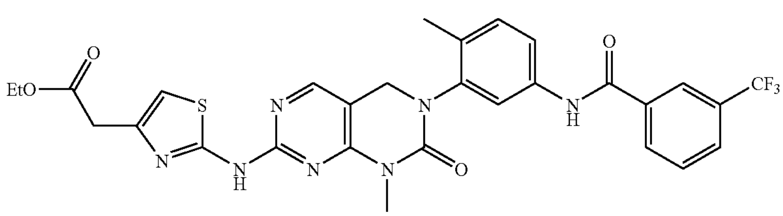 | ¹H NMR 400 MHz (DMSO-d₆) δ 8.28–8.23 (m, 3H), 7.95 (d, 1H), 7.79–7.77 (m, 2H), 7.63 (dd, 1H), 7.30 (dd, 1H), 6.89 (s, 1H), 4.74 (d, 1H), 4.56 (d, 1H), 4.06 (q, 2H), 3.66 (s, 2H), 3.43 (s, 3H), 2.27 (s, 3H), 2.13 (s, 3H); MS m/z 554.3 (M + 1). |
| 269 | 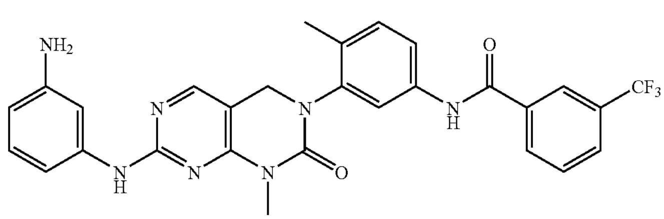 | ¹H NMR 400 MHz (DMSO-d₆) δ 9.22 (s, 1H), 8.29 (s, 1H), 8.25 (d, 1H), 8.10 (s, 1H), 7.95 (d, 1H), 7.78–7.76 (m, 2H), 7.62 (dd, 1H), 7.30 (d, 1H), 7.05 (d, 1H), 6.88 (d, 1H), 6.87 (s, 1H), 6.17 (dd, 1H), 4.92 (s, 2H), 4.67 (d, 1H), 4.49 (d, 1H), 3.33 (s, 3H), 2.12 (s, 3H); MS m/z 548.3 (M + 1). |

TABLE 1-continued

| Compound Number | Structure | Physical Data $^1$H NMR 400 MHz (DMSO-$d_6$) and/or MS (m/z) |
|---|---|---|
| 270 | 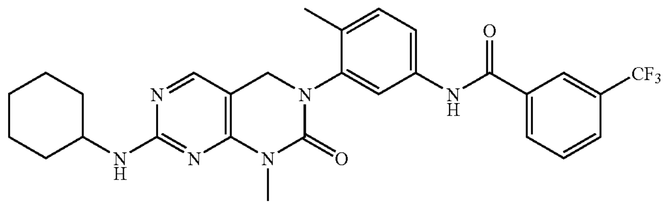 | $^1$H NMR 400 MHz (DMSO-$d_6$) δ 8.28 (s, 1H), 8.24 (d, 1H), 7.95 (d, 1H), 7.93 (s, 1H), 7.77 (t, 1H), 7.73 (d, 1H), 7.51 (dd, 1H), 7.28 (d, 1H), 6.92 (br, 1H), 4.58 (d, 1H), 4.39 (d, 1H), 3.68 (br, 1H), 3.16 (s, 3H), 2.10 (s, 3H), 1.86 (br, 2H), 1.69 (br, 2H), 1.57 (br, 1H), 1.27 (m, 3H), 1.22 (br, 1H); MS m/z 539.3 (M + 1). |
| 271 | 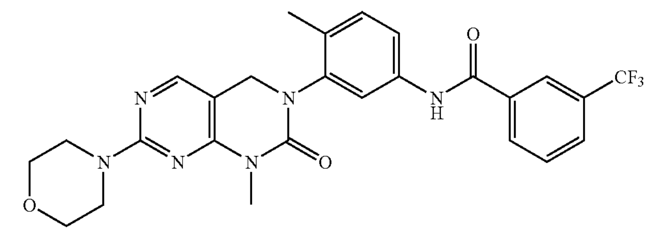 | $^1$H NMR 400 MHz (DMSO-$d_6$) δ 8.28 (s, 1H), 8.24 (d, 1H), 8.05 (s, 1H), 7.95 (d, 1H), 7.75 (t, 1H), 7.74 (s, 1H), 7.61 (dd, 1H), 7.29 (d, 1H), 4.53 (d, 1H), 4.44 (d, 1H), 3.65 (m, 8H), 3.26 (s, 3H), 2.10 (s, 3H); MS m/z 527.3 (M + 1). |
| 272 | 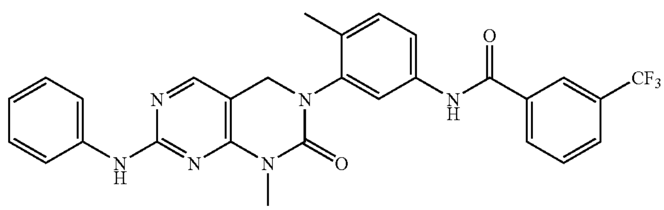 | $^1$H NMR 400 MHz (DMSO-$d_6$) δ 9.53 (s, 1H), 8.29 (s, 1H), 8.24 (d, 1H), 8.14 (s, 1H), 7.95 (d, 1H), 7.79–7.74 (m, 4H), 7.62 (dd, 1H), 7.31–7.25 (m, 3H), 6.93 (t, 1H), 4.68 (d, 1H), 4.52 (d, 1H), 3.34 (s, 3H), 2.13 (s, 3H); MS m/z 533.3 (M + 1). |
| 273 | 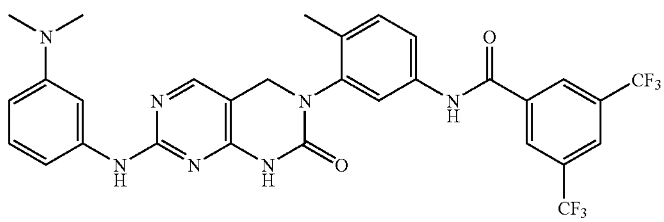 | $^1$H NMR 400 MHz (DMSO-$d_6$) δ 9.15 (s, 1H), 8.60 (s, 2H), 8.36 (s, 1H), 8.10 (s, 1H), 7.73 (d, 1H), 7.66 (d, 1H), 7.32 (d, 1H), 7.20 (s, 1H), 7.14 (d, 1H), 7.01 (t, 1H), 6.31 (dd, 1H), 4.68 (d, 1H), 4.50 (d, 1H), 2.86 (s, 6H), 2.16 (s, 3H); MS m/z 630.3 (M + 1). |
| 274 | 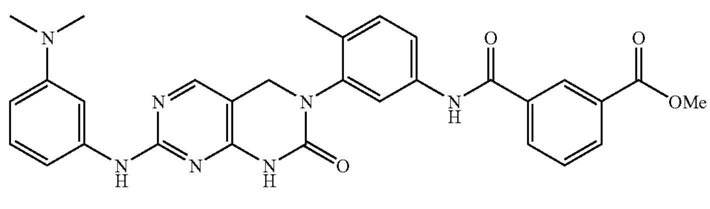 | $^1$H NMR 400 MHz (DMSO-$d_6$) δ 9.14 (s, 1H), 8.53 (s, 1H), 8.22 (d, 1H), 8.14 (d, 1H), 8.09 (s, 1H), 7.77 (d, 1H), 7.69 (d, 1H), 7.65 (d, 1H), 7.28 (d, 1H), 7.20 (t, 1H), 7.13 (d, 1H), 7.01 (t, 1H), 6.30 (d, 1H), 4.68 (d, 1H), 4.50 (d, 1H), 3.88 (s, 3H), 2.86 (s, 6H), 2.15 (s, 3H); MS m/z 552.2 (M + 1). |
| 275 | 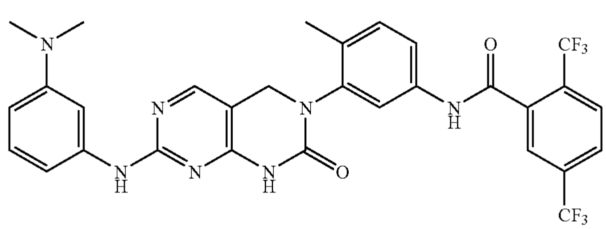 | $^1$H NMR 400 MHz (DMSO-$d_6$) δ 10.72 (s, 1H), 10.21 (s, 1H), 9.14 (s, 1H), 8.15 (s, 1H), 8.09 (s, 2H), 7.67 (s, 1H), 7.49 (d, 1H), 7.29 (d, 1H), 7.20 (s, 1H), 7.13 (d, 1H), 7.01 (t, 1H), 6.31 (dd, 1H), 4.66 (d, 1H), 4.48 (d, 1H), 2.86 (s, 6H), 2.14 (s, 3H); MS m/z 630.1 (M + 1). |

TABLE 1-continued

| Compound Number | Structure | Physical Data $^1$H NMR 400 MHz (DMSO-$d_6$) and/or MS (m/z) |
|---|---|---|
| 276 | 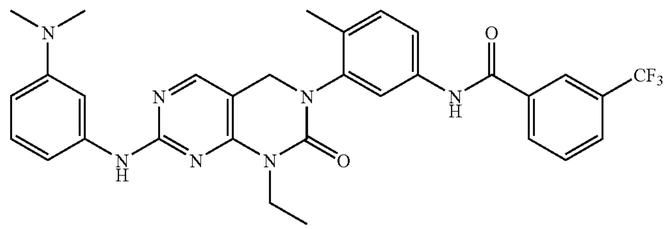 | $^1$H NMR 400 MHz (DMSO-$d_6$) δ 10.51 (s, 1H), 9.29 (s, 1H), 8.29 (s, 1H), 8.25 (d, 1H), 8.12 (s, 1H), 7.95 (d, 1H), 7.79–7.76 (m, 2H), 7.63 (dd, 1H), 7.30 (d, 1H), 7.20 (s, 1H), 7.08–7.03 (m, 2H), 6.34 (dd, 1H), 4.69 (d, 1H), 4.48 (d, 1H), 4.04 (q, 2H), 2.87 (s, 6H), 2.12 (s, 3H), 1.20 (t, 3H); MS m/z 590.3 (M + 1). |
| 277 | 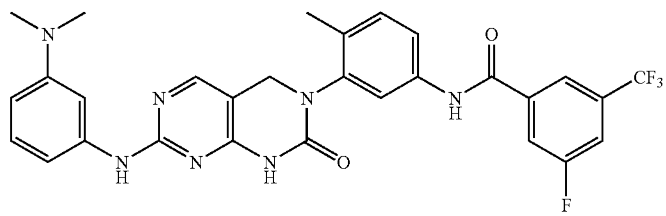 | $^1$H NMR 400 MHz (DMSO-$d_6$) δ 10.53 (s, 1H), 10.22 (s, 1H), 9.14 (s, 1H), 8.17 (s, 1H), 8.10 (d, 1H), 8.09 (s, 1H), 7.94 (d, 1H), 7.74 (s, 1H), 7.63 (dd, 1H), 7.31 (d, 1H), 7.20 (t, 1H), 7.13 (d, 1H), 7.01 (t, 1H), 6.31 (dd, 1H), 4.68 (d, 1H), 4.50 (d, 1H), 2.86 (s, 6H), 2.15 (s, 3H); MS m/z 580.2 (M + 1). |
| 278 | 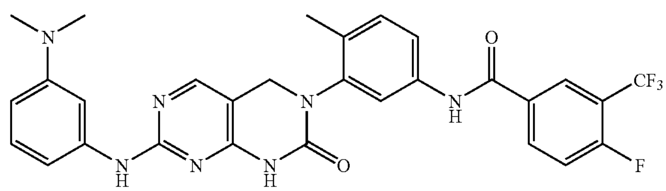 | $^1$H NMR 400 MHz (DMSO-$d_6$) δ 10.49 (s, 1H), 10.22 (s, 1H), 9.14 (s, 1H), 8.36–8.33 (m, 2H), 8.09 (s, 1H), 7.73 (s, 1H), 7.70 (d, 1H), 7.61 (d, 1H), 7.30 (d, 1H), 7.20 (t, 1H), 7.14 (d, 1H), 7.01 (t, 1H), 6.31 (dd, 1H), 4.68 (d, 1H), 4.50 (d, 1H), 2.86 (s, 6H), 2.15 (s, 3H); MS m/z 580.2 (M + 1). |
| 279 | 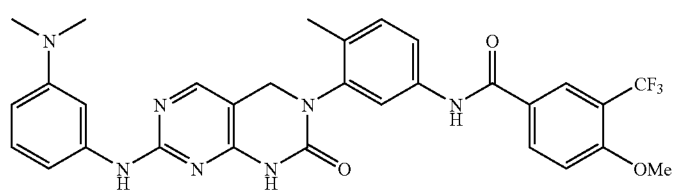 | $^1$H NMR 400 MHz (DMSO-$d_6$) δ 10.33 (s, 1H), 10.21 (s, 1H), 9.14 (s, 1H), 8.28–8.24 (m, 2H), 8.09 (s, 1H), 7.73 (s, 1H), 7.63 (dd, 1H), 7.41 (d, 1H), 7.28 (d, 1H), 7.20 (t, 1H), 7.14 (d, 1H), 7.01 (t, 1H), 6.31 (dd, 1H), 4.68 (d, 1H), 4.50 (d, 1H), 3.97 (s, 6H), 2.86 (s, 6H), 2.14 (s, 3H); MS m/z 592.3 (M + 1). |
| 280 | 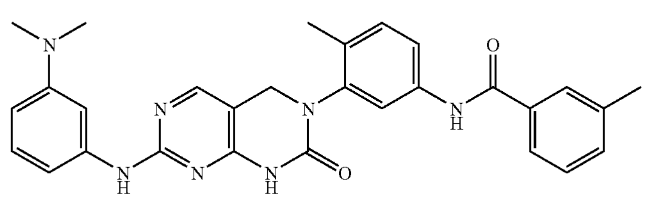 | $^1$H NMR 400 MHz (DMSO-$d_6$) δ 10.23 (s, 1H), 10.22 (s, 1H), 9.16 (s, 1H), 8.10 (m, 1H), 7.78–7.76 (m, 3H), 7.62 (dd, 1H), 7.40 (s, 1H), 7.39 (s, 1H), 7.26 (d, 1H), 7.21 (t, 1H), 7.13 (d, 1H), 7.01 (t, 1H), 6.31 (dd, 1H), 4.68 (d, 1H), 4.49 (d, 1H), 3.97 (s, 6H), 2.86 (s, 6H), 2.38 (s, 3H), 2.14 (s, 3H); MS m/z 508.2 (M + 1). |

TABLE 1-continued

| Compound Number | Structure | Physical Data $^1$H NMR 400 MHz (DMSO-d$_6$) and/or MS (m/z) |
|---|---|---|
| 281 | 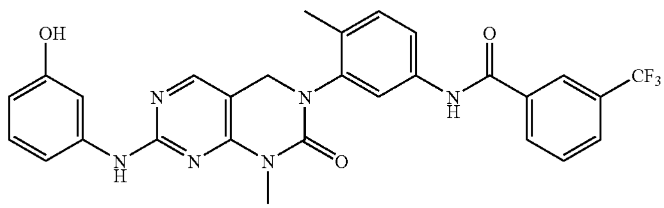 | $^1$H NMR 400 MHz (DMSO-d$_6$) δ 10.51 (s, 1H), 9.43 (s, 1H), 9.22 (s, 1H), 8.29 (s, 1H), 8.25 (d, 1H), 8.12 (s, 1H), 7.96 (d, 1H), 7.80–7.77 (m, 2H), 7.62 (dd, 1H), 7.29–7.31 (m, 2H), 7.13 (d, 1H), 7.02 (t, 1H), 6.34 (d, 1H), 4.68 (d, 1H), 4.51 (d, 1H), 3.34 (s, 3H), 2.12 (s, 3H); MS m/z 549.2 (M + 1). |
| 282 | 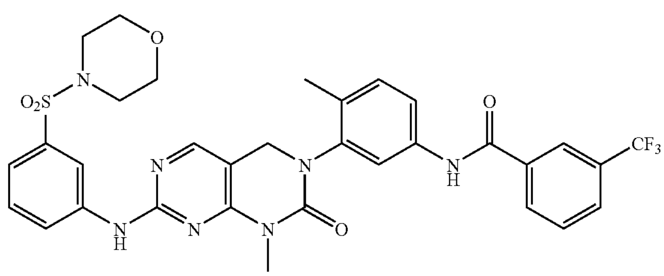 | $^1$H NMR 400 MHz (DMSO-d$_6$) δ 10.50 (s, 1H), 10.01 (s, 1H), 8.53 (s, 1H), 8.29 (s, 1H), 8.25 (d, 1H), 8.20 (s, 1H), 7.95 (d, 1H), 7.90 (d, 1H), 7.80–7.78 (m, 2H), 7.62 (dd, 1H), 7.55 (t, 1H), 7.30 (d, 1H), 7.26 (d, 1H), 4.71 (d, 1H), 4.54 (d, 1H), 3.62 (m, 4H), 3.37 (s, 3H), 2.87 (m, 4H), 2.13 (s, 3H); MS m/z 682.3 (M + 1). |
| 283 | 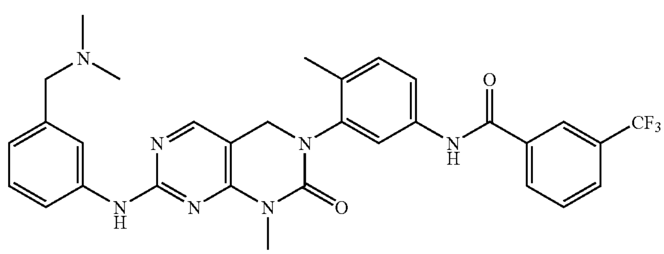 | $^1$H NMR 400 MHz (CD$_3$CN) δ 8.84 (s, 1H), 8.15 (s, 1H), 8.08 (d, 1H), 7.94 (s, 1H), 7.80 (d, 1H), 7.73–7.69 (m, 3H), 7.64 (t, 1H), 7.47 (dd, 2H), 7.23 (d, 1H), 7.19 (t, 1H), 6.87 (d, 1H), 4.61 (d, 1H), 4.39 (d, 1H), 3.34 (s, 2H), 3.32 (s, 3H), 2.13 (s, 6H), 2.10 (s, 3H); MS m/z 590.2 (M + 1). |
| 284 | 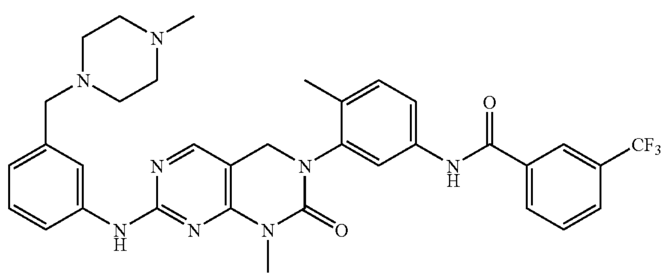 | $^1$H NMR 400 MHz (CD$_3$CN) δ 8.91 (s, 1H), 8.23 (s, 1H), 8.18 (d, 1H), 8.02 (s, 1H), 7.88 (d, 1H), 7.79–7.77 (m, 3H), 7.72 (t, 1H), 7.56 (d, 1H), 7.54 (d, 1H), 7.32 (d, 1H), 7.27 (t, 1H), 6.95 (d, 1H), 4.70 (d, 1H), 4.49 (d, 1H), 3.48 (s, 2H), 3.41 (s, 3H), 2.50–2.30 (br, 8H), 2.20 (s, 3H), 2.19 (s, 3H); MS m/z 645.3 (M + 1). |
| 285 | 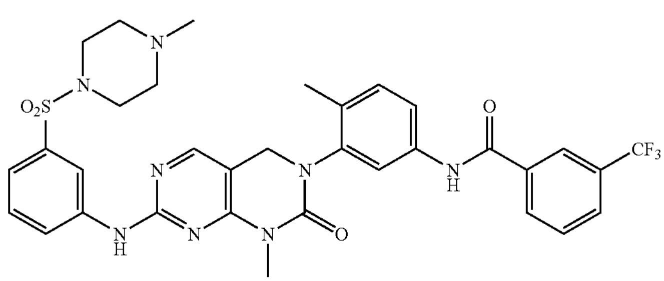 | $^1$H NMR 600 MHz (DMSO-d$_6$) δ 10.54 (s, 1H), 10.10 (s, 1H), 9.50 (br, 1H), 8.58 (s, 1H), 8.30 (s, 1H), 8.27 (d, 1H, J = 8.0 Hz), 8.23 (s, 1H), 7.98 (d, 1H, J = 7.8 Hz), 7.93 (d, 1H, J = 8.1 Hz), 7.84 (d, 1H, J = 1.9 Hz), 7.80 (t, 1H, J = 7.8 Hz), 7.63 (d, 1H, J = 8.5 Hz), 7.61 (t, 1H, J = 8.1 Hz), 7.33 (d, 1H, J = 8.4 Hz), 4.75 (d, 1H, J = 14.3 Hz), 4.57 (d, 1H, J = 14.2 Hz), 3.84 (m, 2H), 3.48 (m, 2H), 3.40 (s, 3H), 3.17 (m, 2H), 2.80 (s, 3H), 2.60 (m, 2H), 2.15 (s, 3H); MS m/z 695.2 (M + 1). |

TABLE 1-continued

| Compound Number | Structure | Physical Data $^1$H NMR 400 MHz (DMSO-$d_6$) and/or MS (m/z) |
|---|---|---|
| 286 | 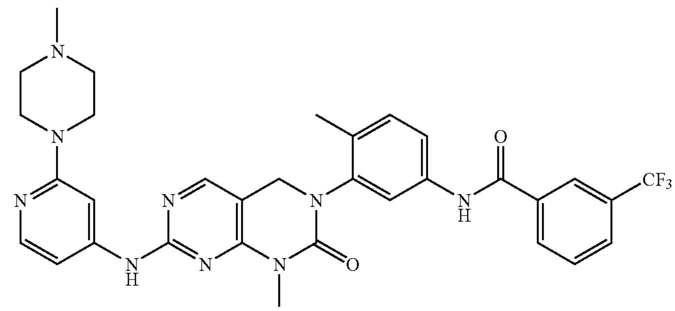 | $^1$H NMR 600 MHz (DMSO-$d_6$) δ 10.56 (s, 1H), 10.50 (br, 1H), 10.25 (br, 1H), 8.31 (s, 2H), 8.27 (d, 1H, J = 8.0 Hz), 8.03 (d, 1H, 6.8 Hz), 7.98 (d, 1H, J = 7.8 Hz), 7.87 (s, 1H), 7.80 (m, 2H), 7.62 (d, 1H, J = 8.2 Hz), 7.33 (d, 1H, J = 8.3 Hz), 7.22 (s, 1H), 4.78 (d, 1H, J = 14.4 Hz), 4.62 (d, 1H, J = 14.5 Hz), 4.20 (m, 2H), 3.96 (m, 4H), 3.17 (m, 2H), 3.40 (s, 3H), 2.87 (s, 3H), 2.15 (s, 3H); MS m/z 632.2 (M + 1). |
| 287 | 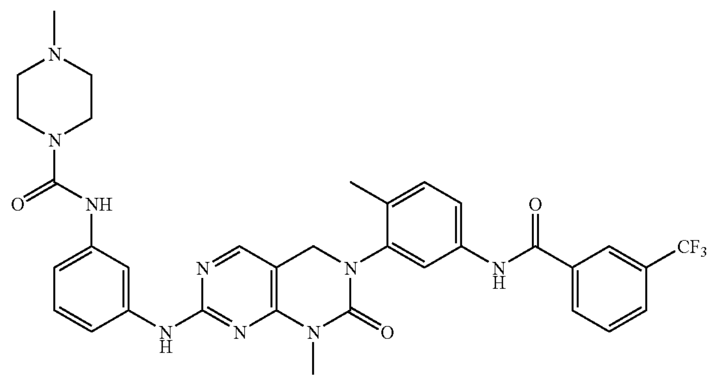 | $^1$H NMR 400 MHz (CD$_3$CN) δ 8.85 (s, 1H), 8.15 (s, 1H), 8.09 (d, 1H), 7.93 (s, 1H), 7.83 (s, 1H), 7.81 (d, 1H), 7.75 (s, 1H), 7.65 (t, 1H), 7.45 (d, 1H), 7.34 (s, 1H), 7.24 (s, 1H), 7.20 (t, 1H), 7.00 (d, 1H), 4.63 (d, 1H), 4.41 (d, 1H), 4.11 (br, 2H), 3.37 (br, 2H), 3.34 (s, 3H), 3.25 (br, 2H), 2.88 (br, 2H), 2.71 (s, 3H), 2.11 (s, 3H); MS m/z 674.3 (M + 1). |
| 288 | 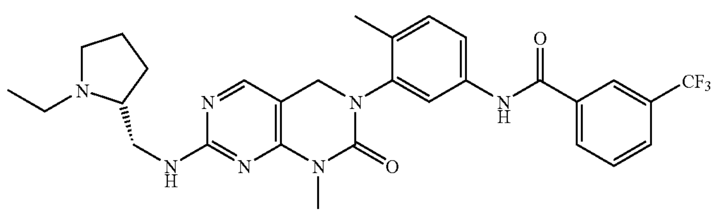 | $^1$H NMR 400 MHz (DMSO-$d_6$) δ 10.48 (s, 1H), 8.28 (s, 1H), 8.24 (d, 1H), 7.95 (d, 1H), 7.94 (s, 1H), 7.77 (t, 1H), 7.73 (s, 1H), 7.61 (dd, 1H), 6.93 (d, 1H), 4.59 (d, 1H), 4.40 (d, 1H), 3.48 (m, 1H), 3.25 (s, 3H), 3.04 (m, 2H), 2.90 (m, 1H), 2.10 (s, 3H), 1.80 (m, 1H), 1.62 (m, 3H), 1.04 (t, 3H); MS m/z 568.2 (M + 1). |
| 289 | 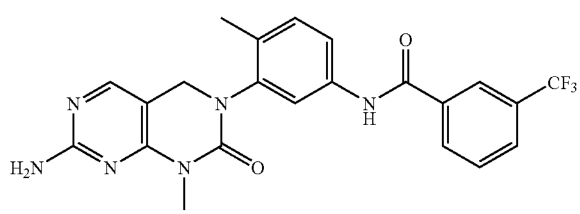 | $^1$H NMR 600 MHz (DMSO-$d_6$) δ 10.50 (s, 1H), 8.30 (s, 1H), 8.26 (d, 1H, J = 7.8 Hz), 7.97 (d, 1H, J = 7.8 Hz), 7.93 (s, 1H), 7.79 (t, 1H, J = 7.8 Hz), 7.75 (d, 2H, J = 2.0 Hz), 7.64 (dd, 1H, J = 8.3, 2.0 Hz), 7.30 (d, 1H, J = 8.4 Hz), 6.57 (s, 2H), 4.59 (d, 1H, J = 13.7 Hz), 4.42(d, 1H, J = 13.7 Hz), 3.29 (s, 3H), 2.12 (s, 3H); MS m/z 457.1 (M + 1). |
| 290 | 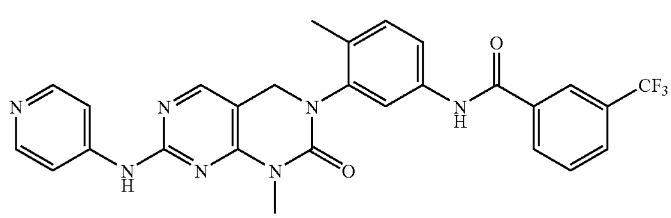 | $^1$H NMR 600 MHz (DMSO-$d_6$) δ 10.53 (s, 1H), 10.12 (s, 1H), 8.37 (d, 1H, J = 6.2 Hz), 8.31 (s, 1H), 8.27 (d, 1H, J = 8.0 Hz), 8.25 (s, 1H), 7.98 (d, 1H, J = 7.8 Hz), 7.82–7.78 (m, 3H), 7.64 (dd, 1H, J = 8.3, 1.7 Hz), 7.33 (d, 1H, J = 8.4 Hz), 4.75 (d, 1H, J = 14.1 Hz), 4.59 (d, 1H, J = 14.1 Hz), 3.39 (s, 3H), 2.15 (s, 3H); MS m/z 534.1 (M + 1). |

TABLE 1-continued

| Compound Number | Structure | Physical Data $^1$H NMR 400 MHz (DMSO-d$_6$) and/or MS (m/z) |
|---|---|---|
| 291 | 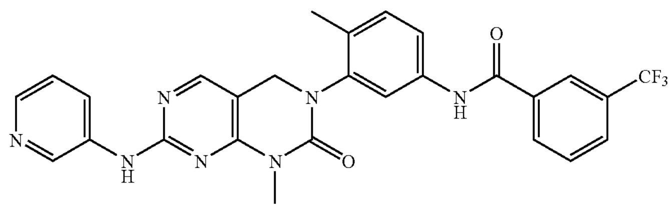 | $^1$H NMR 600 MHz (DMSO-d$_6$) δ 10.52 (s, 1H), 9.76 (s, 1H), 8.92 (d, 1H, J = 2.5 Hz), 8.31 (s, 1H), 8.27 (d, 1H, J = 7.9 Hz), 8.22 (dt, 1H, 7.0, 2.4 Hz), 8.19 (s, 1H), 8.16 (dd, 1H, J = 4.6, 1.2 Hz), 7.98 (d, 1H, J = 7.8 Hz), 7.81–7.78 (m, 2H), 7.64 (dd, 1H, J = 8.3, 2.1 Hz), 7.33 (d, 1H, J = 8.2 Hz), 7.32 (d, 1H, J = 8.3 Hz), 4.72 (d, 1H, J = 14.1 Hz), 4.55 (d, 1H, J = 14.1 Hz), 3.33 (s, 3H), 2.15 (s, 3H); MS m/z 534.2 (M + 1). |
| 292 | 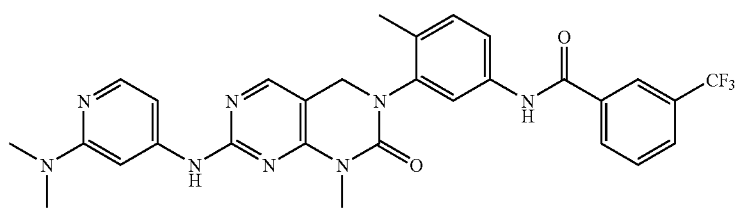 | $^1$H NMR 600 MHz (DMSO-d$_6$) δ 10.53 (s, 1H), 9.72 (s, 1H), 8.30 (s, 1H), 8.27 (d, 1H), 8.20 (s, 1H), 7.98 (d, 1H), 7.88 (d, 1H), 7.78 (m, 2H), 7.64 (dd, 1H), 7.33 (d, 1H), 7.28 (s, 1H), 6.90 (d, 1H), 4.75 (d, 1H, J = 14.1 Hz), 4.59 (d, 1H, J = 14.1 Hz), 3.39 (s, 3H), 3.00 (s, 6H), 2.15 (s, 3H); MS m/z 577.2 (M + 1). |
| 293 | 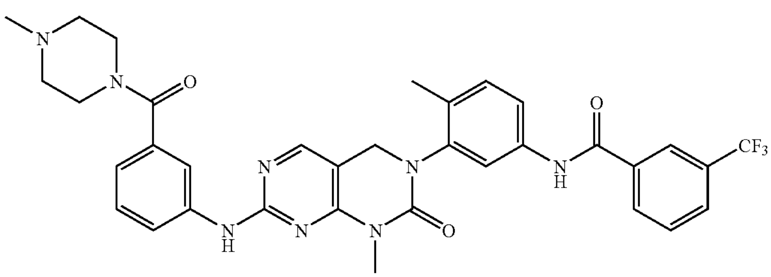 | $^1$H NMR 600 MHz (DMSO-d$_6$) δ 10.53 (s, 1H), 9.96 (br, 1H), 9.78 (s, 1H), 8.30 (s, 1H), 8.27 (d, 1H, J = 7.9 Hz), 8.19 (s, 1H), 7.98 (d, 1H, J = 7.8 Hz), 7.91 (s, 1H), 7.87 (d, 1H, J = 9.0 Hz), 7.83 (s, 1H), 7.78 (t, 1H, J = 7.8 Hz), 7.62 (dd, 1H, J = 8.2, 1.8 Hz), 7.40 (t, 1H, J = 7.8 Hz), 7.33 (d, 1H, J = 8.4 Hz), 7.03 (d, 1H, 8.5 Hz), 4.73 (d, 1H, J = 14.1 Hz), 4.55 (d, 1H, J = 14.1 Hz), 3.74 (m, 2H), 3.56 (m, 4H), 3.36 (s, 3H), 3.17 (m, 2H), 2.84 (s, 3H), 2.15 (s, 3H); MS m/z 659.2 (M + 1). |
| 294 | 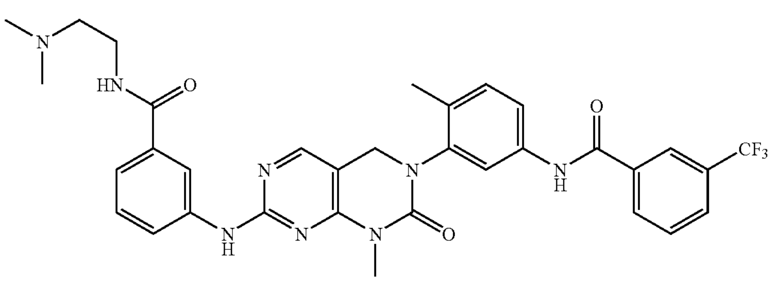 | $^1$H NMR 600 MHz (DMSO-d$_6$) δ 10.54 (s, 1H), 9.78 (s, 1H), 9.39 (br, 1H), 8.61 (t, 1H, J = 5.5 Hz), 8.44 (s, 1H), 8.31 (s, 1H), 8.27 (d, 1H, J = 7.8 Hz), 7.18 (s, 1H), 7.98 (d, 1H, J = 7.8 Hz), 7.84 (d, 1H, J = 8.1 Hz), 7.83 (s, 1H), 7.80 (t, 1H, J = 7.9 Hz), 7.63 (dd, 1H, J = 8.2, 1.8 Hz), 7.43 (d, 1H, J = 7.7 Hz), 7.40 (t, 1H, J = 7.8 Hz), 7.33 (d, 1H, 8.4 Hz), 4.73 (d, 1H, J = 14.1 Hz), 4.55 (d, 1H, J = 14.1 Hz), 3.61 (m, 2H), 3.38 (s, 3H), 3.27 (m, 2H), 2.86 (s, 6H), 2.15 (s, 3H); MS m/z 647.2 (M + 1). |

| Compound Number | Structure | Physical Data<br>$^1$H NMR 400 MHz<br>(DMSO-$d_6$) and/or MS (m/z) |
|---|---|---|
| 295 | 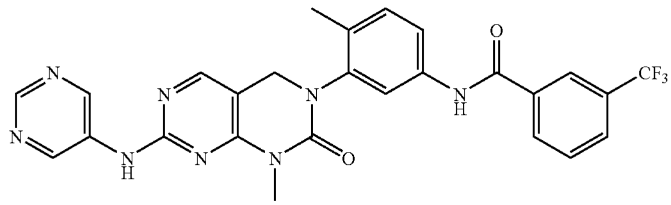 | $^1$H NMR 600 MHz (DMSO-$d_6$) δ 10.53 (s, 1H), 9.98 (s, 1H), 9.17 (s, 2H), 8.76 (s, 1H), 8.29 (s, 1H), 8.25 (d, 1H, J = 7.5 Hz), 8.21 (s, 1H), 7.96 (d, 1H, J = 7.2 Hz), 7.79 (m, 2H), 7.63 (d, 1H, J = 7.2 Hz), 7.30 (d, 1H, J = 7.8 Hz), 4.73 (d, 1H, J = 13.5 Hz), 4.55 (d, 1H, J = 13.5 Hz), 3.34 (s, 3H), 2.13 (s, 3H); MS m/z 535.2 (M + 1). |
| 296 | 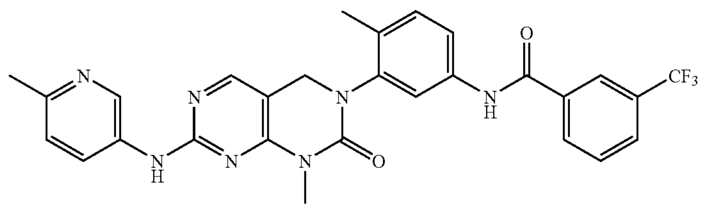 | $^1$H NMR 600 MHz (DMSO-$d_6$) δ 10.57 (s, 1H), 10.42 (s, 1H), 9.24 (s, 1H), 8.49 (d, 1H, J = 9.1 Hz), 8.35 (s, 1H), 8.28–8.33 (m, 2H), 8.28 (s, 1H), 7.97 (d, 1H, J = 7.9 Hz), 7.85 (s, 1H), 7.80 (t, 1H, J = 8.0 Hz), 7.63 (d, 1H, J = 8.2 Hz), 7.33 (d, 1H, J = 8.4 Hz), 4.77 (d, 1H, J = 14.3 Hz), 4.60 (d, 1H, J = 14.3 Hz), 3.36 (s, 3H), 2.65 (s, 3H), 2.15 (s, 3H); MS m/z 548.2 (M + 1). |
| 297 | 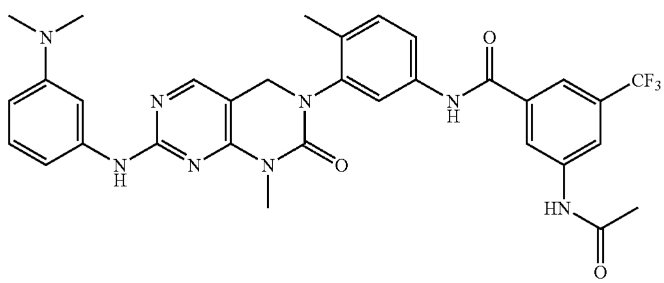 | $^1$H NMR (DMSO-$d_6$) δ 10.51 (s, 1H), 10.48 (s, 1H) 9.34 (s, 1H), 8.30 (m, 2H), 8.14 (s, 1H), 8.00 (s, 1H), 7.78 (d, J = 1.9 Hz, 1H), 7.64 (dd, J = 8.2, 1.8 Hz, 1H), 7.31 (m, 2H), 7.06 (m, 2H), 6.36 (d, J = 6.7 Hz, 1H), 4.70 (d, J = 14 Hz, 1H), 4.53 (d, J = 14 Hz, 1H), 3.37 (s, 3H), 2.90 (s, 6H), 2.28 (s, 3H), 2.15 (s, 3H); m/z [M$^+$ + 1] 633.2. |
| 298 | 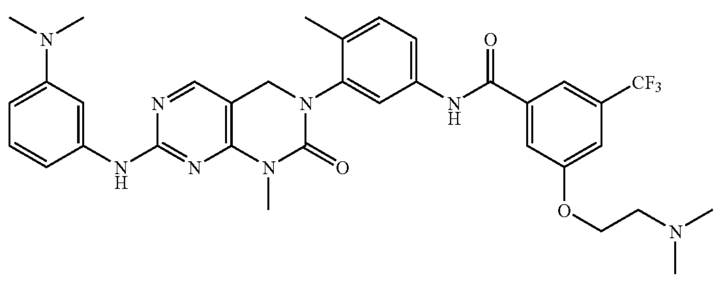 | $^1$H NMR (DMSO-$d_6$) δ 10.47 (s, 1H), 9.34 (s, 1H), 8.14 (s, 1H), 7.91 (s, 1H), 7.84 (s, 1H), 7.77 (d, J = 2.0 Hz, 1H), 7.66 (dd, J = 8.2, 2.0 Hz, 1H), 7.51 (s, 1H), 7.32 (m, 2H), 7.07 (m, 2H), 6.35 (d, J = 7.6 Hz, 1H), 4.69 (d, J = 14.0 Hz, 1H), 4.52 (d, J = 14.0 Hz, 1H), 4.32 (t, J = 5.4 Hz, 2H), 2.95 (bs, 2H), 2.90 (s, 6H), 2.50 (s, 3H), 2.44 (s, 6H), 2.15 (s, 3H); m/z [M$^+$ + 1]663.3. |
| 299 | 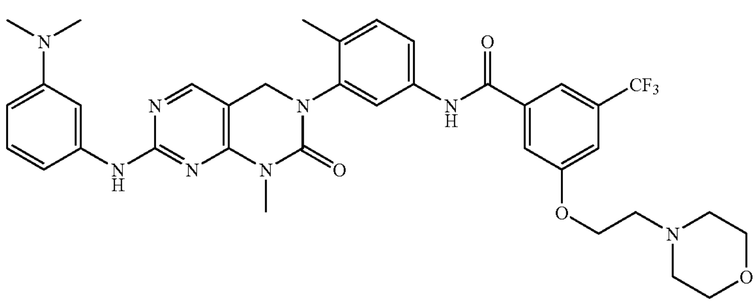 | $^1$H NMR (DMSO-$d_6$) δ 10.46 (s, 1H), 9.34 (s, 1H), 8.14 (s, 1H), 7.87 (s, 1H), 7.84 (s, 1H), 7.78 (d, J = 2.0 Hz, 1H), 7.66 (dd, J = 8.3, 2.0 Hz, 1H), 7.50 (s, 1H), 7.32 (d, J = 2.5 Hz, 1H), 7.31 (s, 1H), 7.06 (m, 2H), 6.35 (m, 1H), 4.69 (d, J = 14 Hz, 1H), 4.52 (d, J = 14 Hz, 1H), 4.27 (t, J = 5.6 Hz, 2H), 3.58 (m, 4H), 3.32 (s, 3H), 2.88 (s, 6H), 2.74 (m, 2H), 2.50 (m, 4H), 2.15 (s, 3H); m/z [M$^+$ + 1] 705.3. |

TABLE 1-continued

| Compound Number | Structure | Physical Data $^1$H NMR 400 MHz (DMSO-d$_6$) and/or MS (m/z) |
|---|---|---|
| 300 | 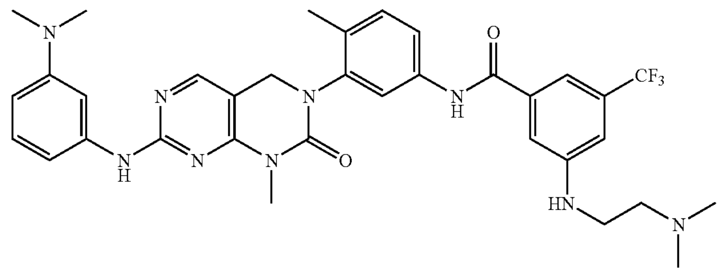 | $^1$H NMR (DMSO-d$_6$) δ 10.44 (s, 1H), 9.34 (s, 1H), 8.15 (s, 1H), 7.81 (d, J = 2.0 Hz, 1H), 7.69 (dd, J = 8.3, 2.0 Hz, 1H), 7.50 (s, 1H), 7.45 (s, 1H), 7.31 (m, 2H), 7.09 (s, 1H), 7.06 (m, 2H), 6.67 (m, 1H), 6.35 (d, J = 7.3 Hz, 1H), 4.69 (d, J = 14 Hz, 1H), 4.52 (d, J = 14 Hz, 1H), 3.56 (m, 2H), 3.37 (s, 3H), 3.15 (bs, 2H), 2.90 (s, 6H), 2.79 (bs, 6H), 2.14 (s, 3H); m/z [M$^+$ + 1] 662.3. |
| 301 | 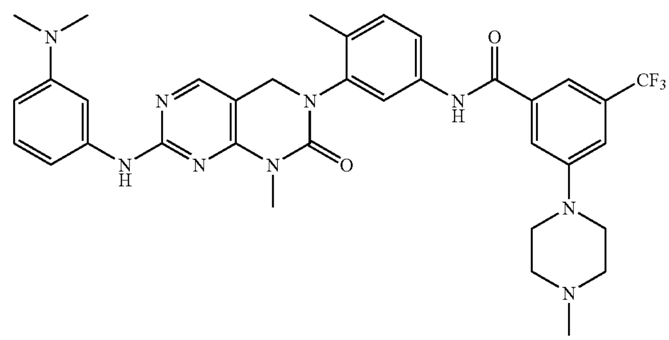 | $^1$H NMR (DMSO-d$_6$) δ 10.43 (s, 1H), 9.34 (s, 1H), 8.15 (s, 1H), 7.81 (m, 2H), 7.66 (d, J = 6.2 Hz, 1H), 7.65 (m, 1H), 7.45 (s, 1H), 7.32 (m, 2H), 7.06 (m, 2H), 6.36 (d, J = 7.5 Hz, 1H), 4.69 (d, J = 14 Hz, 1H), 3.44 (s, 3H), 3.31 (s, 3H), 3.09 (m, 2H), 2.90 (s, 6H), 2.68 (bs, 4H), 2.44 (bs, 2H), 2.15 (s, 3H); m/z [M$^+$ + 1] 674.3. |
| 302 | 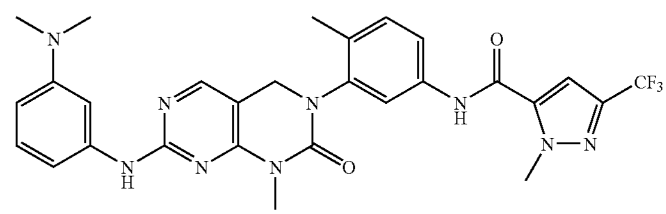 | $^1$H NMR (DMSO-d$_6$) δ 10.45 (s, 1H), 9.34 (s, 1H), 8.14 (s, 1H), 7.76 (d, J = 1.9 Hz, 1H), 7.56 (dd, J = 8.2, 2.0 Hz, 1H), 7.51 (s, 1H), 7.33 (s, 1H), 7.32 (s, 1H), 7.06 (m, 2H), 6.35 (d, J = 7.6 Hz, 1H), 4.69 (d, J = 14.0 Hz, 1H), 4.51 (d, J = 14.0 Hz, 1H), 3.35 (s, 3H), 2.90 (s, 6H), 2.14 (s, 3H); m/z [M$^+$ + 1] 580.2. |

Assays

Compounds of the present invention are assayed to measure their capacity to selectively inhibit cell proliferation of 32D cells expressing BCR-Abl (32D-p210) compared with parental 32D cells. Compounds selectively inhibiting the proliferation of these BCR-Abl transformed cells are tested for anti-proliferative activity on Ba/F3 cells expressing either wild type or the mutant forms of Bcr-abl. In addition, compounds are assayed to measure their capacity to inhibit Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and Tie2 kinases.

Inhibition of Cellular BCR-Abl Dependent Proliferation (High Throughput Method)

The murine cell line used is the 32D hemopoietic progenitor cell line transformed with BCR-Abl cDNA (32D-p210). These cells are maintained in RPMI/10% fetal calf serum (RPMI/FCS) supplemented with penicillin 50 μg/mL, streptomycin 50 μg/mL and L-glutamine 200 mM. Untransformed 32D cells are similarly maintained with the addition of 15% of WEHI conditioned medium as a source of IL3.

50 μl of a 32D or 32D-p210 cells suspension are plated in Greiner 384 well microplates (black) at a density of 5000 cells per well. 50 nl of test compound (1 mM in DMSO stock solution) is added to each well (STI571 is included as a positive control). The cells are incubated for 72 hours at 37° C., 5% CO$_2$. 10 μl of a 60% Alamar Blue solution (Tek diagnostics) is added to each well and the cells are incubated for an additional 24 hours. The fluorescence intensity (Excitation at 530 nm, Emission at 580 nm) is quantified using the Acquest™ system (Molecular Devices).

Inhibition of Cellular BCR-Abl Dependent Proliferation 32D-p210 cells are plated into 96 well TC plates at a density of 15,000 cells per well. 50 μL of two fold serial dilutions of the test compound (C$_{max}$ is 40 μM) are added to each well (ST1571 is included as a positive control). After incubating the cells for 48 hours at 37° C., 5% CO$_2$, 15 μL of MTT (Promega) is added to each well and the cells are incubated for an additional 5 hours. The optical density at 570 nm is quantified spectrophotometrically and IC$_{50}$ values, the concentration of compound required for 50% inhibition, determined from a dose response curve.

Effect on Cell Cycle Distribution 32D and 32D-p210 cells are plated into 6 well TC plates at 2.5×10$^6$ cells per well in 5 ml of medium and test compound at 1 or 10 μM is added (STI571 is included as a control). The cells are then incubated for 24 or 48 hours at 37° C., 5% $CO_2$. 2 ml of cell suspension is washed with PBS, fixed in 70% EtOH for 1 hour and treated with PBS/EDTA/RNase A for 30 minutes. Propidium iodide (Cf=10 μg/ml) is added and the fluorescence intensity is quantified by flow cytometry on the FACScalibur™ system (BD Biosciences). Test compounds of the present invention demonstrate an apoptotic effect on the 32D-p210 cells but do not induce apoptosis in the 32D parental cells.

Effect on Cellular BCR-Abl Autophosphorylation

BCR-Abl autophosphorylation is quantified with capture Elisa using a c-abl specific capture antibody and an antiphosphotyrosine antibody. 32D-p210 cells are plated in 96 well TC plates at $2\times10^5$ cells per well in 50 μL of medium. 50 μL of two fold serial dilutions of test compounds ($C_{max}$ is 10 μM) are added to each well (STI571 is included as a positive control). The cells are incubated for 90 minutes at 37° C., 5% $CO_2$. The cells are then treated for 1 hour on ice with 150 μL of lysis buffer (50 mM Tris-HCl, pH 7.4, 150 mM NaCl, 5 mM EDTA, 1 mM EGTA and 1% NP-40) containing protease and phosphatase inhibitors. 50 μL of cell lysate is added to 96 well optiplates previously coated with anti-abl specific antibody and blocked. The plates are incubated for 4 hours at 4° C. After washing with TBS-Tween 20 buffer, 50 μL of alkaline-phosphatase conjugated anti-phosphotyrosine antibody is added and the plate is further incubated overnight at 4° C. After washing with TBS-Tween 20 buffer, 90 μL of a luminescent substrate are added and the luminescence is quantified using the Acquest™ system (Molecular Devices). Test compounds of the invention that inhibit the proliferation of the BCR-Abl expressing cells, inhibit the cellular BCR-Abl autophosphorylation in a dose-dependent manner.

Effect on Proliferation of Cells Expressing Mutant Forms of Bcr-abl

Compounds of the invention are tested for their antiproliferative effect on Ba/F3 cells expressing either wild type or the mutant forms of BCR-Abl (G250E, E255V, T315I, F317L, M351T) that confers resistance or diminished sensitivity to STI571. The antiproliferative effect of these compounds on the mutant-BCR-Abl expressing cells and on the non transformed cells were tested at 10, 3.3, 1.1 and 0.37 μM as described above (in media lacking IL3). The $IC_{50}$ values of the compounds lacking toxicity on the untransformed cells were determined from the dose response curves obtained as describe above.

b-Raf

Compounds of the invention are tested for their ability to inhibit the activity of b-Raf. The assay is carried out in 384-well MaxiSorp plates (NUNC) with black walls and clear bottom. The substrate, IκBα is diluted in DPBS (1:750) and 15 μl is added to each well. The plates are incubated at 4° C. overnight and washed 3 times with TBST (25 mM Tris, pH 8.0, 150 mM NaCl and 0.05% Tween-20) using the EMBLA plate washer. Plates are blocked by Superblock (15 μl/well) for 3 hours at room temperature, washed 3 times with TBST and pat-dried. Assay buffer containing 20 μM ATP (10 μl) is added to each well followed by 100 nl or 500 nl of compound. B-Raf is diluted in the assay buffer (1 μl into 25 μl) and 10 μl of diluted b-Raf is added to each well (0.4 μg/well). The plates are incubated at room temperature for 2.5 hours. The kinase reaction is stopped by washing the plates 6 times with TBST. Phosph-IκBα (Ser32/36) antibody is diluted in Superblock (1:10, 000) and 15 μl is added to each well. The plates are incubated at 4° C. overnight and washed 6 times with TBST. AP-conjugated goat-anti-mouse IgG is diluted in Superblock (1:1,500) and 15 μl is added to each well. Plates are incubated at room temperature for 1 hour and washed 6 times with TBST. 15 μl of Attophos AP substrate is added to each well and plates are incubated at room temperature for 15 minutes. Plates are read on Acquest or Analyst GT using a Fluorescence Intensity Nanxin BBT anion (505 dichroic mirror).

FGFR3 (Enzymatic Assay)

Kinase activity assay with purified FGFR3 (Upstate) is carried out in a final volume of 10 μL containing 0.25 μg/mL of enzyme in kinase buffer (30 mM Tris-HCl pH7.5, 15 mM $MgCl_2$, 4.5 mM $MnCl_2$, 15 μM $Na_3VO_4$ and 50 μg/mL BSA), and substrates (5 μg/mL biotin-poly-EY(Glu, Tyr) (CIS-US, Inc.) and 3 μM ATP). Two solutions are made: the first solution of 5 μl contains the FGFR3 enzyme in kinase buffer was first dispensed into 384-format Proxiplate® (Perkin-Elmer) followed by adding 50 nL of compounds dissolved in DMSO, then 5 μl of second solution containing the substrate (poly-EY) and ATP in kinase buffer was added to each well. Reactions are incubated at room temperature for one hour, stopped by adding 10 μL of HTRF detection mixture, which contains 30 mM Tris-HCl pH7.5, 0.5 M KF, 50 mM EDTA, 0.2 mg/mL BSA, 15 μg/mL streptavidin-XL665 (CIS-US, Inc.) and 150 ng/mL cryptate conjugated anti-phosphotyrosine antibody (CIS-US, Inc.). After one hour of room temperature incubation to allow for streptavidin-biotin interaction, time resolved florescent signals are read on Analyst GT (Molecular Devices Corp.). $IC_{50}$ values are calculated by linear regression analysis of the percentage inhibition of each compound at 12 concentrations (1:3 dilution from 50 μM to 0.28 nM).

FGFR3 (Cellular Assay)

Compounds of the invention are tested for their ability to inhibit transformed Ba/F3-TEL-FGFR3 cell proliferation, which is depended on FGFR3 cellular kinase activity. Ba/F3-TEL-FGFR3 are cultured up to 800,000 cells/mL in suspension, with RPMI 1640 supplemented with 10% fetal bovine serum as the culture medium. Cells are dispensed into 384-well format plate at 5000 cell/well in 50 μL culture medium. Compounds of the invention are dissolved and diluted in dimethylsufoxide (DMSO). Twelve points 1:3 serial dilutions are made into DMSO to create concentrations gradient ranging typically from 10 mM to 0.05 μM. Cells are added with 50 nL of diluted compounds and incubated for 48 hours in cell culture incubator. Alamar-Blue® (TREK Diagnostic Systems), which can be used to monitor the reducing environment created by proliferating cells, is added to cells at final concentration of 10%. After additional four hours of incubation in a 37° C. cell culture incubator, fluorescence signals from reduced AlamarBlue® Excitation at 530 nm, Emission at 580 nm) are quantified on Analyst GT (Molecular Devices Corp.). $IC_{50}$ values are calculated by linear regression analysis of the percentage inhibition of each compound at 12 concentrations.

FLT3 (Cellular Assay)

The effects of compounds of the invention on the cellular activity of FLT3 are conducted using identical methods as described above for FGFR3 cellular activity, except that Ba/F3-FLT3-ITD is used instead of Ba/F3-TEL-FGFR3.

Upstate KinaseProfiler™—Radio-Enzymatic Filter Binding Assay

Compounds of the invention are assessed for their ability to inhibit individual members of a panel of kinases (a partial, non-limiting list of kinases includes: Abl, Bmx, c-Raf, CSK, BCR-Abl, JNK, Trk, FGFR3, Fes, Ikk, IR, Lck, Mkk, PKC, PKD, Rsk, SAPK, Syk, BTK, Src, EGFR, IGF, Mek, Ros and Tie2). The compounds are tested in duplicates at a final concentration of 10 μM following this generic protocol. Note that the kinase buffer composition and the substrates vary for the different kinases included in the "Upstate KinaseProfiler™" panel. The compounds are tested in duplicates at a final concentration of 10 μM following this generic protocol. Note that the kinase buffer composition and the substrates vary for the different kinases included in the "Upstate KinaseProfiler™" panel. Kinase buffer (2.5 μL, 10×—containing MnCl$_2$ when required), active kinase (0.001-0.01 Units; 2.5 μL), specific or Poly(Glu4-Tyr) peptide (5-500 μM or 0.01 mg/ml) in kinase buffer and kinase buffer (50 μM; 5 μL) are mixed in an eppendorf on ice. A Mg/ATP mix (10 μL; 67.5 (or 33.75) mM MgCl$_2$, 450 (or 225) μM ATP and 1 μCi/μl [γ-$^{32}$P]-ATP (3000 Ci/mmol)) is added and the reaction is incubated at about 30° C. for about 10 minutes. The reaction mixture is spotted (20 μL) onto a 2 cm×2 cm P81 (phosphocellulose, for positively charged peptide substrates) or Whatman No. 1 (for Poly (Glu4-Tyr) peptide substrate) paper square. The assay squares are washed 4 times, for 5 minutes each, with 0.75% phosphoric acid and washed once with acetone for 5 minutes. The assay squares are transferred to a scintillation vial, 5 ml scintillation cocktail are added and $^{32}$P incorporation (cpm) to the peptide substrate is quantified with a Beckman scintillation counter. Percentage inhibition is calculated for each reaction.

Compounds of Formula I, in free form or in pharmaceutically acceptable salt form, exhibit valuable pharmacological properties, for example, as indicated by the in vitro tests described in this application. For example, compounds of Formula I preferably show an IC$_{50}$ in the range of 1×10$^{-10}$ to 1×10$^{-5}$ M) preferably less than 50 nM for wild type BCR-Abl and G250E, E255V, T3151, F317L and M351T BCR-Abl mutants. Compounds of Formula I preferably show an IC$_{50}$ in the range of 1×10$^{-10}$ to 1×10$^{-5}$ M, preferably less than 50 nM for FGFR3. Compounds of Formula I, at a concentration of 10 μM, preferably show a percentage inhibition of greater than 50%, preferably greater than about 70%, against Abl, BCR-Abl, Bmx, c-Raf, Csk, Fes, FGFR, Flt3, Ikk, IR, JNK, Lck, Mkk, PKC, PKD, Rsk, SAPK, Syk, Trk, BTK, Src, EGFR, IGF, Mek, Ros and Tie2 kinases. For example N-{3-[7-(3-amino-phenylamino)-2-oxo-1,4-dihydro-2H-pyrimido[4,5-d]pyrimidin-3-yl]-4-methylphenyl}-3-trifluoromethylbenzamide N-{3-[7-(3-amino-phenylamino)-2-oxo-1,4-dihydro-2H-pyrimido[4,5-d]pyrimidin-3-yl]-4-methylphenyl}-3-trifluoromethyl-benzamide (Example 2) has an IC$_{50}$ of 5 nM, 2 nM, 5 nM, 3 nM 5 nM and 5 nM for wild type, G250E, E255V, T315I, F317L and M351T Bcr-abl, respectively.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

We claim:
1. A compound of Formula I:

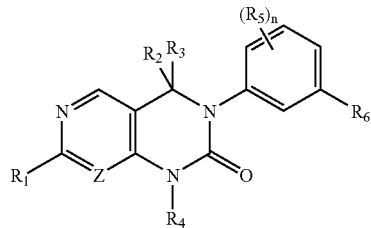

in which:

n is selected from 0, 1, 2, 3 and 4;

Z is N;

$R_1$ is selected from hydrogen, —$R_8$, —$OR_8$, —$S(O)_{0-2}R_8$, —$NR_7R_8$ and —$NR_7NR_7R_8$; wherein $R_7$ is independently selected from hydrogen and $C_{1-6}$alkyl; $R_8$ is selected from hydrogen, $C_{1-6}$alkyl, $C_{2-6}$alkenyl, $C_{6-10}$aryl-$C_{0-4}$alkyl, $C_{5-10}$heteroaryl-$C_{0-4}$alkyl, $C_{3-10}$cycloalkyl-$C_{0-4}$alkyl and $C_{3-10}$heterocycloalkyl-$C_{0-4}$alkyl; or $R_7$ and $R_8$ together with the nitrogen atom to which $R_7$ and $R_8$ are attached form $C_{3-10}$heterocycloalkyl or $C_{5-10}$heteroaryl; wherein any alkyl or alkenyl of $R_8$ is optionally substituted by one to three radicals independently selected from halo, hydroxy, $C_{1-6}$alkyl and —$NR_9R_{10}$; wherein any $C_{3-10}$heterocycloalkyl or $C_{3-10}$heteroaryl of $R_8$ is selected from pyrimidinyl, 2-oxo-pyrrolidin-1-yl, piperazinyl, thiazolyl, oxazolyl, pyridinyl, pyrazolyl, piperidinyl, pyrrolidinyl, morpholino, [1,2,4]triazin-3-yl and [1,3,4]thiadiazolyl; wherein any aryl, heteroaryl, cycloalkyl or heterocycloalkyl of $R_8$, or the combination of $R_7$ and $R_8$, is optionally substituted by one to three radicals selected from halo, hydroxy, cyano, $C_{1-6}$alkyl, $C_{1-6}$alkoxy, $C_{2-6}$alkenyl, trifluoromethyl, —$XNR_9R_{10}$, —$XOXNR_9R_{10}$, —$XNR_9S(O)_{0-2}R_{10}$, —$XC(O)NR_9R_{10}$, —$XNR_9C(O)XOR_9$, —$XNR_9C(O)NR_9R_{10}$, —$XNR_9XNR_9R_{10}$, —$XC(O)NR_9XNR_9R_{10}$, —$XNR_9XOR_9$, —$XOR_9$, —$XNR_9C(=NR_9)NR_9R_{10}$, —$XS(O)_{0-2}R_{11}$, —$XNR_9C(O)R_9$, —$XNR_9C(O)XNR_9R_{10}$, —$XNR_9C(O)R_{11}$, —$XC(O)R_{11}$, —$XR_{11}$, —$XC(O)OR_{10}$ and —$XS(O)_{0-2}NR_9R_{10}$; wherein X is a bond or $C_{1-4}$alkylene; $R_9$ and $R_{10}$ are independently selected from hydrogen, $C_{1-6}$alkyl and $C_{3-12}$cycloalkyl; and $R_{11}$ is selected from piperazinyl, morpholino and pyrrolidinyl; wherein $R_{11}$ is optionally substituted with 1 to 3 radicals selected from $C_{1-6}$alkyl, —$XNR_9R_{10}$, —$XNR_9XNR_9R_9$, $XNR_9XOR_9$ and —$XOR_9$; wherein X, $R_9$ and $R_{10}$ are as described above;

$R_2$ and $R_3$ are hydrogen or $R_2$ and $R_3$ together form =O or =S;

$R_4$ is selected from hydrogen, hydroxy, amino, $C_{1-6}$alkyl, —$XOR_9$, —$XC(O)OR_9$, —$XC(O)NR_9R_{10}$, $C_{3-10}$cycloalkyl-$C_{0-4}$alkyl, pyridinyl-$C_{0-4}$alkyl, $C_{6-10}$aryl-$C_{0-4}$alkyl and morpholino-$C_{0-4}$alkyl; wherein X, $R_9$ and $R_{10}$ are as described above;

$R_5$ is selected from $C_{1-6}$alkyl, $C_{2-6}$alkenyl, $C_{1-6}$alkoxy, and trifluoromethyl;

$R_6$ is selected from —$NR_{12}Y(O)R_{13}$ and —$Y(O)NR_{12}R_{13}$; wherein Y is selected from C, P(O), and S(O); $R_{12}$ is selected from hydrogen and $C_{1-6}$alkyl; and $R_{13}$ is selected from $C_{6-10}$aryl, $C_{3-10}$cycloalkyl, pyrazolyl and pyridinyl; wherein any aryl, cycloalkyl, or pyridinyl of $R_{13}$ is substituted by one to three radicals independently selected from halo, hydroxy, nitro, cyano, trifluoromethyl, $C_{1-6}$alkyl, $C_{1-6}$alkoxy, —$XNR_9R_9$, —$XNR_9XNR_9R_9$, —$XNR_9C(O)R_9$, —$XC(O)OR_9$, —$XNR_9S(O)_2R_9$, —$XNR_9S(O)R_9$, —$XNR_9SR_9$ and —$XR_{14}$; wherein X and $R_9$ are as defined above and $R_{14}$ is selected from $C_{5-10}$heteroaryl-$C_{0-4}$alkyl and $C_{3-10}$heterocycloalkyl-$C_{0-4}$alkyl; wherein said $C_{5-10}$heteroaryl of $R_{14}$ is selected from imidazolyl and 1,3,4-triazinyl; wherein said $C_{3-10}$heterocycloalkyl of $R_{14}$ is selected from morpholino, piperazinyl and pyrrolidinyl; wherein any heteroaryl or heterocycloalkyl of $R_{14}$ is optionally substituted with a radical selected from $C_{1-6}$alkyl, trifluoromethyl, —NR$_9$R$_9$ and —C(O)OR$_9$; wherein R$_9$ is as described above; and the pharmaceutically acceptable salts thereof.

2. The compound of claim 1 in which:
n is selected from 0, 1 and 2;
Z is N;
R$_1$ is selected from hydrogen, —R$_8$, —OR$_8$, —S(O)$_{0-2}$R$_8$, —NR$_7$R$_8$ and —NR$_7$NR$_7$R$_8$; wherein R$_7$ is independently selected from hydrogen and C$_{1-6}$alkyl; R$_8$ is selected from hydrogen, C$_{1-6}$alkyl, C$_{2-6}$alkenyl, C$_{6-10}$aryl-C$_{0-4}$alkyl, C$_{5-10}$heteroaryl-C$_{0-4}$alkyl, C$_{3-10}$cycloalkyl-C$_{0-4}$alkyl and C$_{3-10}$heterocycloalkyl-C$_{0-4}$alkyl; or R$_7$ and R$_8$ together with the nitrogen atom to which R$_7$ and R$_8$ are attached form C$_{3-10}$heterocycloalkyl or C$_{5-10}$heteroaryl; wherein any alkyl or alkenyl of R$_8$ is optionally substituted by one to three radicals independently selected from halo, hydroxy, C$_{1-6}$alkyl and —NR$_9$R$_{10}$; wherein any C$_{3-10}$heterocycloalkyl or C$_{5-10}$heteroaryl of R$_8$ is selected from pyrimidinyl, 2-oxo-pyrrolidin-1-yl, piperazinyl, thiazolyl, oxazolyl, pyridinyl, pyrazolyl, piperidinyl, pyrrolidinyl, morpholino, [1,2,4]triazin-3-yl and [1,3,4]thiadiazolyl; wherein any aryl, heteroaryl, cycloalkyl or heterocycloalkyl of R$_8$, or the combination of R$_7$ and R$_8$, is optionally substituted by one to three radicals selected from halo, hydroxy, cyano, C$_{1-6}$alkyl, C$_{1-6}$alkoxy, C$_{2-6}$alkenyl, trifluoromethyl, —XNR$_9$R$_{10}$, —XOXNR$_9$R$_{10}$, —XNR$_9$S(O)$_{0-2}$R$_{10}$, —XC(O)NR$_9$R$_{10}$, —XNR$_9$C(O)XOR$_9$, —XNR$_9$C(O)NR$_9$R$_{10}$, —XNR$_9$XNR$_9$R$_{10}$, —XC(O)NR$_9$XNR$_9$R$_{10}$, —XNR$_9$XOR$_9$, —XOR$_9$, —XNR$_9$C(=NR$_9$)NR$_9$R$_{10}$, —XS(O)$_{0-2}$R$_{11}$, —XNR$_9$C(O)R$_9$, —XNR$_9$C(O)XNR$_9$R$_{10}$, —XNR$_9$C(O)R$_{11}$, —XC(O)R$_{11}$, —XR$_{11}$, —XC(O)OR$_{10}$ and —XS(O)$_{0-2}$NR$_9$R$_{10}$; wherein X is a bond or C$_{1-4}$alkylene; R$_9$ and R$_{10}$ are independently selected from hydrogen, C$_{1-6}$alkyl and C$_{3-12}$cycloalkyl; and R$_{11}$ is selected from piperazinyl, morpholino and pyrrolidinyl; wherein R$_{11}$ is optionally substituted with 1 to 3 radicals selected from C$_{1-6}$alkyl, —XNR$_9$R$_{10}$, —XNR$_9$XNR$_9$R$_9$, —XNR$_9$XOR$_9$ and —XOR$_9$; wherein X, R$_9$ and R$_{10}$ are as described above;

R$_2$ and R$_3$ are hydrogen or R$_2$ and R$_3$ together form =O;
R$_4$ is selected from hydrogen, C$_{1-6}$alkyl, —XOR$_9$, —XC(O)OR$_9$, —XC(O)NR$_9$R$_{10}$, C$_{3-10}$cycloalkyl-C$_{0-4}$alkyl, pyridinyl-C$_{0-4}$alkyl, and morpholino-C$_{0-4}$alkyl; wherein X, R$_9$ and R$_{10}$ are as described above;
R$_5$ is selected from C$_{1-6}$alkyl, C$_{2-6}$alkenyl, C$_{1-6}$alkoxy;
R$_6$ is selected from —NR$_{12}$C(O)R$_{13}$ and —C(O)NR$_{12}$R$_{13}$; wherein R$_{12}$ is selected from hydrogen and C$_{1-6}$alkyl; and R$_{13}$ is selected from C$_{6-10}$aryl, C$_{3-10}$cycloalkyl, pyrazolyl pyridinyl; wherein any aryl, cycloalkyl, pyrazolyl or pyridinyl of R$_{13}$ is substituted by one to three radicals independently selected from halo, hydroxy, nitro, cyano, trifluoromethyl, C$_{1-6}$alkyl, C$_{1-6}$alkoxy, —XNR$_9$R$_9$, —XNR$_9$XNR$_9$R$_9$, —XNR$_9$C(O)R$_9$, —XC(O)OR$_9$, —XNR$_9$S(O)$_2$R$_9$, —XNR$_9$S(O)R$_9$, —XNR$_9$SR$_9$ and —XR$_{14}$; wherein X and R$_9$ are as defined above and R$_{14}$ is selected from C$_{5-10}$heteroaryl-C$_{0-4}$alkyl and C$_{3-10}$heterocycloalkyl-C$_{0-4}$alkyl; wherein said C$_{5-10}$heteroaryl of R$_{14}$ is selected from imidazolyl and 1,3,4-triazinyl; wherein said C$_{3-10}$heterocycloalkyl of R$_{14}$ is selected from morpholino, piperazinyl and pyrrolidinyl; wherein any heteroaryl or heterocycloalkyl of R$_{14}$ is optionally substituted with a radical selected from C$_{1-6}$alkyl, trifluoromethyl, —NR$_9$R$_9$ and —C(O)OR$_9$; wherein R$_9$ is as described above.

3. The compound of claim 2 in which R$_1$ is selected from hydrogen, —R$_8$, —OR$_8$, —S(O)$_2$R$_8$, —NHR$_8$ and —NHNHR$_8$; wherein R$_8$ is selected from hydrogen, methyl, ethyl, isopropyl, cyclopropyl, cyclobutyl, cyclopentyl, cyclohexyl, pyrimidinyl, 3-hydroxy-1-methyl-propyl hydroxy-ethyl, phenyl, morpholino, benzyl, [1,2,4]triazol-4-yl, allyl, 2-methyl-allyl, 2-(2-oxo-pyrrolidin-1-yl)-ethyl, piperazinyl-ethyl, piperazinyl-propyl, thiazolyl, oxazolyl, pyridinyl, pyrazolyl, piperidinyl, thiazolyl, ethyl-pyrrolidinyl-methyl, morpholino-propyl, dimethyl-amino-propyl, diethyl-amino-propyl, diethyl-amino-butyl, ethoxy-carbonyl-methyl and [1,2,4]triazin-3-yl, [1,3,4]thiadiazolyl; wherein any aryl, heteroaryl, cycloalkyl or heterocycloalkyl is optionally substituted with 1 to 3 radicals independently selected from methyl, ethyl, cyano, hydroxy, methoxy, amino-carbonyl-amino, hydroxy-methyl, methyl-piperazinyl, methyl-piperazinyl-carbonyl, ethyl-piperazinyl, methyl-piperazinyl-methyl, morpholino-sulfonyl, methyl-piperazinyl-sulfonyl, methyl-piperazinyl-carbonyl-amino, methyl-sulfonyl-amino, amino-carbonyl, amino-sulfonyl, hydroxy-ethyl, hydroxy-methyl-carbonyl-amino, formyl-amino, dimethyl-amino, dimethyl-amino-methyl, dimethyl-amino-ethyl, isopropyl-amino-ethyl, carboxy, amino-ethyl-amino, methyl-amino-ethyl, morpholino-ethyl, morpholino-methyl, amino-ethyl, imidazolyl-propyl, piperazinyl-ethyl, piperazinyl, trifluoromethyl, diethyl-amino-ethyl, fluoro, morpholino, dimethyl-amino-ethyl-amino-carbonyl, diethyl-amino-ethoxy, 2-amino-propionylamino, dimethyl-amino-pyrrolidinyl, (2-dimethylamino-ethyl)-methyl-amino, 2-dimethylamino-1-methyl-ethoxy and diethyl-amino.

4. The compound of claim 3 in which R$_6$ is selected from —NHC(O)R$_{13}$ and —C(O)NHR$_{13}$; wherein R$_{13}$ is selected from methyl, phenyl, pyrazolyl and pyridinyl; wherein any aryl or heteroaryl is optionally substituted with 1 to 2 radicals independently selected from trifluoromethyl, dimethylamino, nitro, amino, morpholino, methyl-piperazinyl-methyl, ethyl-piperazinyl-methyl, methyl-carbonyl-amino, methoxy, methoxy-carbonyl, methyl-piperazinyl, ethyl-piperazinyl, morpholino-methyl, methyl-imidazolyl, dimethy-lamino-ethoxy, methyl-imidazolyl, diethyl-amino-ethyl, [1,2,4]triazolyl and pyrrolidinyl-methyl.

5. The compound of claim 4 in which R$_4$ is selected from hydrogen, methyl, hydroxy-ethyl, cyclopropyl, carboxymethyl, methoxy-carbonyl-methyl, methyl-amino-carbonyl-methyl, ethyl, morpholino-ethyl, pyridinyl-ethyl, amino-carbonyl-methyl, ethyl-amino-carbonyl-methyl, dimethyl-amino-carbonyl-methyl, cyclopropyl-amino-carbonyl-methyl and isopropyl-amino-carbonyl-methyl.

6. The compound of claim 5 selected from: N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Amino-phenylamino)-1-methyl-2-oxo-1,4-dihydro-2H-pyrimido[4,5-d]pyrimidin-3-yl]-4-methyl-phenyl}-3-trifluoromethyl-benzamide;

N-[4-Methyl-3-(1-methyl-7-methylamino-2,4-dioxo-1,4-dihydro-2H-pyrimido[4,5-d]pyrimidin-3-yl)-phenyl]-3-trifluoromethyl-benzamide;

N-[3-(7-Benzylamino-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-2-oxo-7-(3-ureido-phenylamino)-1,4-dihydro-2H-pyrimido[4,5-d]pyrimidin-3-yl]-phenyl}-3-trifluoromethyl-benzamide;

N-{3-[7-(3-Hydroxymethyl-phenylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(4-methyl-piperazin-1-ylmethyl)-phenylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-2-oxo-7-(3-sulfamoyl-phenylamino)-1,4-dihydro-2H-pyrimido[4,5-d]pyrimidin-3-yl]-phenyl}-3-trifluoromethyl-benzamide;

N-(3-{7-[3-(2-Hydroxy-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[3-(4-methyl-piperazin-1-yl)-phenylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-2-oxo-7-(N'-phenyl-hydrazino)-1,4-dihydro-2H-pyrimido[4,5-d]pyrimidin-3-yl]-phenyl}-3-trifluoromethyl-benzamide;

N-(3-{7-[3-(2-Hydroxy-acetylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-{4-Methyl-3-[1-methyl-2-oxo-7-([1,2,4]triazol-4-ylamino)-1,4-dihydro-2H-pyrimido[4,5-d]pyrimidin-3-yl]-phenyl}-3-trifluoromethyl-benzamide;

N-{4-Methyl-3-[1-methyl-7-(4-methyl-piperazin-1-ylamino)-2-oxo-1,4-dihydro-2H-pyrimido[4,5-d]pyrimidin-3-yl]-phenyl}-3-trifluoromethyl-benzamide;

N-{3-[7-(3-Formylamino-phenylamino)-1-methyl-2-oxo-1,4-dihydro-2H-pyrimido[4,5-d]pyrimidin-3-yl]-4-methyl-phenyl}-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-trifluoromethyl-benzamide;

N-[3-(7-Cyclopropylamino-1-methyl-2-oxo-1,4-dihydro-2H-pyrimido[4,5-d]pyrimidin-3-yl)-4-methyl-phenyl]-3-trifluoromethyl-benzamide;

N-{3-[7-(2-Hydroxy-ethylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Dimethylamino-phenylamino)-1-(2-hydroxy-ethyl)-2-oxo-1,4-dihydro-2H-pyrimido[4,5-d]pyrimidin-3-yl]-4-methyl-phenyl}-3-trifluoromethyl-benzamide;

N-(3-{7-[3-(2-Isopropylamino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-[3-(7-Methanesulfonyl-1-methyl-2-oxo-1,4-dihydro-2H-pyrimido[4,5-d]pyrimidin-3-yl)-4-methyl-phenyl]-3-trifluoromethyl-benzamide;

3-{8-Methyl-6-[2-methyl-5-(3-trifluoromethyl-benzoylamino)-phenyl-7-oxo-5,6,7,8-tetrahydro-pyrimido[4,5-d]pyrimidin-2-ylamino}-benzoic acid;

N-[3-(7-Cyclobutylamino-1-methyl-2-oxo-1,4-dihydro-2H-pyrimido[4,5-d]pyrimidin-3-yl)-4-methyl-phenyl]-3-trifluoromethyl-benzamide;

N-[3-(7-Cyclopentylamino-1-methyl-2-oxo-1,4-dihydro-2H-pyrimido[4,5-d]pyrimidin-3-yl)-4-methyl-phenyl]-3-trifluoromethyl-benzamide;

N-{3-[7-(2-Hydroxy-1-methyl-ethylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2-Hydroxy-1-methyl-ethylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Allylamino-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-7-(2-methyl-allylamino)-2-oxo-1,4-dihydro-2H-pyrimido[4,5-d]pyrimidin-3-yl]-phenyl}-3-trifluoromethyl-benzamide;

N-(4-Methyl-3-{1-methyl-2-oxo-7-[3-(2-oxo-pyrrolidin-1-yl)-propylamino]-1,4-dihydro-2H-pyrimido(4,5-d]pyrimidin-3-yl}-phenyl)-3-trifluoromethyl-benzamide;

3-Dimethylamino-N-(4-methyl-3-{1-methyl-7-[3-(4-methyl-piperazin-1-ylmethyl)-phenylamino]-2-oxo-1,4-dihydro-2H-pyrimido[4,5-d]pyrimidin-3-yl}-phenyl)-5-trifluoromethyl-benzamide;

3-Dimethylamino-N-{3-[7-(3-dimethylaminomethyl-phenylamino)-1-methyl-2-oxo-1,4-dihydro-2H-pyrimido[4,5-d]pyrimidin-3-yl]-4-methyl-phenyl}-5-trifluoromethyl-benzamide;

N-(3-{7-[3-(2-Dimethylamino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[3-(2-Amino-ethylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[3-(2-methylamino-ethyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[3-(2-morpholin-4-yl-ethyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[4-(2-morpholin-4-yl-ethyl)-phenylamino]-2-oxo-1,4-dihydro-2H-pyrimido[4,5-d]pyrimidin-3-yl}-phenyl)-3-trifluoromethyl-benzamide;

N-(3-{7-[4-(2-Amino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[4-(2-methylamino-ethyl)-phenylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-7-(3-morpholin-4-ylmethyl-phenylamino)-2-oxo-1,4-dihydro-2H-pyrimido[4,5-d]pyrimidin-3-yl]-phenyl}-3-trifluoromethyl-benzamide;

N-(3-{7-[3-(2-Amino-ethyl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-2-oxo-7-[3-(2-piperazin-1-yl-ethyl)-phenylamino]-1,4-dihydro-2H-pyrimido[4,5-d]pyrimidin-3-yl}-phenyl)-3-trifluoromethyl-benzamide;

N-{3-[7-(3-Imidazol-1-yl-propylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(3-methyl-isoxazol-5-ylamino)-2-oxo-1,4-dihydro-2H-pyrimido[4,5-d]pyrimidin-3-yl]-phenyl}-3-trifluoromethyl-benzamide;

N-(4-Methyl-3-{1-methyl-2-oxo-7-[4-(2-piperazin-1-yl-ethyl)-phenylamino]-1,4-dihydro-2H-pyrimido[4,5-d]pyrimidin-3-yl}-phenyl)-3-trifluoromethyl-benzamide N-{4-Methyl-3-[1-methyl-2-oxo-7-(3-piperazin-1-ylmethyl-phenylamino)-1,4-dihydro-2H-pyrimido[4,5-d]pyrimidin-3-yl]-phenyl}-3-trifluoromethyl-benzamide;

N-{4-Methyl-3-[1-methyl-2-oxo-7-(4-piperazin-1-yl-phenylamino)-1,4-dihydro-2H-pyrimido[4,5-d]pyrimidin-3-yl]-phenyl}-3-trifluoromethyl-benzamide;

N-(3-{7-[4-(4-Ethyl-piperazin-1-yl)-phenylamino]-1-methyl-2-oxo-1,4-dihydro-2H-pyrimido[4,5-d]pyrimidin-3-yl}-4-methyl-phenyl)-3-trifluoromethyl-benzamide;

N-{3-[7-(3-Dimethylamino-phenylamino)-2,4-dioxo-1,4-dihydro-2H-pyrimido[4,5-d]pyrimidin-3-yl]-4-methyl-phenyl}-3-trifluoromethyl-benzamide;

N-{4-Methoxy-3-[1-methyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(6-Ethyl-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Dimethylamino-phenylamino)-1-methyl-2,4-dioxo-1,4-dihydro-2H-pyrimido[4,5-d]pyrimidin-3-yl]-4-methyl-phenyl}-3-trifluoromethyl-benzamide;

N-{4-Methyl-3-[1-methyl-2-oxo-7-(6-trifluoromethyl-pyridin-3-ylamino)-1,4-dihydro-2H-pyrimido[4,5-d]pyrimidin-3-yl]-phenyl}-3-trifluoromethyl-benzamide;

N-{4-Methyl-3-[1-methyl-2-oxo-7-(6-vinyl-pyridin-3-ylamino)-1,4-dihydro-2H-pyrimido[4,5-d]pyrimidin-3-yl]-phenyl}-3-trifluoromethyl-benzamide;

N-{3-[7-(3-Diethylamino-propylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(3-Diethylamino-propylamino)-1-methyl-2-oxo-1,4-dihydro-2H-pyrido[4,3-d]pyrimidin-3-yl]-4-methyl-phenyl}-3-trifluoromethyl-benzamide; N-(3-{7-[6-(2-Diethylamino-ethyl)-pyridin-3-ylamino]-1-methyl-2-oxo-1,4-dihydro-2H-pyrimido[4,5-d]pyrimidin-3-yl}-4-methyl-phenyl)-3-trifluoromethyl-benzamide;

N-{4-Methyl-3-[1-methyl-7-(6-methyl-pyridin-3-ylamino)-2,4-dioxo-1,4-dihydro-2H-pyrimido[4,5-d]pyrimidin-3-yl]-phenyl}-3-trifluoromethyl-benzamide;

N-{3-[7-(4-Fluoro-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(6-methyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(2,5-dimethyl-2H-pyrazol-3-ylamino)-2-oxo-1,4-dihydro-2H-pyrimido[4,5-d]pyrimidin-3-yl]-4-methyl-phenyl}-3-trifluoromethyl-benzamide;

4-Methyl-3-[1-methyl-7-(6-methyl-pyridin-3-ylamino)-2-oxo-1,4-dihydro-2H-pyrimido[4,5-d]pyrimidin-3-yl]-N-(3-trifluoromethyl-phenyl)benzamide;

{7-(6-Methyl-pyridin-3-ylamino)-3-[2-methyl-5-(3-trifluoromethyl-benzoylamino)-phenyl]-2-oxo-3,4-dihydro-2H-pyrimido[4,5-d]pyrimidin-1-yl}-acetic acid methyl ester;

N-{4-Methyl-3-[1-methyl-2-oxo-7-(piperidin-4-ylamino)-1,4-dihydro-2H-pyrimido[4,5-d]pyrimidin-3-yl]-phenyl}-3-trifluoromethyl-benzamide;

{7-(6-Methyl-pyridin-3-ylamino)-3-[2-methyl-5-(3-trifluoromethyl-benzoylamino)-phenyl]-2-oxo-3,4-dihydro-2H-pyrimido[4,5-d]pyrimidin-1-yl }-acetic acid;

N-{4-Methyl-3-[1-methylcarbamoylmethyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[1-Cyclopropyl-7-(4-fluoro-phenylamino)-2-oxo-1,4-dihydro-2H-pyrimido[4,5-d]pyrimidin-3-yl]-4-methyl-phenyl}-3-trifluoromethyl-benzamide;

3-[7-(2,6-Dimethyl-pyridin-3-ylamino)-1-methyl-2-oxo-1,4-dihydro-2H-pyrimido[4,5-d]pyrimidin-3-yl]-N-(3-trifluoromethyl-phenyl)-4-vinyl-benzamide;

N-{3-[1-Cyclopropyl-7-(3-methyl-isoxazol-5-ylamino)-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(4-morpholin-4-yl-phenylamino)-2-oxo-1,4-dihydro-2H-pyrimido[4,5-d]pyrimidin-3-yl]-phenyl}-3-trifluoromethyl-benzamide;

N-(3-{1-Cyclopropyl-7-[4-(2-morpholin-4-yl-ethyl)-phenylamino]-2-oxo-1,4-dihydro-2H-pyrimido[4,5-d]pyrimidin-3-yl}-4-methyl-phenyl)-3-trifluoromethyl-benzamide;

N-{3-[1-Cyclopropyl-7-(2,6-dimethyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(2-methyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-7-(4,6-dimethyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[1-Cyclopropyl-2-oxo-7-(pyridin-3-ylamino)-1,4-dihydro-2H-pyrimido[4,5-d]pyrimidin-3-yl]-4-methyl-phenyl}-3-trifluoromethyl-benzamide;

N-[3-(1-Ethyl-7-methylamino-2-oxo-1,4-dihydro-2H-pyrimido[4,5-d]pyrimidin-3-yl)-4-methyl-phenyl]-3-trifluoromethyl-benzamide;

N-[3-(1-Ethyl-7-ethylamino-2-oxo-1,4-dihydro-2H-pyrimido[4,5-d]pyrimidin-3-yl)-4-methyl-phenyl]-3-trifluoromethyl-benzamide;

N-{3-[7-(2,6-Dimethyl-pyridin-3-ylamino)-1-ethyl-2-oxo-1,4-dihydro-2H-pyrimido[4,5-d]pyrimidin-3-yl]-4-methyl-phenyl}-3-trifluoromethyl-benzamide;

N-{3-[1-Ethyl-7-(2-methyl-pyridin-3-ylamino)-2-oxo-1,4-dihydro-2H-pyrimido[4,5-d]pyrimidin-3-yl]-4-methyl-phenyl}-3-trifluoromethyl-benzamide;

N-{3-[7-(2,6-Dimethyl-pyridin-3-ylamino)-1-methyl-2-oxo-1,4-dihydro-2H-pyrimido[4,5-d]pyrimidin-3-yl]-4-ethyl-phenyl}-3-trifluoromethyl-benzamide;

N-[3-Methoxy-5-(1-methyl-7-methylamino-2-oxo-1,4-dihydro-2H-pyrimido[4,5-d]pyrimidin-3-yl)-phenyl]-3-trifluoromethyl-benzamide;

N-(3-Methoxy-5-{1-methyl-2-oxo-7-[3-(2-oxo-pyrrolidin-1-yl)-propylamino]-1,4-hydro-2H-pyrimido[4,5-d]pyrimidin-3-yl}-phenyl)-3-trifluoromethyl-benzamide;

N-[3-Methoxy-5-(1-methyl-7-methylamino-2-oxo-1,4-dihydro-2H-pyrimido[4,5-]pyrimidin-3-yl)-phenyl]-3-morpholin-4-yl-5-trifluoromethyl-benzamide;

N-(3-Methoxy-5-{1-methyl-2-oxo-7-[3-(2-oxo-pyrrolidin-1-yl)-propylamino]-1,4-dihydro-2H-pyrimido[4,5-d]pyrimidin-3-yl}-phenyl)-3-morpholin-4-yl-5-trifluoromethyl-benzamide;

N-[4-Methyl-3-(1-methyl-7-methylamino-2,4-dioxo-1,4-dihydro-2H-pyrimido[4,5-]pyrimidin-3-yl)-phenyl]-3-trifluoromethyl-benzamide;

N-[3-(7-Amino-1-methyl-2,4-dioxo-1,4-dihydro-2H-pyrimido[4,5-d]pyrimidin-3-yl)-4-methyl-phenyl]-3-trifluoromethyl-benzamide;

N-{3-[7-(2,6-Dimethyl-pyridin-3-ylamino)-1-methyl-2,4-dioxo-1,4-dihydro-2H-pyrimido[4,5-d]pyrimidin-3-yl]-4-methyl-phenyl}-3-trifluoromethyl-benzamide;

4-(4-Ethyl-piperazin-1-ylmethyl)-N-[3-methoxy-5-(1-methyl-7-methylamino-2-oxo-1,4-dihydro-2H-pyrimido[4,5-d]pyrimidin-3-yl)-phenyl]-3-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-4-(4-ethyl-piperazin-1-yl)-3-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-3-(4-ethyl-piperazin-1-yl)-5-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-3-morpholin-4-yl-5-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-4-(4-ethyl-piperazin-1-ylmethyl)-3-trifluoromethyl-benzamide;

N-[3-(1-Ethyl-7-methylamino-2-oxo-1,4-dihydro-2H-pyrimido[4,5-d]pyrimidin-3-yl)-5-methoxy-phenyl]-4-morpholin-4-ylmethyl-3-trifluoromethyl-benzamide;

N-[4-Methyl-3-(1-methyl-7-methylamino-2,4-dioxo-1,4-dihydro-2H-pyrimido[4,5-d]pyrimidin-3-yl)-phenyl]-3-morpholin-4-yl-5-trifluoromethyl-benzamide;

4-(4-Ethyl-piperazin-1-yl)-N-[4-methyl-3-(1-methyl-7-methylamino-2,4-dioxo-1,4-dihydro-2H-pyrimido[4,5-d]pyrimidin-3-yl)-phenyl]-3-trifluoromethyl-benzamide;

3-(4-Ethyl-piperazin-1-yl)-N-[4-methyl-3-(1-methyl-7-methylamino-2,4-dioxo-1,4-dihydro-2H-pyrimido[4,5-d]pyrimidin-3-yl)-phenyl]-5-trifluoromethyl-benzamide;

4-(4-Ethyl-piperazin-1-ylmethyl)-N-[4-methyl-3-(1-methyl-7-methylamino-2,4-dioxo-1,4-dihydro-2H-pyrimido[4,5-d]pyrimidin-3-yl)-phenyl]-3-trifluoromethyl-benzamide;

N-[4-Methyl-3-(1-methyl-7-methylamino-2,4-dioxo-1,4-dihydro-2H-pyrimido[4,5-d]pyrimidin-3-yl)-phenyl]-4-morpholin-4-ylmethyl-3-trifluoromethyl-benzamide;

N-(2-Hydroxy-5-trifluoromethyl-pyridin-3-yl)-4-methyl-3-[1-methyl-7-(6-methyl-pyridin-3-ylamino)-2-oxo-1,4-dihydro-2H-pyrimido[4,5-d]pyrimidin-3-yl]-benzamide;

N-[3-(1-Ethyl-7-methylamino-2-oxo-1,4-dihydro-2H-pyrimido[4,5-d]pyrimidin-3-yl)-5-methoxy-phenyl]-4-(4-ethyl-piperazin-1-ylmethyl)-benzamide;

N-{3-Methoxy-5-[7-methylamino-1-(2-morpholin-4-yl-ethyl)-2-oxo-1,4-dihydro-2H-pyrimido[4,5-d]pyrimidin-3-yl]-phenyl}-3-trifluoromethyl-benzamide;

N-{3-[7-Ethylamino-1-(2-morpholin-4-yl-ethyl)-2-oxo-1,4-dihydro-2H-pyrimido[4,5-d]pyrimidin-3-yl]-5-methoxy-phenyl}-3-trifluoromethyl-benzamide;

N-{3-[7-Cyclopropylamino-1-(2-morpholin-4-yl-ethyl)-2-oxo-1,4-dihydro-2H-pyrimido[4,5-d]pyrimidin-3-yl]-5-methoxy-phenyl}-3-trifluoromethyl-benzamide;

N-{3-Methoxy-5-[7-(2-methyl-allylamino)-1-(2-morpholin-4-yl-ethyl)-2-oxo-1,4-dihydro-2H-pyrimido[4,5-d]pyrimidin-3-yl]-phenyl}-3-trifluoromethyl-benzamide;

N-{3-Methoxy-5-[1-(2-morpholin-4-yl-ethyl)-2-oxo-7-phenylamino-1,4-dihydro-2H-pyrimido[4,5-d]pyrimidin-3-yl]-phenyl}-3-trifluoromethyl-benzamide;

N-{3-Methoxy-5-[1-(2-morpholin-4-yl-ethyl)-7-(4-morpholin-4-yl-phenylamino)-2-oxo-1,4-dihydro-2H-pyrimido[4,5-d]pyrimidin-3-yl]-phenyl}-3-trifluoromethyl-benzamide;

N-{3-Methoxy-5-[7-methylamino-2-oxo-1-(2-pyridin-2-yl-ethyl)-1,4-dihydro-2H-pyrimido[4,5-d]pyrimidin-3-yl]-phenyl}-3-trifluoromethyl-benzamide;

N-{3-[7-Ethylamino-2-oxo-1-(2-pyridin-2-yl-ethyl)-1,4-dihydro-2H-pyrimido[4,5-d]pyrimidin-3-yl]-5-methoxy-phenyl}-3-trifluoromethyl-benzamide;

N-{3-[7-Cyclopropylamino-2-oxo-1-(2-pyridin-2-yl-ethyl)-1,4-dihydro-2H-pyrimido[4,5-d]pyrimidin-3-yl]-5-methoxy-phenyl}-3-trifluoromethyl-benzamide;

N-{3-Methoxy-5-[7-(2-methyl-pyridin-3-ylamino)-1-(2-morpholin-4-yl-ethyl)-2-oxo-1,4-dihydro-2H-pyrimido[4,5-d]pyrimidin-3-yl]-phenyl}-3-trifluoromethyl-benzamide;

N-[3-(1-Ethyl-7-ethylamino-2-oxo-1,4-dihydro-2H-pyrimido[4,5-d]pyrimidin-3-yl)-5-methoxy-phenyl]-4-(4-ethyl-piperazin-1-ylmethyl)-3-trifluoromethyl-benzamide;

N-[3-(1-Ethyl-7-isopropylamino-2-oxo-1,4-dihydro-2H-pyrimido[4,5-d]pyrimidin-3-yl)-5-methoxy-phenyl]-4-(4-ethyl-piperazin-1-ylmethyl)-3-trifluoromethyl-benzamide;

{3-[3-Methoxy-5-(3-trifluoromethyl-benzoylamino)-phenyl]-7-methylamino-2-oxo-,3,4-dihydro-2H-pyrimido[4,5-d]pyrimidin-1-yl}-acetic acid methyl ester;

N-[3-Methoxy-5-(7-methylamino-1-methylcarbamoylmethyl-2-oxo-1,4-dihydro-2H-pyrimido[4,5-d]pyrimidin-3-yl)-phenyl]-3-trifluoromethyl-benzamide;

{3-[3-Methoxy-5-(3-trifluoromethyl-benzoylamino)-phenyl-7-methylamino-2-oxo-3,4-dihydro-2H-pyrimido[4,5-d]pyrimidin-1-yl}-acetic acid;

N-[3-(1-Carbamoylmethyl-7-methylamino-2-oxo-1,4-dihydro-2H-pyrimido[4,5-d]pyrimidin-3-yl)-5-methoxy-phenyl]-3-trifluoromethyl-benzamide;

N-[3-(1-Ethylcarbamoylmethyl-7-methylamino-2-oxo-1,4-dihydro-2H-pyrimido[4,5-d]pyrimidin-3-yl)-5-methoxy-phenyl]-3-trifluoromethyl-benzamide;

N-[3-(1-Dimethylcarbamoylmethyl-7-methylamino-2-oxo-1,4-dihydro-2H-pyrimido[4,5-d]pyrimidin-3-yl)-5-methoxy-phenyl]-3-trifluoromethyl-benzamide;

N-[3-(1-Cyclopropylcarbamoylmethyl-7-methylamino-2-oxo-1,4-dihydro-2H-pyrimido[4,5-d]pyrimidin-3-yl)-S-methoxy-phenyl]-3-trifluoromethyl-benzamide;

N-{3-[1-(Isopropylcarbamoyl-methyl)-7-methylamino-2-oxo-1,4-dihydro-2H-pyrimido[4,5-d]pyrimidin-3-yl]-5-methoxy-phenyl}-3-trifluoromethyl-benzamide;

N-[3-(7-Ethylamino-1-methylcarbamoylmethyl-2-oxo-1,4-dihydro-2H-pyrimido[4,5-d]pyrimidin-3-yl)-5-methoxy-phenyl]-3-trifluoromethyl-benzamide;

N-{3-[7-(2,5-Dimethyl-2H-pyrazol-3-ylamino)-1-methylcarbamoylmethyl-2-oxo-1,4-dihydro-2H-pyrimido[4,5-d]pyrimidin-3-yl]-5-methoxy-phenyl}-3-trifluoromethyl-benzamide;

N-{3-[7-(4,6-Dimethyl-pyridin-3-ylamino)-1-methylcarbamoylmethyl-2-oxo-1,4-dihydro-2H-pyrimido[4,5-d]pyrimidin-3-yl]-5-methoxy-phenyl}-3-trifluoromethyl-benzamide;

N-{3-Methoxy-5-[1-methylcarbamoylmethyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

3-(7-Amino-1-ethyl-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxy-benzamide;

3-(1-Ethyl-7-methylamino-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxy-benzamide;

3-(1-Ethyl-7-ethylamino-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxybenzamide;

3-(1-Ethyl-7-isopropylamino-2-oxo-1,4-dihydro-2H-pyrimido[4,5-d]pyrimidin-3-yl)-N-[4-(4-ethyl-piperazin-1-ylmethyl)-3-trifluoromethyl-phenyl]-5-methoxybenzamide;

3-(7-Cyclopropylamino-1-ethyl-2-oxo-1,4-dihydro-2H-pyrimido[4,5-d]pyrimidin-3-yl)-N-[4-(4-ethyl-piperazin-1-ylmethyl)3-trifluoromethyl-phenyl]-5-methoxy-benzamide;

3-(1-Ethyl-7-methylamino-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-[1-Ethyl-7-(6-methyl-pyridin-3-ylamino)-2-oxo-1,4-dihydro-2H-pyrimido[4,5-d]pyrimidin-3-yl]-N-[4-(4-ethyl-piperazin-1-ylmethyl)-3-trifluoromethyl-phenyl]-5-methoxy-benzamide;

3-(7-Amino-1-ethyl-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-(1-Ethyl-7-ethylamino-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-(7-Cyclopropylamino-1-ethyl-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

3-(1-Ethyl-7-isopropylamino-2-oxo-1,4-dihydro-2H-pyrimido[4,5-d]pyrimidin-3-yl)-5-methoxy-N-[4-(2-methyl-imidazol-1-yl)-3-trifluoromethyl-phenyl]-benzamide;

N-[3-(7-Amino-1-ethyl-2-oxo-1,4-dihydro-2H-pyrimido[4,5-d]pyrimidin-3-yl)-2,5-dimethoxy-phenyl]-acetamide;

N-{3-[1-Ethyl-7-(4-morpholin-4-yl-phenylamino)-2-oxo-1,4-dihydro-2H-pyrimido[4,5-d]pyrimidin-3-yl]-2,5-dimethoxy-phenyl}-acetamide;

N-[3-(1-Ethyl-7-ethylamino-2-oxo-1,4-dihydro-2H-pyrimido[4,5-d]pyrimidin-3-yl)-2,5-dimethoxy-phenyl]-acetamide;

N-[3-(1-Ethyl-7-methylamino-2-oxo-1,4-dihydro-2H-pyrimido[4,5-d]pyrimidin-3-yl)-2,5-dimethoxy-phenyl]-acetamide;

N-[3-(7-Cyclopropylamino-1-ethyl-2-oxo-1,4-dihydro-2H-pyrimido[4,5-d]pyrimidin-3-yl)-2,5-dimethoxy-phenyl]-acetamide;

N-{3-[1-Ethyl-7-(2-ethyl-2H-pyrazol-3-ylamino)-2-oxo-1,4-dihydro-2H-pyrimido[4,5-d]pyrimidin-3-yl]-5-methoxy-phenyl}-3-trifluoromethyl-benzamide;

N-{3-[7-(2,5-Dimethyl-2H-pyrazol-3-ylamino)-1-ethyl-2-oxo-1,4-dihydro-2H-pyrimido[4,5-d]pyrimidin-3-yl]-5-methoxy-phenyl}-3-trifluoromethyl-benzamide;

N-[4-Dimethyl-aminoethyl-amino-carbonyl-3-(1-methyl-2-oxo-7-p-tolylamino-1,4-dihydro-2H-pyrimido[4,5-d]pyrimidin-3-yl)-phenyl]-3-trifluoromethyl-benzamide;

N-(4-Methyl-3-{1-methyl-7-[4-(4-methyl-piperazin-1-yl)-phenylamino]-2-oxo-1,4-dihydro-2H-pyrimido[4,5-d]pyrimidin-3-yl}-phenyl)-3-trifluoromethyl-benzamide;

N-[3-(7-Hydroxy-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-7-(2-methyl-pyridin-4-ylamino)-2-oxo-1,4-dihydro-2H-pyrimido[4,5-d]pyrimidin-3-yl]-phenyl}-3-trifluoromethyl-benzamide;

N-[4-Methyl-3-(1-methyl-2-oxo-7-pyridin-3-yl-1,4-dihydro-2H-pyrimido[4,5-d]pyrimidin-3-yl)-phenyl]-3-trifluoromethyl-benzamide;

N-{3-[1-Ethyl-7-(2-methyl-pyridin-3-ylamino)-2-oxo-1,4-dihydro-2H-pyrimido[4,5-d]pyrimidin-3-yl]-5-methoxy-phenyl}-3-trifluoromethyl-benzamide;

N-{3-[7-(4,6-Dimethyl-pyridin-3-ylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(2,6-Dimethyl-pyridin-3-ylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[1-Ethyl-7-(6-methyl-pyridin-3-ylamino)-2-oxo-1,4-dihydro-2H-pyrimido[4,5-d]pyrimidin-3-yl]-5-methoxy-phenyl}-3-trifluoromethyl-benzamide;

N-{3-[7-(5-Dimethylaminomethyl-thiazol-2-ylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[4-(4-methyl-piperazin-1-ylmethyl)-phenylamino]-2-oxo-1,4-dihydro-2H-pyrimido[4,5-d]pyrimidin-3-yl }-phenyl)-3-trifluoromethyl-benzamide;

N-{3-[7-(4-Dimethylaminomethyl-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Cyano-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(5-Cyano-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2,6-Dimethyl-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(4,6-Dimethyl-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(4-Methoxy-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2-Methoxy-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(2-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(2,4-Dimethyl-thiazol-5-ylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Amino-1,4-dimethyl-2-oxo-1,4-dihydro-2H-pyrimido[4,5-d]pyrimidin-3-yl)-4-methyl-phenyl]-3-trifluoromethyl-benzamide;

N-[3-(7-Amino-1,4-dimethyl-2-oxo-1,4-dihydro-2H-pyrimido[4,5-d]pyrimidin-3-yl)-phenyl]-3-trifluoromethyl-benzamide;

N-{3-[1,4-Dimethyl-2-oxo-7-(pyridin-3-ylamino)-1,4-dihydro-2H-pyrimido[4,5-d]pyrimidin-3-yl]-4-methyl-phenyl}-3-trifluoromethyl-benzamide;

N-{3-[1,4-Dimethyl-2-oxo-7-(pyridin-3-ylamino)-1,4-dihydro-2H-pyrimido[4,5-d]pyrimidin-3-yl]-phenyl}-3-trifluoromethyl-benzamide;

N-{4-Methyl-3-[7-methylamino-1-(2-morpholin-4-yl-ethyl)2-oxo-1,4-dihydro-2H-pyrimido[4,5-d]pyrimidin-3-yl]-phenyl}-3-trifluoromethyl-benzamide;

N-{3-[7-Amino-1-(2-morpholin-4-yl-ethyl)-2-oxo-1,4-dihydro-2H-pyrimido[4,5-d]pyrimidin-3-yl]-4-methyl-phenyl}-3-trifluoromethyl-benzamide;

N-[3-(7-Amino-1-methyl-2-oxo-1,4-dihydro-2H-pyrimido[4,5-d]pyrimidin-3-yl)-5-methoxy-phenyl]-3-trifluoromethyl-benzamide;

N-[3-(7-Ethylamino-1-methyl-2-oxo-1,4-dihydro-2H-pyrimido[4,5-d]pyrimidin-3-yl)-5-methoxy-phenyl]-3-trifluoromethyl-benzamide;

N-(3-{7-[4-(2-Diethylamino-ethoxy)-phenylamino]-1-methyl-2-oxo-1,4-dihydro-2H-pyrimido[4,5-d]pyrimidin-3-yl}-5-methoxy-phenyl)-3-trifluoromethyl-benzamide;

N-[3-(7-Amino-1-ethyl-2-oxo-1,4-dihydro-2H-pyrimido[4,5-d]pyrimidin-3-yl)-5-methoxy-phenyl]-3-trifluoromethyl-benzamide;

N-[3-(1-Ethyl-7-ethylamino-2-oxo-1,4-dihydro-2H-pyrimido[4,5-d]pyrimidin-3-yl)-5-methoxy-phenyl]-3-trifluoromethyl-benzamide;

N-{3-[1-Ethyl-7-(3-morpholin-4-yl-propylamino)-2-oxo-1,4-dihydro-2H-pyrimido[4,5-d]pyrimidin-3-yl]-5-methoxy-phenyl}-3-trifluoromethyl-benzamide;

N-{3-[1-Ethyl-7-(4-morpholin-4-yl-phenylamino)-2-oxo-1,4-dihydro-2H-pyrimido[4,5-d]pyrimidin-3-yl]-5-methoxy-phenyl}-3-trifluoromethyl-benzamide;

N-{3-[1-Ethyl-2-oxo-7-(pyridin-3-ylamino)-1,4-dihydro-2H-pyrimido[4,5-d]pyrimidin-3-yl]-5-methoxy-phenyl}-3-trifluoromethyl-benzamide;

N-[3-(7-Cyclopropylamino-1-ethyl-2-oxo-1,4-dihydro-2H-pyrimido[4,5-d]pyrimidin-3-yl)-5-methoxy-phenyl]-3-trifluoromethyl-benzamide;

N-{3-[1-Ethyl-7-(2-methyl-allylamino)-2-oxo-1,4-dihydro-2H-pyrimido[4,5-d]pyrimidin-3-yl]-5-methoxy-phenyl}-3-trifluoromethyl-benzamide;

N-{3-[7-(3-Diethylamino-propylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(4-Diethylamino-butylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(3-Dimethylamino-phenylamino)-1-ethyl-2-oxo-1,4-dihydro-2H-pyrimido[4,5-d]pyrimidin-3-yl]-5-methoxy-phenyl}-3-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-nitro-5-trifluoromethyl-benzamide;

3-Amino-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

N-(3-{7-[3-(2-Amino-propionylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[3-(2-Amino-3-methyl-butyrylamino)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[6-(3-Dimethylamino-pyrrolidin-1-yl)-pyridin-3-ylamino]-1-methyl-2-oxo-1,4-dihydro-2H-pyrimido[4,5-d]pyrimidin-3-yl}-4-methyl-phenyl)-3-trifluoromethyl-benzamide;

N-[3-(7-{6-[(2-Dimethylamino-ethyl)-methyl-amino]-pyridin-3-ylamino}-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-2-oxo-7-(pyrimidin-2-ylamino)-1,4-dihydro-2H-pyrimido[4,5-d]pyrimidin-3-yl]-phenyl}-3-trifluoromethyl-benzamide;

N-{3-[7-(5,6-Dimethyl-[1,2,4]triazin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-2-oxo-7-(pyrazin-2-ylamino)-1,4-dihydro-2H-pyrimido[4,5-d]pyrimidin-3-yl]-phenyl}-3-trifluoromethyl-benzamide;

N-{3-[7-(2,5-Dimethyl-2H-pyrazol-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(3-methyl-isothiazol-5-ylamino)-2-oxo-1,4-dihydro-2H-pyrimido[4,5-d]pyrimidin-3-yl]-phenyl}-3-trifluoromethyl-benzamide;

N-{3-[7-(2-Ethyl-2H-pyrazol-3-ylamino)-1-methyl-2-oxo-1,4-dihydro-2H-pyrimido[4,5-d]pyrimidin-3-yl]-4-methyl-phenyl}-3-trifluoromethyl-benzamide;

N-(3-{7-[6-(2-Dimethylamino-1-methyl-ethoxy)-pyridin-3-ylamino]-1-methyl-2-oxo-1,4-dihydro-2H-pyrimido[4,5-d]pyrimidin-3-yl}-4-methyl-phenyl)-3-trifluoromethyl-benzamide;

N-(3-{7-[4-(2-Diethylamino-ethoxy)-phenylamino]-1-methyl-2-oxo-1,4-dihydro-2H-pyrimido[4,5-d]pyrimidin-3-yl}-4-methyl-phenyl)-3-trifluoromethyl-benzamide;

N-(4-Methyl-3-{1-methyl-7-[3-(4-methyl-piperazin-1-yl)-propylamino]-2-oxo-1,4-dihydro-2H-pyrimido[4,5-d]pyrimidin-3-yl}-phenyl)-3-trifluoromethyl-benzamide;

N-{4-Methyl-3-[1-methyl-2-oxo-7-(pyridin-3-ylamino)-1,4-dihydro-2H-pyrido[4,3-d]pyrimidin-3-yl]-phenyl}-3-trifluoromethyl-benzamide;

N-{4-Methyl-3-[1-methyl-7-(4-methyl-pyridin-3-ylamino)-2-oxo-1,4-dihydro-2H-pyrimido[4,5-d]pyrimidin-3-yl]-phenyl}-3-trifluoromethyl-benzamide;

N-{4-Methyl-3-[1-methyl-7-(3-methyl-pyridin-4-ylamino)-2-oxo-1,4-dihydro-2H-pyrimido[4,5-d]pyrimidin-3-yl]-phenyl}-3-trifluoromethyl-benzamide;

N-{4-Methyl-3-[1-methyl-7-(5-morpholin-4-ylmethyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(6-Diethylamino-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(6-Ethylamino-pyridin-3-ylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(2,6-Dimethyl-pyridin-4-ylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(4-methyl-imidazol-1-yl)-5-trifluoromethyl-benzamide;

N-{3-[7-(5-Ethyl-[1,3,4]thiadiazol-2-ylamino)-1-methyl-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(6-methyl-pyridin-3-ylamino)-2-oxo-1,4-dihydro-2H-pyrido[4,3-d]pyrimidin-3-yl]-phenyl}-3-trifluoromethyl-benzamide;

N-{4-Methyl-3-[7-(6-methyl-pyridin-3-ylamino)-2-oxo-1,4-dihydro-2H-pyrimido[4,5-d]pyrimidin-3-yl]-phenyl}-3-trifluoromethyl-benzamide;

N-{3-[7-(2,5-Dimethyl-2H-pyrazol-3-ylamino)-2-oxo-1,4-dihydro-2H-pyrimido[4,5-d]pyrimidin-3-yl]-4-methyl-phenyl}-3-trifluoromethyl-benzamide;

N-{4-Methyl-3-[1-methyl-7-(5-methyl-1H-pyrazol-3-ylamino)-2-oxo-1,4-dihydro-2H-pyrimido[4,5-d]pyrimidin-3-yl]-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-[1,2,4]triazol-4-yl-5-trifluoromethyl-benzamide;

N-{3-[7-(2,5-Dimethyl-2H-pyrazol-3-ylamino)-1-methyl-2-oxo-1,4-dihydro-2H-pyrido[4,3-d]pyrimidin-3-yl]-4-methyl-phenyl}-3-trifluoromethyl-benzamide;

N-{4-Methyl-3-[1-methyl-7-(1-methyl-1H-pyrazol-3-ylamino)-2-oxo-1,4-dihydro-2H-pyrimido[4,5-d]pyrimidin-3-yl]-phenyl}-3-trifluoromethyl-benzamide;

N-{4-Methyl-3-[1-methyl-7-(2-methyl-2H-pyrazol-3-ylamino)-2-oxo-1,4-dihydro-2H-pyrimido[4,5-d]pyrimidin-3-yl]-phenyl}-3-trifluoromethyl-benzamide;

N-{3-[7-(2,4-Dimethyl-thiazol-5-ylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-morpholin-4-yl-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-(2-methyl-imidazol-1-yl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-morpholin-4-yl-3-trifluoromethyl-benzamide;

N-{4-Methyl-3-[1-methyl-2-oxo-7-(pyrazin-2-ylamino)-1,4-dihydro-2H-pyrido[4,3-d]pyrimidin-3-yl]-phenyl}-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-dimethylamino-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-diethylaminomethyl-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-morpholin-4-ylmethyl-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-morpholin-4-yl-5-trifluoromethyl-benzamide;

3-Dimethylamino-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-[1,2,4]triazol-4-yl-5-trifluoromethyl-benzamide;

4-(2-Methyl-imidazol-1-yl)-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-morpholin-4-yl-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-(4-methyl-piperazin-1-yl)-3-trifluoromethyl-benzamide;

4-(4-Ethyl-piperazin-1-yl)-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

4-Cyclopropylaminomethyl-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

4-(4-Ethyl-piperazin-1-ylmethyl)-N-[4-methyl-3-(1-methyl-7-methylamino-2-oxo-1,4-dihydro-2H-pyrimido[4,5-d]pyrimidin-3-yl)-phenyl]-3-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-pyrrolidin-1-ylmethyl-3-trifluoromethyl-benzamide;

N-[4-Methyl-3-(1-methyl-7-methylamino-2-oxo-1,4-dihydro-2H-pyrimido[4,5-]pyrimidin-3-yl)-phenyl]-4-morpholin-4-ylmethyl-3-trifluoromethyl-benzamide;

4-Diethylaminomethyl-N-[4-methyl-3-(1-methyl-7-methylamino-2-oxo-1,4-dihydro-H-pyrimido[4,5-d]pyrimidin-3-yl)-phenyl]-3-trifluoromethyl-benzamide;

N-[3-(7-Amino-1-methyl-2-oxo-1,4-dihydro-2H-pyrimido[4,5-d]pyrimidin-3-yl)-4-ethyl-phenyl]-4-(4-methyl-piperazin-1-yl)-3-trifluoromethyl-benzamide;

N-[3-(7-Amino-1-methyl-2-oxo-1,4-dihydro-2H-pyrimido[4,5-d]pyrimidin-3-yl)-4-ethyl-phenyl]-4-(4-ethyl-piperazin-1-yl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-(4-ethyl-piperazin-1-ylmethyl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-pyrrolidin-1-ylmethyl-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-4-(4-methyl-piperazin-1-ylmethyl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(4-methyl-piperazin-1-yl)-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(3-dimethylamino-pyrrolidin-1-yl)-5-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-(4-ethyl-piperazin-1-yl)-5-trifluoromethyl-benzamide;

3-(4-Methyl-imidazol-1-yl)-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

3-(4-Ethyl-piperazin-1-yl)-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

3-(3-Dimethylamino-pyrrolidin-1-yl)-N-[4-methyl-3-(1-methyl-7-methylamino-2-oxo-1,4-dihydro-2H-pyrimido[4,5-d]pyrimidin-3-yl)-phenyl]-5-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-3-(4-methyl-piperazin-1-yl)-5-trifluoromethyl-benzamide;

N-[4-Methyl-3-(1-methyl-7-methylamino-2-oxo-1,4-dihydro-2H-pyrimido[4,5-d]pyrimidin-3-yl)-phenyl]-4-(4-methyl-piperazin-1-ylmethyl)-3-trifluoromethyl-benzamide;

N-{4-Methyl-3-[1-methyl-7-(3-morpholin-4-yl-propylamino)-2-oxo-1,4-dihydro-2H-pyrido[4,3-d]pyrimidin-3-yl]-phenyl}-3-trifluoromethyl-benzamide;

N-{3-[7-(3-Diethylamino-propylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(4-Diethylamino-butylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(4,6-Dimethyl-pyridin-3-ylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(2,6-Dimethyl-pyridin-3-ylamino)-1-methyl-2-oxo-1,4-dihydro-2H-pyrido[4,3-d]pyrimidin-3-yl]-4-methyl-phenyl}-3-trifluoromethyl-benzamide;

N-{3-[7-(2,6-Dimethyl-pyridin-4-ylamino)-1-methyl-2-oxo-1,4-dihydro-2H-pyrido[4,3-d]pyrimidin-3-yl]-4-methyl-phenyl}-3-trifluoromethyl-benzamide;

N-[4-Methyl-3-(1-methyl-2-oxo-1,4-dihydro-2H-pyrido[4,3-d]pyrimidin-3-yl)-phenyl]-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-4-(4-methyl-piperazin-1-ylmethyl)-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-trifluoromethyl-benzamide;

N-{3-[7-(3-Carbamoyl-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(2-Fluoro-5-trifluoromethyl-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(2-Fluoro-3-trifluoromethyl-phenylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Methanesulfonylamino-phenylamino)-1-methyl-2-oxo-1,4-dihydro-2H-pyrimido[4,5-d]pyrimidin-3-yl]-4-methyl-phenyl}-3-trifluoromethyl-benzamide;

N-{3-[7-(3-Methanesulfonylamino-phenylamino)-1-methyl-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-propylamino)-2-oxo-1,4-dihydro-2H-pyrimido[4,5-d]pyrimidin-3-yl]-4-methyl-phenyl}-3-(4-methyl-imidazol-1-yl)-5-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-acetamide;

N-{3-[7-(3-Dimethylamino-phenylamino)-2-oxo-1,4-dihydro-2H-pyrimido[4,5-d]pyrimidin-3-yl]-4-methyl-phenyl}-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-fluoro-benzamide;

N-{4-Methyl-3-[1-methyl-7-(4-methyl-thiazol-2-ylamino)-2-oxo-1,4-dihydro-2H-pyrimido[4,5-d]pyrimidin-3-yl]-phenyl}-3-trifluoromethyl-benzamide;

(2-{8-Methyl-6-[2-methyl-5-(3-trifluoromethyl-benzoylamino)-phenyl]-7-oxo-5,6,7,8-tetrahydro-pyrimido[4,5-d]pyrimidin-2-ylamino}-thiazol-4-yl)-acetic acid ethyl ester;

N-{3-[7-(3-Amino-phenylamino)-1-methyl-2-oxo-1,4-dihydro-2H-pyrimido[4,5-d]pyrimidin-3-yl]-4-methyl-phenyl}-3-trifluoromethyl-benzamide;

N-[3-(7-Cyclohexylamino-1-methyl-2-oxo-1,4-dihydro-2H-pyrimido[4,5-d]pyrimidin-3-yl)-4-methyl-phenyl]-3-trifluoromethyl-benzamide;

N-[4-Methyl-3-(1-methyl-7-morpholin-4-yl-2-oxo-1,4-dihydro-2H-pyrimido[4,5-d]pyrimidin-3-yl)-phenyl]-3-trifluoromethyl-benzamide;

N-[4-Methyl-3-(1-methyl-2-oxo-7-phenylamino-1,4-dihydro-2H-pyrimido[4,5-d]pyrimidin-3-yl)-phenyl]-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3,5-bis-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-isophthalamic acid methyl ester;

N-{3-[7-(3-Dimethylamino-phenylamino)-2-oxo-1,4-dihydro-2H-pyrimido[4,5-d]pyrimidin-3-yl]-4-methyl-phenyl}-2,5-bis-trifluoromethyl-benzamide;

N-{3-[7-(3-Dimethylamino-phenylamino)-1-ethyl-2-oxo-1,4-dihydro-2H-pyrimido[4,5-d]pyrimidin-3-yl]-4-methyl-phenyl}-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-fluoro-5-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-4-fluoro-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-4-methoxy-3-trifluoromethyl-benzamide;

N-{3-[7-(3-Dimethylamino-phenylamino)-2-oxo-1,4-dihydro-2H-pyrimido[4,5-d]pyrimidin-3-yl]-4-methyl-phenyl}-3-methyl-benzamide;

N-{3-[7-(3-Hydroxy-phenylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(morpholine-4-sulfonyl)-phenylamino]-2-oxo-1,4-dihydro-2H-pyrimido[4,5-d]pyrimidin-3-yl}-phenyl)-3-trifluoromethyl-benzamide;

N-{3-[7-(3-Dimethylaminomethyl-phenylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(4-methyl-piperazin-1-ylmethyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[3-(4-methyl-piperazine-1-sulfonyl)-phenylamino]-2-oxo-1,4-dihydro-2H-pyrimido[4,5-d]pyrimidin-3-yl}-phenyl)-3-trifluoromethyl-benzamide;

N-(4-Methyl-3-{1-methyl-7-[2-(4-methyl-piperazin-1-yl)-pyridin-4-ylamino]-2-oxo-1,4-dihydro-2H-pyrimido[4,5-d]pyrimidin-3-yl}-phenyl)-3-trifluoromethyl-benzamide;

4-Methyl-piperazine-1-carboxylic acid (3-{8-methyl-6-[2-methyl-5-(3-trifluoromethyl-benzoylamino)-phenyl]-7-oxo-5,6,7,8-tetrahydro-pyrimido[4,5-d]pyrimidin-2-ylamino}-phenyl)-amide;

N-(3-{7-[(1-Ethyl-pyrrolidin-2-ylmethyl)-amino]-1-methyl-2-oxo-1,4-dihydro-2H-pyrimido[4,5-d]pyrimidin-3-yl}-4-methyl-phenyl)-3-trifluoromethyl-benzamide;

N-[3-(7-Amino-1-methyl-2-oxo-1,4-dihydro-2H-pyrimido[4,5-d]pyrimidin-3-yl)-4-methyl-phenyl]-3-trifluoromethyl-benzamide;

N-{4-Methyl-3-[1-methyl-2-oxo-7-(pyridin-4-ylamino)-1,4-dihydro-2H-pyrimido[4,5-d]pyrimidin-3-yl]-phenyl}-3-trifluoromethyl-benzamide;

N-{4-Methyl-3-[1-methyl-2-oxo-7-(pyridin-3-ylamino)-1,4-dihydro-2H-pyrimido[4,5-]pyrimidin-3-yl]-phenyl}-3-trifluoromethyl-benzamide;

N-{3-[7-(2-Dimethylamino-pyridin-4-ylamino)-1-methyl-2-oxo-1,4-dihydro-2H-pyrimido[4,5-d]pyrimidin-3-yl]-4-methyl-phenyl}-3-trifluoromethyl-benzamide;

N-(4-Methyl-3-{1-methyl-7-[3-(4-methyl-piperazine-1-carbonyl)-phenylamino]-2-oxo-1,4-dihydro-2H-pyrimido[4,5-d]pyrimidin-3-yl }-phenyl)-3-trifluoromethyl-benzamide;

N-{4-Methyl-3-[1-methyl-2-oxo-7-(pyrimidin-5-ylamino)-1,4-dihydro-2H-pyrimido[4,5-d]pyrimidin-3-yl]-phenyl}-3-trifluoromethyl-benzamide;

N-{4-Methyl-3-[1-methyl-7-(6-methyl-pyridin-3-ylamino)-2-oxo-1,4-dihydro-2H-pyrimido[4,5-d]pyrimidin-3-yl]-phenyl}-3-trifluoromethyl-benzamide;

3-Acetylamino-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

3-(2-Dimethylamino-ethoxy)-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(2-morpholin-4-yl-ethoxy)-5-trifluoromethyl-benzamide;

3-(2-Dimethylamino-ethylamino)-N-{3-[7-(3-dimethylamino-phenylamino)-1-methyl-2-oxo-1,4-dihydro-2H-pyrimido[4,5-d]pyrimidin-3-yl]-4-methyl-phenyl}-5-trifluoromethyl-benzamide;

N-{3-[7-(3-Dimethylamino-phenylamino)-1-methyl-2-oxo-1,4-dihydro-2H-pyrimido[4,5-d]pyrimidin-3-yl]-4-methyl-phenyl}-3-(4-methyl-piperazin-1-yl)-5-trifluoromethyl-benzamide; and 2-Methyl-5-trifluoromethyl-2H-pyrazole-3-carboxylic acid -{3-[7-(3-dimethylamino-phenylamino)-1-methyl-2-oxo-1,4-dihydro-2H-pyrimido[4,5-d]pyrimidin-3 -yl]-4-methyl-phenyl}-amide.

7. A pharmaceutical composition comprising a therapeutically effective amount of a compound of claim 1 in combination with a pharmaceutically acceptable excipient.

* * * * *